United States Patent
Jeon et al.

(10) Patent No.: US 8,410,475 B2
(45) Date of Patent: Apr. 2, 2013

(54) COMPOUNDS AND ORGANIC LIGHT EMITTING DIODE USING THE SAME

(75) Inventors: Byung-Sun Jeon, Seoul (KR); Jeung-Gon Kim, Daejeon (KR); Wook-Dong Cho, Daejeon (KR); Chang-Hwan Kim, Jeju-si (KR); Hyun Nam, Seoul (KR)

(73) Assignee: LG Chem, Ltd., Seoul (KR)

( * ) Notice: Subject to any disclaimer, the term of this patent is extended or adjusted under 35 U.S.C. 154(b) by 798 days.

(21) Appl. No.: 12/312,847

(22) PCT Filed: Dec. 3, 2007

(86) PCT No.: PCT/KR2007/006176
§ 371 (c)(1),
(2), (4) Date: May 29, 2009

(87) PCT Pub. No.: WO2008/066357
PCT Pub. Date: Jun. 5, 2008

(65) Prior Publication Data
US 2010/0065827 A1    Mar. 18, 2010

(30) Foreign Application Priority Data
Dec. 1, 2006   (KR) .................. 10-2006-0120560

(51) Int. Cl.
*H01L 29/00* (2006.01)
(52) U.S. Cl. .......................................... 257/40; 257/103
(58) Field of Classification Search ................ 257/40, 257/103, E51.032
See application file for complete search history.

(56) References Cited

U.S. PATENT DOCUMENTS

| | | | |
|---|---|---|---|
| 7,838,129 B2 * | 11/2010 | Cho et al. | 428/690 |
| 2004/0219381 A1 * | 11/2004 | Kanakura et al. | 428/523 |
| 2004/0219386 A1 | 11/2004 | Thoms | |

FOREIGN PATENT DOCUMENTS

| | | |
|---|---|---|
| JP | 07-145372 | 6/1995 |
| JP | 2005-085599 | 3/2005 |
| WO | WO 2006/033564 A1 | 3/2006 |
| WO | WO 2006/080640 A1 | 8/2006 |
| WO | WO 2006/080644 | 8/2006 |

* cited by examiner

*Primary Examiner* — Howard Weiss
*Assistant Examiner* — Steven Rao
(74) *Attorney, Agent, or Firm* — McKenna Long & Aldridge, LLP

(57) ABSTRACT

Disclosed are new compounds and an organic light emitting diode using the same. The organic light emitting diode using the new compound according to the present invention exhibits excellent characteristics in terms of actuating voltage, light efficiency, and lifespan.

16 Claims, 1 Drawing Sheet

COMPOUNDS AND ORGANIC LIGHT EMITTING DIODE USING THE SAME

This application claims priority from International Application No. PCT/KR2007/006176, filed on Dec. 3, 2007, and Korean Patent Application No. 10-2006-0120560 filed on Dec. 1, 2006 in the KIPO, both of which are incorporated herein by reference in its entirety.

TECHNICAL FIELD

The present invention relates to new compounds which are capable of significantly improving a lifespan, efficiency, electrochemical stability and thermal stability of an organic light emitting diode, and an organic light emitting diode in which the compound is contained in an organic compound layer.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting diode which is based on the above mechanism typically comprises a cathode, an anode, and organic material layer(s), for example, organic material layers including a hole injection layer, a hole transport layer, a light emitting layer, and an electron transport layer, interposed therebetween.

The materials used in the organic light emitting diode are mostly pure organic materials or complexes of organic material and metal. The material used in the organic light emitting diode may be classified as a hole injection material, a hole transport material, a light emitting material, an electron transport material, or an electron injection material, according to its use. In connection with this, an organic material having a p-type property, which is easily oxidized and is electrochemically stable when it is oxidized, is mostly used as the hole injection material or the hole transport material. Meanwhile, an organic material having an n-type property, which is easily reduced and is electrochemically stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting diode further have the following properties.

First, it is preferable that the material used in the organic light emitting diode have excellent thermal stability. The reason is that joule heat is generated by movement of electric charges in the organic light emitting diode. NPB (N,N-di(naphthalene-1-yl)-N,N-diphenyl-benzidene), which has recently been used as the hole transport layer material, has a glass transition temperature of 100° C. or lower, thus it is difficult to apply to an organic light emitting diode requiring a high current.

Second, in order to produce an organic light emitting diode that is capable of being actuated at low voltage and has high efficiency, holes and electrons which are injected into the organic light emitting diode must be smoothly transported to a light emitting layer, and must not be released out of the light emitting layer. To achieve this, a material used in the organic light emitting diode must have a proper band gap and a proper HOMO (highest occupied molecular orbital) or LUMO (lowest unoccupied molecular orbital) energy levels. A LUMO energy level of PEDOT (poly(3,4-ethylenedioxythiophene)):PSS (poly(styrenesulfonate)), which is currently used as a hole transport material of an organic light emitting diode produced using a solution coating method, is lower than that of an organic material used as a light emitting layer material, thus it is difficult to produce an organic light emitting diode having high efficiency and a long lifespan.

Moreover, the material used in the organic light emitting diode must have excellent chemical stability, electric charge mobility, and interfacial characteristic with an electrode or an adjacent layer. That is to say, the material used in the organic light emitting diode must be little deformed by moisture or oxygen. Furthermore, proper hole or electron mobility must be assured so as to balance densities of the holes and of the electrons in the light emitting layer of the organic light emitting diode to maximize the formation of excitons. Additionally, it has to be able to have a good interface with an electrode including metal or metal oxides so as to assure stability of the device.

Accordingly, there is a need to develop an organic material having the above-mentioned requirements in the art.

DISCLOSURE OF INVENTION

Technical Problem

Therefore, an object of the present inventions is to provide a new compound which is capable of satisfying conditions required of a material usable for an organic light emitting diode, for example, a proper energy level, electrochemical stability, and thermal stability, and which has a chemical structure capable of playing various roles required in the organic light emitting diode, depending on a substituent group, and an organic light emitting diode containing the same.

Technical Solution

The present invention provides a new compound represented by the following Formula 1.

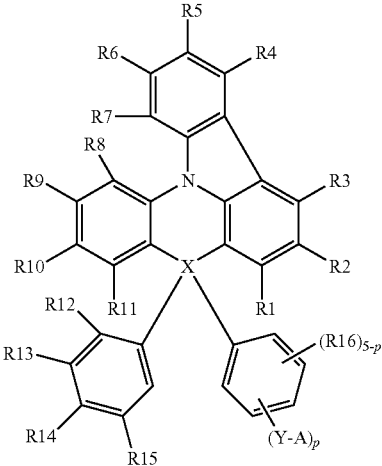

[Formula 1]

wherein, X is C or Si,

Ys may be directly connected to each other; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups, R1 to R11 may be the same or different from each other, and each independently hydrogen, a substituted or unsubstituted alkyl group, a substituted or unsubstituted alkoxy group, a substituted or unsubstituted alkenyl group, a substituted or un-substituted aryl group, a substituted or unsubstituted arylamine group, a substituted or unsubstituted heterocyclic group, an amino group, a nitrile group, a nitro group, a halogen group, an amide group, or an ester group, in which they may form aliphatic, aromatic or hetero condensation rings along with adjacent groups, R12 and R16 may be the same or different from each other, and each independently hydrogen, a substituted or unsubstituted alkyl group, a substituted or unsubstituted alkoxy group, a substituted or unsubstituted alkenyl group, a substituted or un-substituted aryl group, a substituted or unsubstituted heterocyclic group, an amino group, a nitrile group, a nitro group, a halogen group, an amide group, or an ester group, in which they may form aliphatic, aromatic or hetero condensation rings along with adjacent groups, R7 and R8 may be directly connected to each other, or may form a condensation ring along with a group selected from the group consisting of O, S, NR, PR, C=O, CRR' and SiRR' in which R and R' are the same or different from each other, each independently hydrogen, a substituted or unsubstituted alkyl group, a substituted or un-substituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, or an ester group, and may form a condensation ring to form a spiro compound, p is an integer of 1 to 5, A is

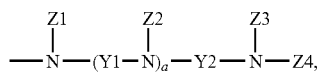

a is an integer of 0 to 10,

Y1 and Y2 may be the same or different from each other, and each independently bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy and amino groups, and Z1 to Z4 may be the same or different from each other, and each independently hydrogen; aliphatic hydrocarbons having 1 to 20 carbon atoms; aromatic hydrocarbons; aromatic hydrocarbons which are substituted with at least one substituent group selected from the group consisting of nitro, nitrile, halogen, alkyl, alkoxy, amino, aromatic hydrocarbon, and heterocyclic groups; a silicon group substituted with aromatic hydrocarbons; a heterocyclic group; a heterocyclic group which is substituted with at least one substituent group selected from the group consisting of nitro, nitrile, halogen, alkyl, alkoxy, amino, aromatic hydrocarbon, and heterocyclic groups; a thiophene group which is substituted with aliphatic hydrocarbons having 1 to 20 carbon atoms or aromatic hydrocarbons having 6 to 20 carbon atoms; or a boron group which is substituted with aromatic hydrocarbons.

Further, the present invention provides an organic light emitting diode which comprises a first electrode, at least one organic material layer, and a second electrode, wherein the first electrode, the organic material layer(s), and the second electrode form a layered structure and at least one layer of the organic material layers includes a compound represented by Formula 1 of the present invention.

Advantageous Effects

The compound of the present invention can be used as an organic material layer material, particularly, hole injection and/or transport materials in an organic light emitting diode, and when applied to an organic light emitting diode it is possible to reduce the actuating voltage of the device, to improve the light efficiency thereof, and to improve the lifespan of the device through the thermal stability of the compound.

BEST MODE FOR CARRYING OUT THE INVENTION

Figure 1:
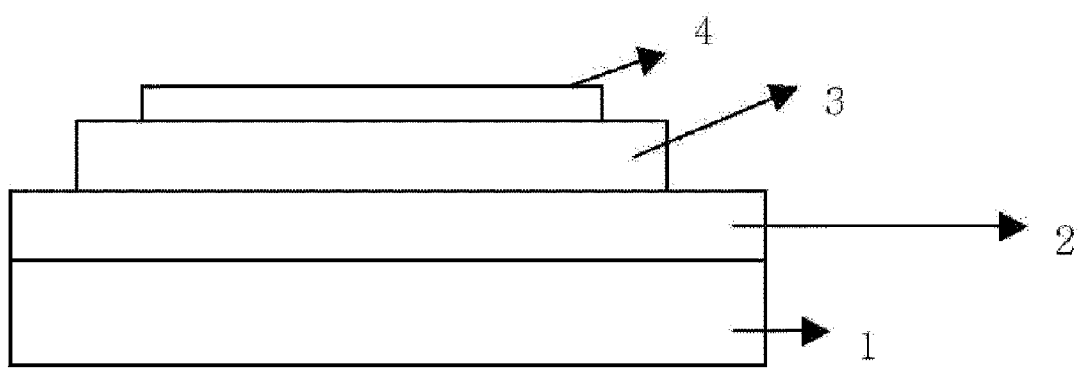
FIG. 1 illustrates an example of an organic light emitting diode comprising a substrate 1, an anode 2, a light emitting layer 3, and a cathode 4.
Figure 2:
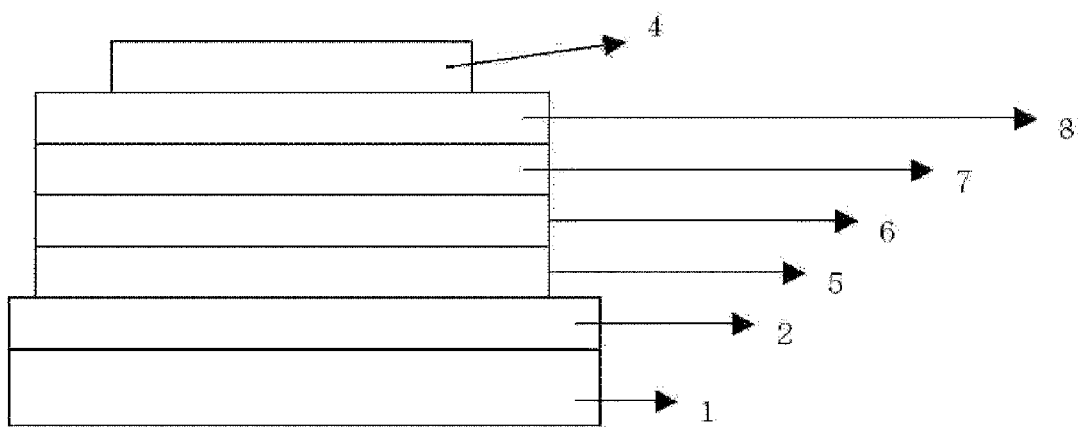
FIG. 2 illustrates an example of an organic light emitting diode comprising a substrate 1, an anode 2, a hole injection layer 5, a hole transport layer 6, a light emitting layer 7, an electron transport layer 8, and a cathode 4.

Hereinafter, a detailed description will be given of the present invention.

Substituent groups of Formula 1 will be described in detail, below.

In Y, Y1 and Y2 of Formula 1, examples of the bivalent aromatic hydrocarbons include monocyclic aromatic rings such as phenylene, biphenylene and terphenylene, and multicyclic aromatic rings such as naphthylene, anthracenylene, pyrenylene and perylenylene, but are not limited thereto.

In Y, Y1 and Y2 of Formula 1, examples of the bivalent heterocyclic group include thiophenylene, furylene, pyrrolylene, imidazolylene, thiazolylene, oxazolylene, oxadiazolylene, thiadiazolylene, triazolylene, pyridylene, pyridazylene, pyrazinylene, quinolylene and isoquinolylene, but are not limited thereto.

In Z1 to Z4 of Formula 1, examples of the aromatic hydrocarbons include monocyclic aromatic rings such as phenyl, biphenyl and terphenyl, and multicyclic aromatic rings such as naphthyl, anthracenyl, pyrenyl and perylenyl, but are not limited thereto.

In Z1 to Z4 of Formula 1, examples of the heterocyclic group include thiophene, furan, pyrrole, imidazole, thiazole, oxazole, oxadiazole, thiadiazole, triazole, pyridyl, pyridazyl, pyrazine, quinoline and isoquinoline, but are not limited thereto.

In Z1 to Z4 of Formula 1, aliphatic hydrocarbons having 1 to 20 carbon atoms include straight chain aliphatic hydrocarbons, branched chain aliphatic hydrocarbons, saturated aliphatic hydrocarbons, and unsaturated aliphatic hydrocarbons. They are exemplified by an alkyl group such as a methyl group, an ethyl group, an n-propyl group, an iso-propyl group, an n-butyl group, a sec-butyl group, an iso-butyl group, a ter-butyl group, a pentyl group, and a hexyl group; an alkenyl group having a double bond such as styryl; and an alkynyl group having a triple bond such as an acetylene group, but are not limited thereto.

In R1 to R16 of Formula 1, the carbon number of the alkyl, alkoxy, and alkenyl groups is not limited, but is preferably 1 to 20.

The length of the alkyl group contained in the compound does not affect the conjugation length of the compound, but may affect the method of applying the compound to the organic light emitting diode, for example, a vacuum deposition method or a solution coating method.

In R1 to R16 of Formula 1, examples of the aryl group include monocyclic aromatic rings such as a phenyl group, a biphenyl group, a terphenyl group and a stilbene group, and multicyclic aromatic rings such as a naphthyl group, an anthracenyl group, a phenanthrene group, a pyrenyl group, and a perylenyl group, but are not limited thereto.

In R1 to R11 of Formula 1, examples of the arylamine group include a diphenylamine group, a dinaphthylamine group, a dibiphenylamine group, a phenylnaphthylamine group, a phenyldiphetylamine group, a ditolylamine group, a phenyltolylamine group, a carbazolyl group, and a triphenylamine group, but are not limited thereto.

In R1 to R16 of Formula 1, examples of the heterocyclic group include a thiophene group, a furan group, a pyrrole group, an imidazole group, a thiazole group, an oxazole group, an oxadiazole group, a triazole group, a pyridyl group, a pyridazine group, a quinolinyl group, an isoquinoline group, and an acridyl group, but are limited thereto.

In R1 to R16 of Formula 1, if the alkyl, alkoxy, alkenyl, aryl, arylamine, and heterocyclic groups have other substituent group, the substituent group may be aliphatic hydrocarbons having 1 to 20 carbon atoms, an alkoxy group, an arylamine group, an aryl group, a heterocyclic group, a nitrile group, an acetylene group or the like.

In addition, in R1 to R16 of Formula 1, specific examples of the alkenyl, aryl, arylamine, and heterocyclic groups include compounds shown in the following Formulae, but are not limited thereto.

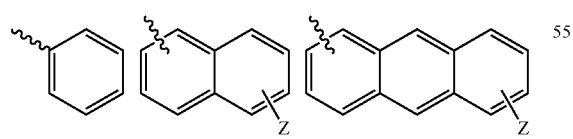

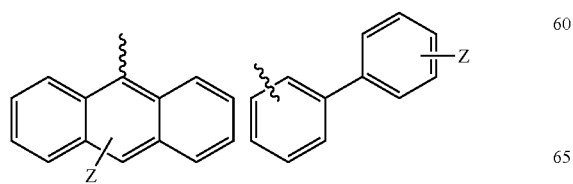

-continued

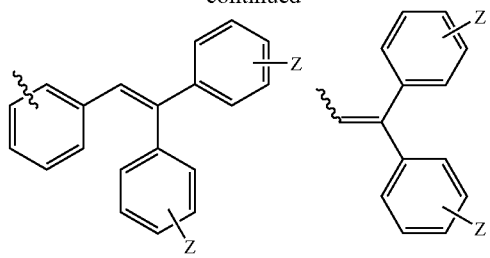

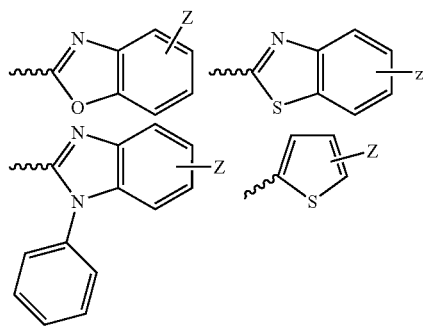

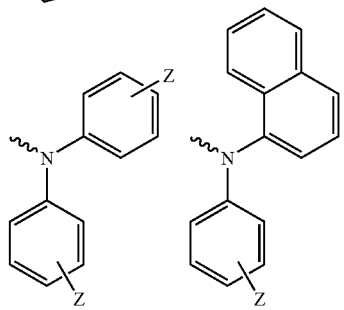

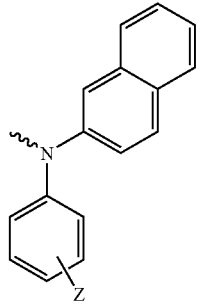

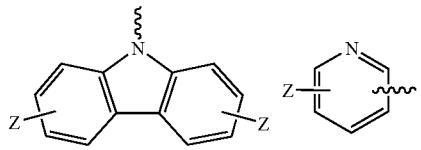

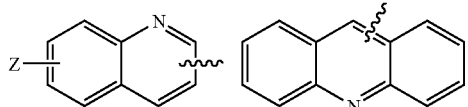

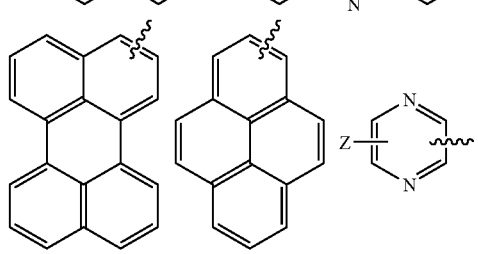

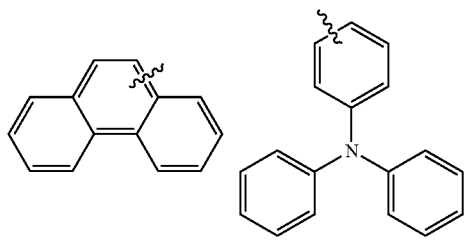

In the above Formulae, Z is a group selected from the group consisting of hydrogen, aliphatic hydrocarbons having 1 to 20 carbon atoms, an alkoxy group, an arylamine group, an aryl group, a heterocyclic group, a nitrile group, and an acetylene group. Specific examples of the arylamine, aryl, and heterocyclic groups of Z are as shown in the above-mentioned substituent groups of R1 to R16.

According to a preferred embodiment of the present invention, in Formula 1, X is C, R7 and R8 may be directly connected to each other, or form a condensation ring along with a group selected from the group consisting of O, S, NR, PR, C=O, CRR' and SiRR' (R and R' are as defined in Formula 1).

According to another preferred embodiment of the present invention, in Formula 1, X is Si, R7 and R8 may be directly connected to each other, or form a condensation ring along with a group selected from the group consisting of O, S, NR, PR, CRR' and SiRR' (R and R' are as defined in Formula 1).

According to still another preferred embodiment of the present invention, the compound of Formula 1 can be represented by any one of the following Formulae 2 to 7.

[Formula 2]

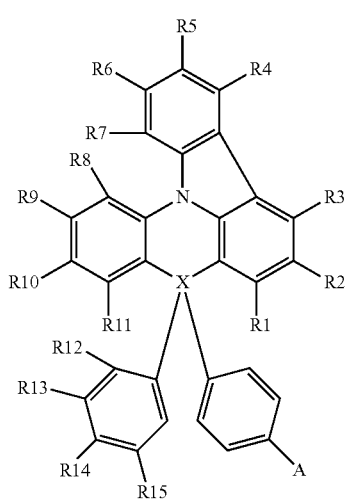

[Formula 3]

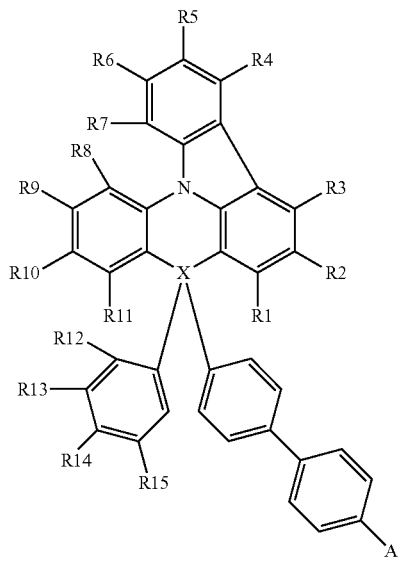

[Formula 4]

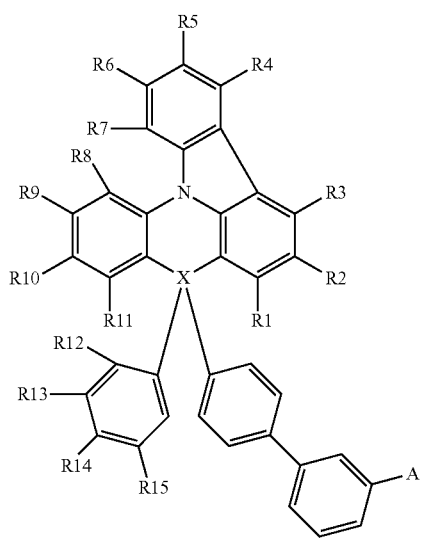

[Formula 5]

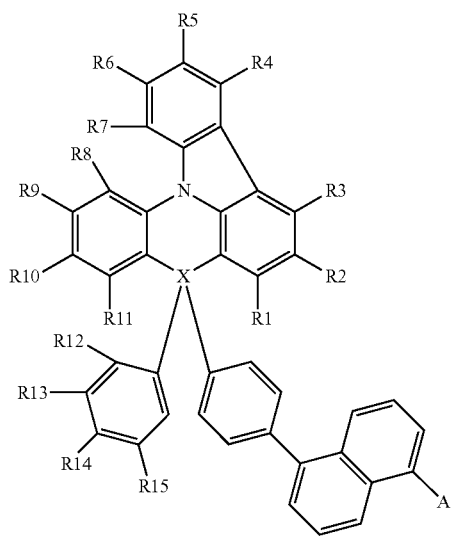

[Formula 6]
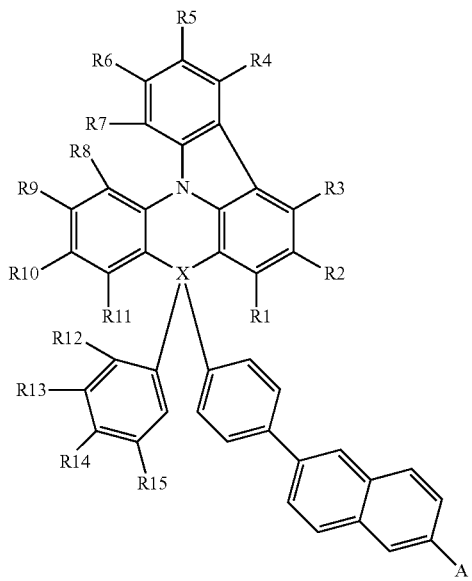
Examples of A of Formula 1 are preferably as follows, but are not limited thereto. Combination of the compounds of Formulae 2 to 7 and the following groups can form various derivative compounds.
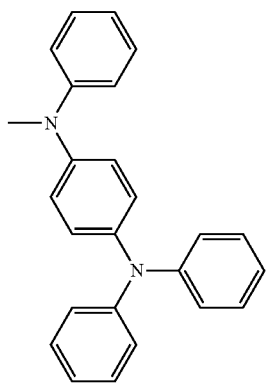
1
[Formula 7]
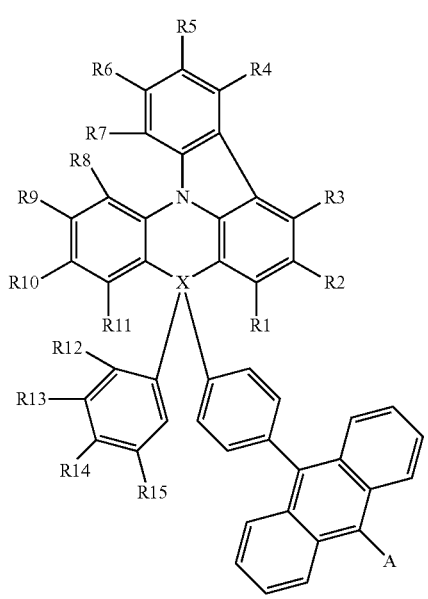
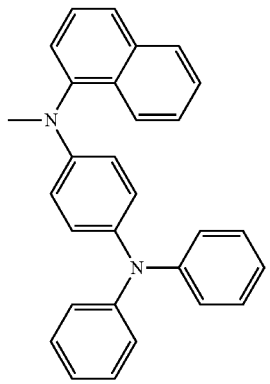
2
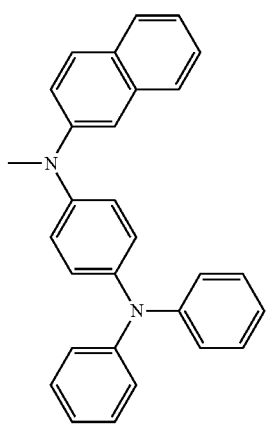
3
In the above Formulae, X, R1 to R15, and A are as defined in Formula 1.

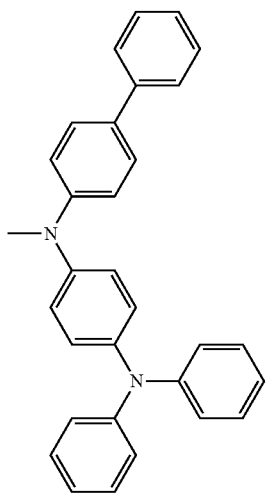
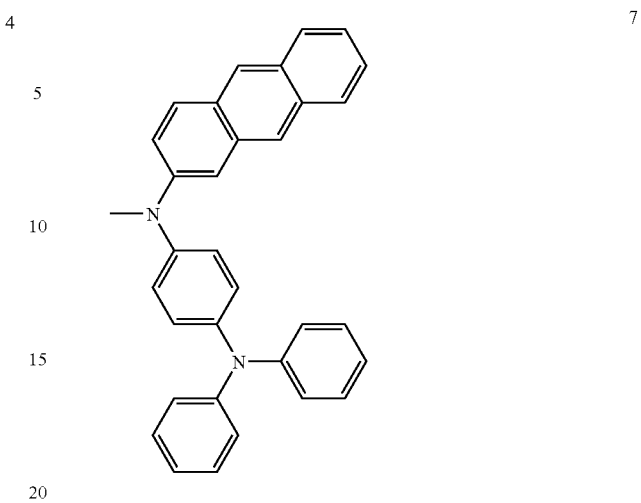
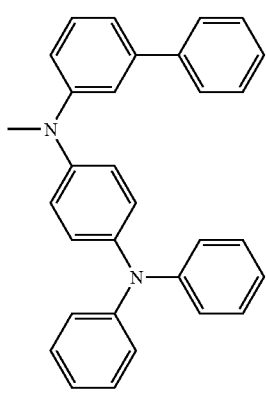
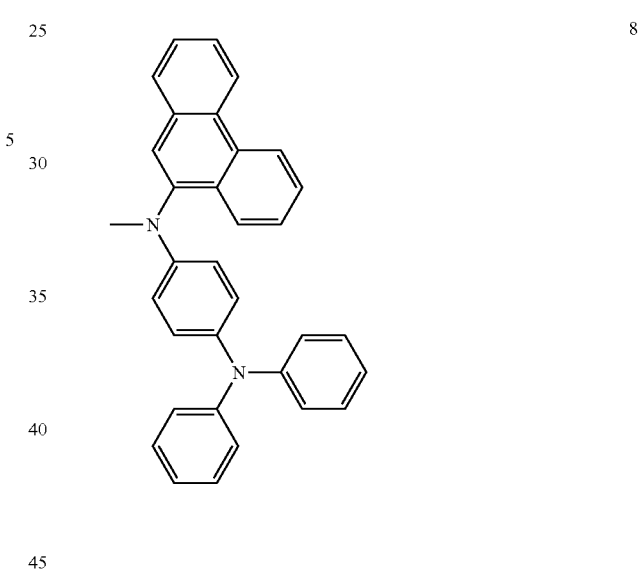
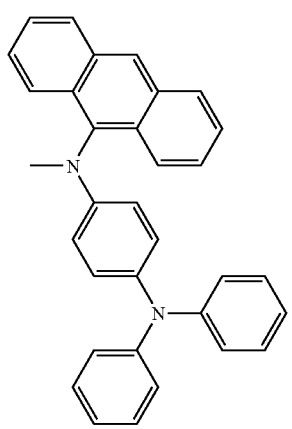
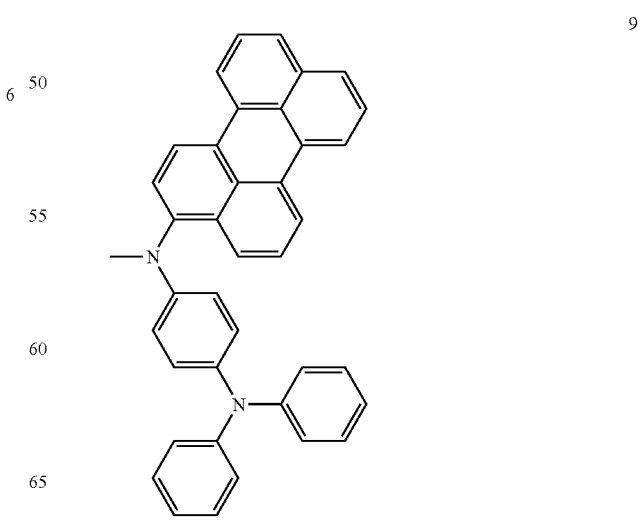

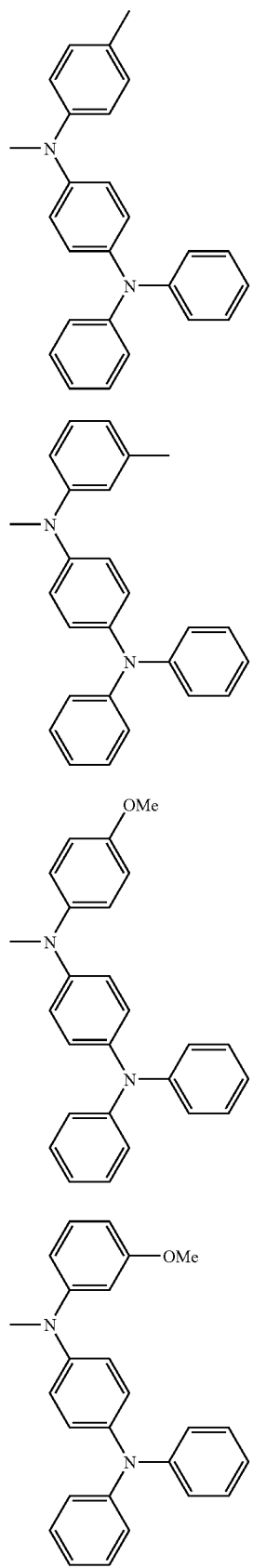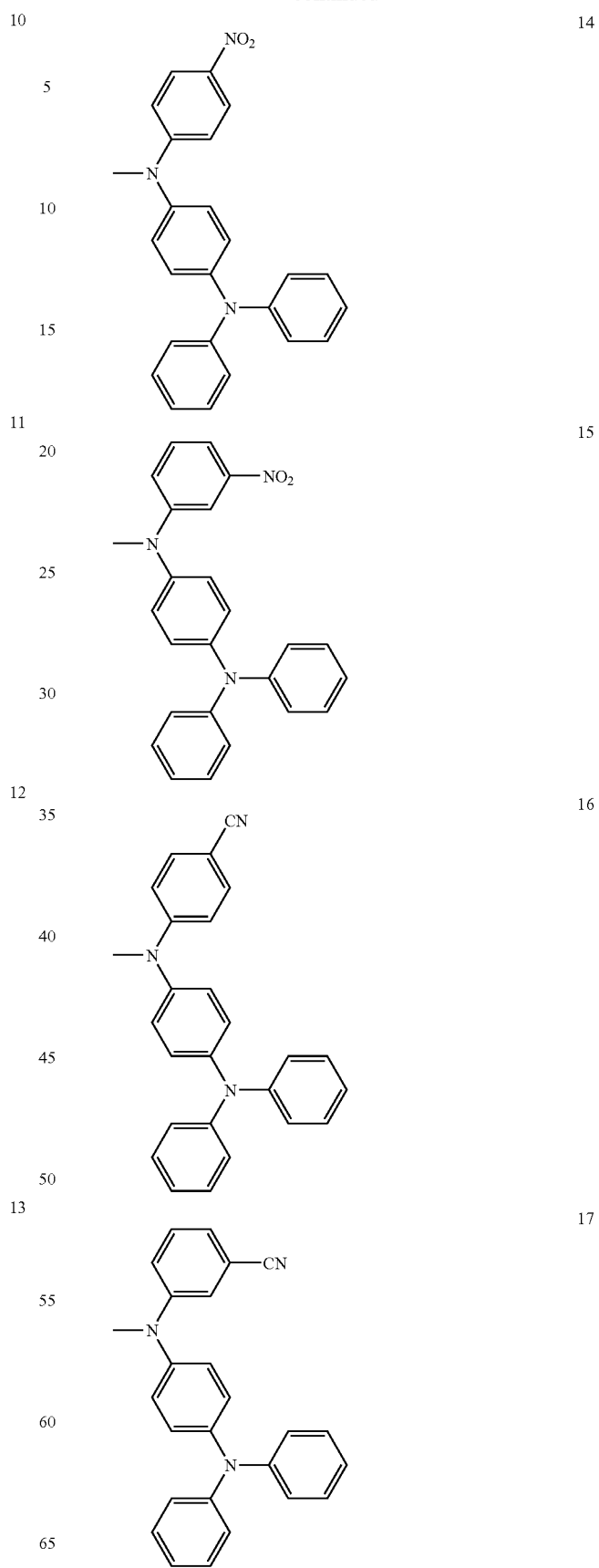

18
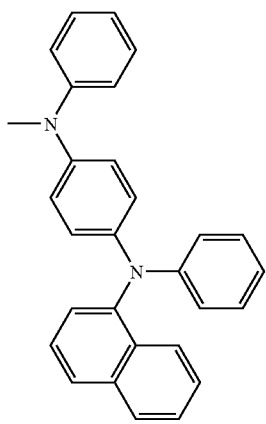
19
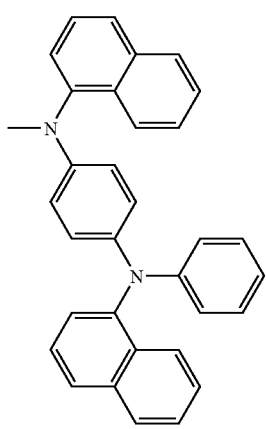
20
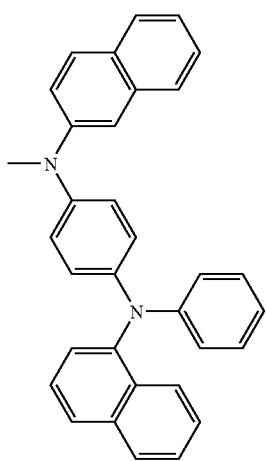
21
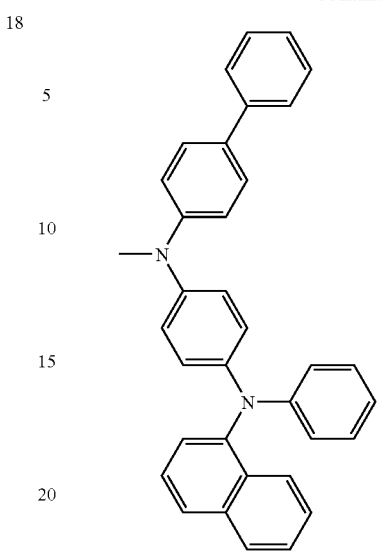
22
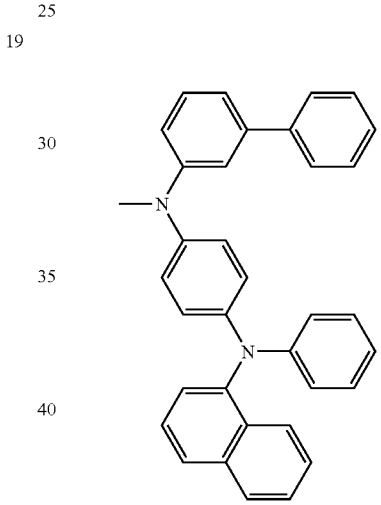
23
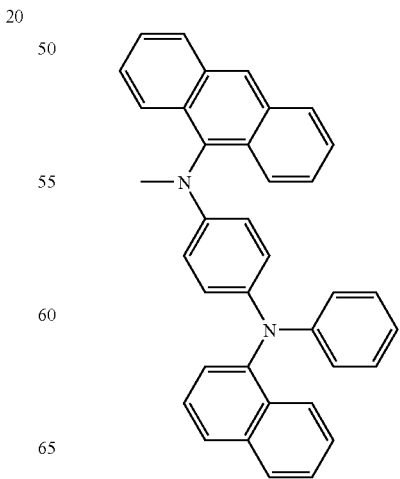

24
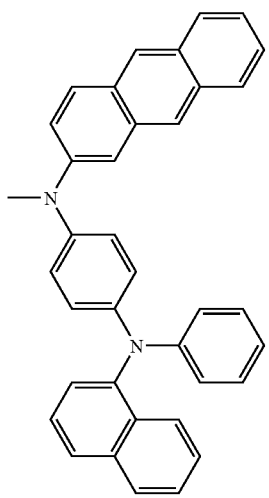
25
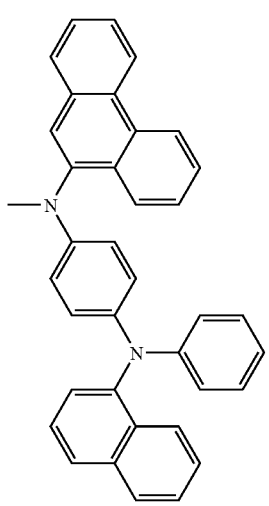
26
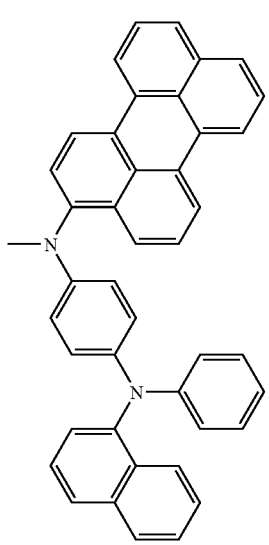
27
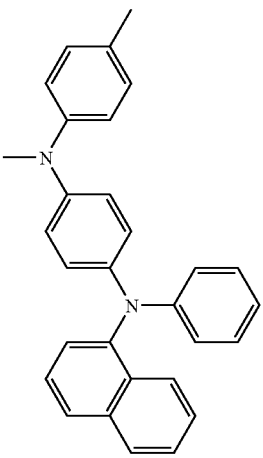
28
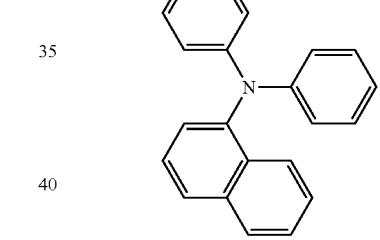
29
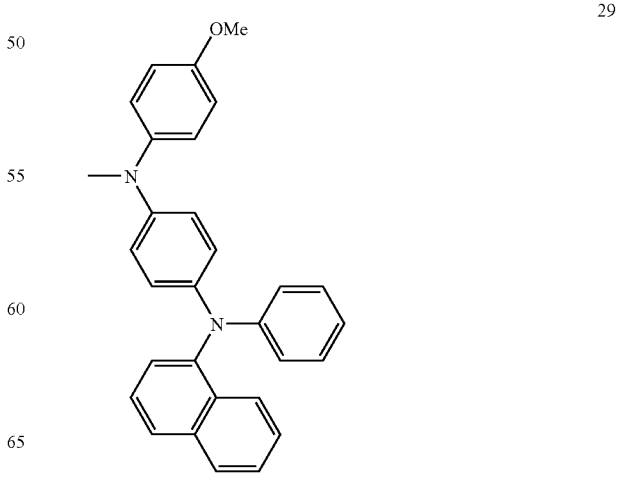

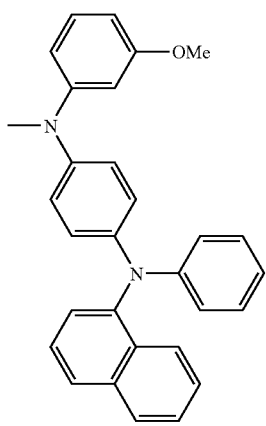
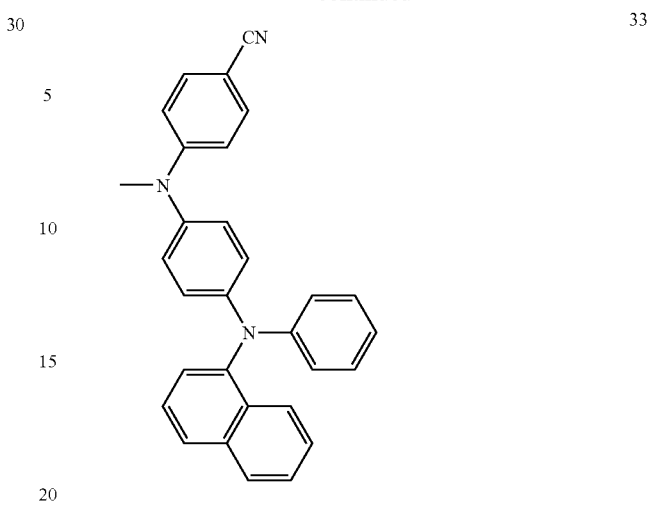
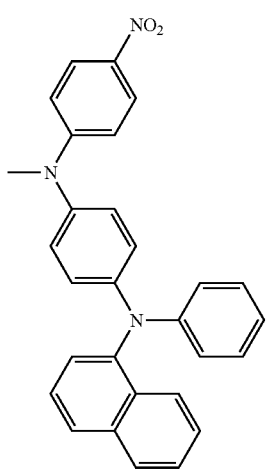
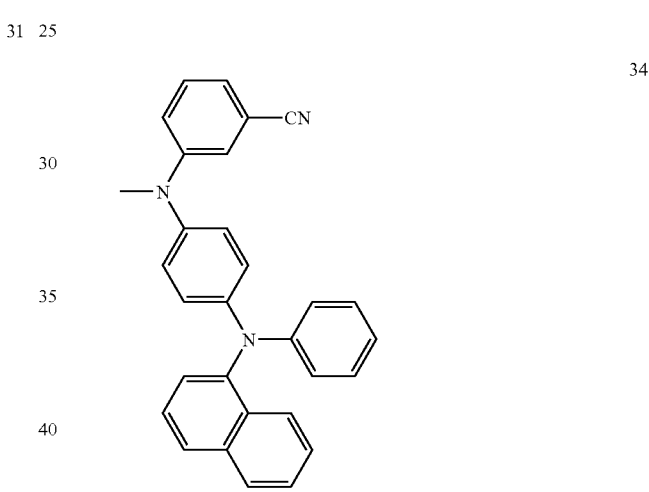
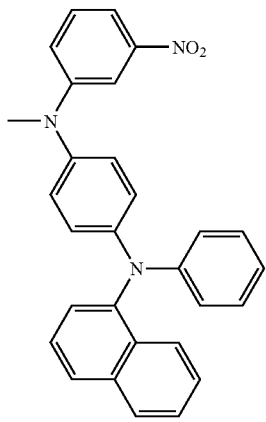
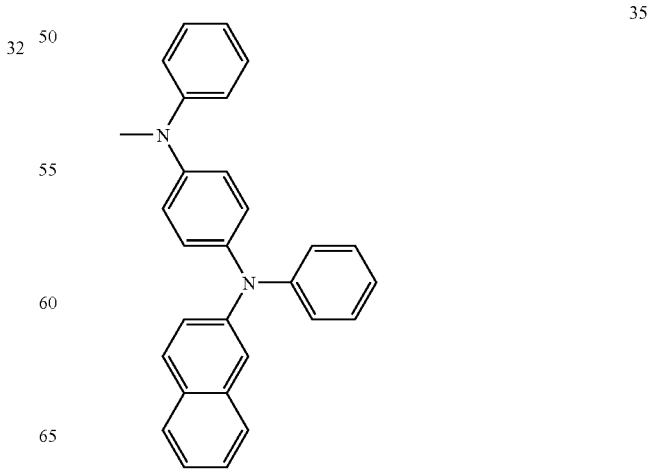

36
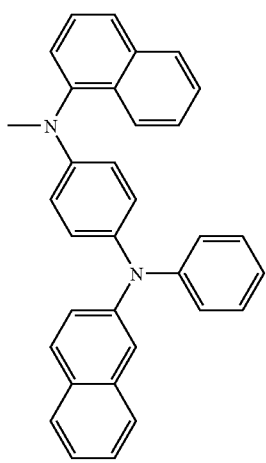
37
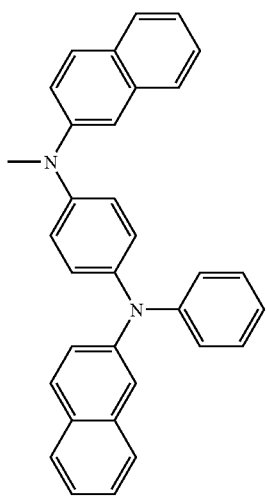
38
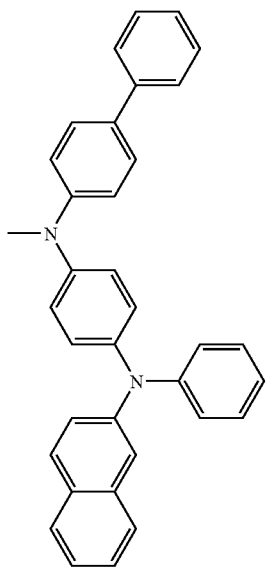
39
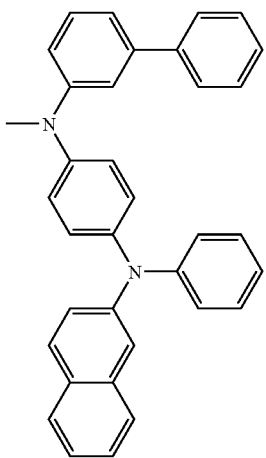
40
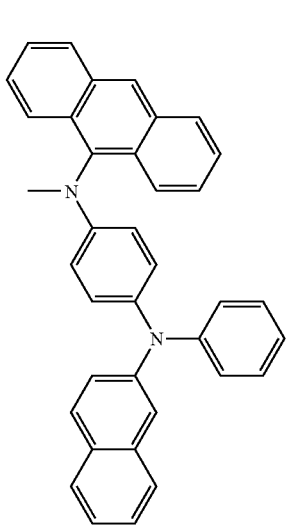
41
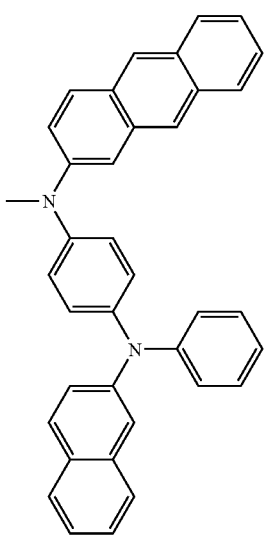

42
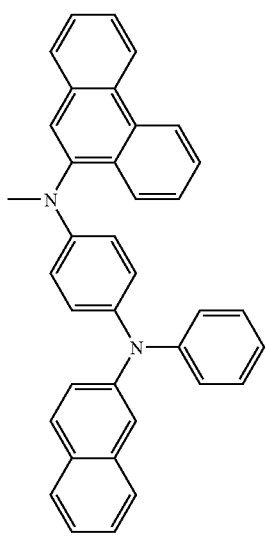
43
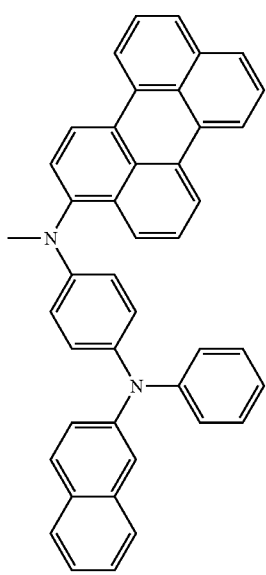
44
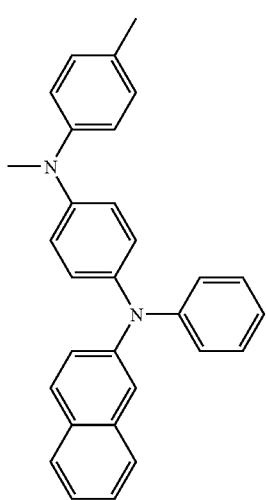
45
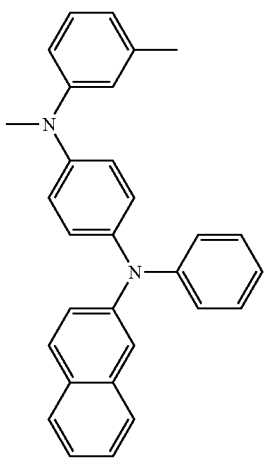
46
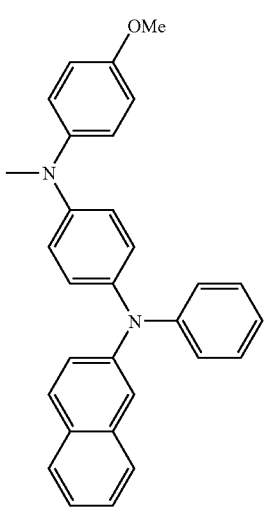
47
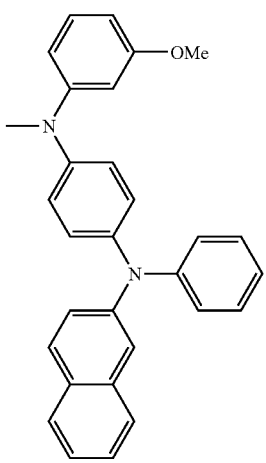

48
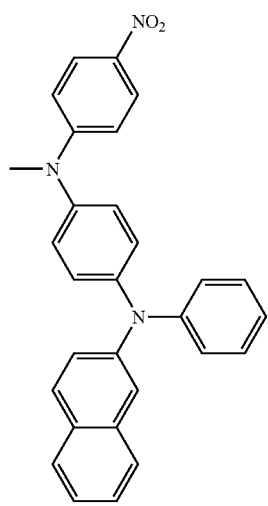
51
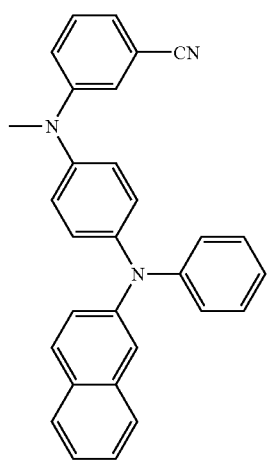
49
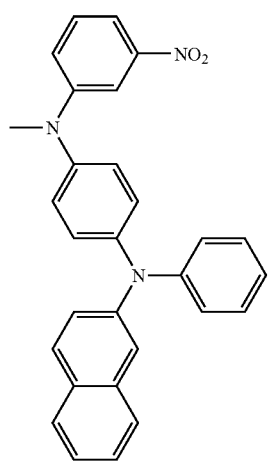
52
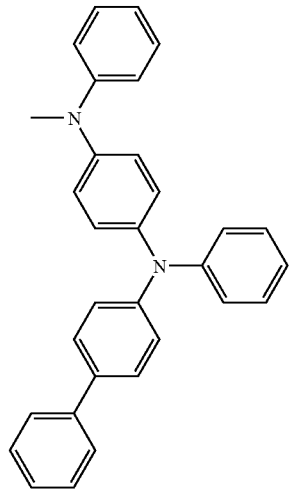
50
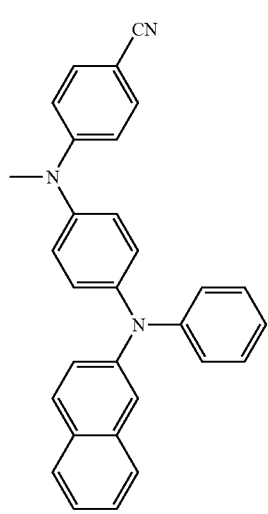
53
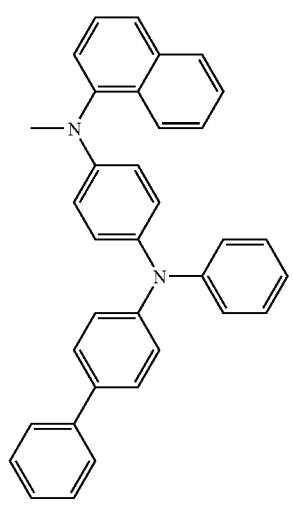

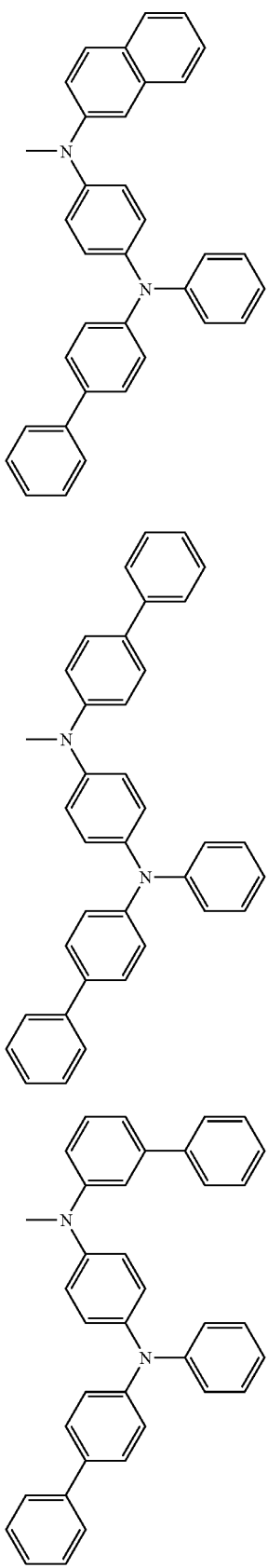
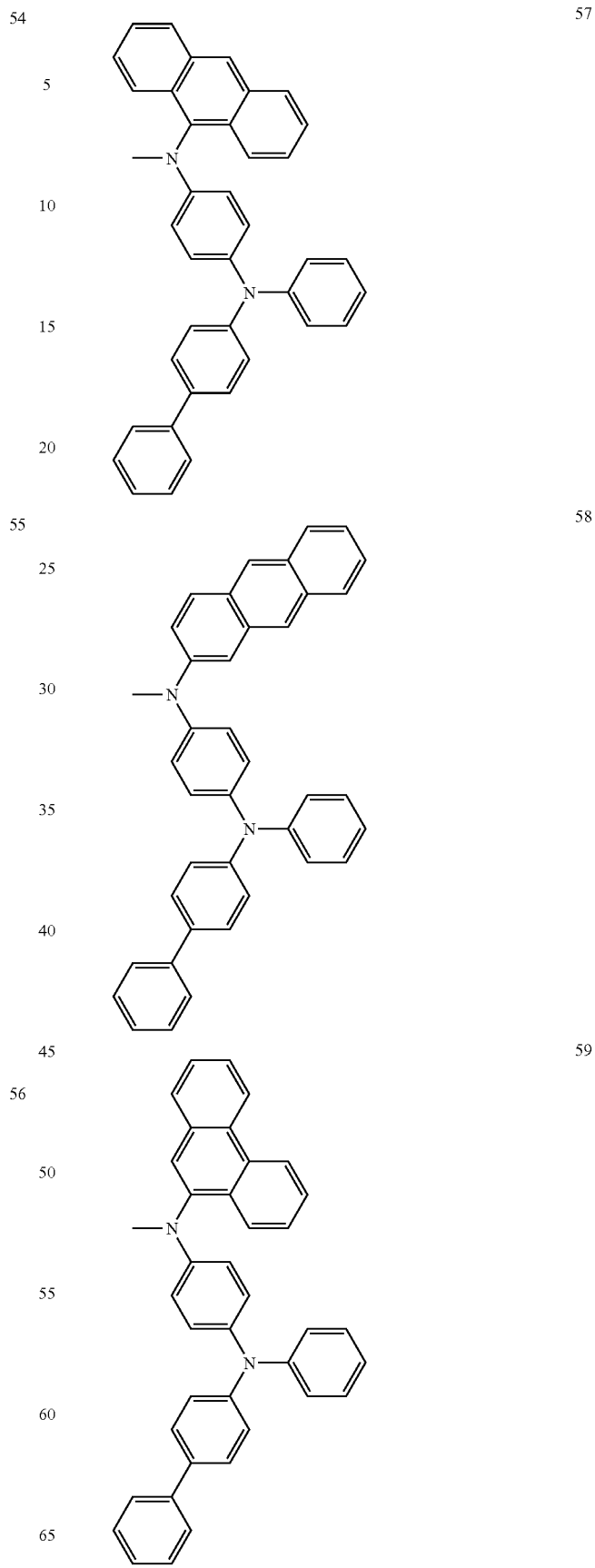

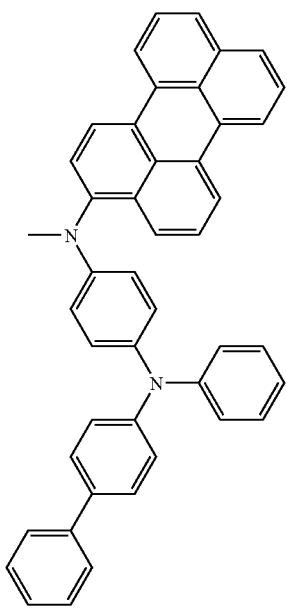
60
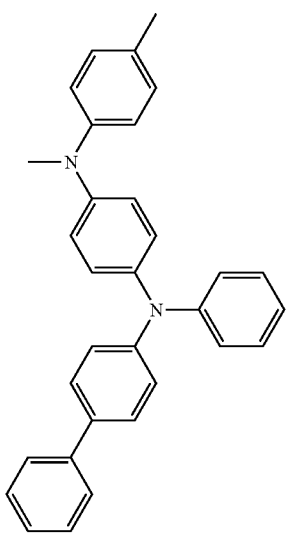
61
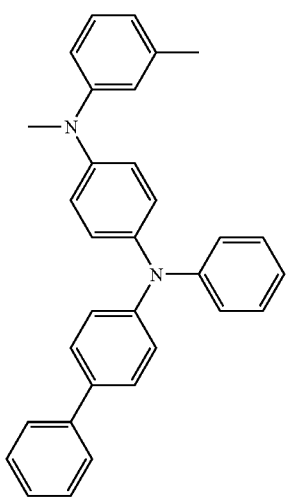
62
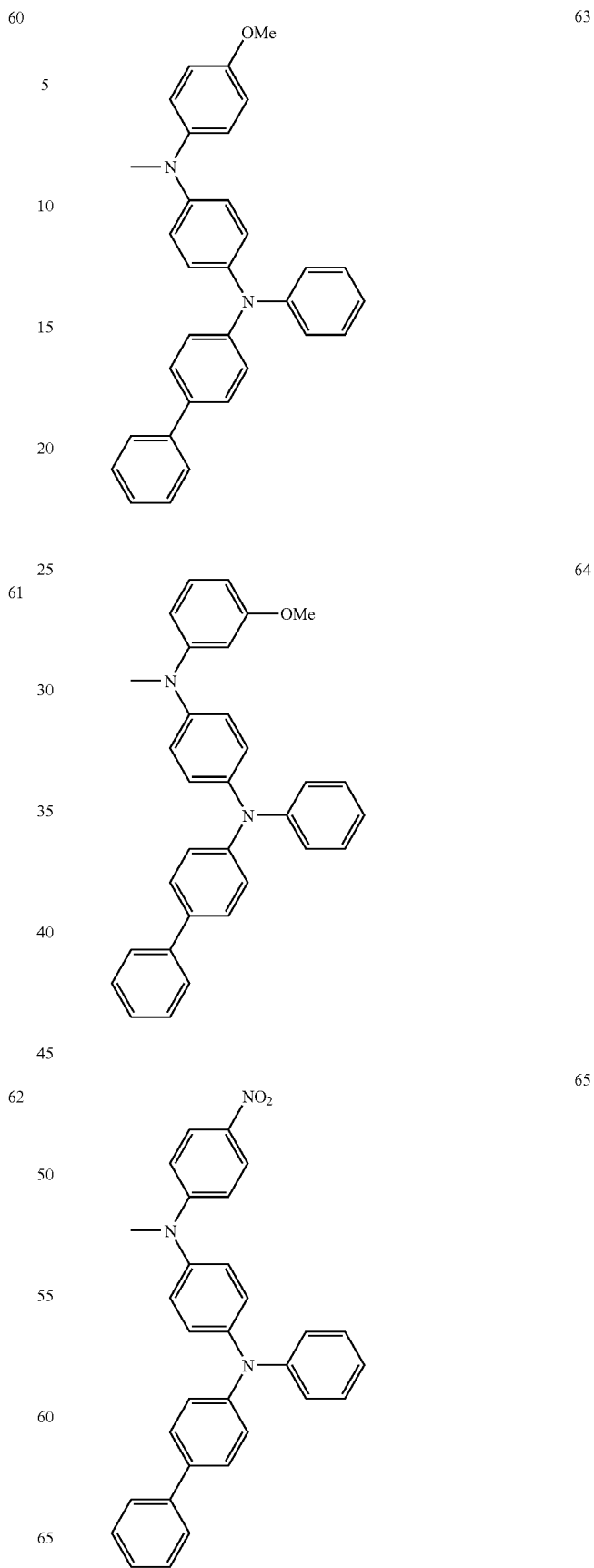

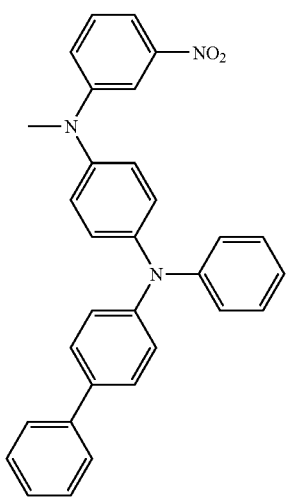
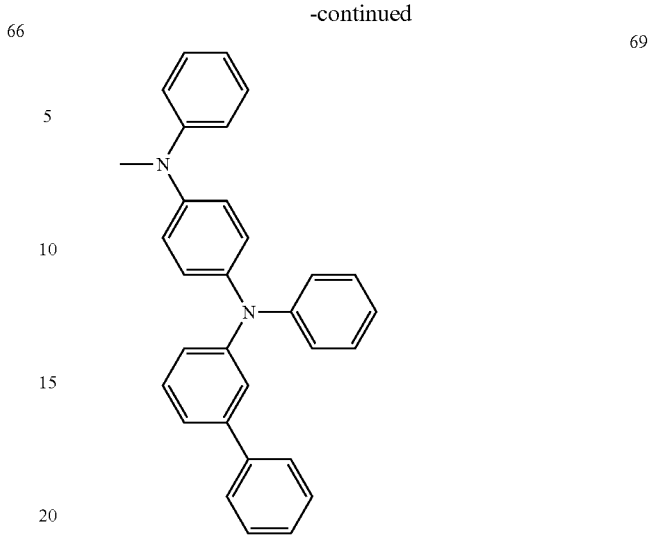
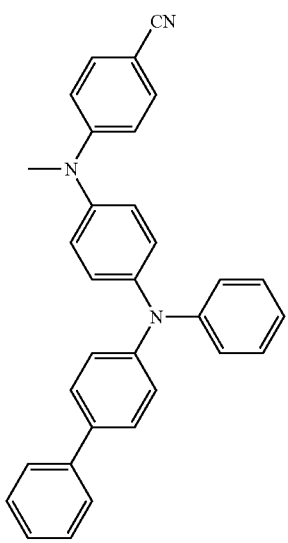
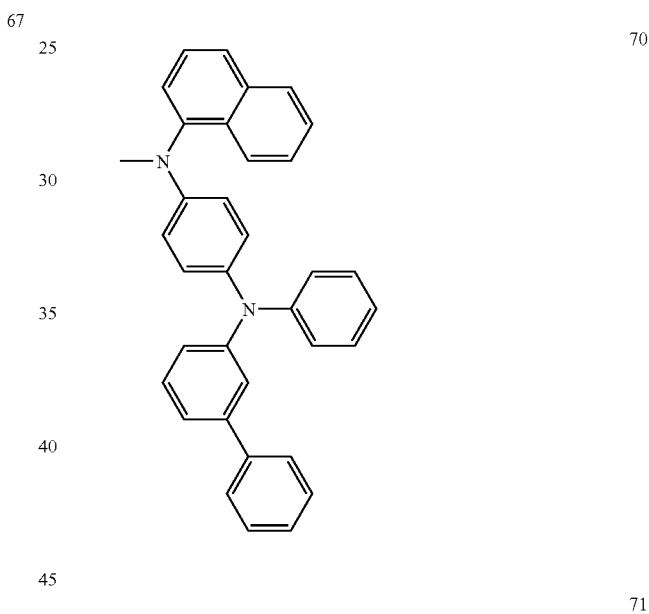
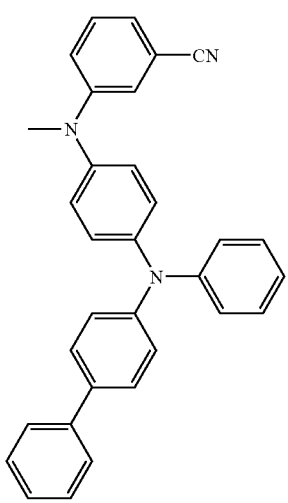
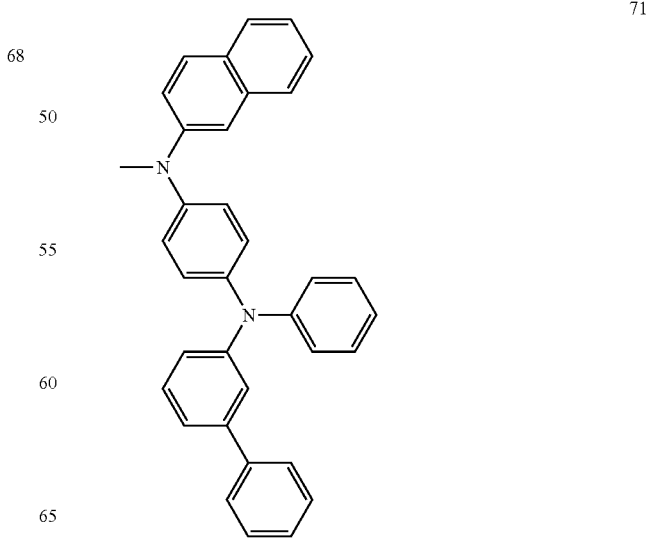

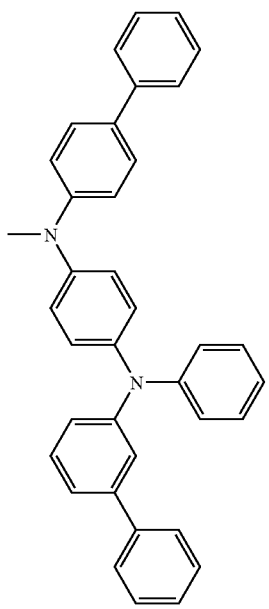
72
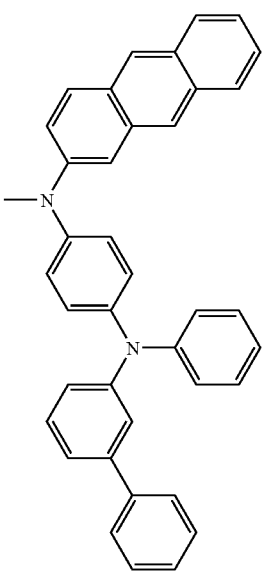
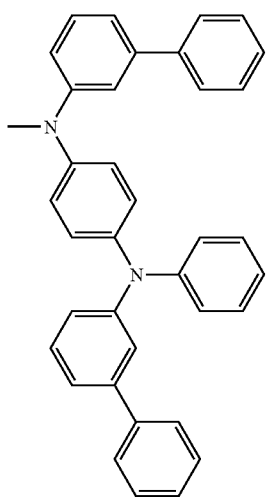
73
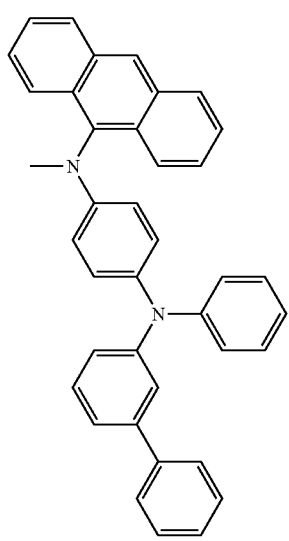
74
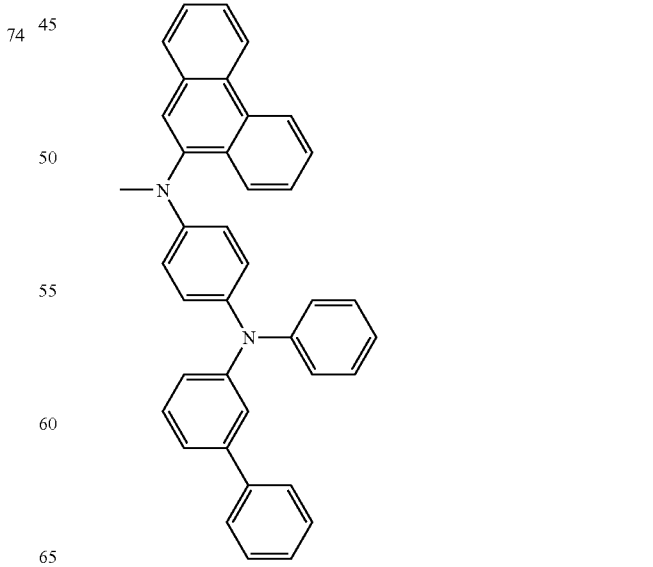
75
76

77
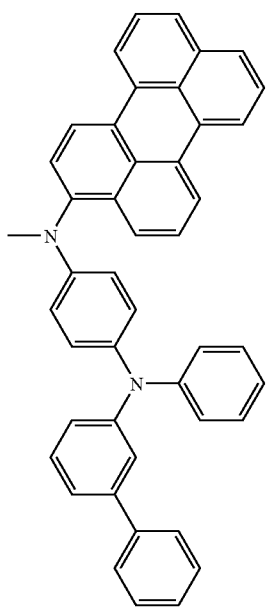
78
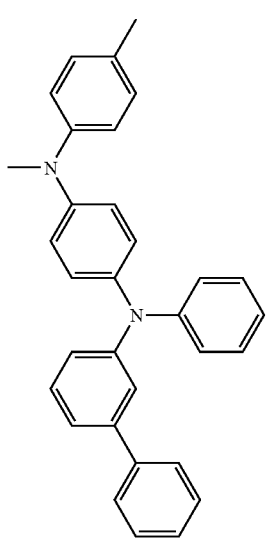
79
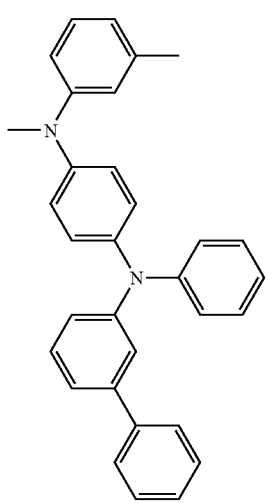
80
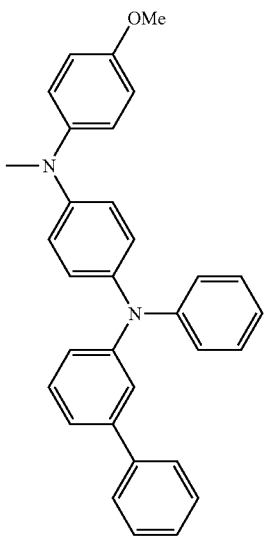
81
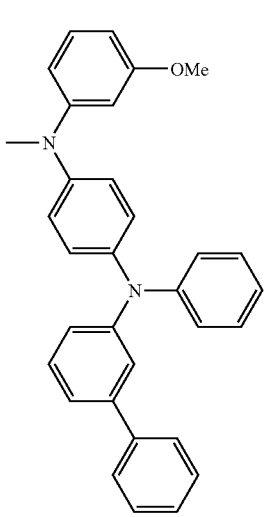
82
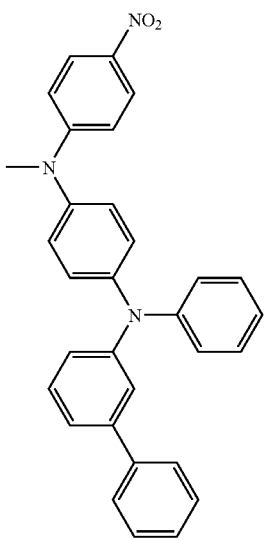

83
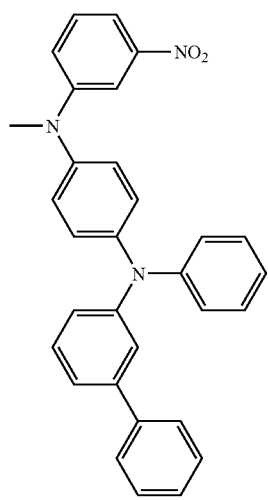
84
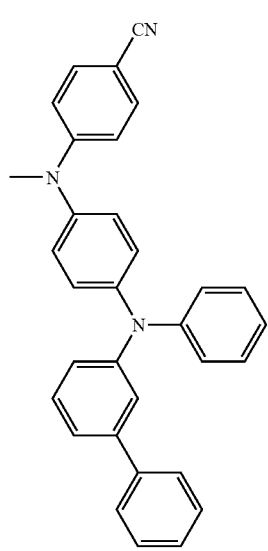
85
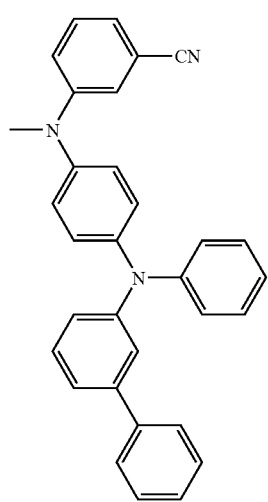
86
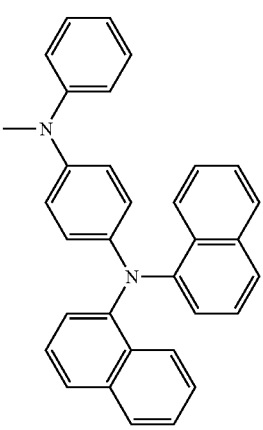
87
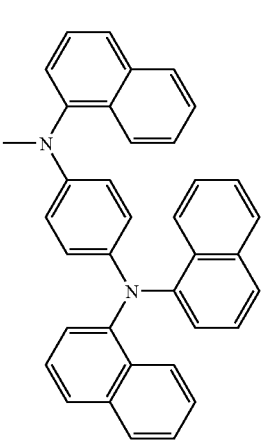
88
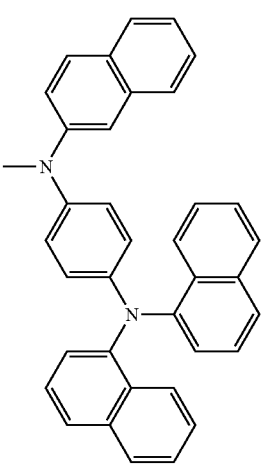

89
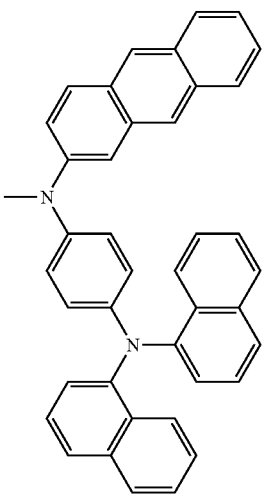
90
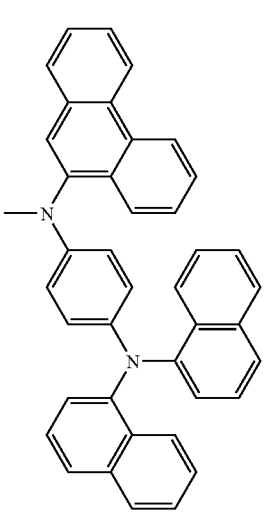
91
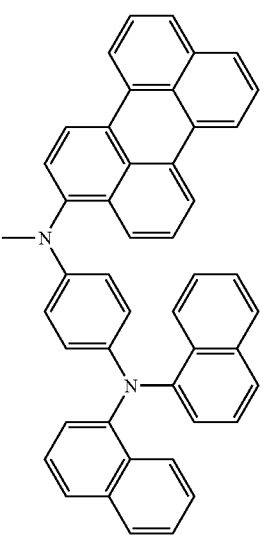
92
93
94
-continued
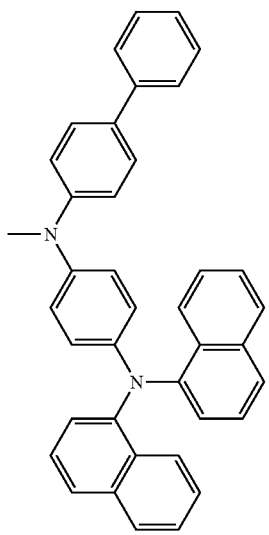
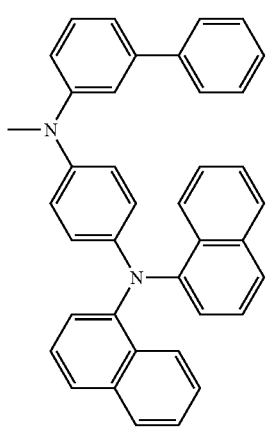
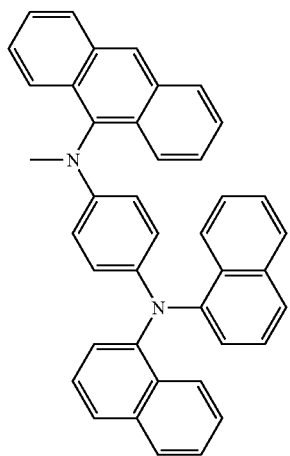

95
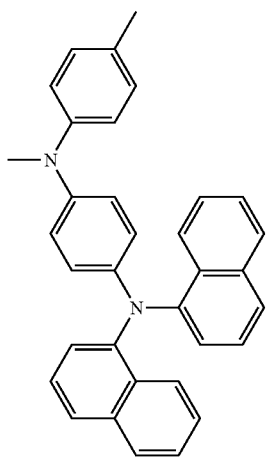
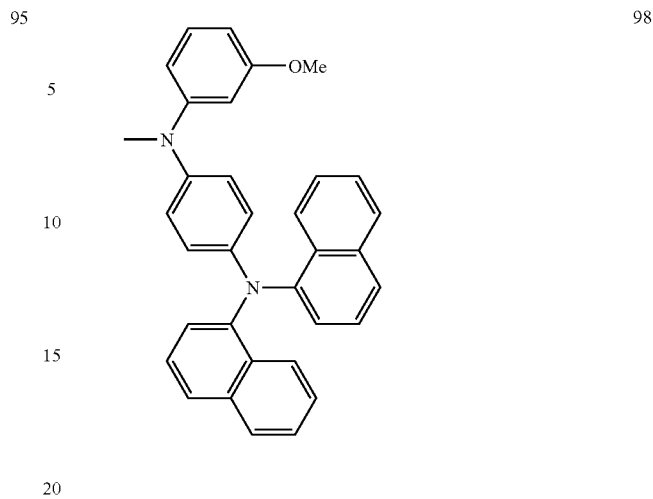
96
97
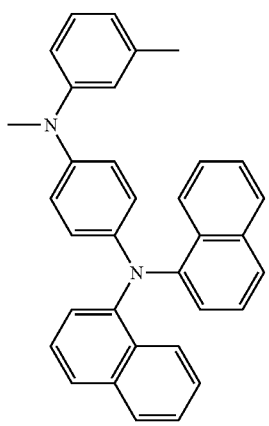
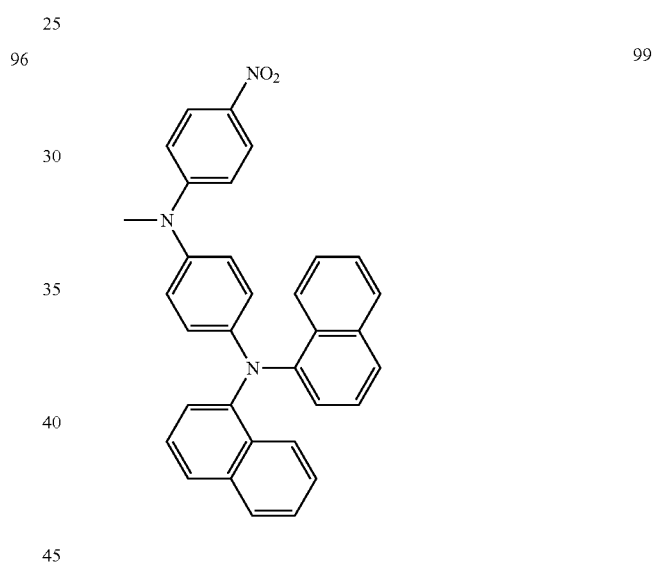
98
99
100
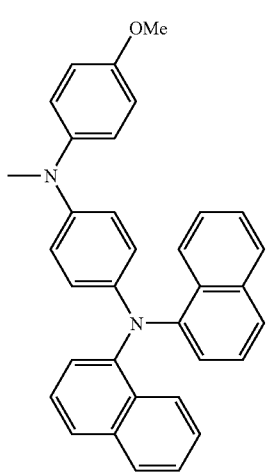
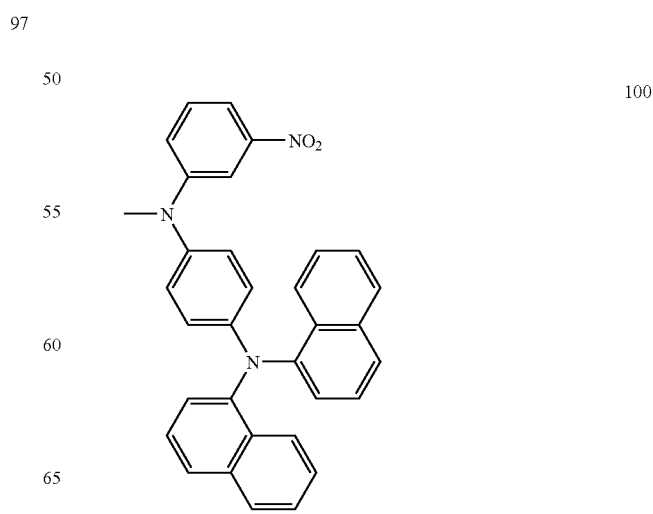

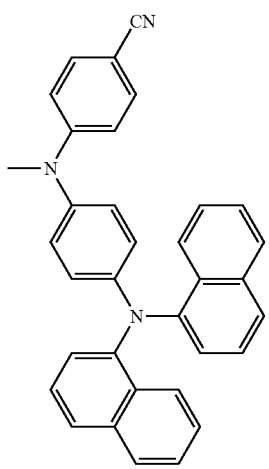
101
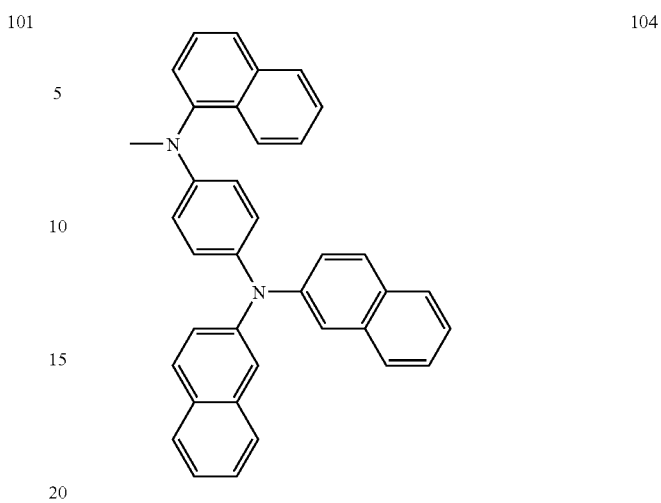
104
102
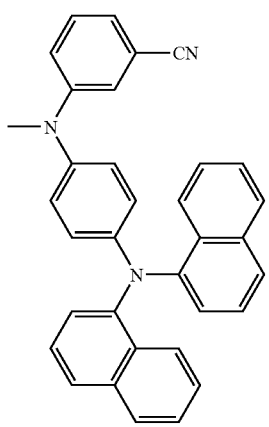
105
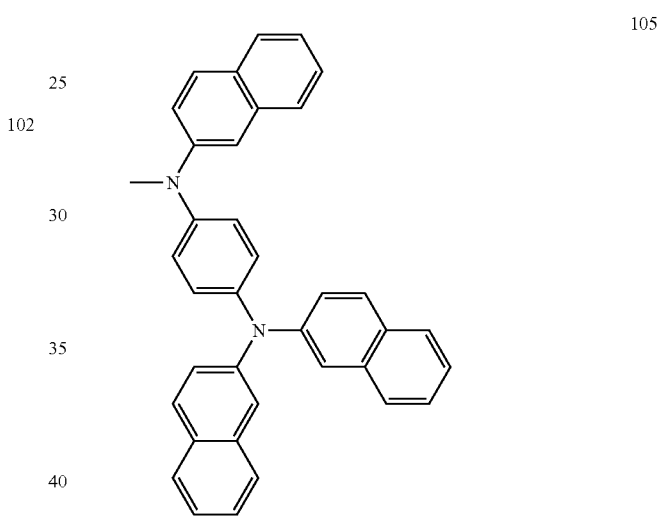
103
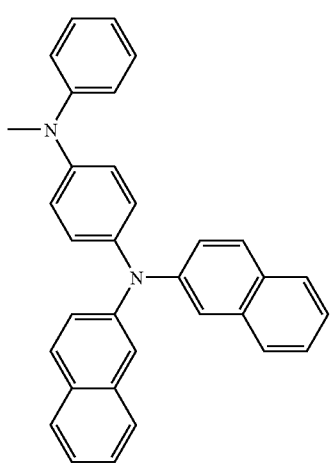
106
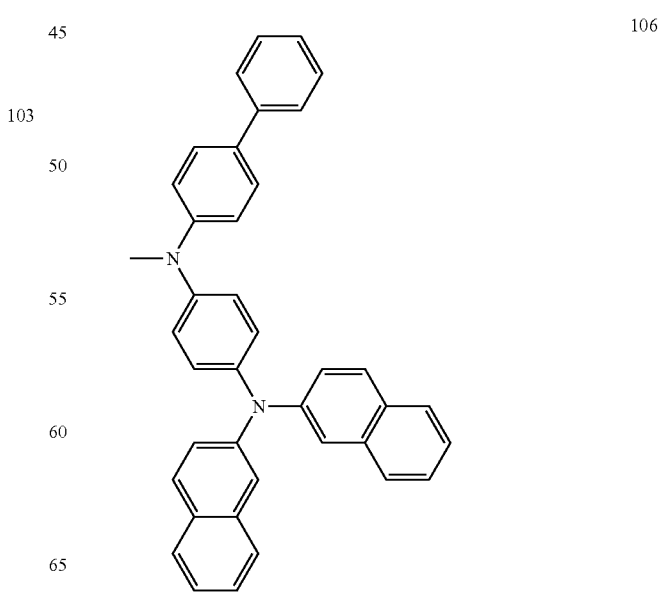

107
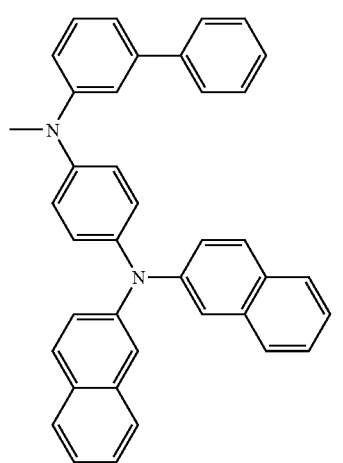
108
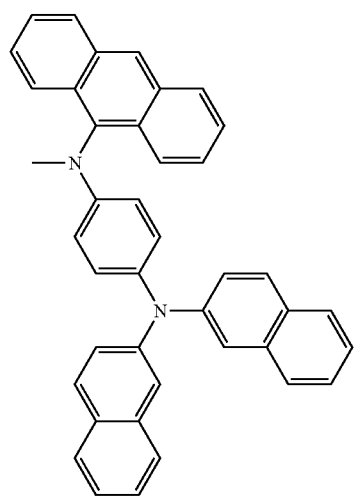
109
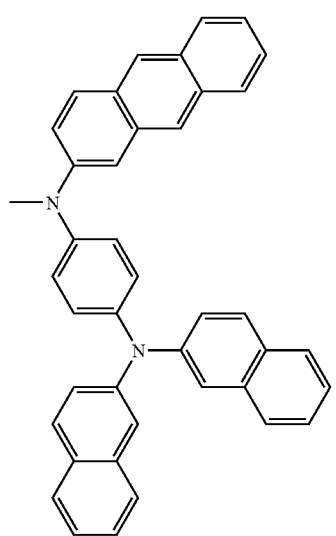
110
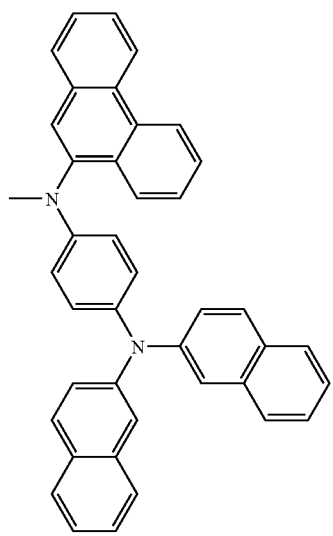
111
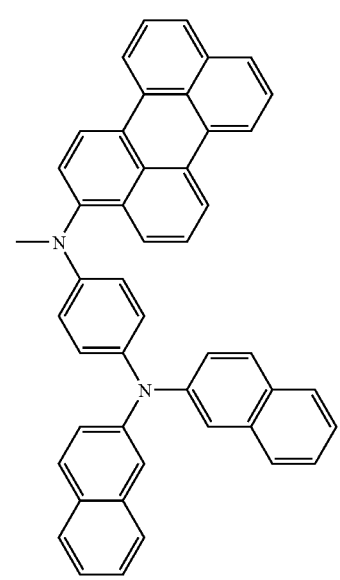
112
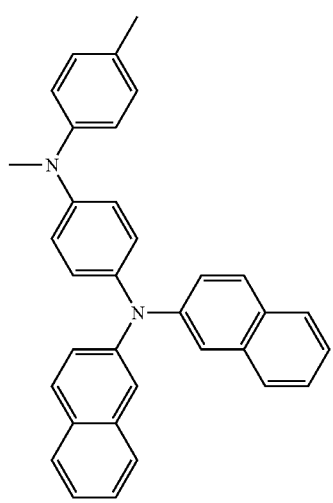

113
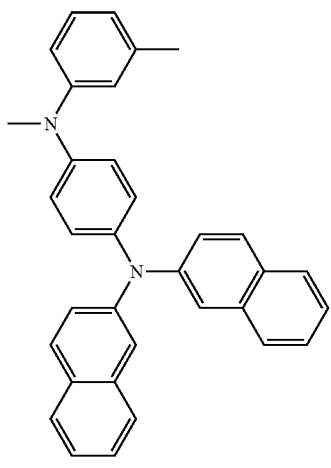
114
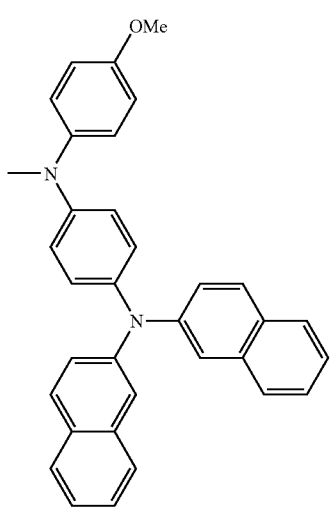
115
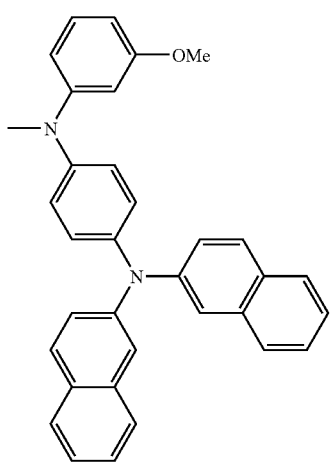
116
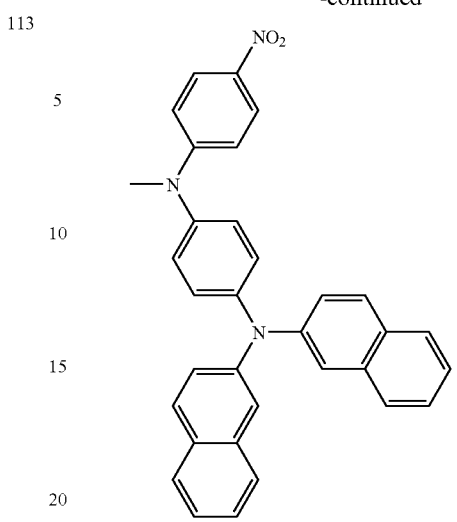
117
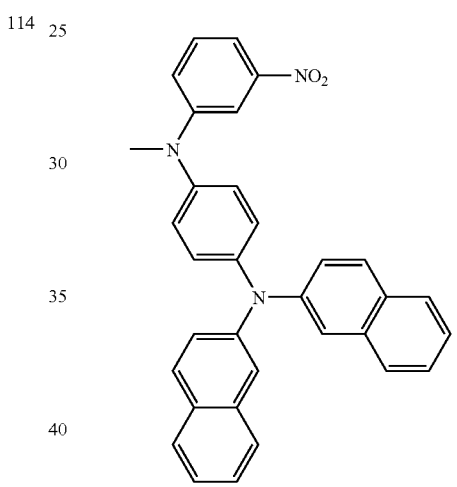
118
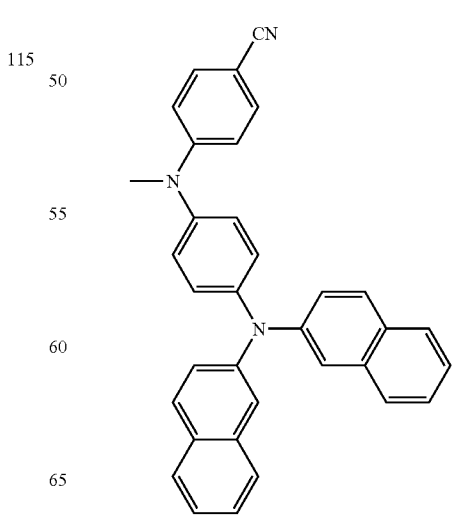

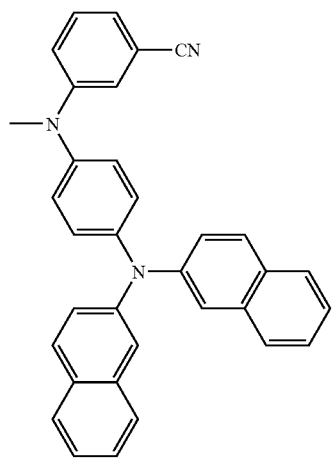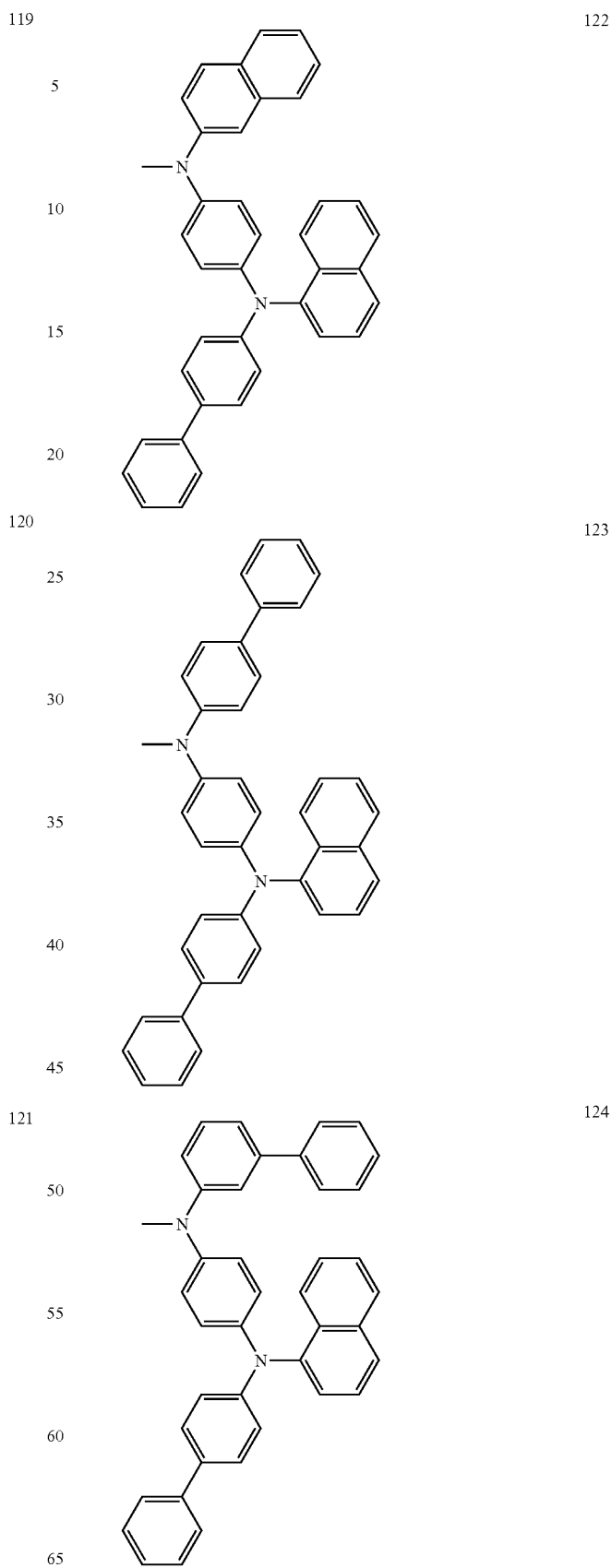

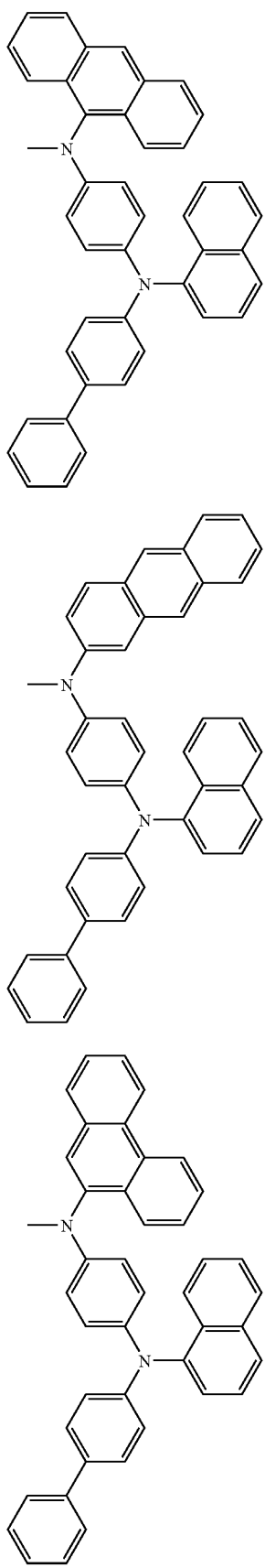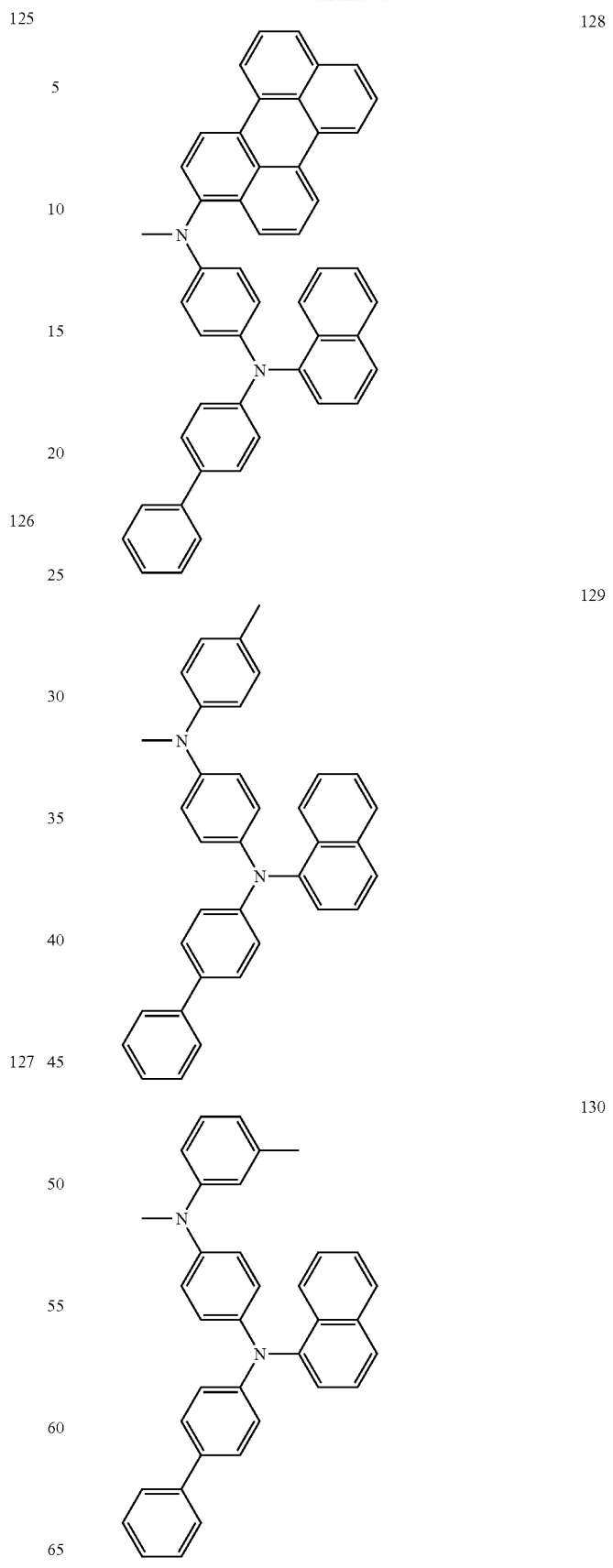

131 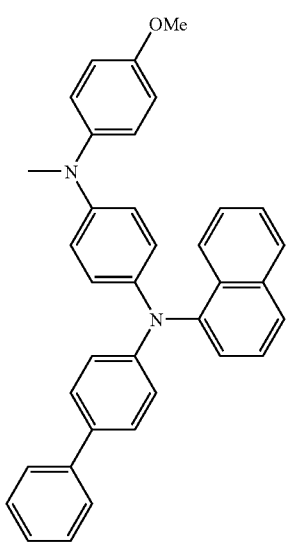
132 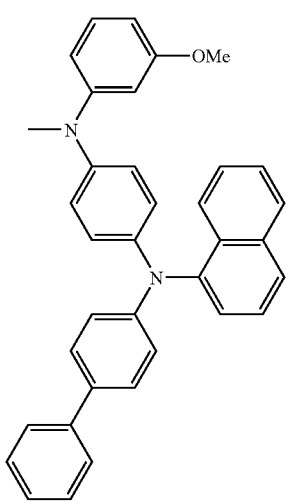
133 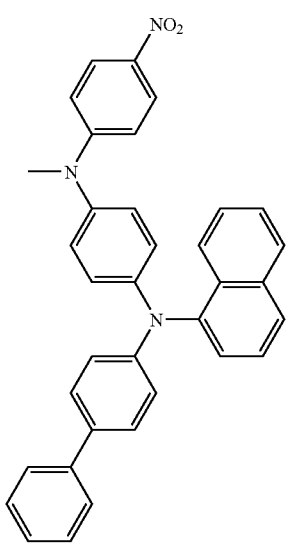
134 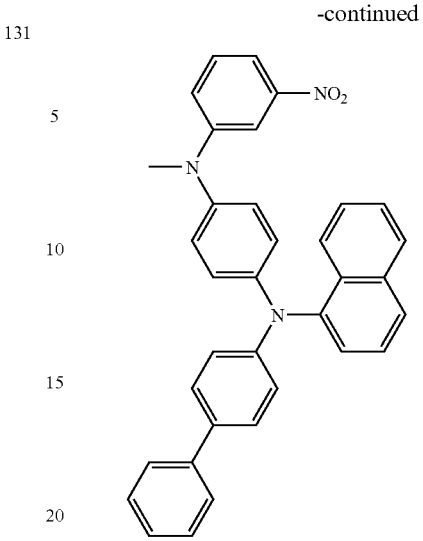
135 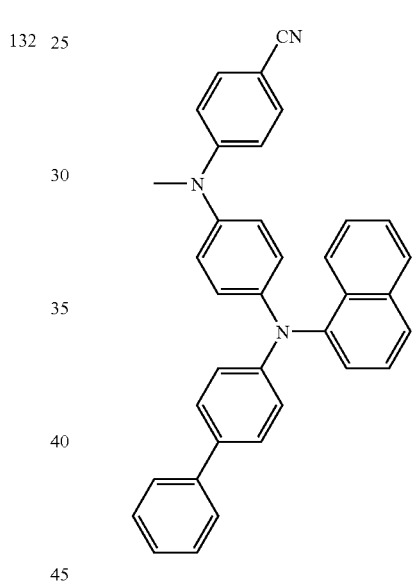
136 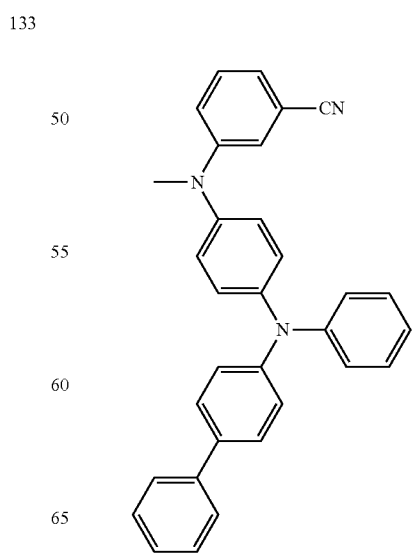

137
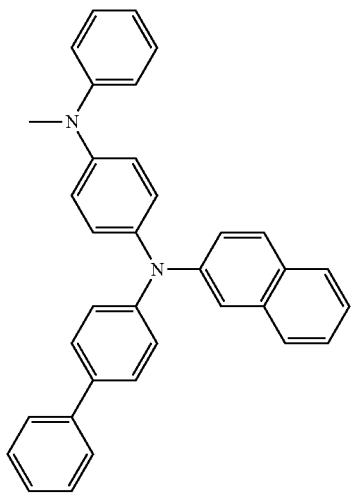
138
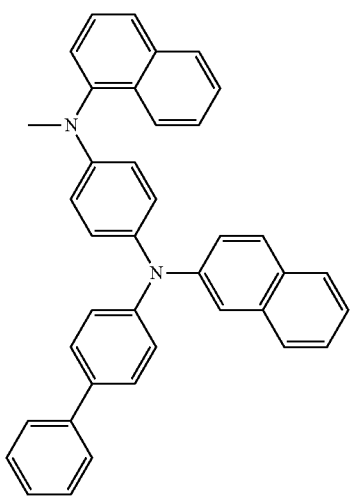
139
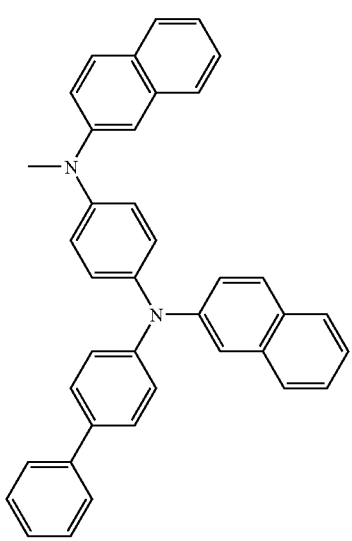
140
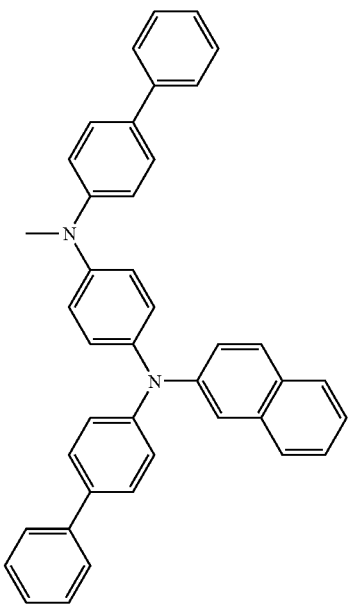
141
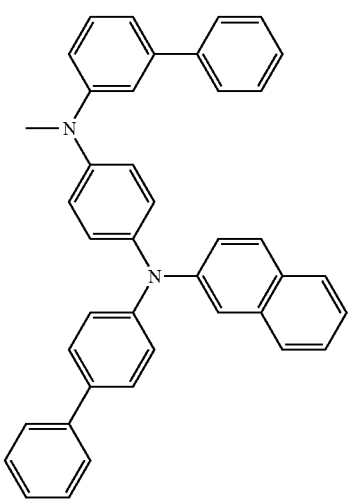
142
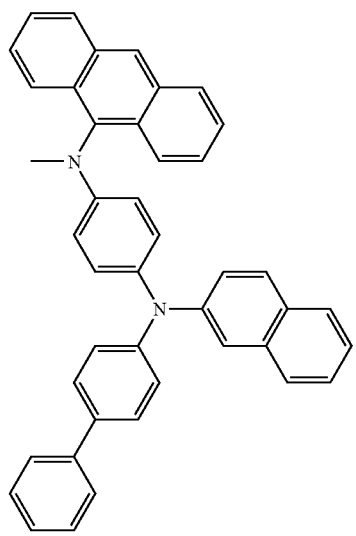

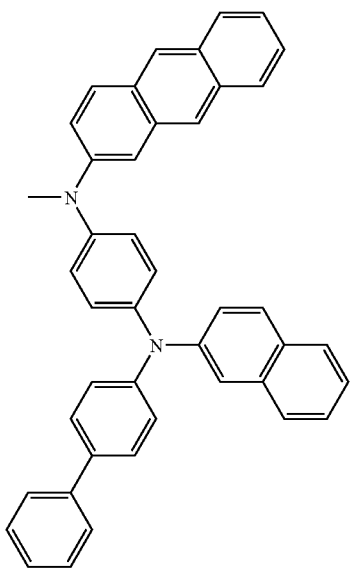
143
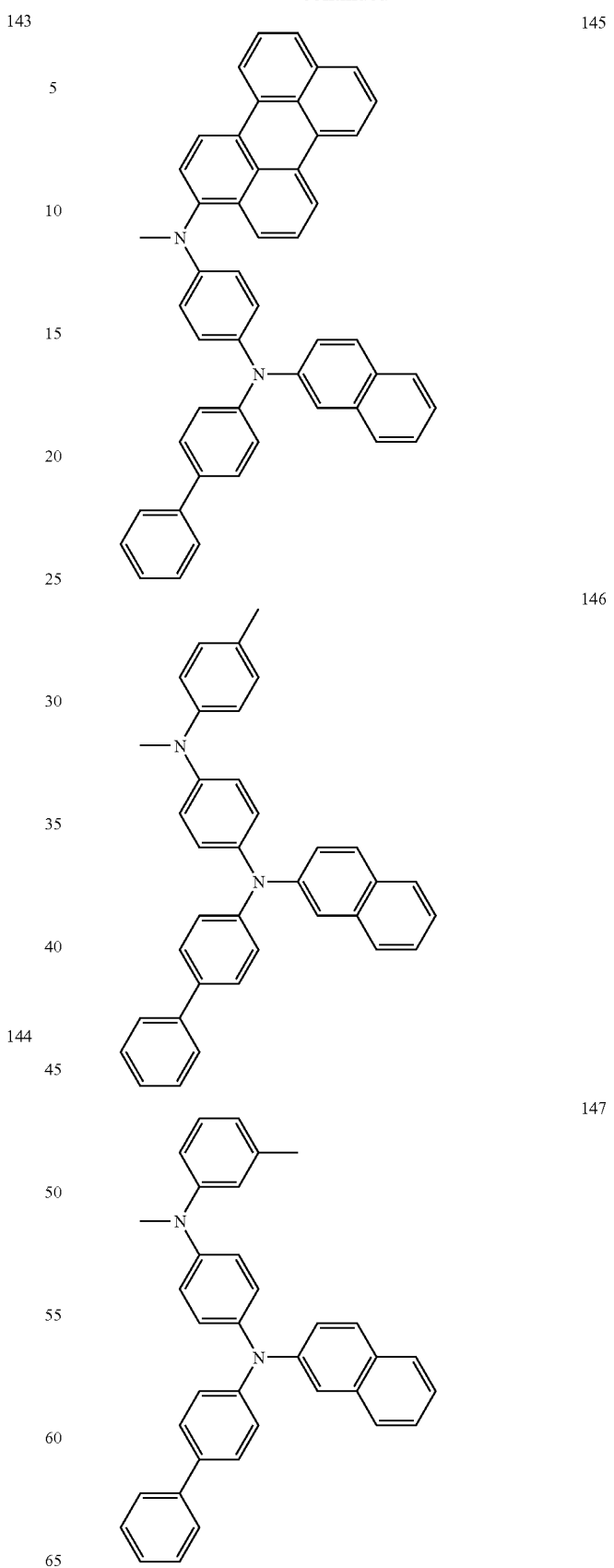
144

148
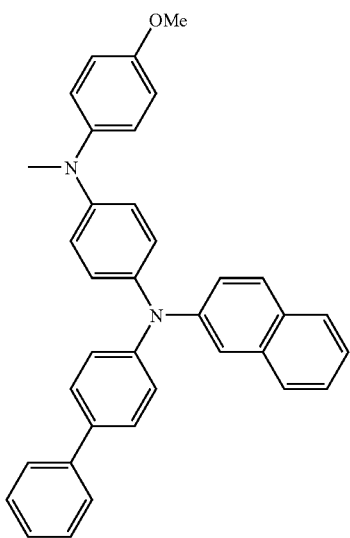
149
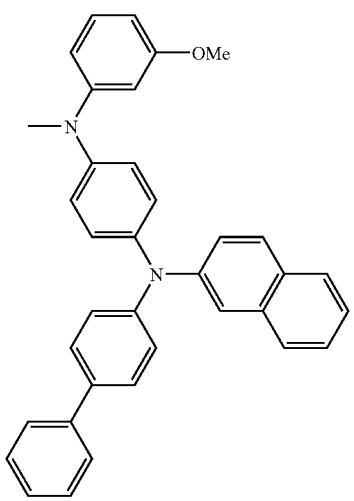
150
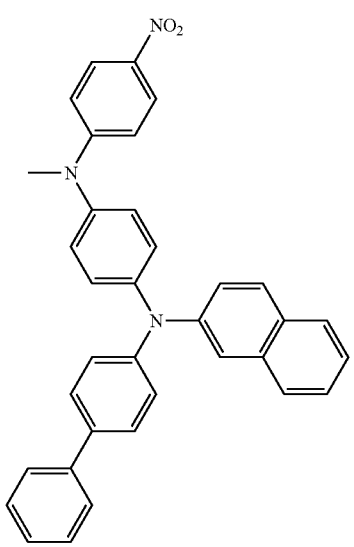
151
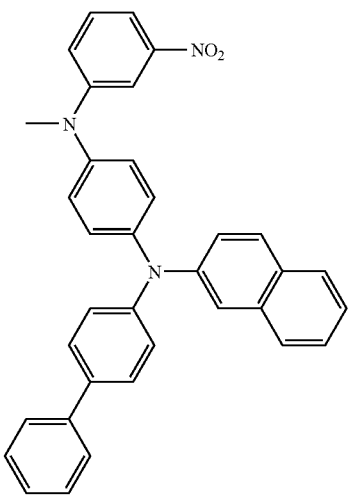
152
153
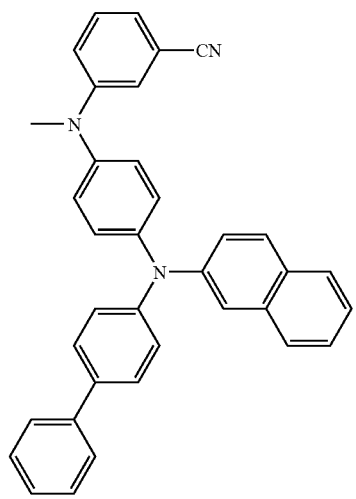

154
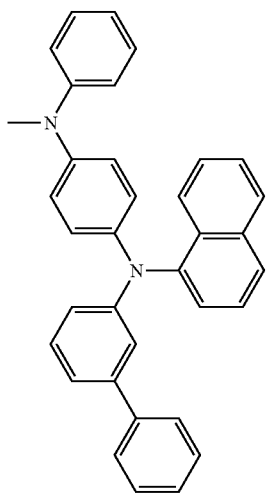
155
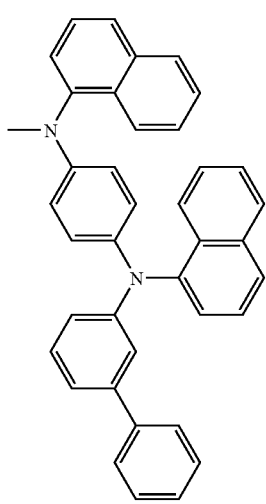
156
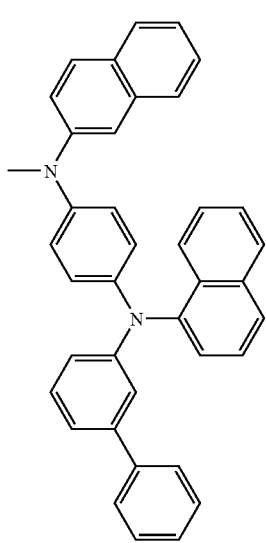
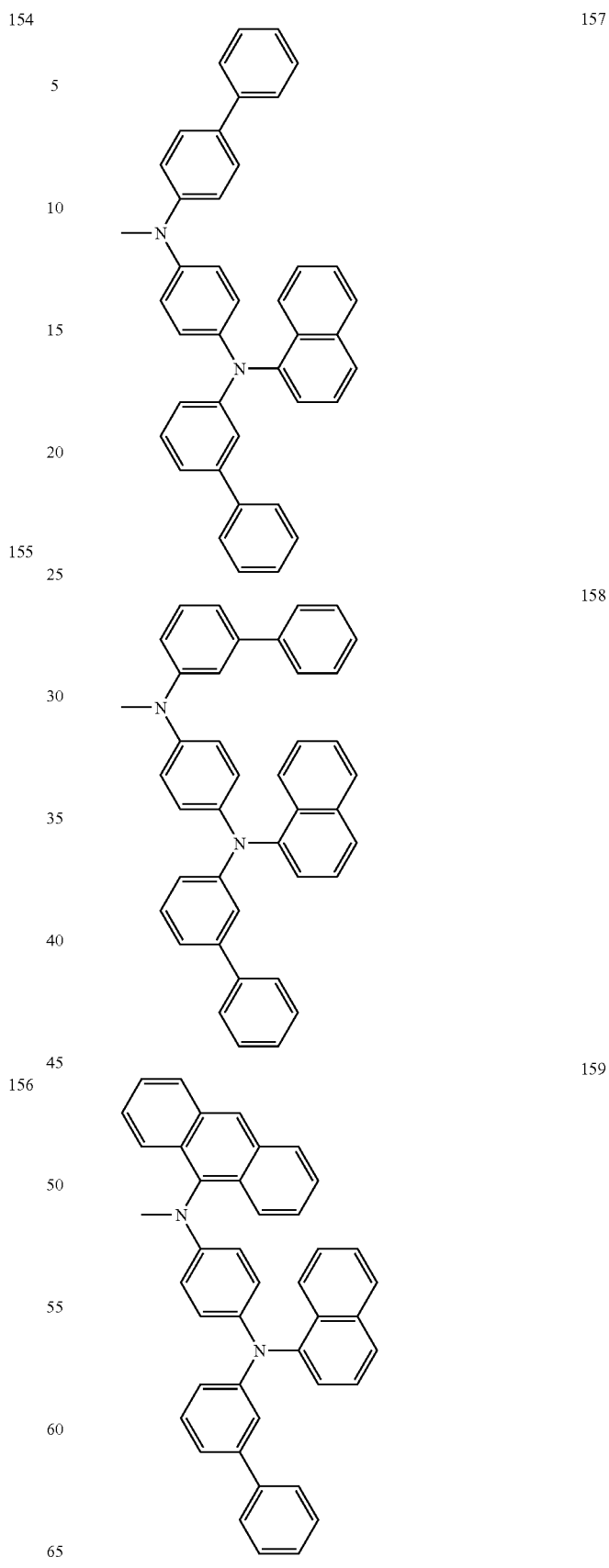

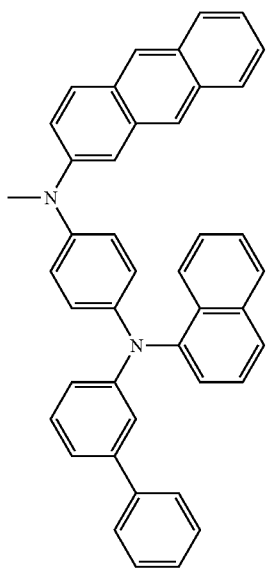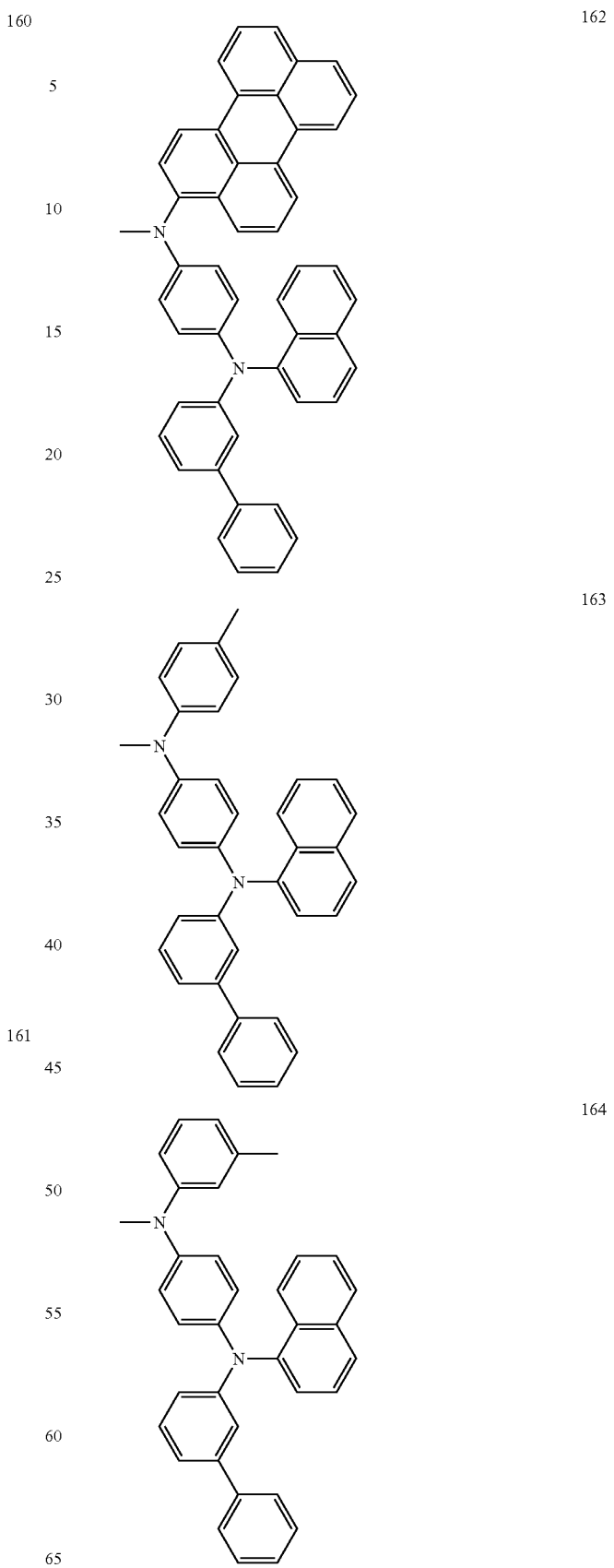

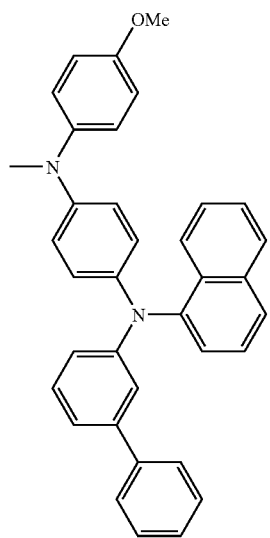
165
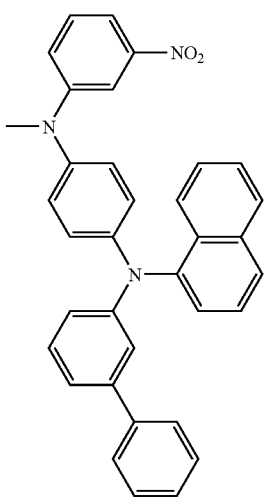
168
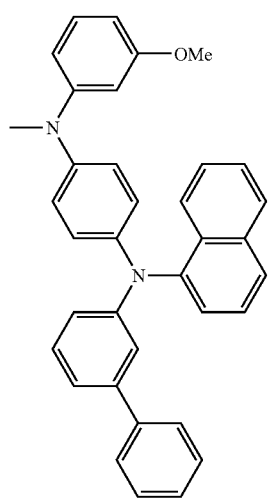
166
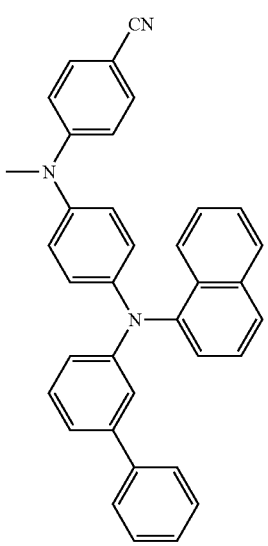
169
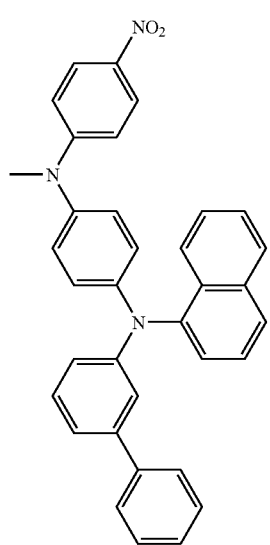
167
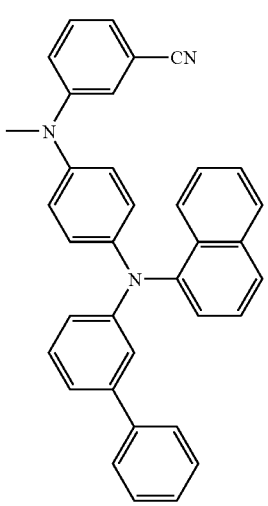
170

171 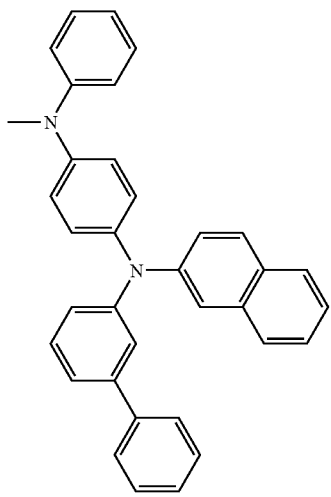
172 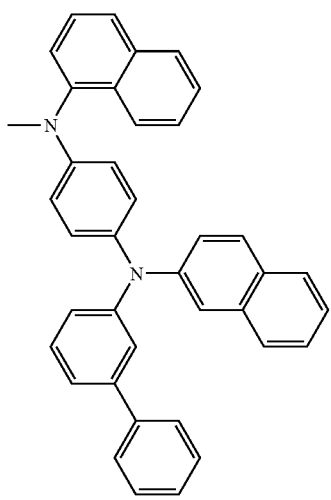
173 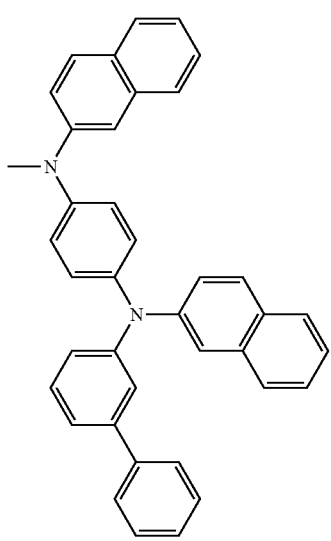
174 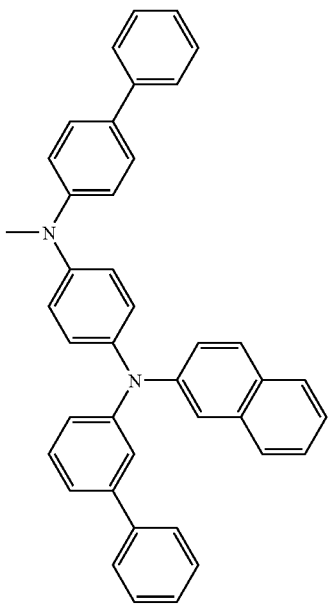
175 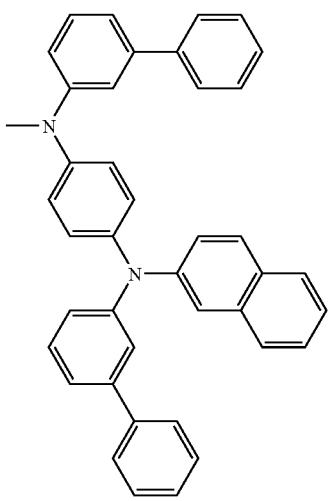
176 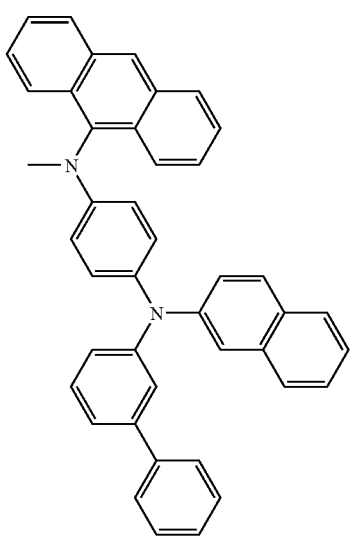

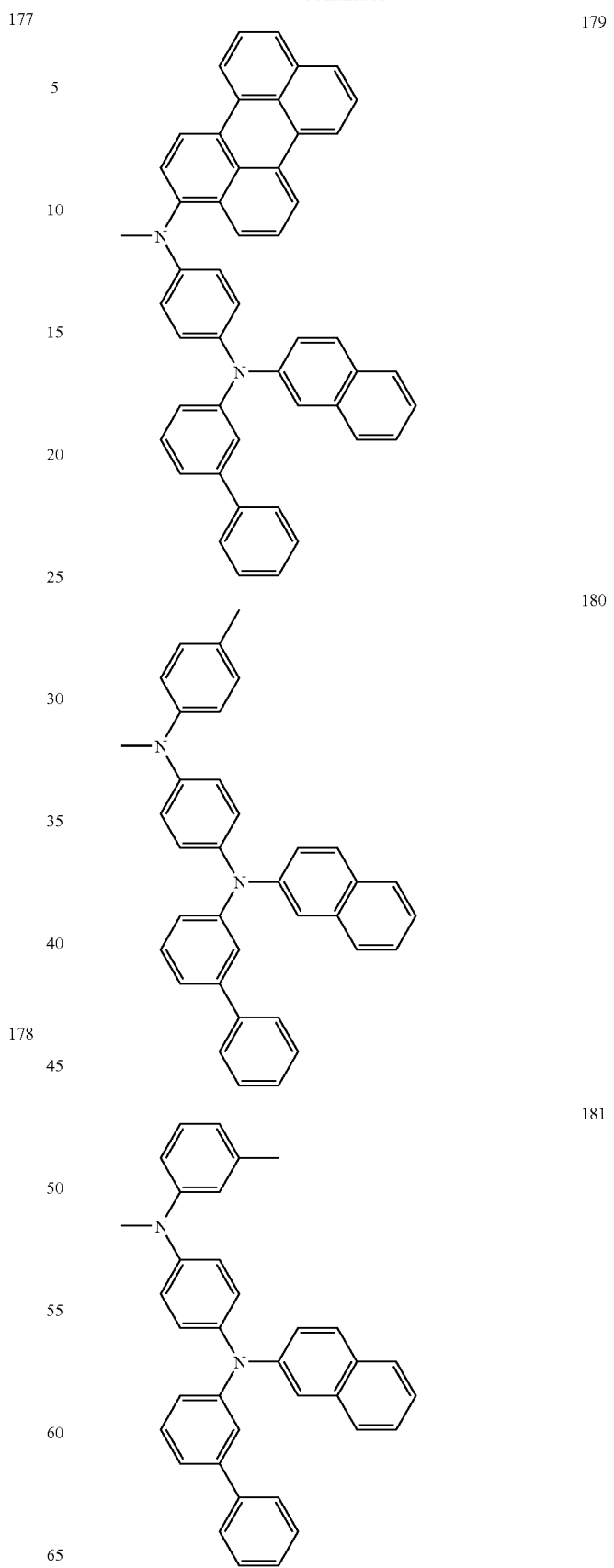

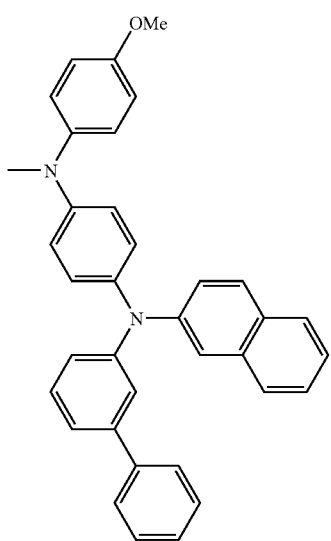
182
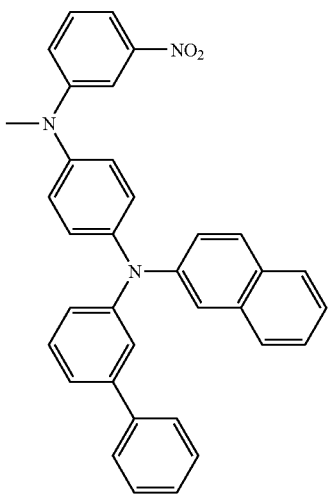
185
183
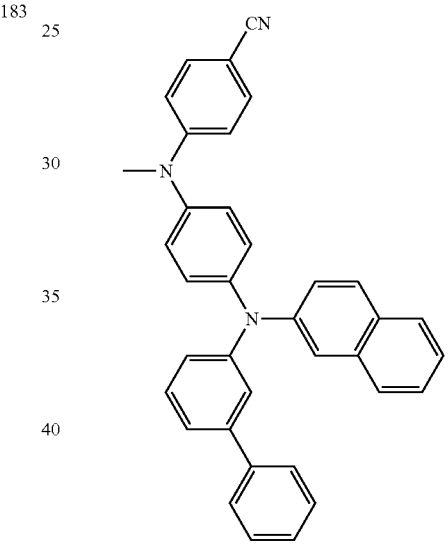
186
184
187
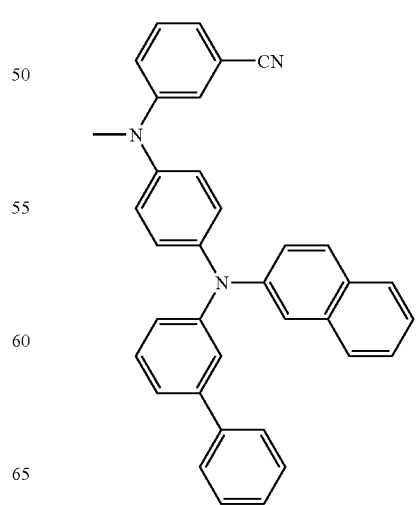

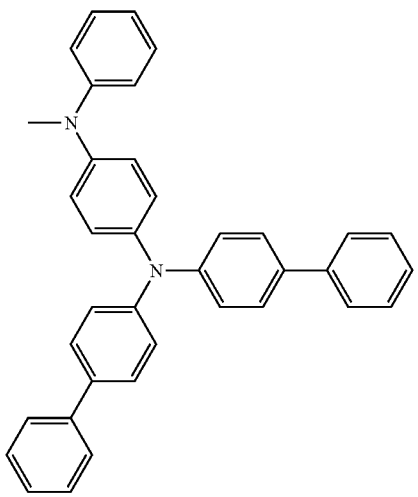
188
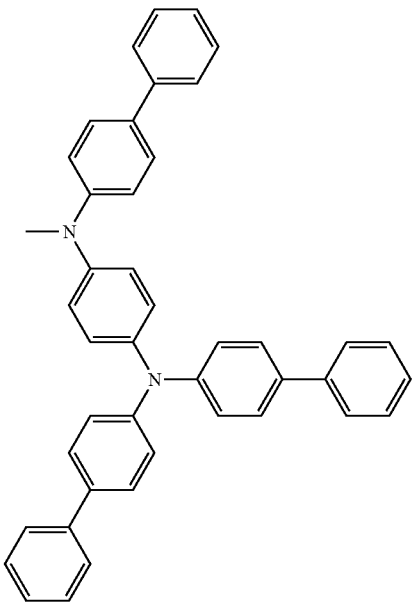
191
189
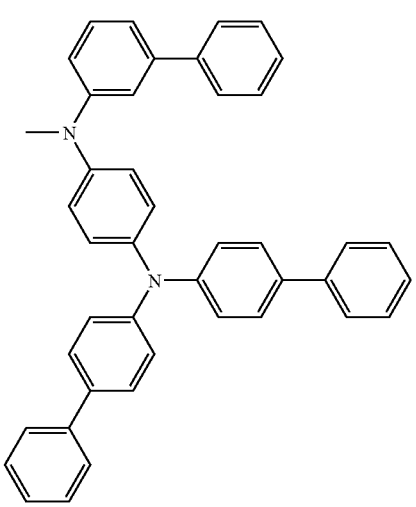
192
190
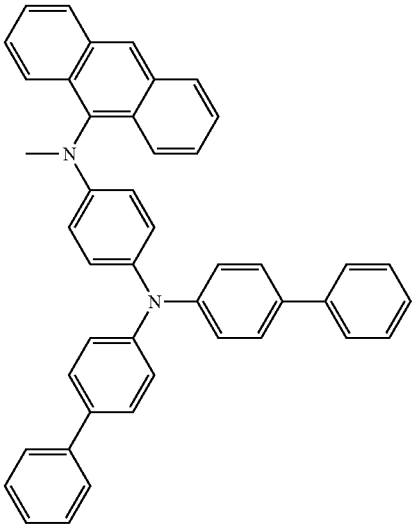
193

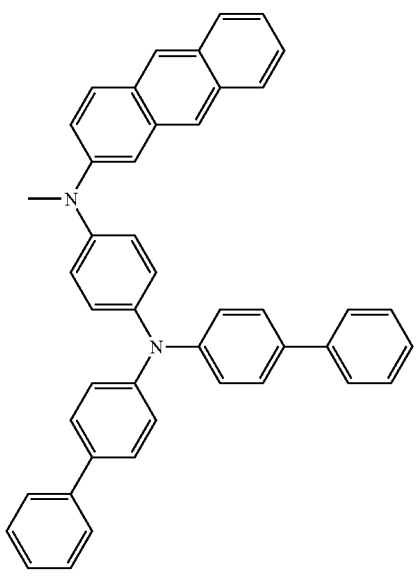
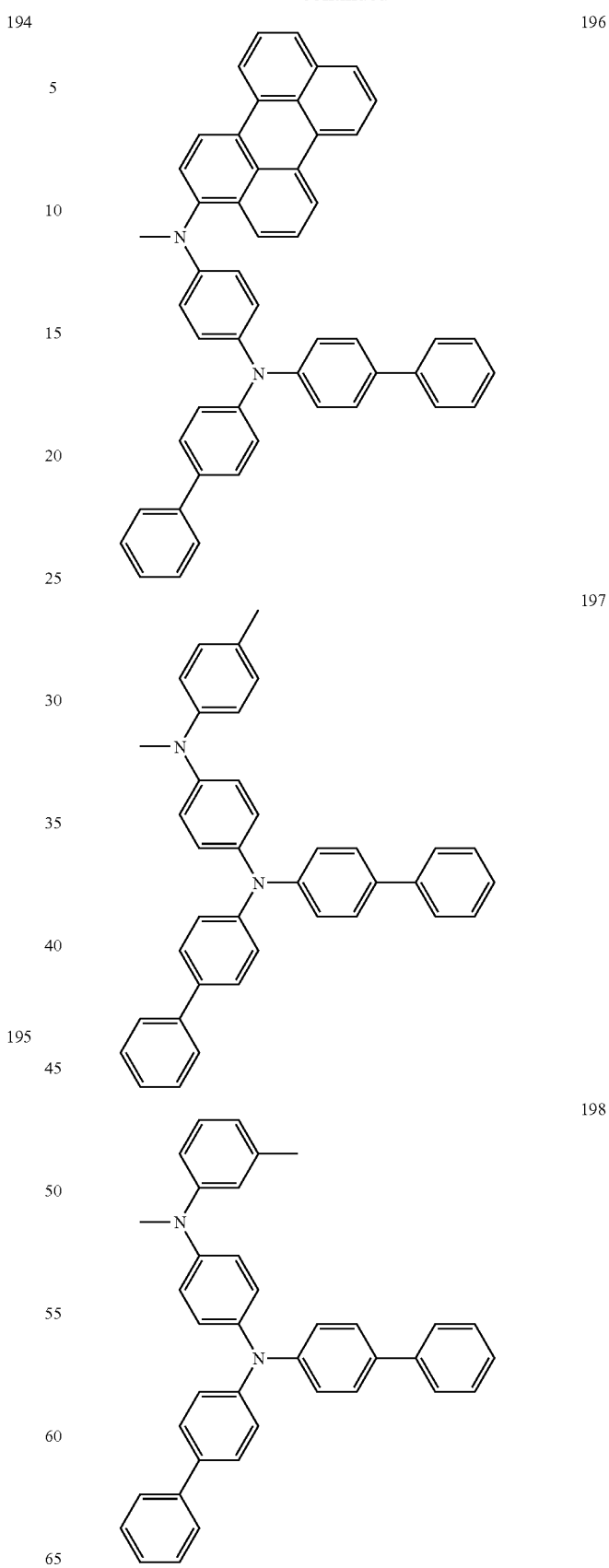

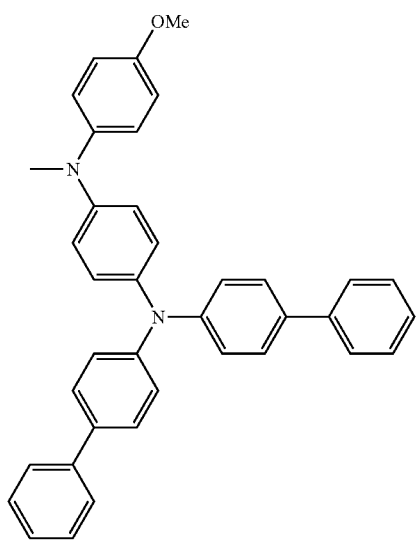
199
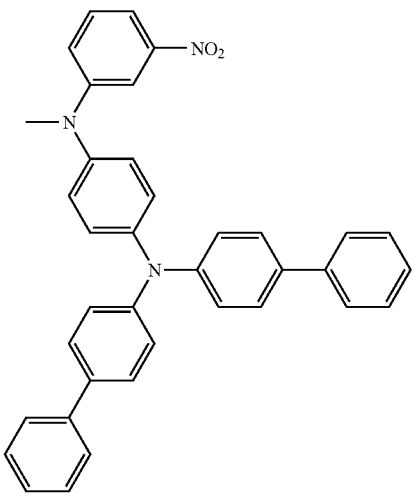
202
200
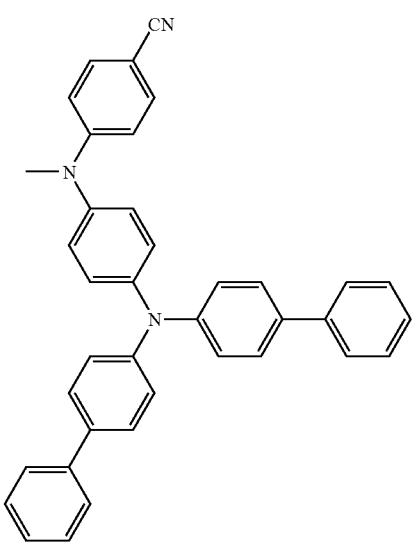
203
201
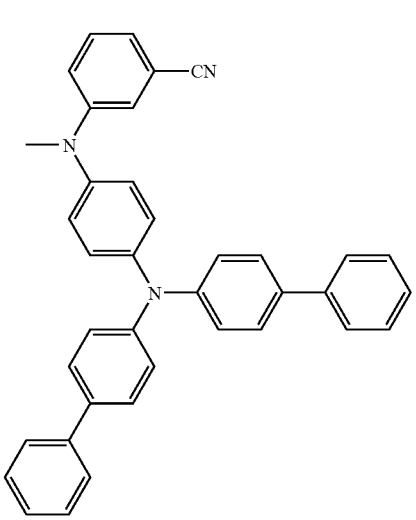
204

205
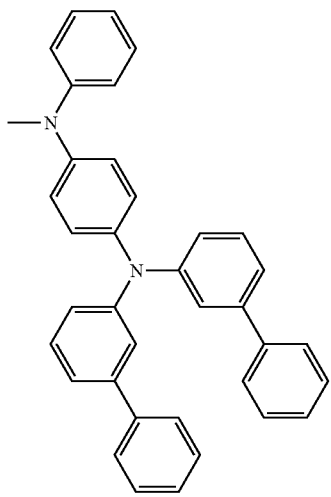
206
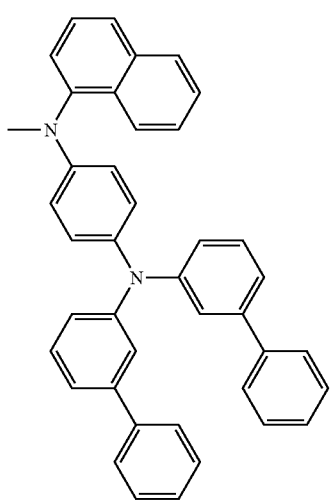
207
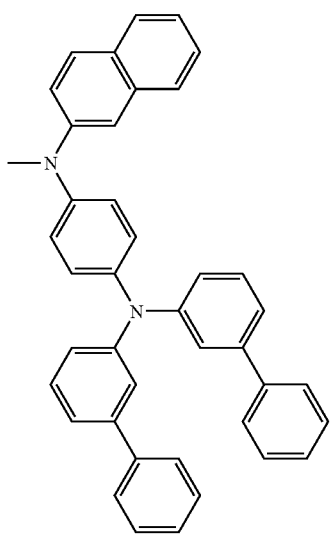
208
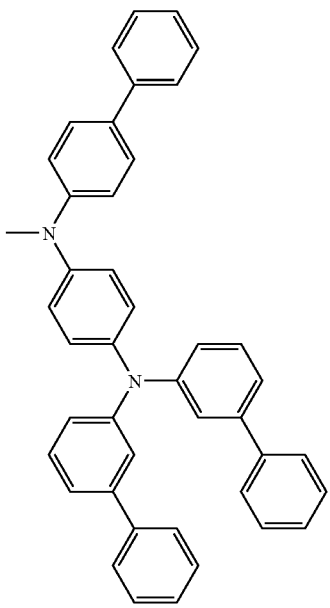
209
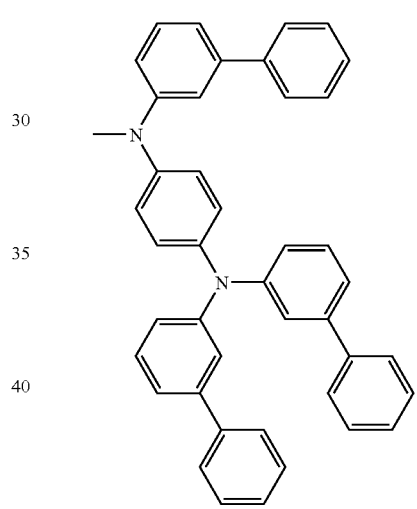
210
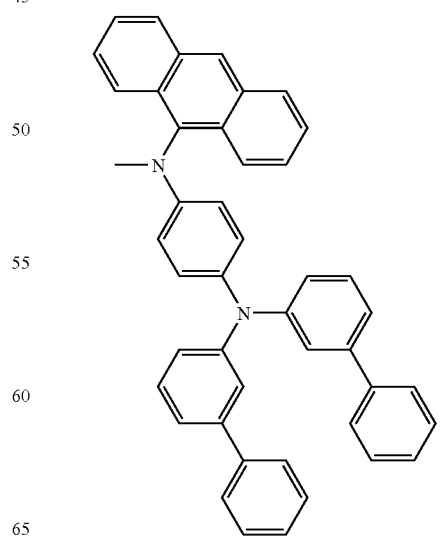

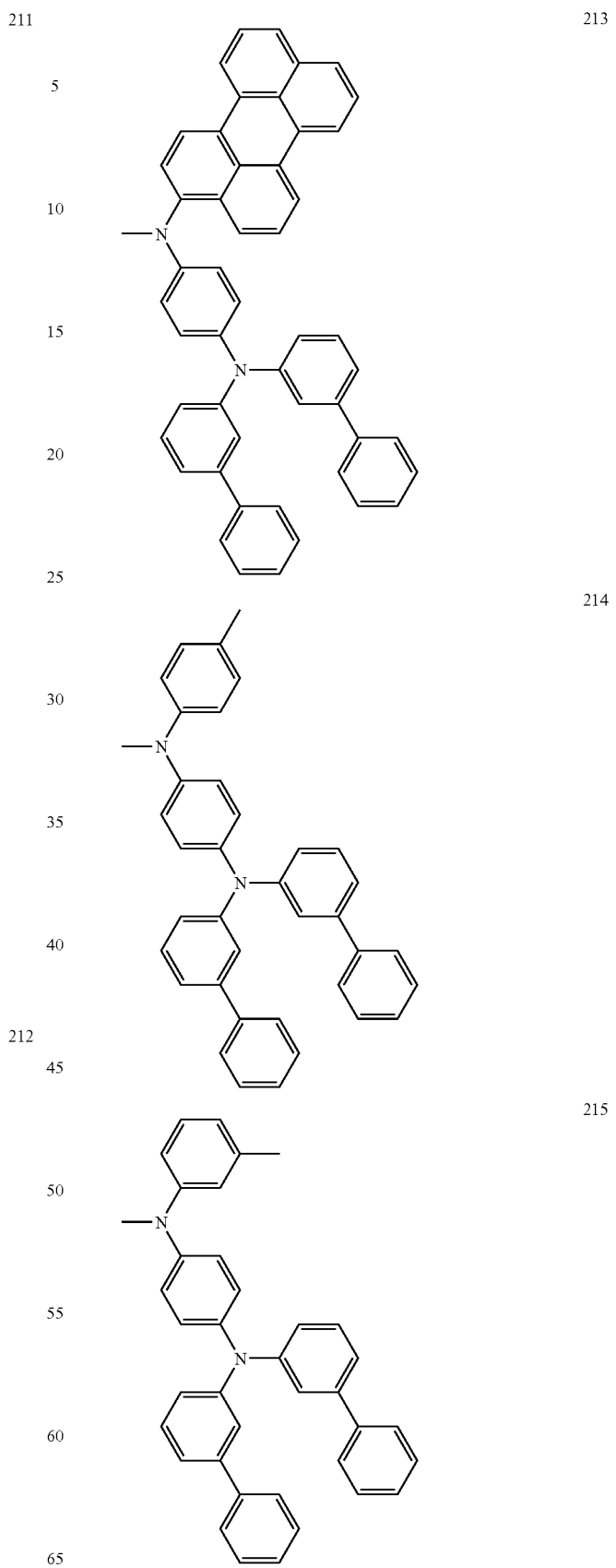

216
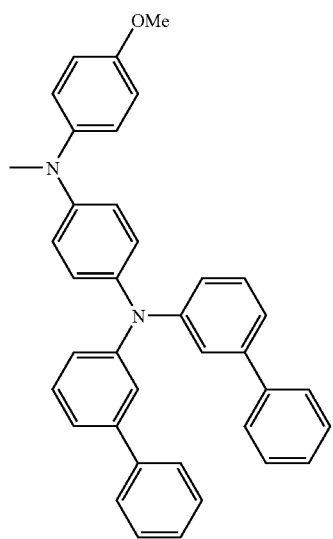
217
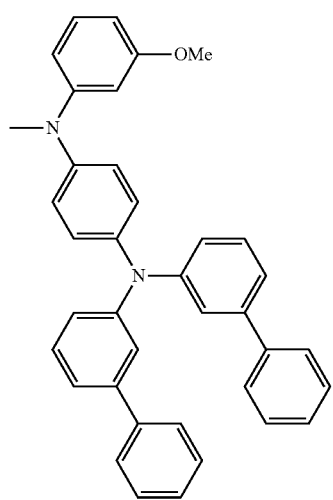
218
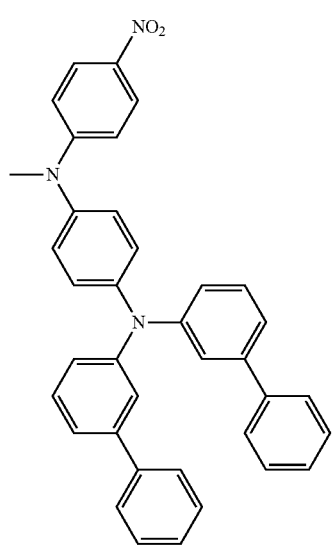
219
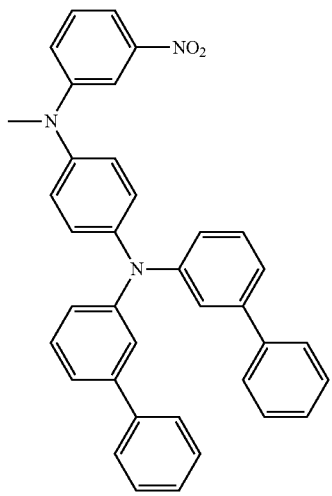
220
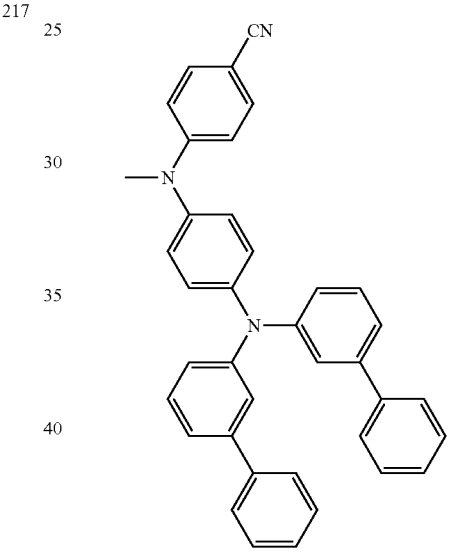
221
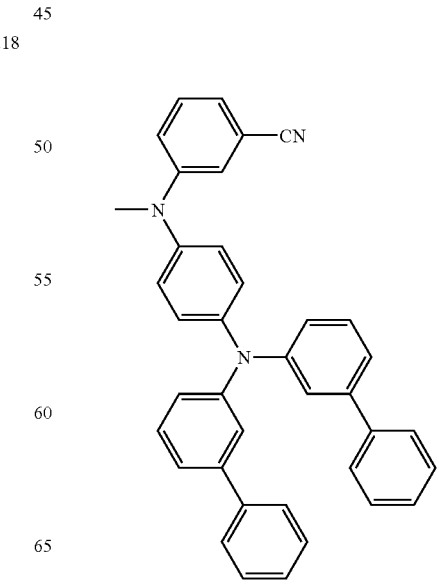

222
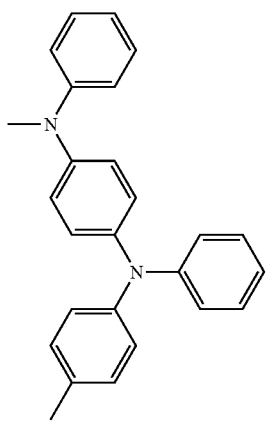
223
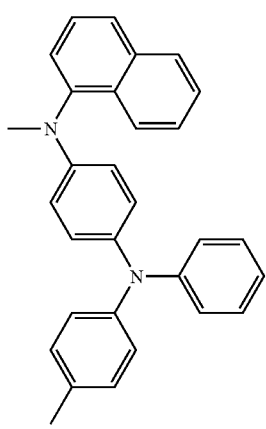
224
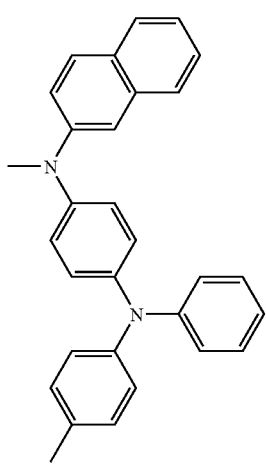
225
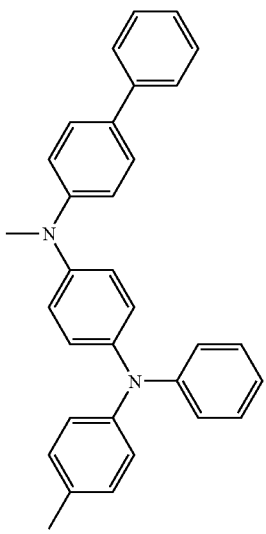
226
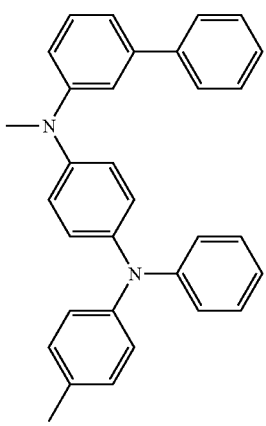
227
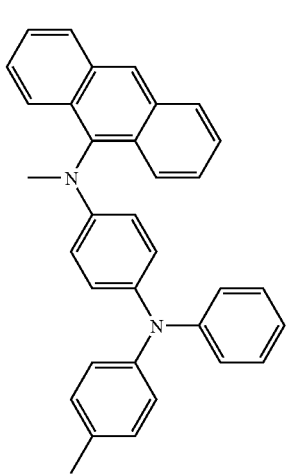

228
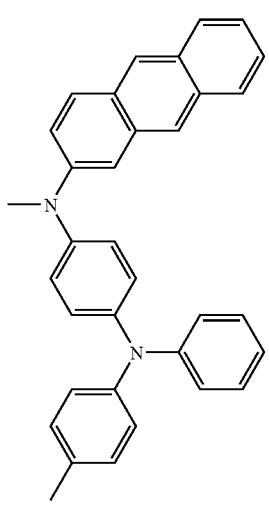
229
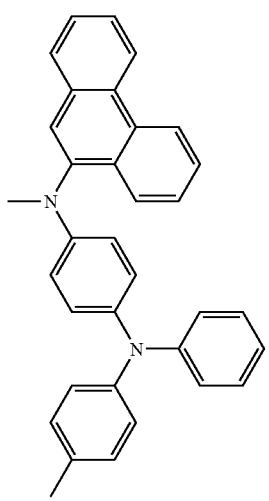
230
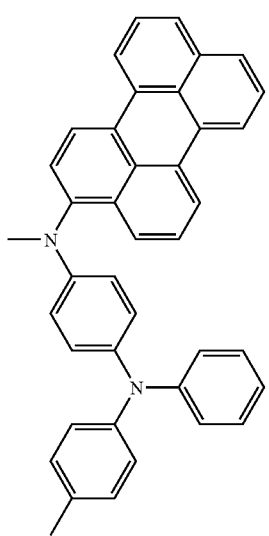
231
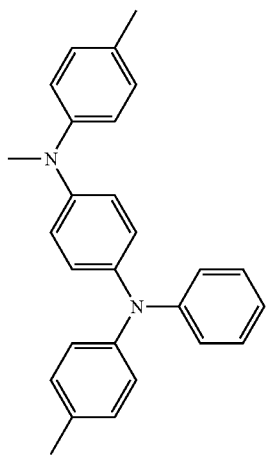
232
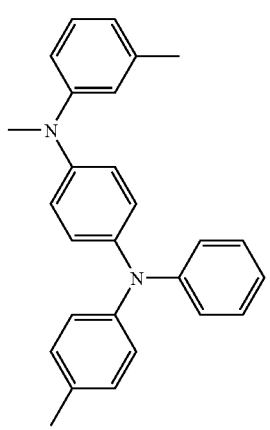
233
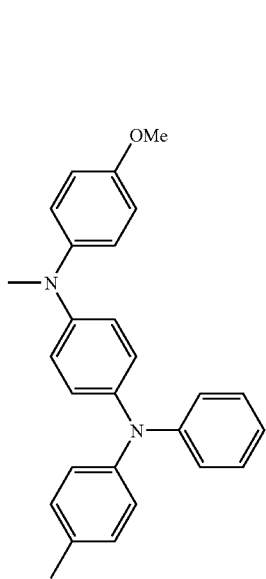

234
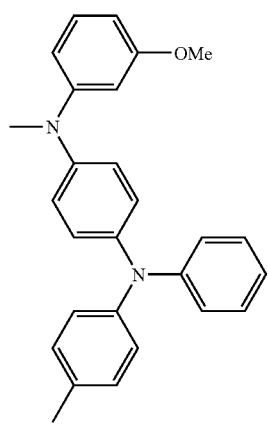
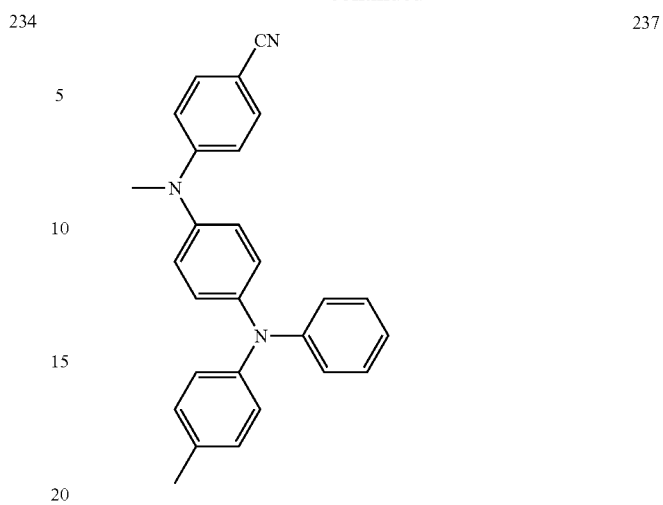
235
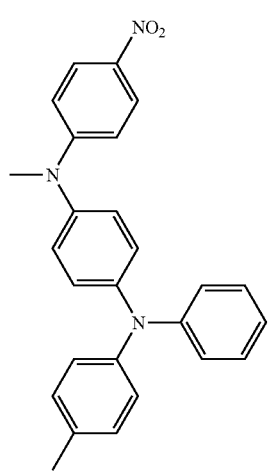
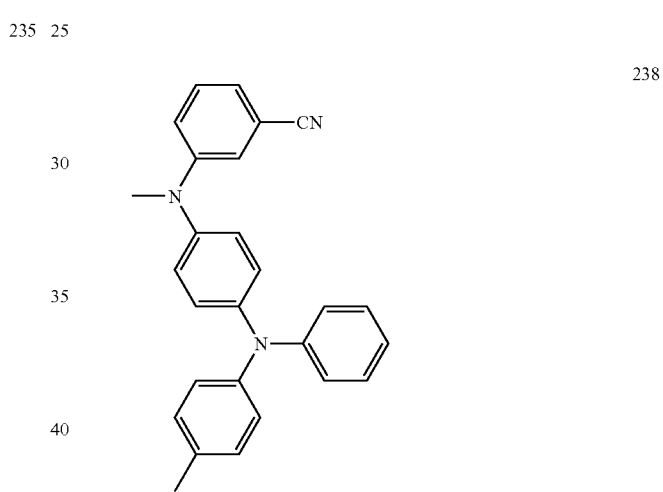
236
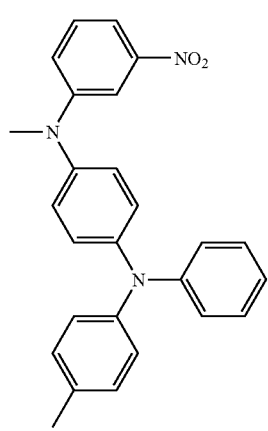
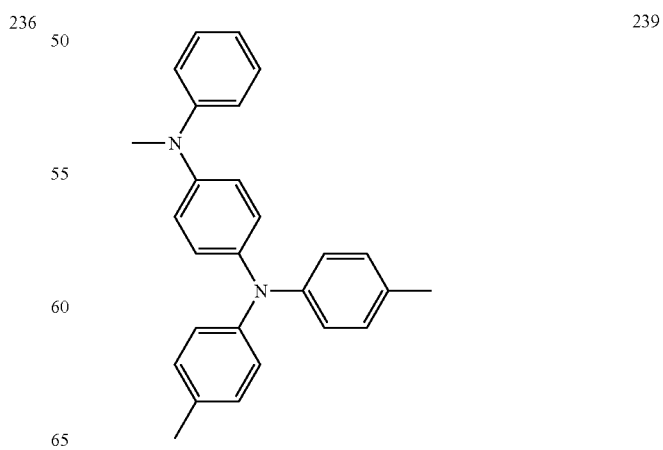

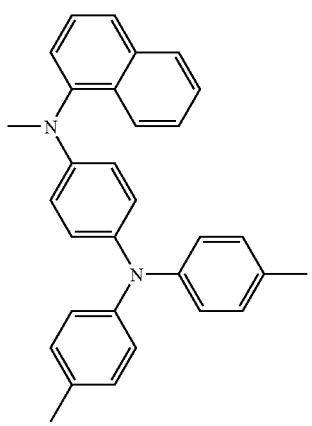
240
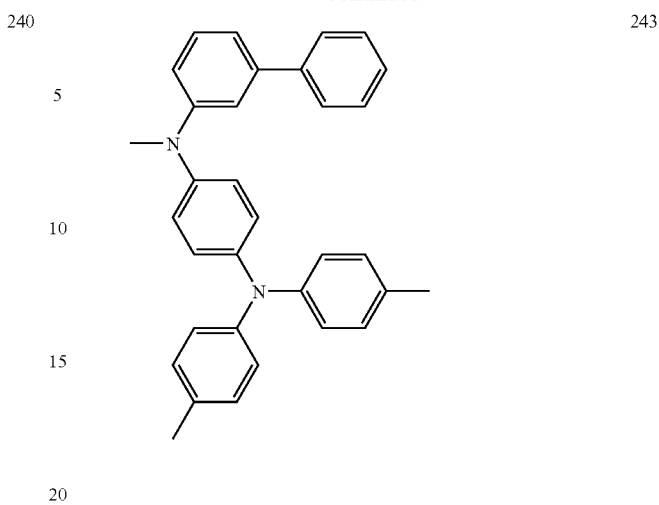
243
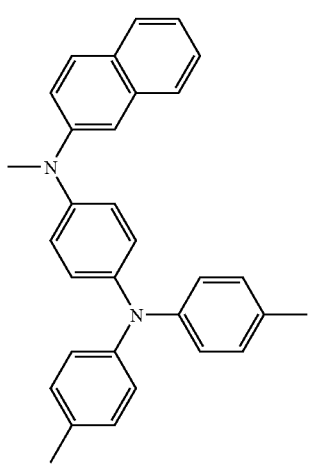
241
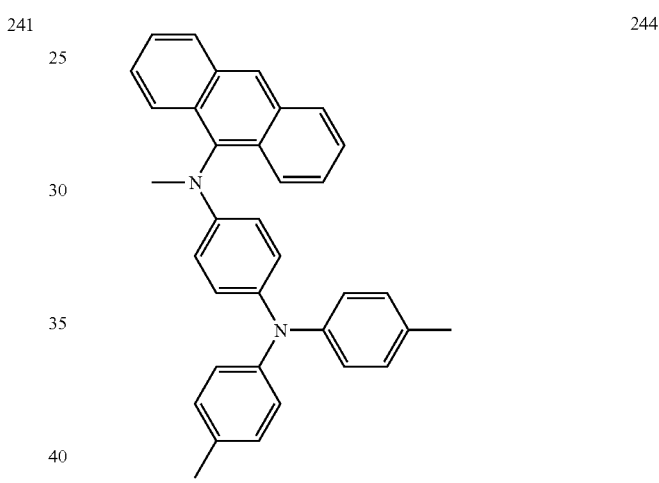
244
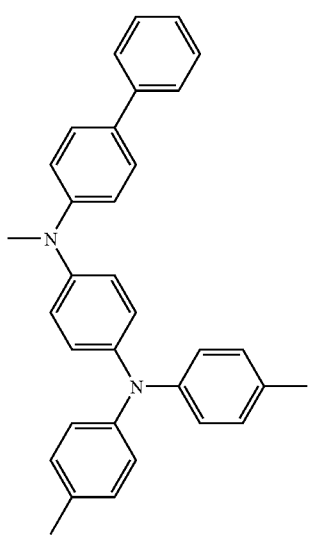
242
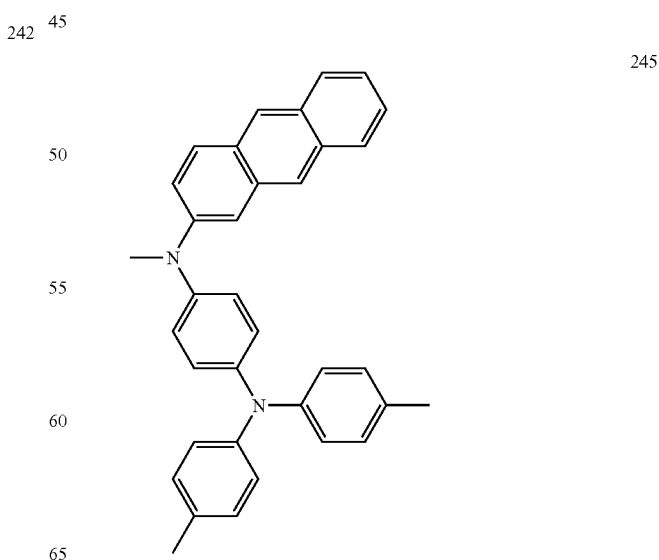
245

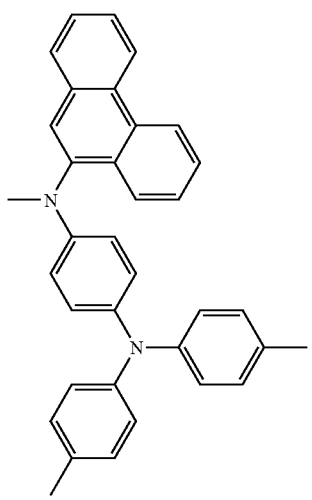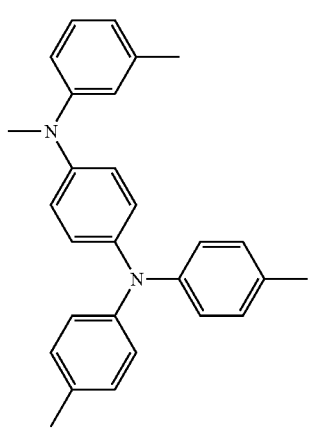

252
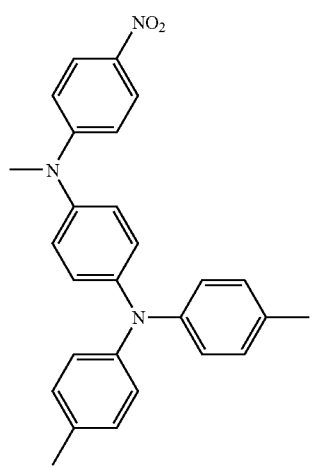
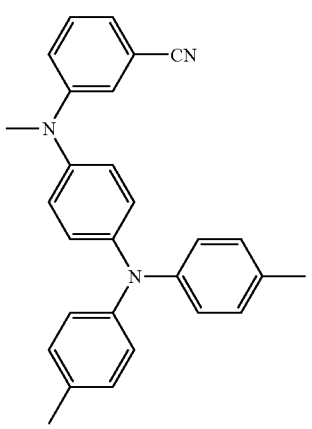
255
253
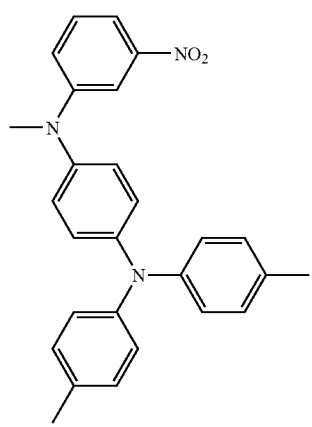
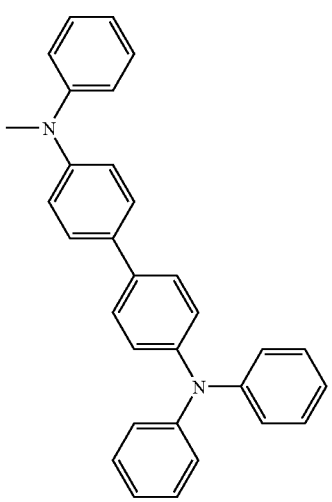
256
254
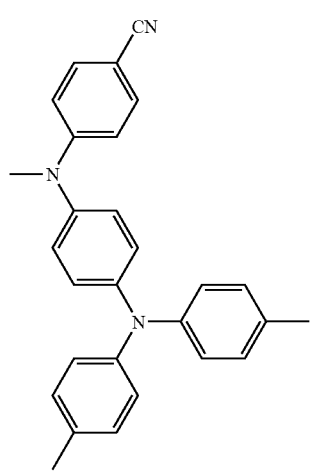
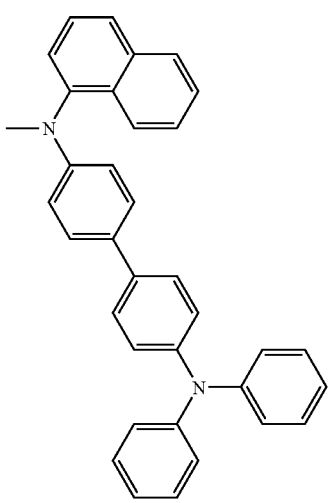
257

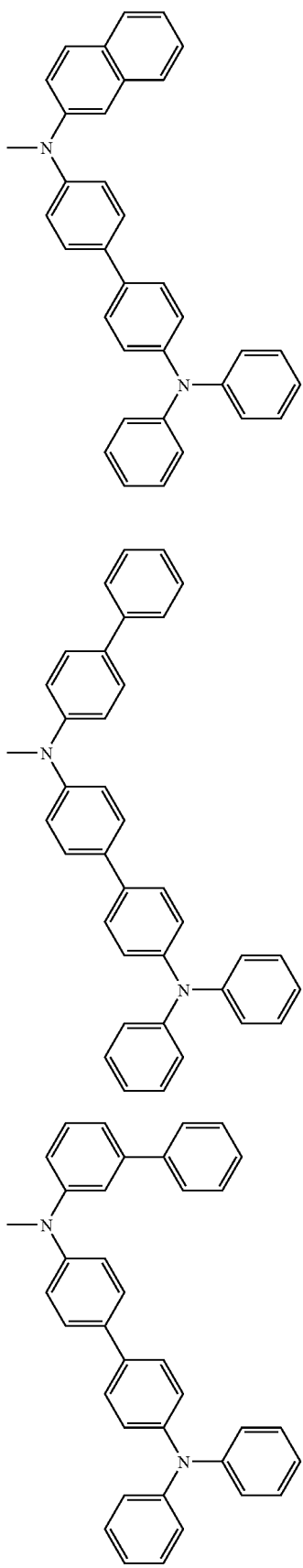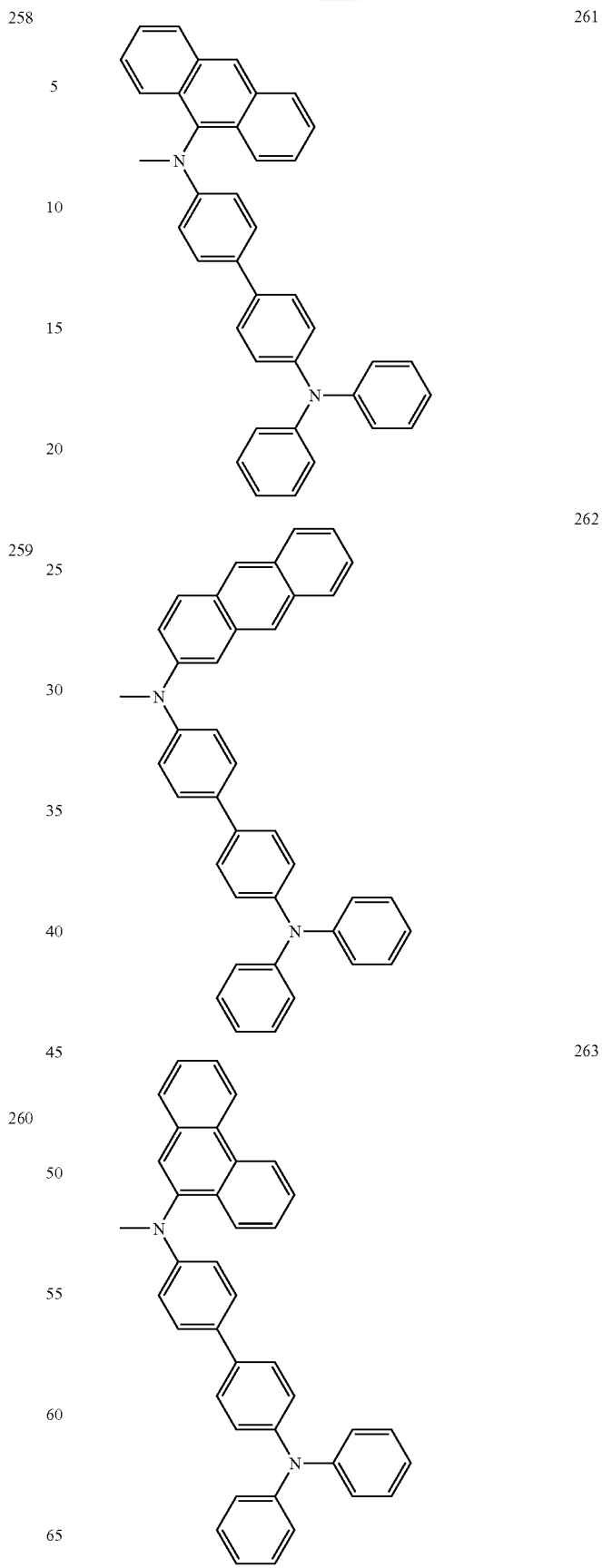

264
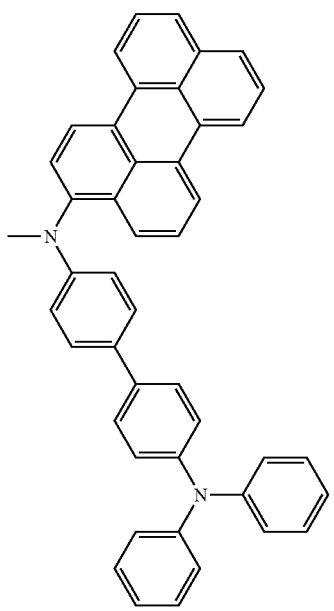
265
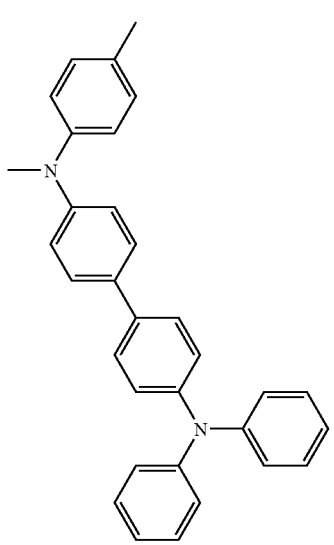
266
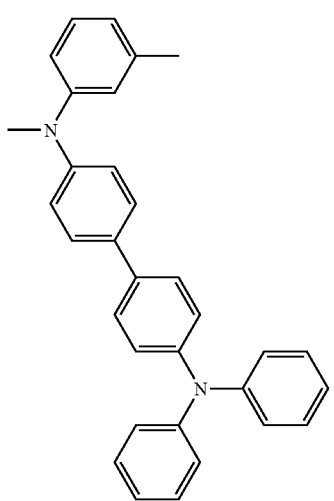
267
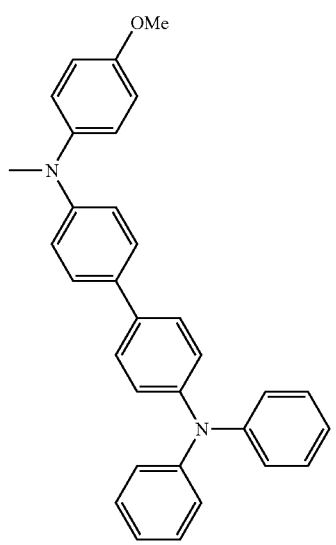
268
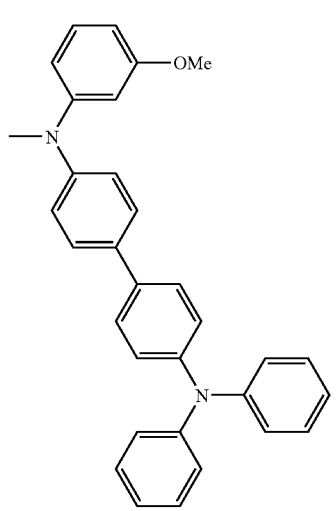
269
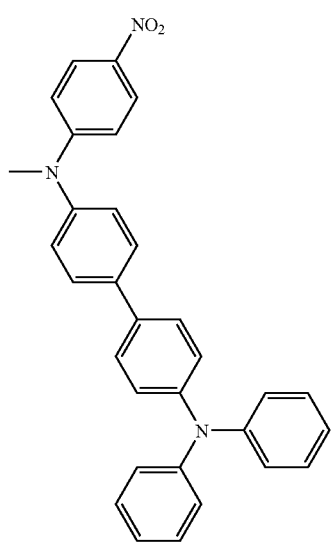

101
-continued
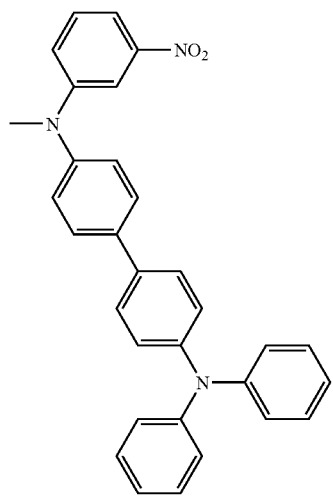
270
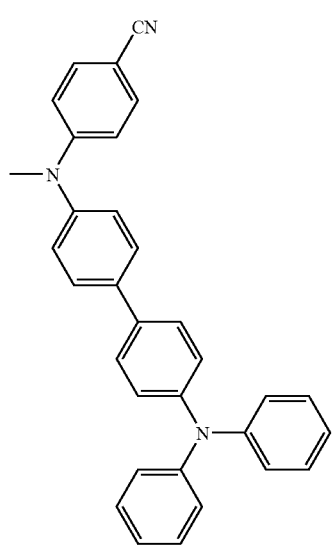
271
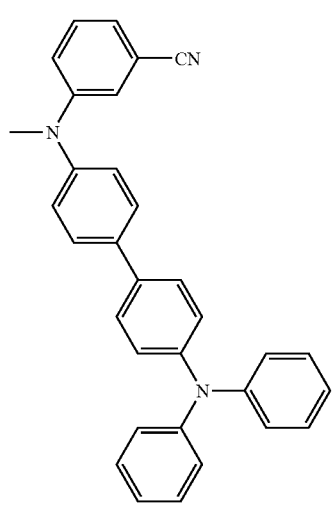
272
102
-continued
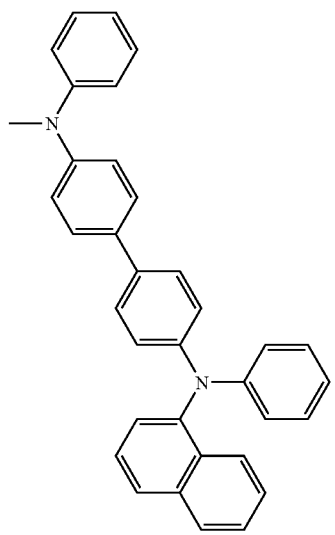
273
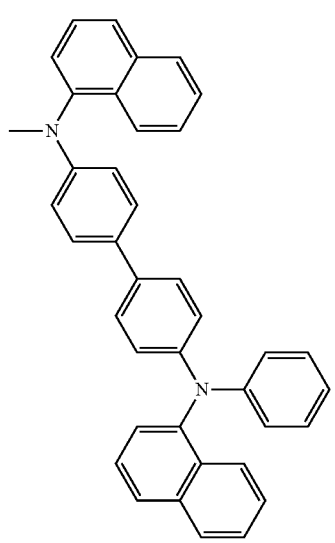
274
275

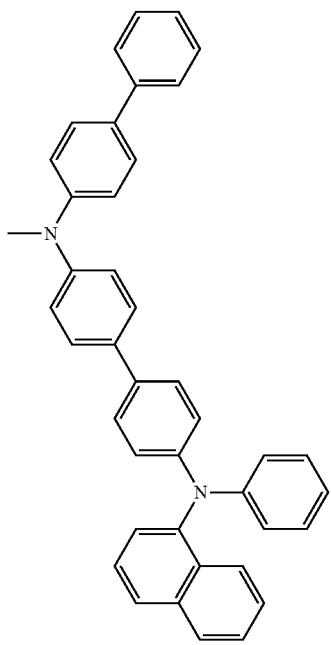
276
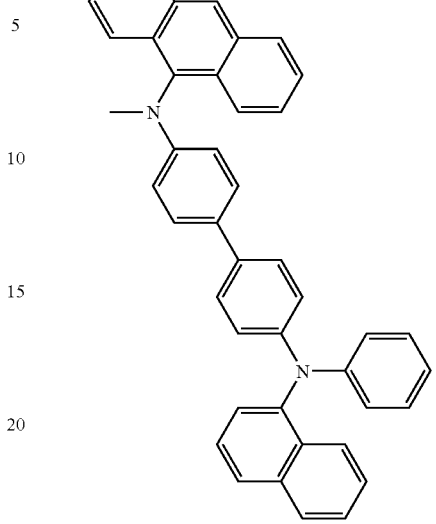
278
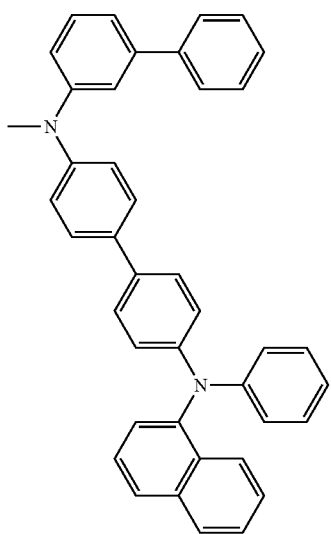
277
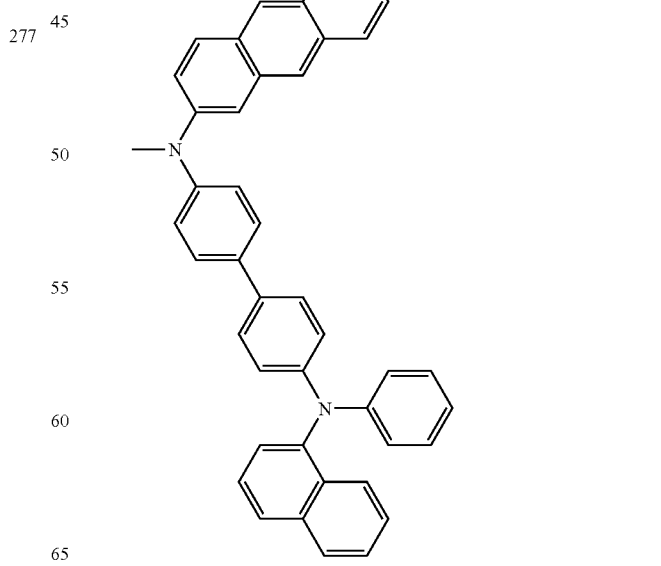
279

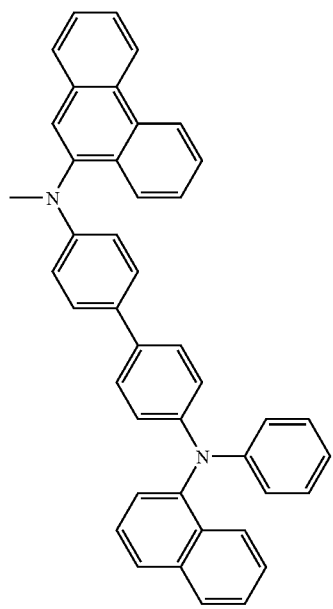
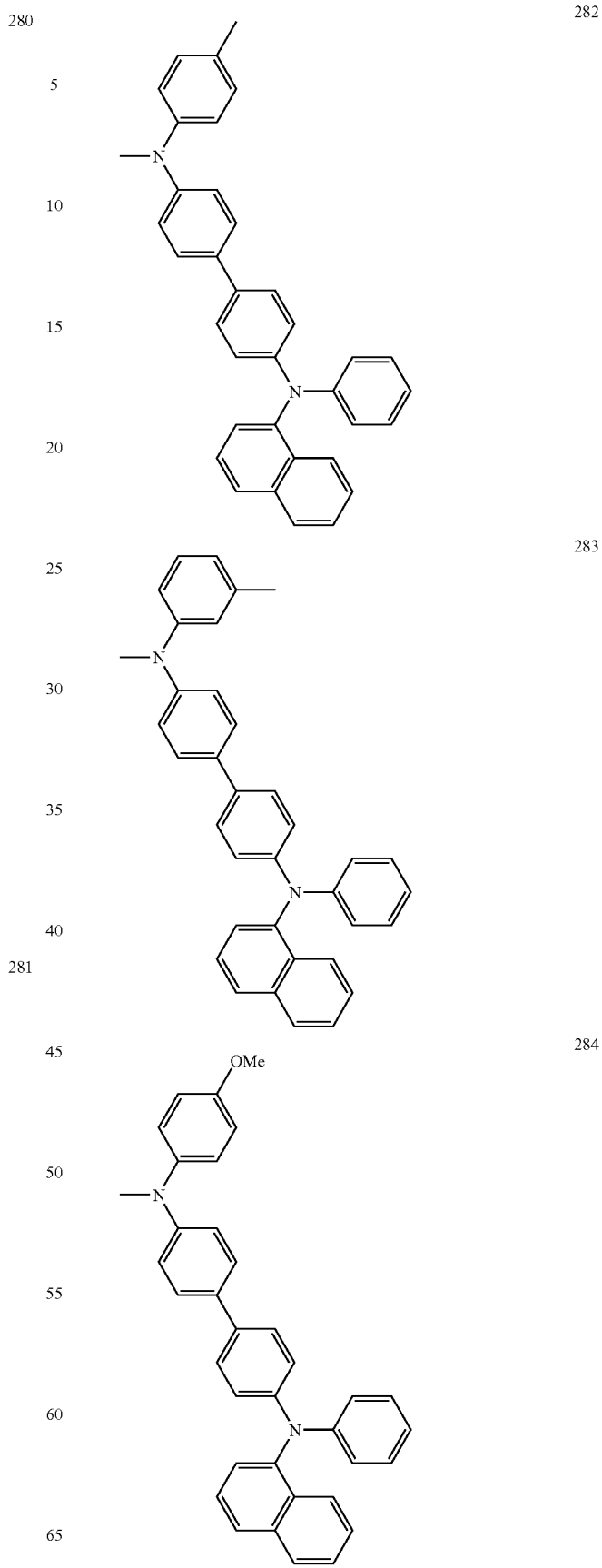

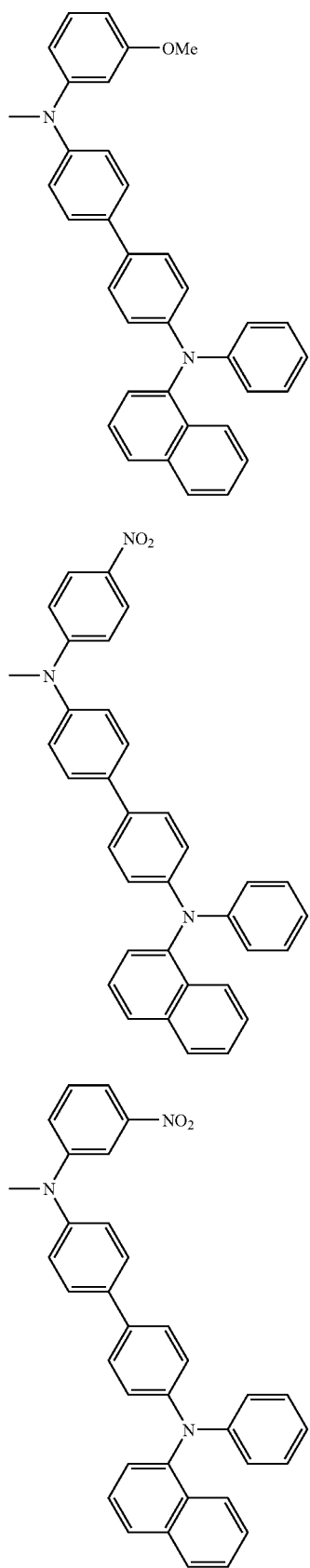
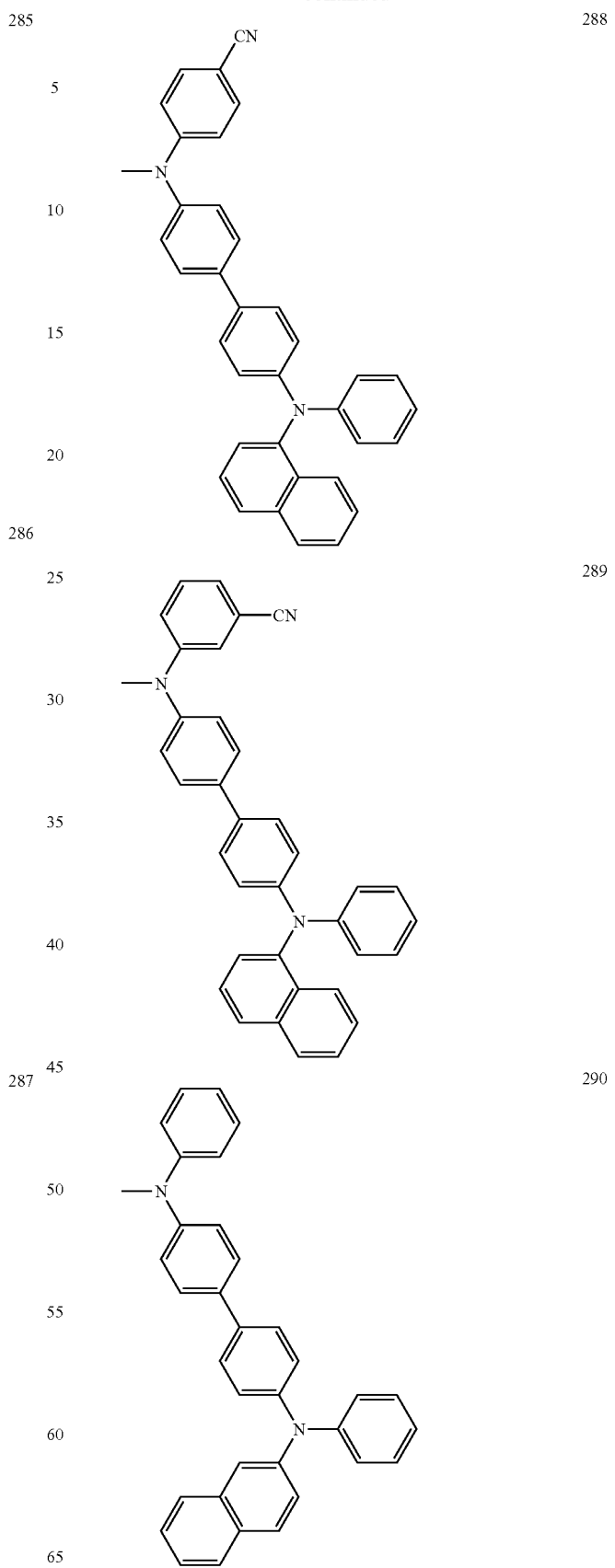

109
-continued
291
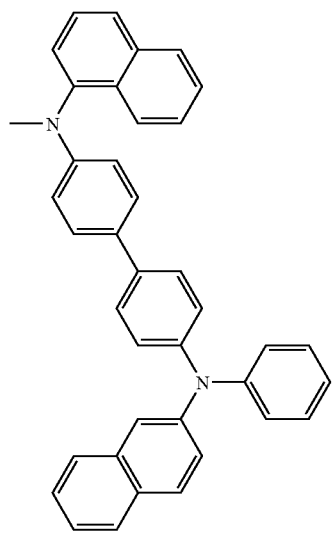
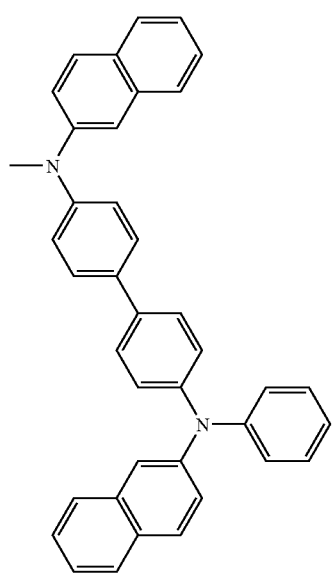
292
110
-continued
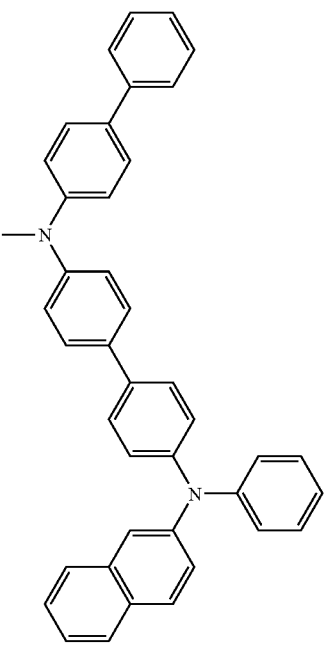
293
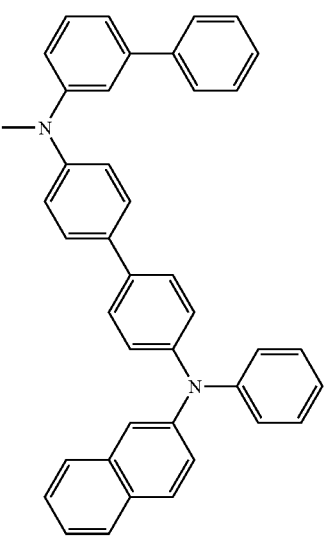
294

295
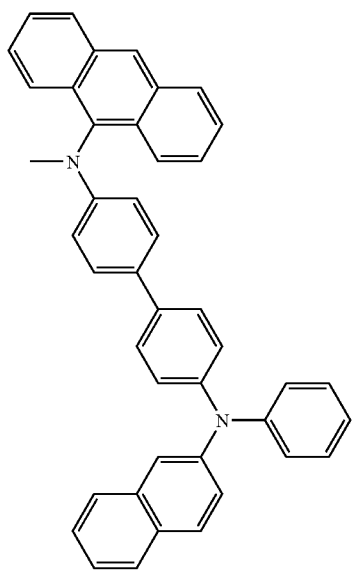
296
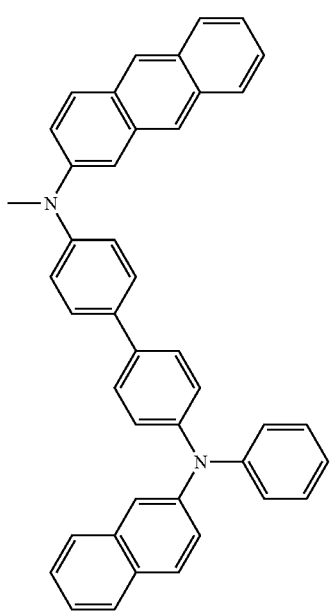
297
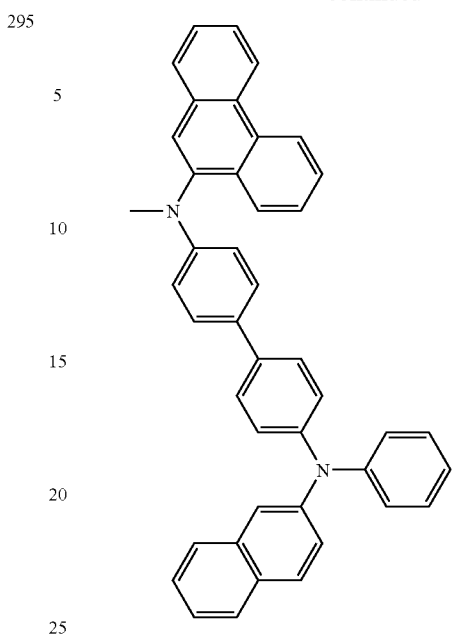
298
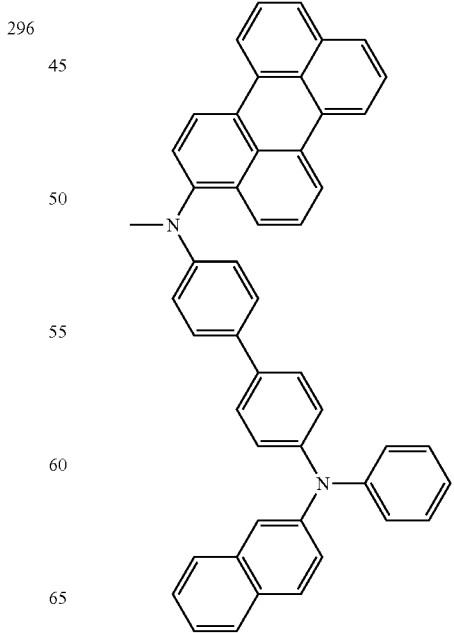

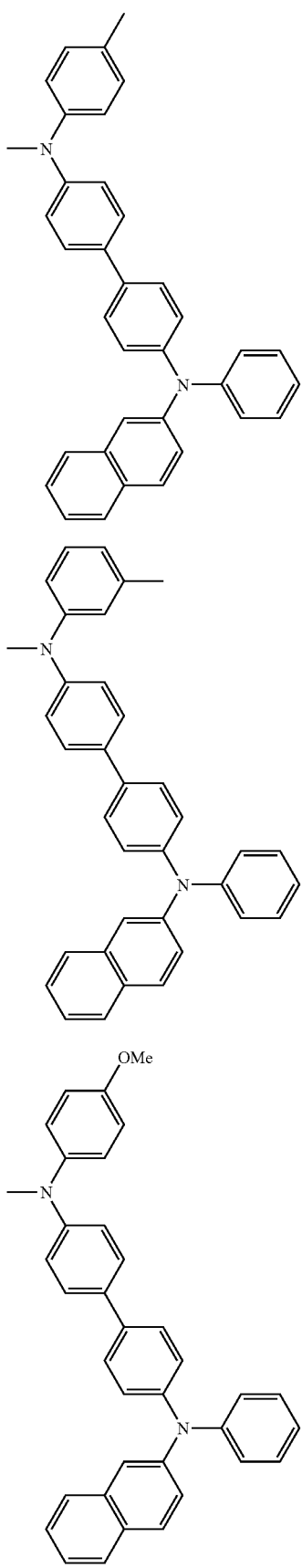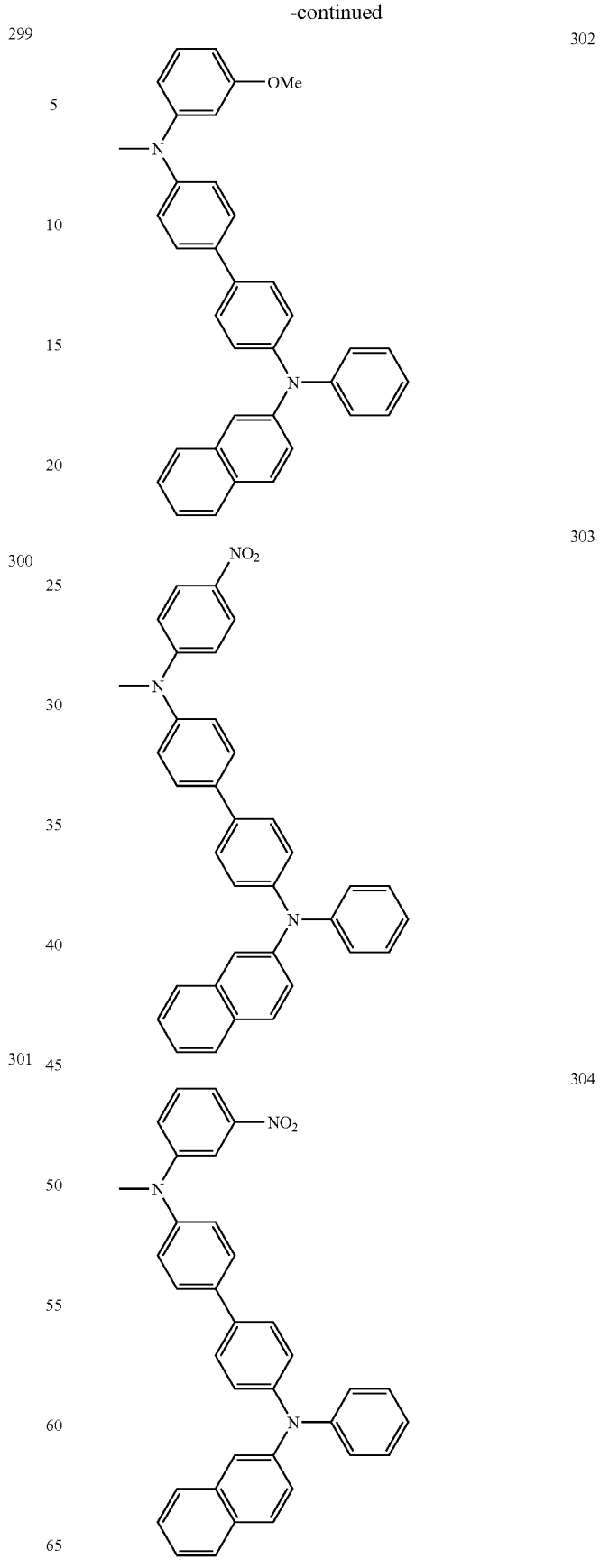

115
-continued
305
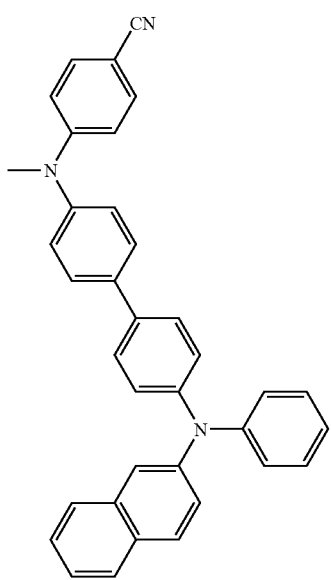
306
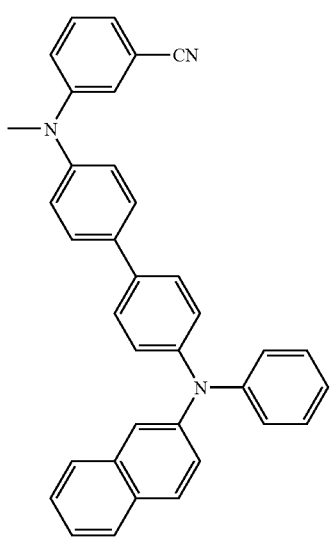
116
-continued
307
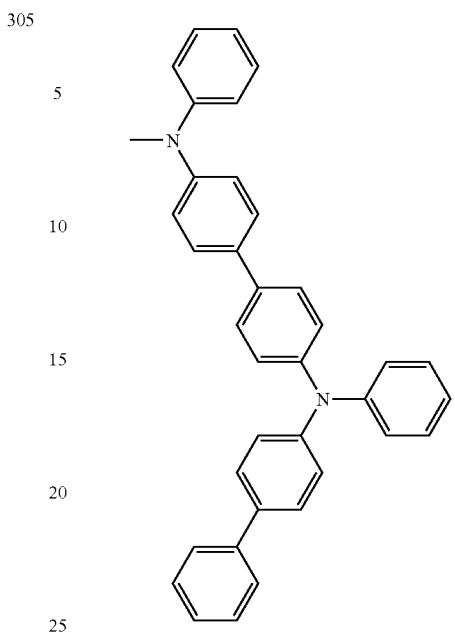
308
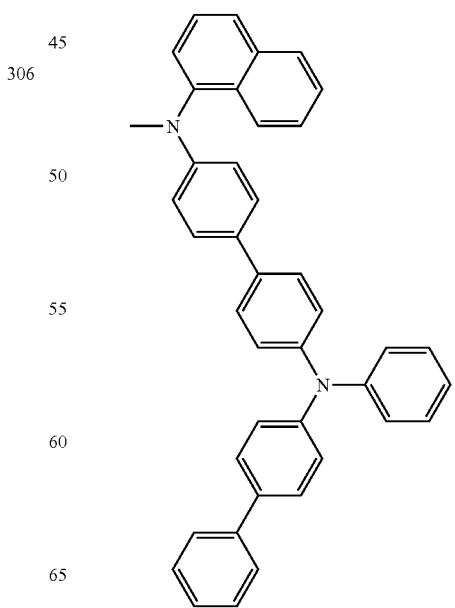

117
-continued
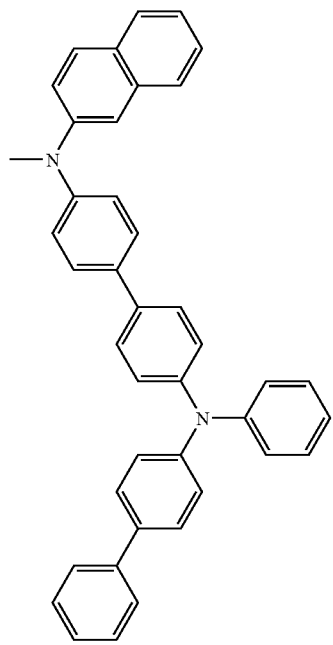
309
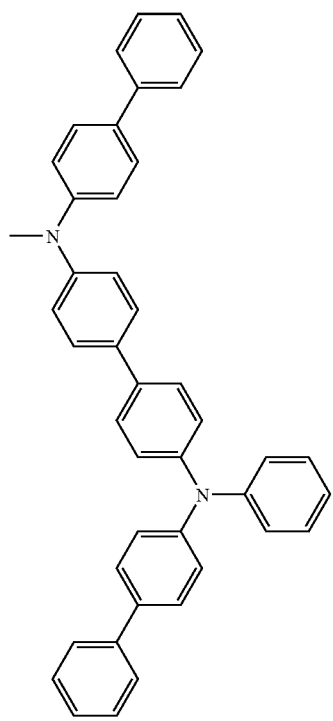
310
118
-continued
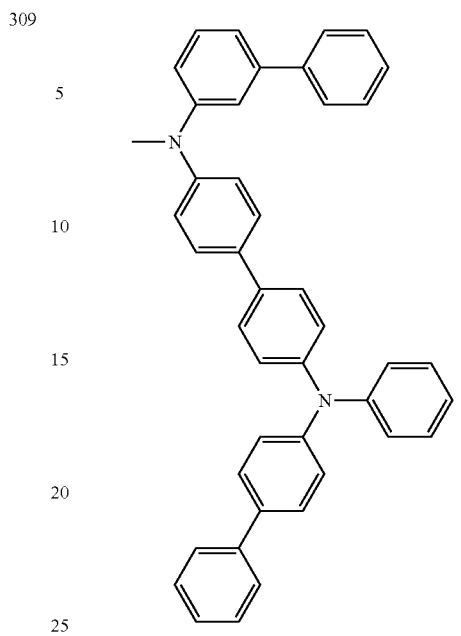
311
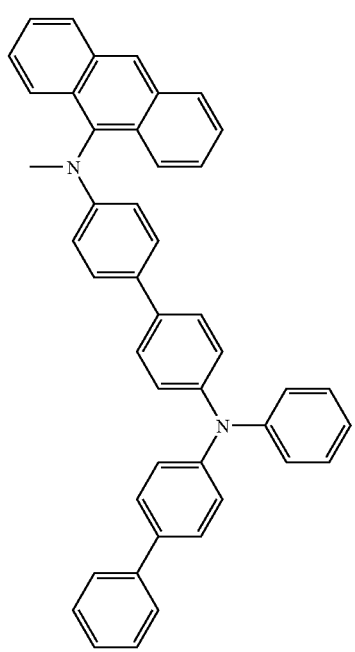
312

119
-continued
313
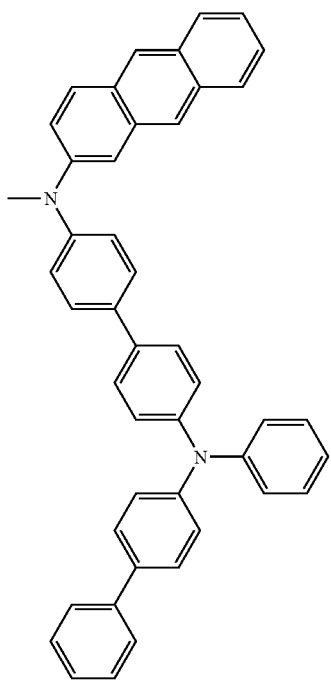
314
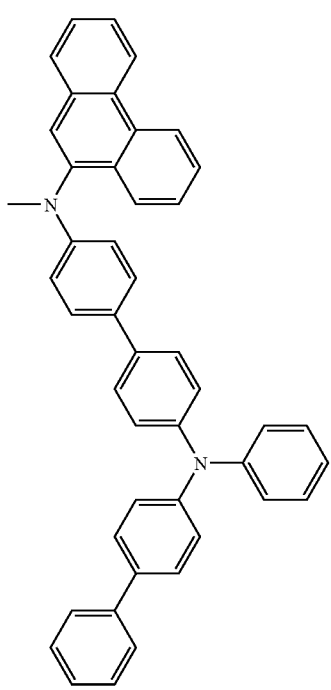
120
-continued
315
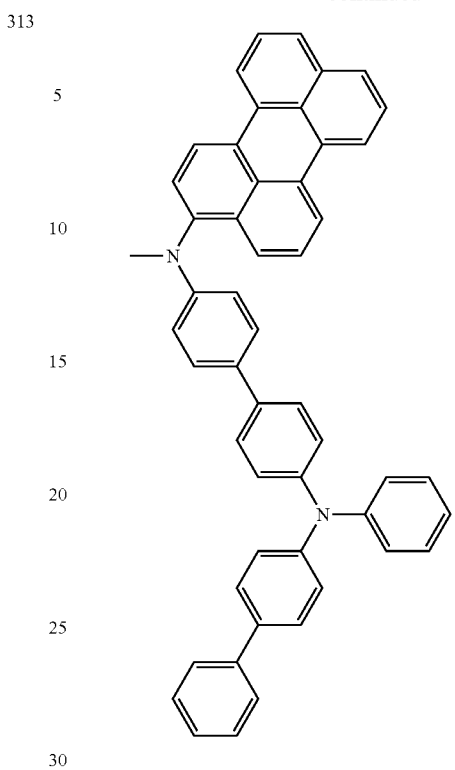
316
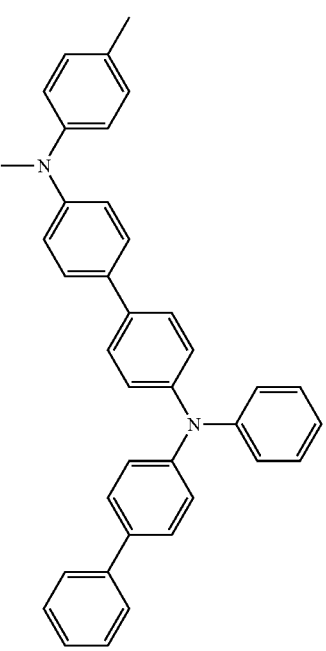

121
-continued
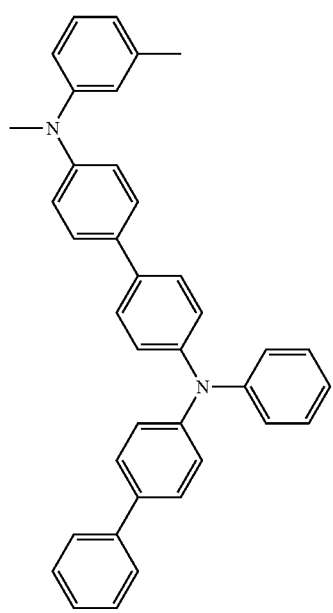
317
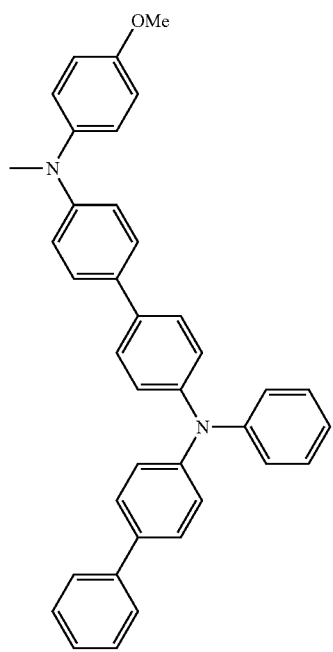
318
122
-continued
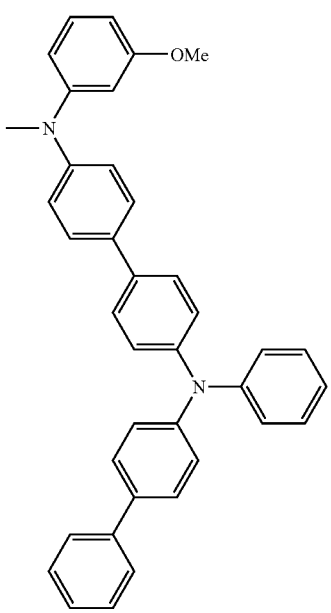
319
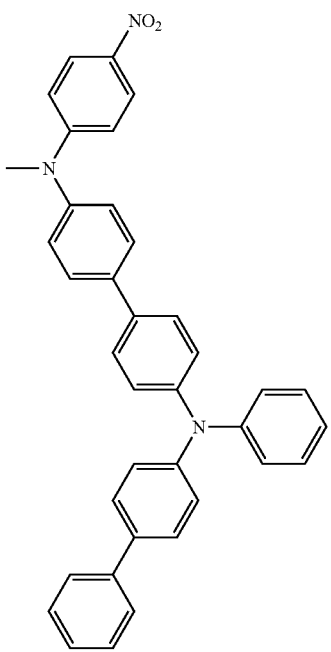
320

123
-continued
124
-continued
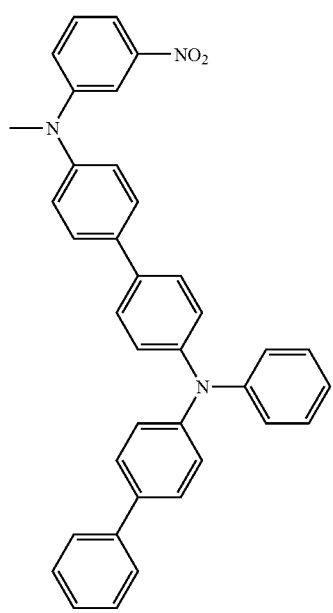
321
322
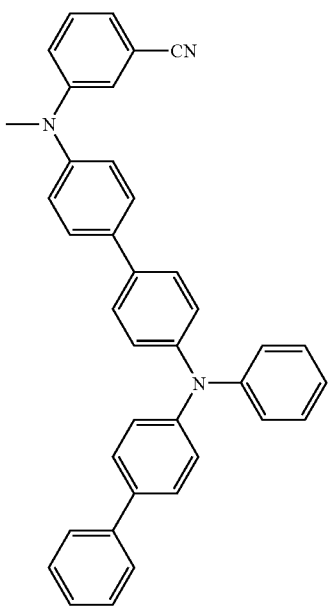
323
324

125
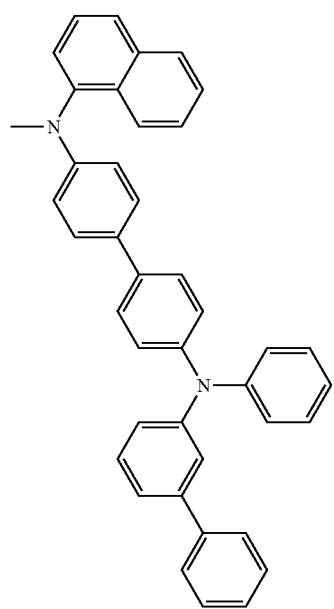
325
126
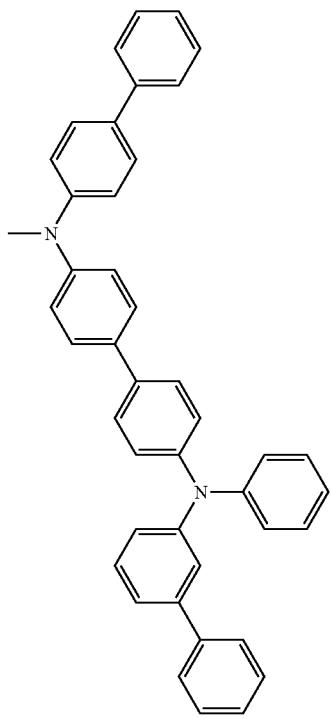
327
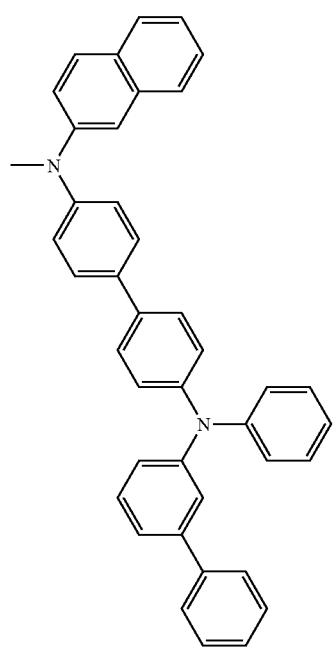
326
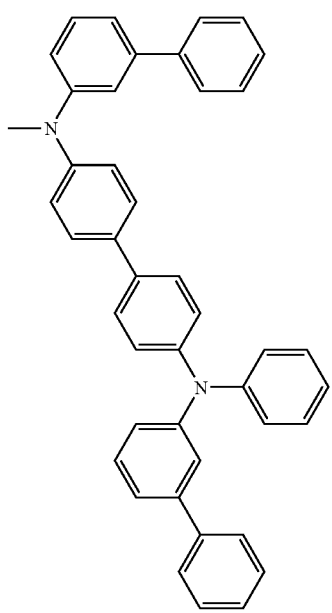
328

127
-continued
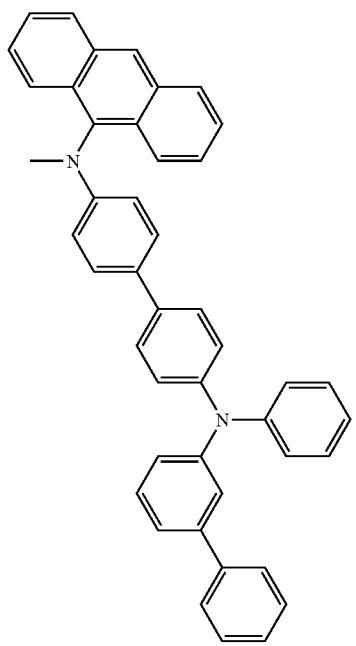
329
128
-continued
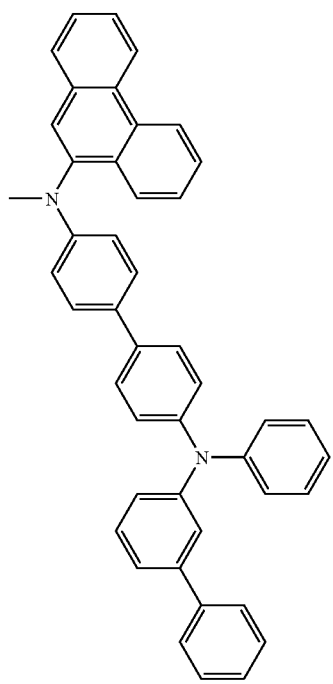
331
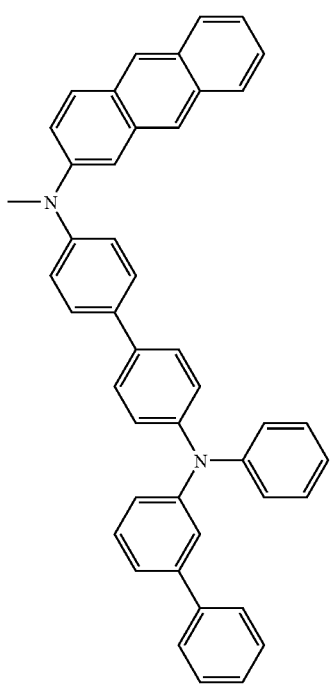
330
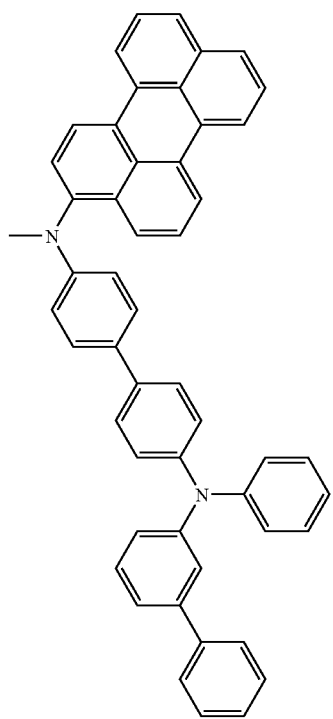
332

129
-continued
333
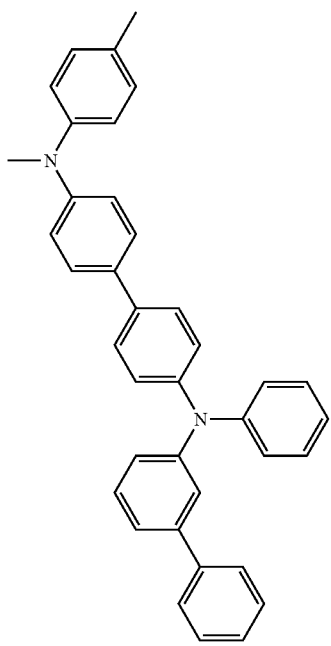
334
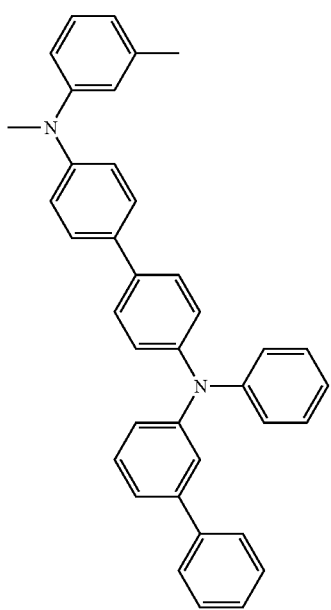
130
-continued
335
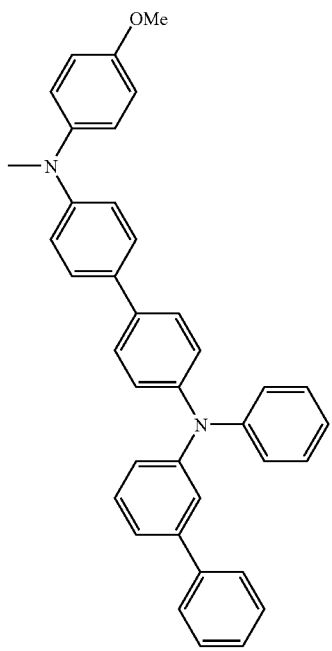
336
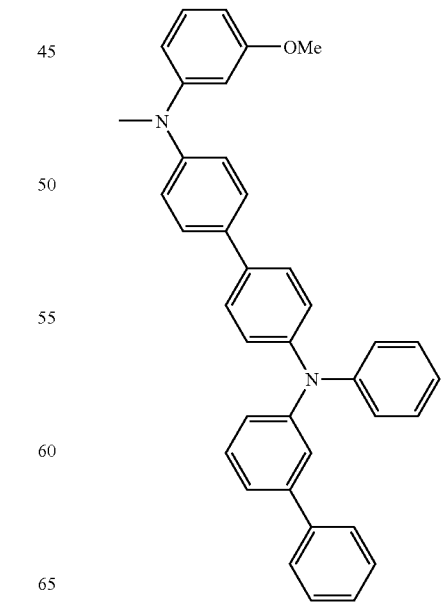

131
-continued
337
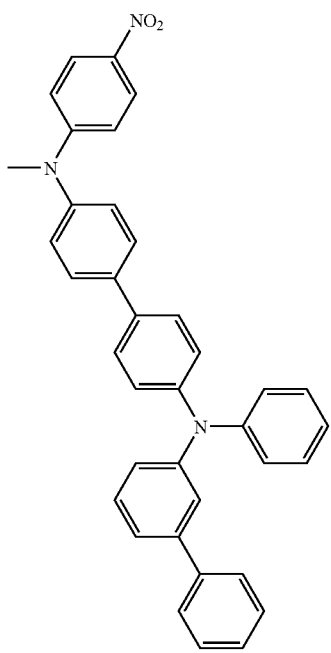
338
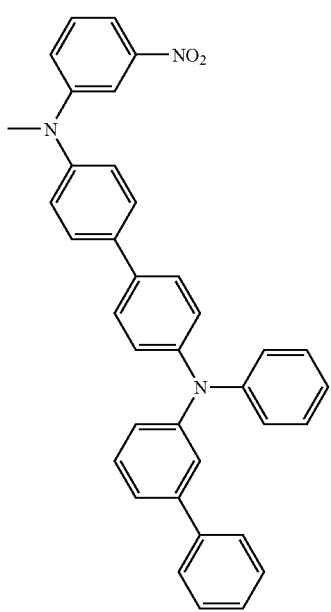
132
-continued
339
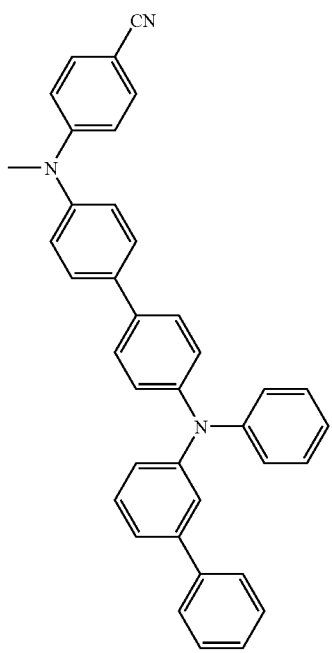
340
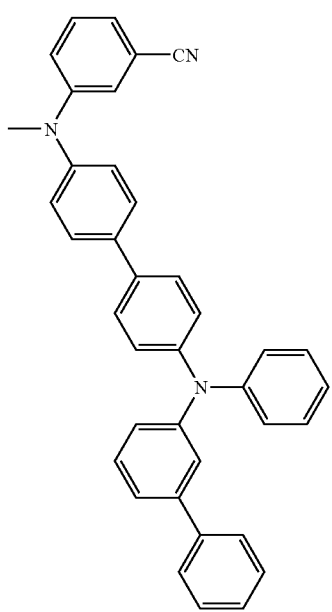

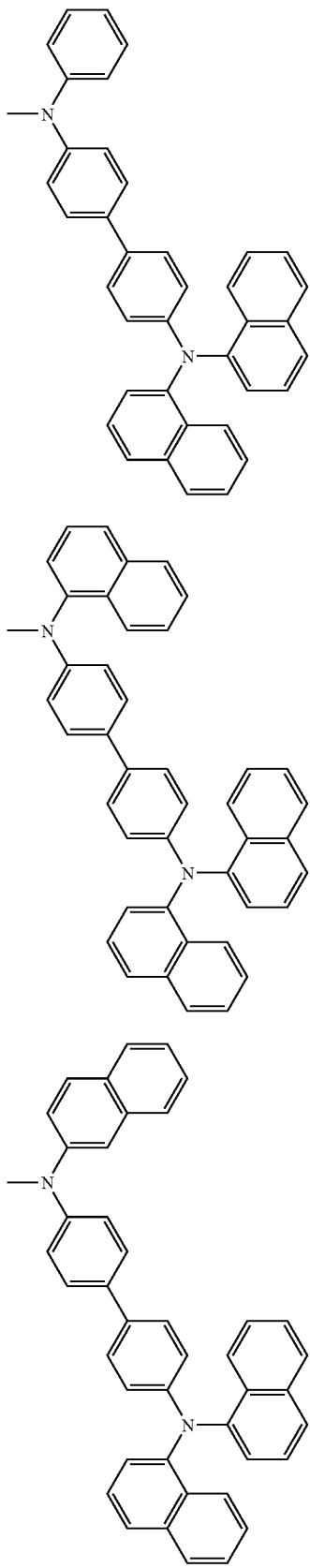
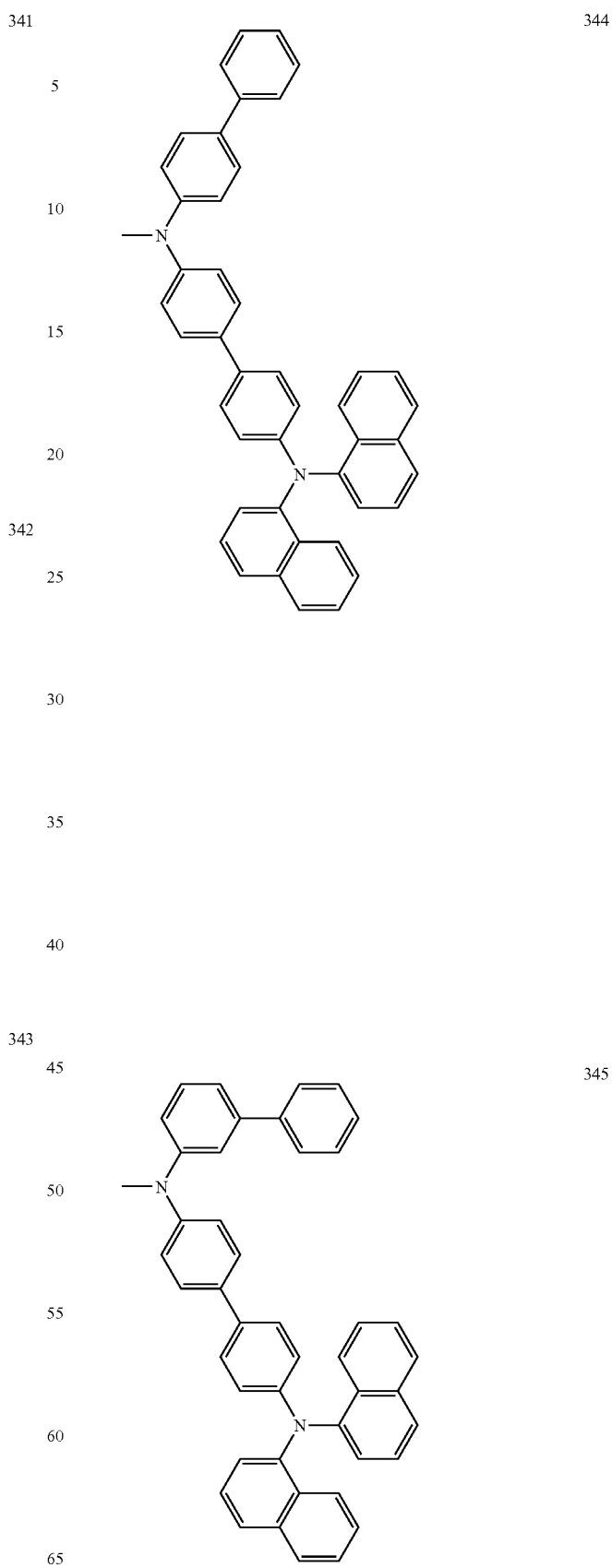

135
-continued
346
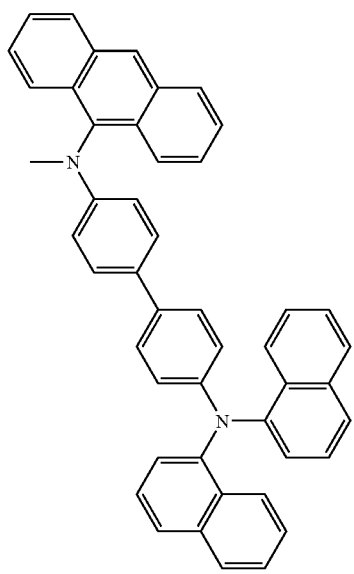
347
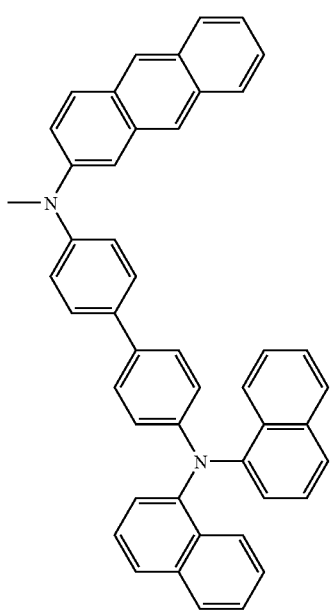
136
-continued
348
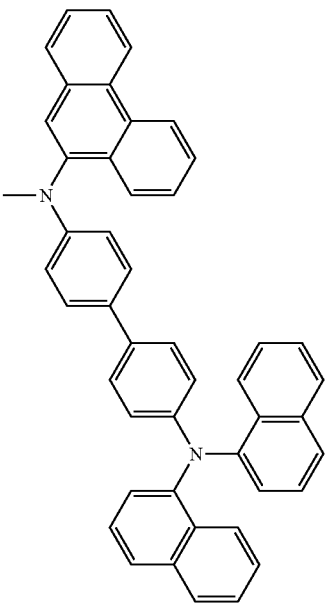
349
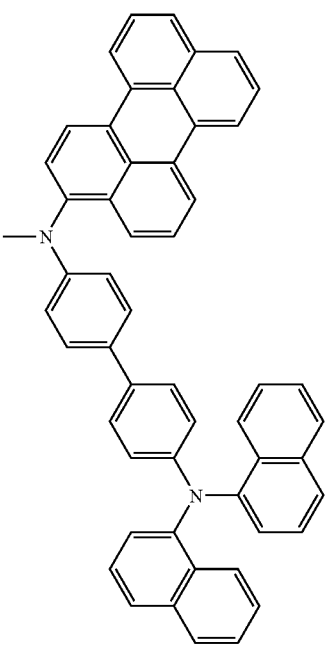

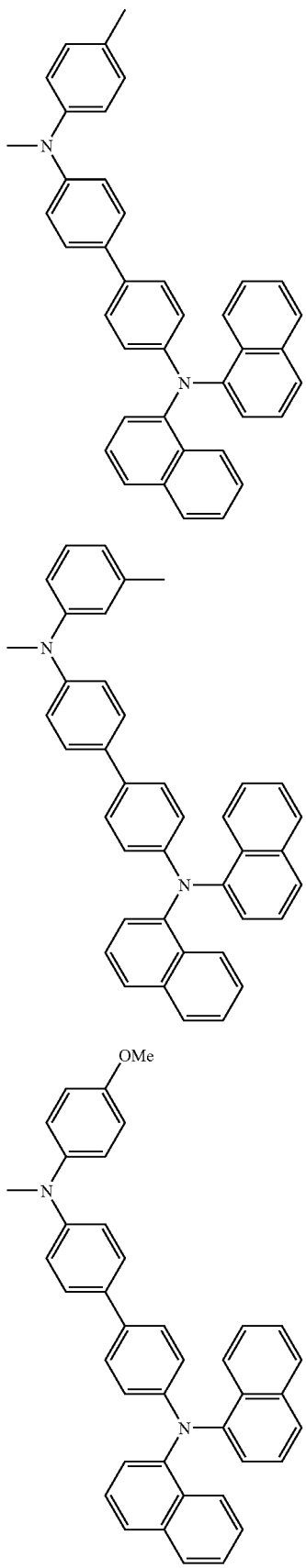
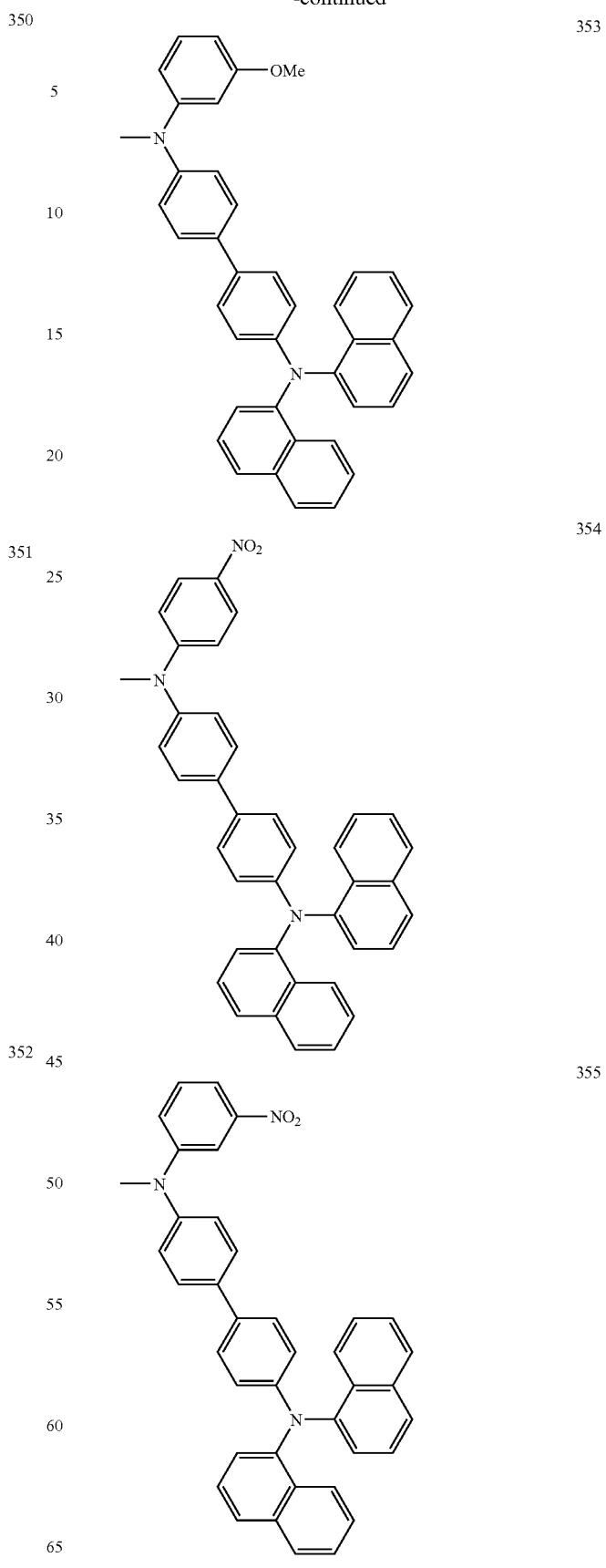

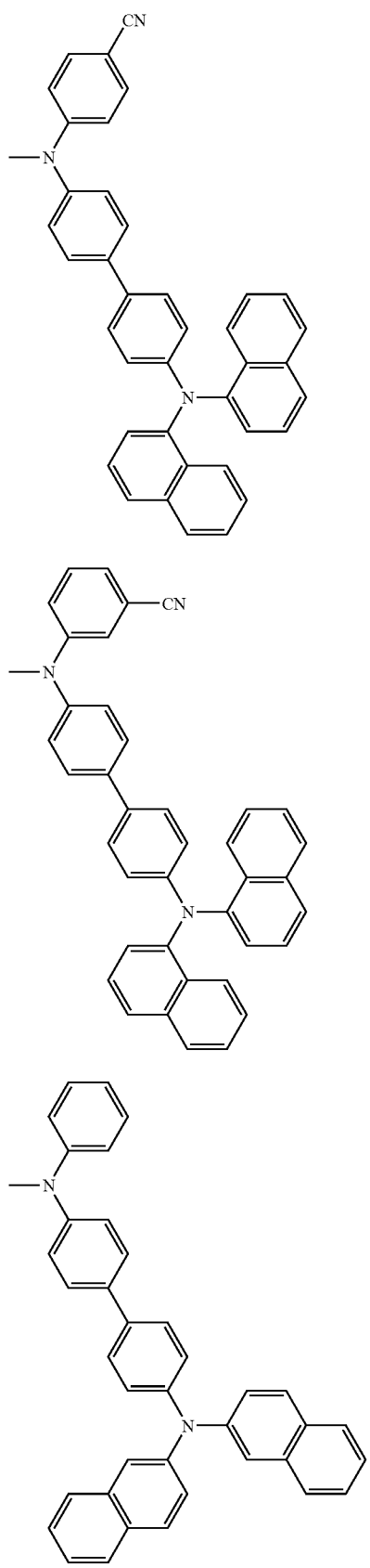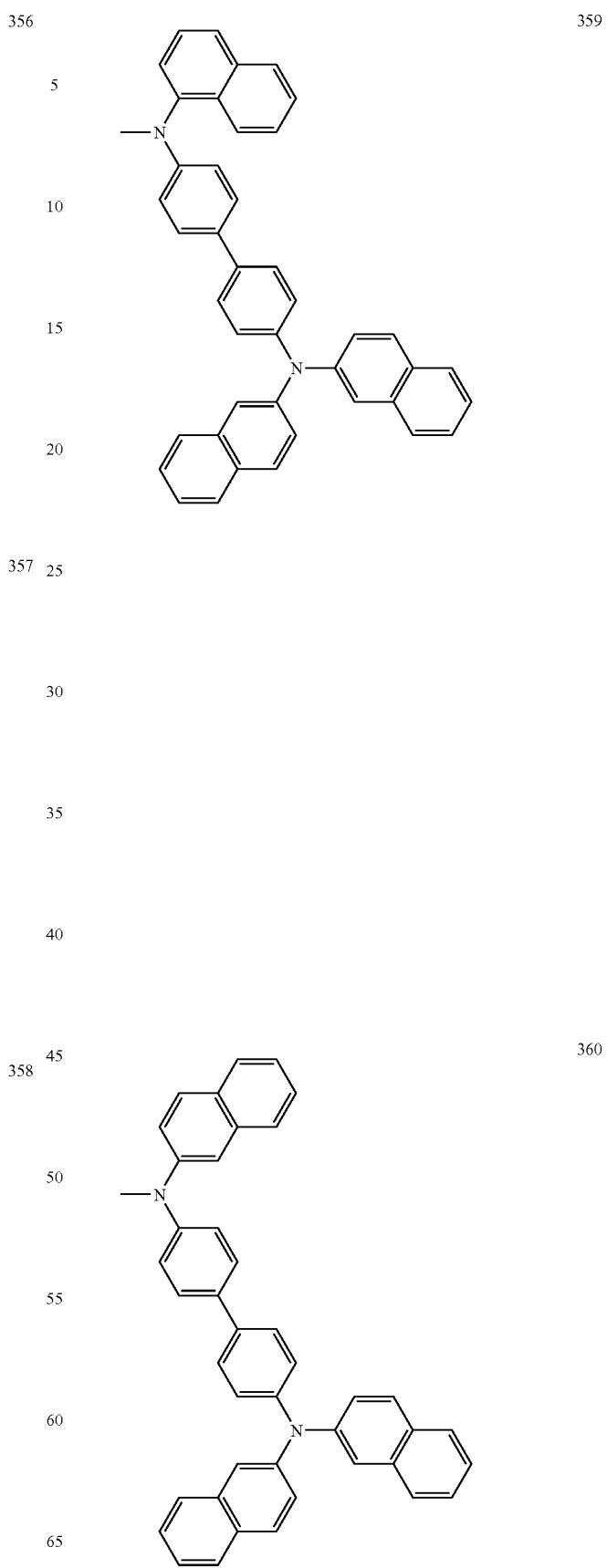

361
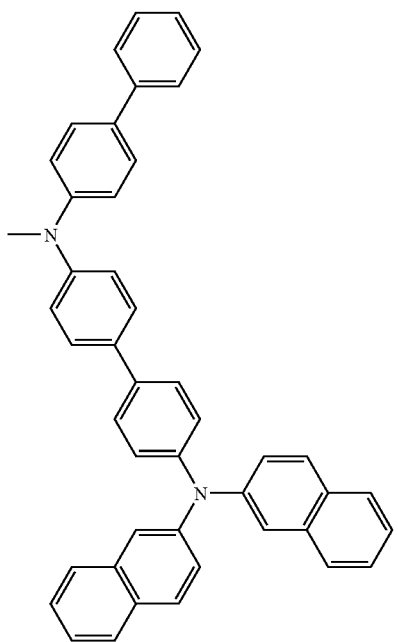
362
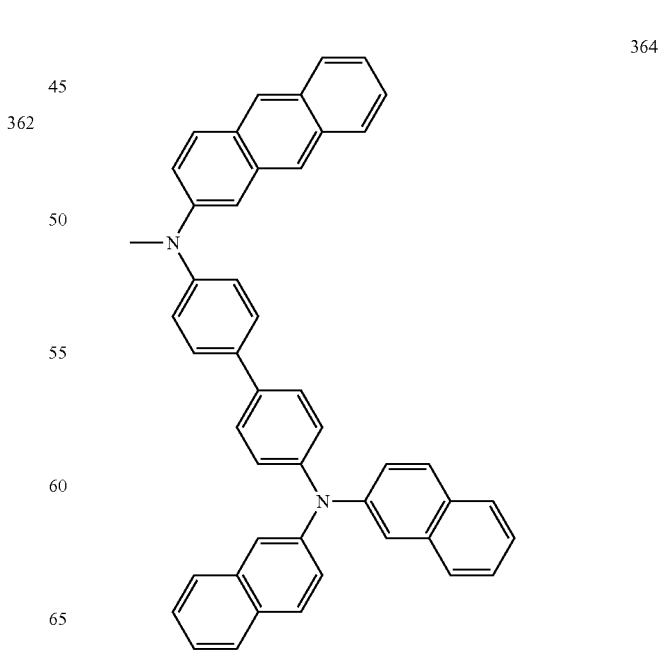
363
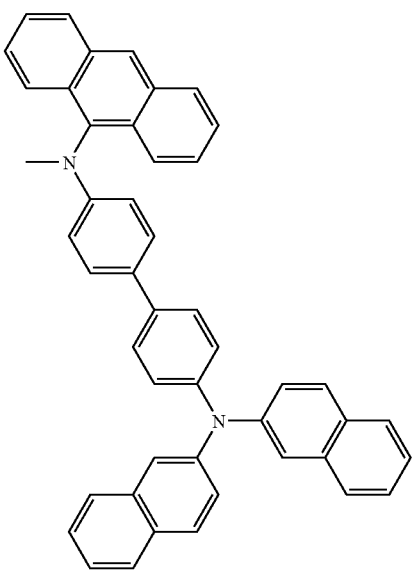
364

143
-continued
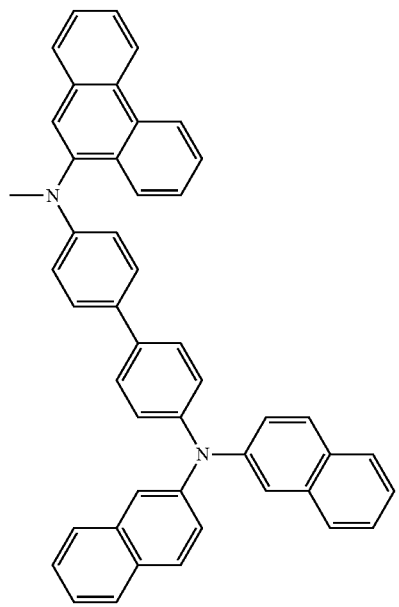
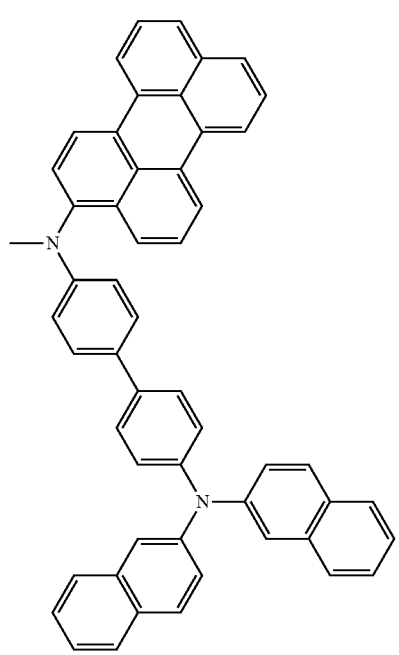
144
-continued
365
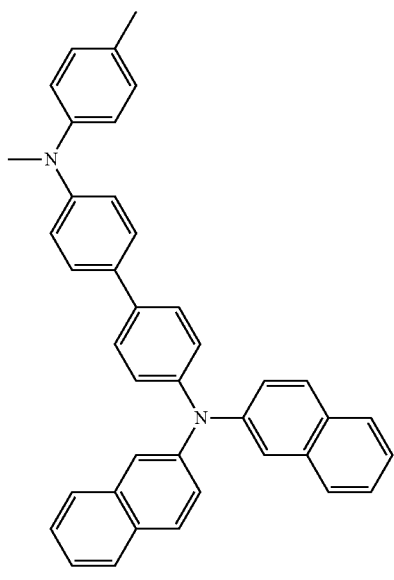
366
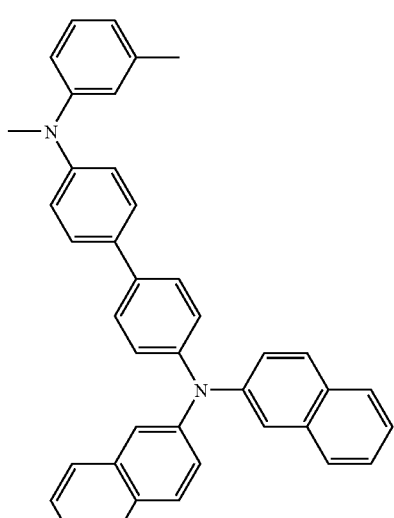
367
368
369
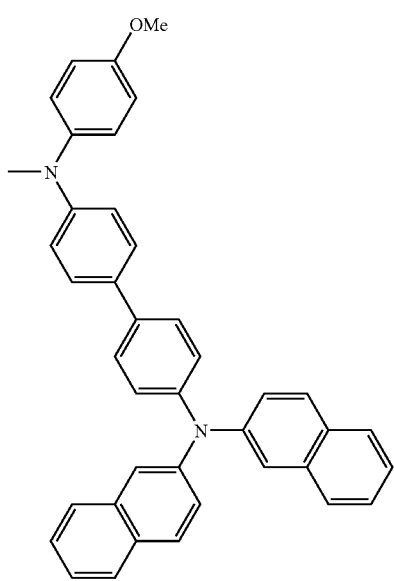

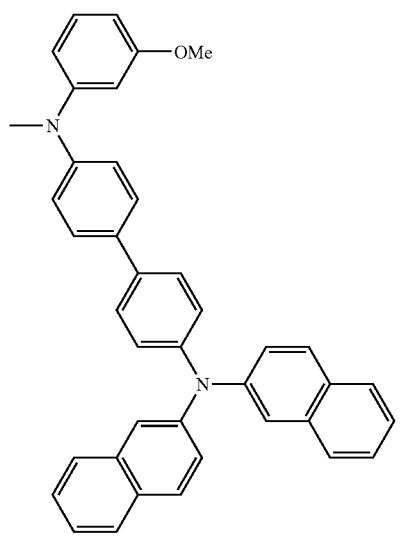
370
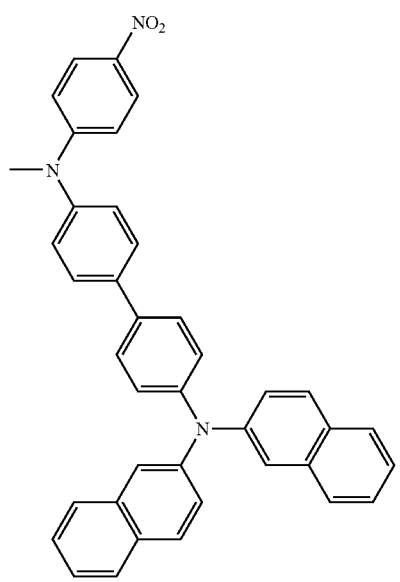
371
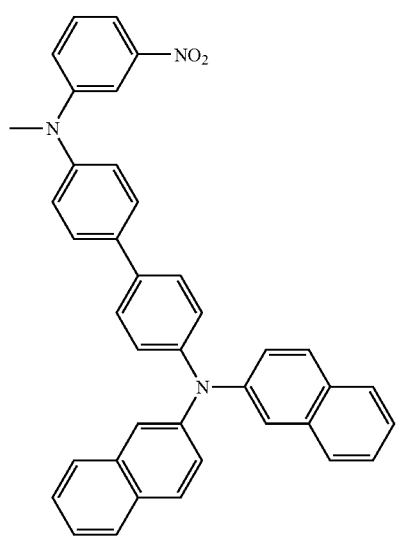
372
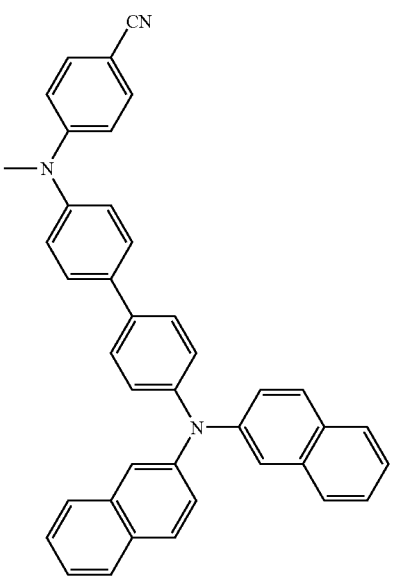
373
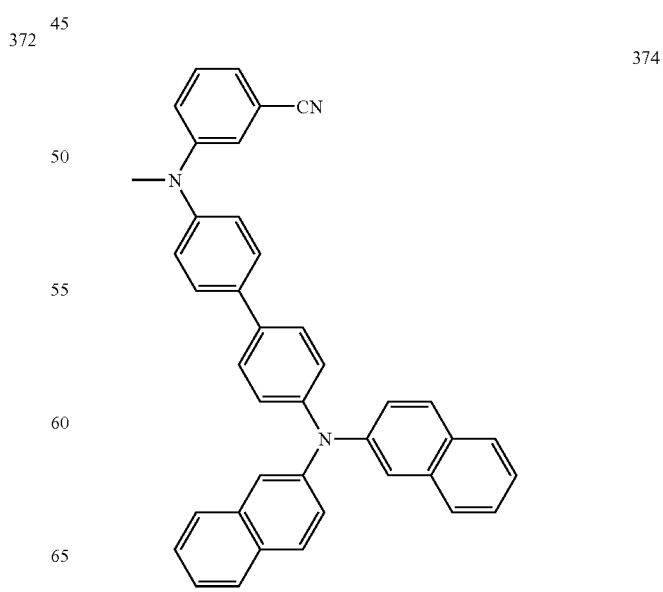
374

375
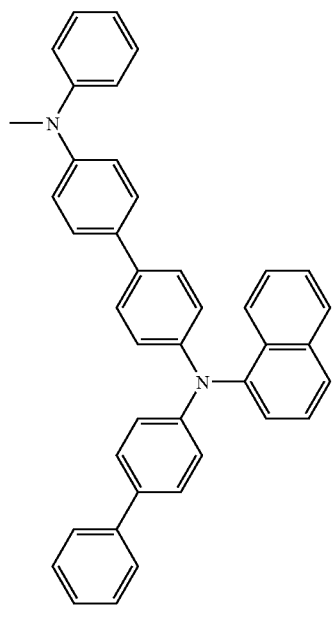
376
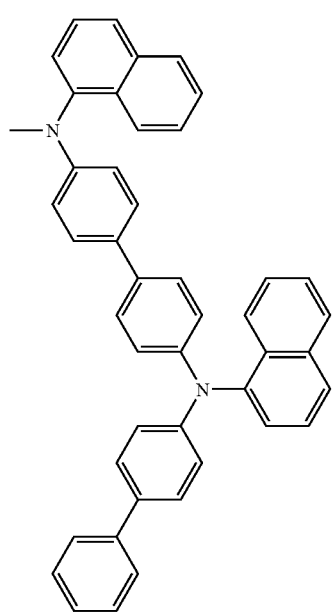
377
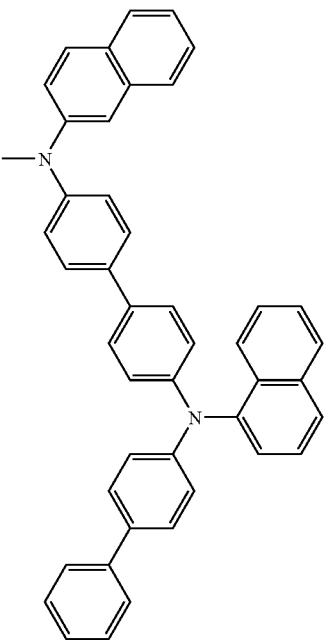
378
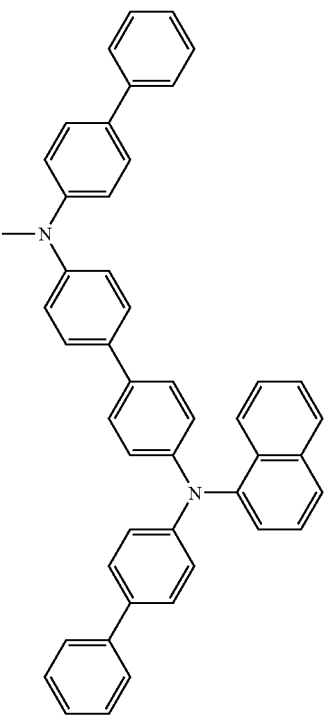

149
-continued
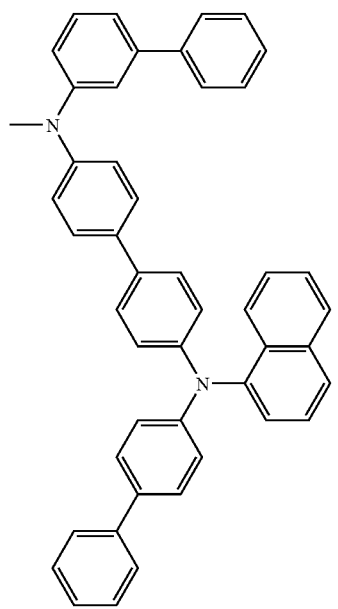
379
150
-continued
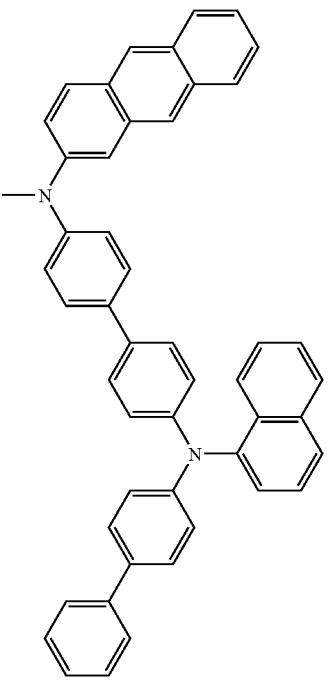
381
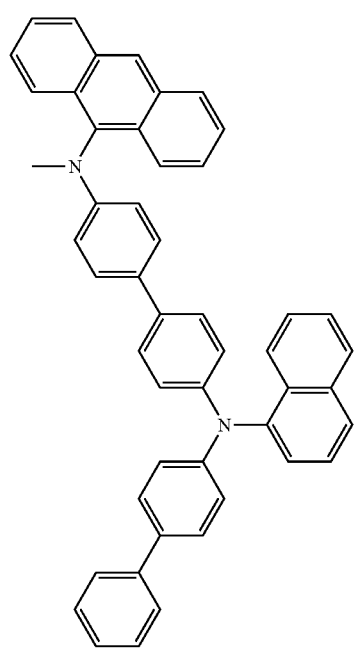
380
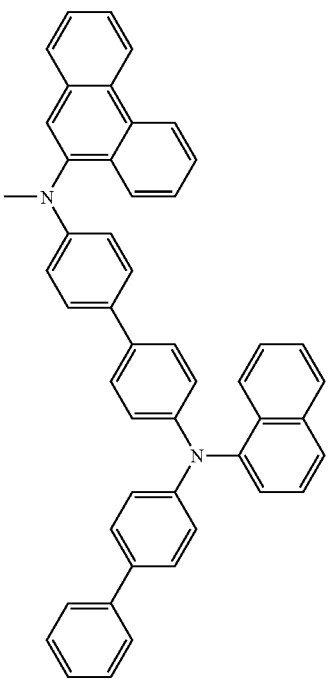
382

151
-continued
383
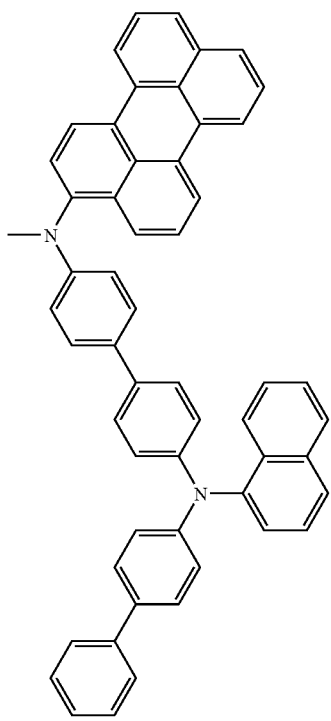
384
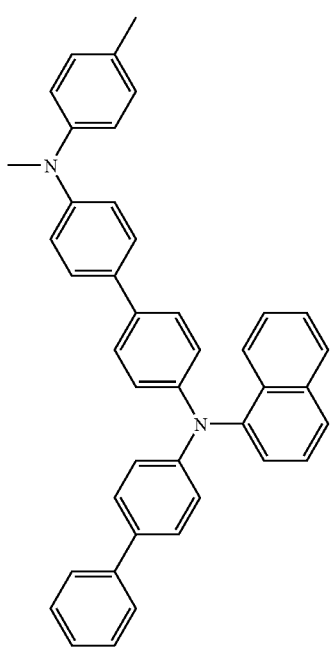
152
-continued
385
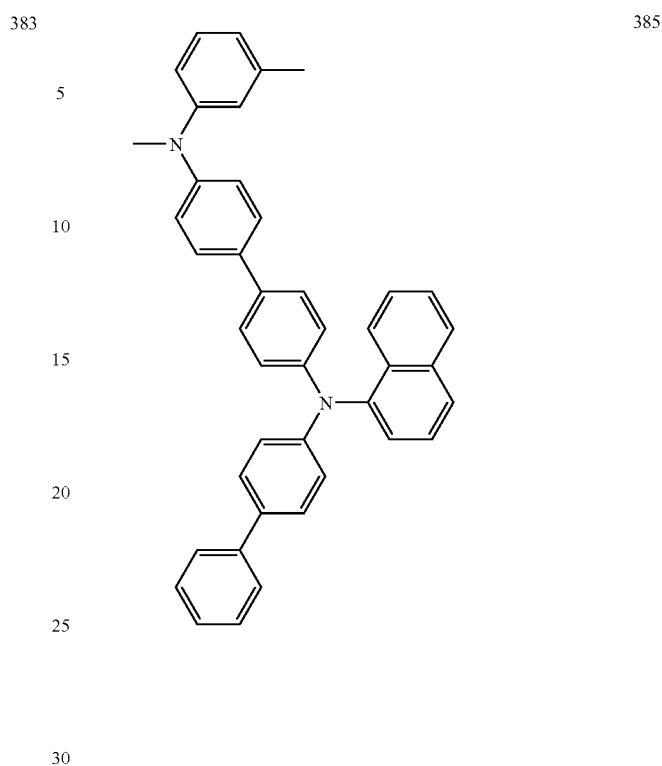
386
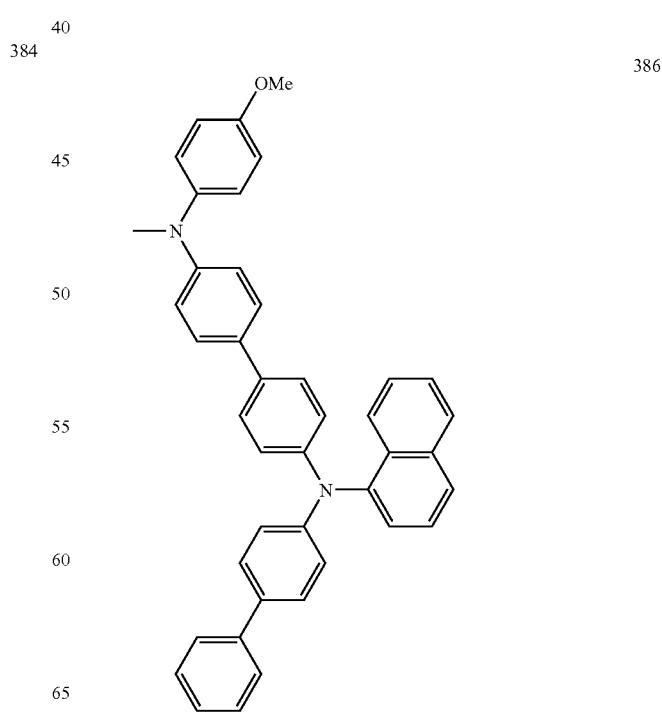

153
-continued
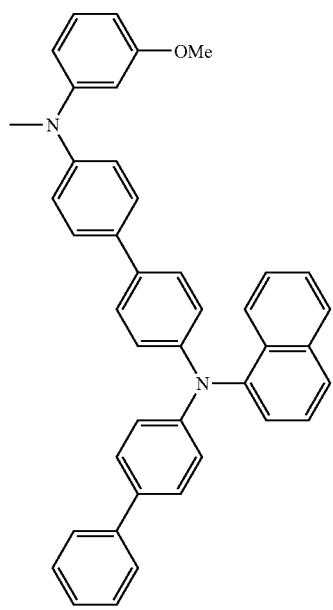
387
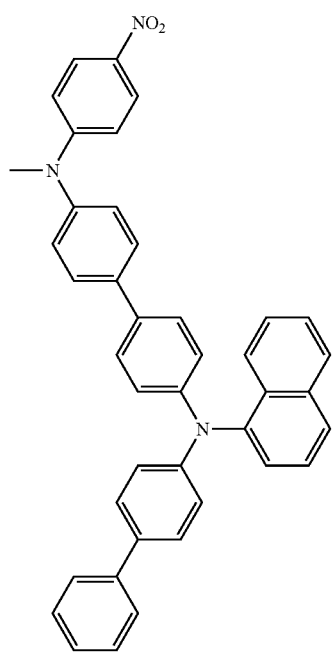
388
154
-continued
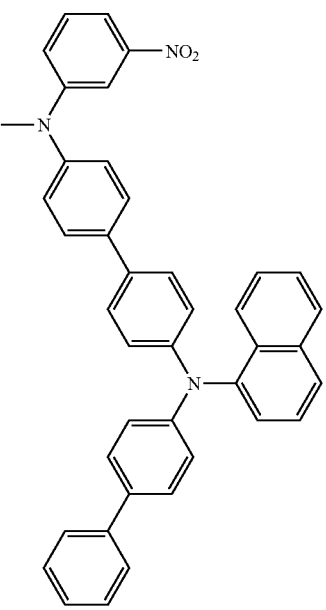
389
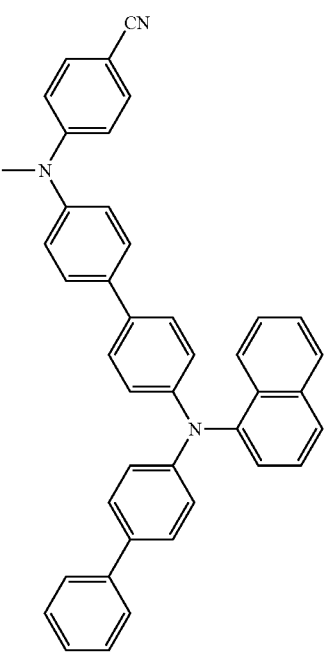
390

155
-continued
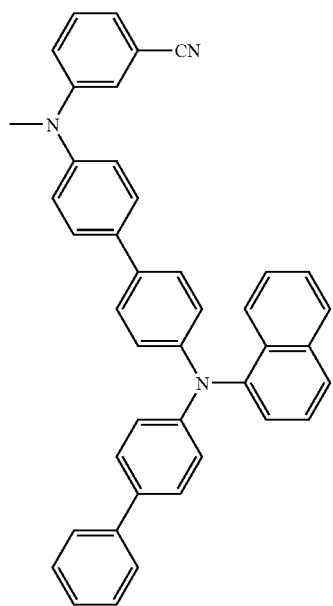
391
156
-continued
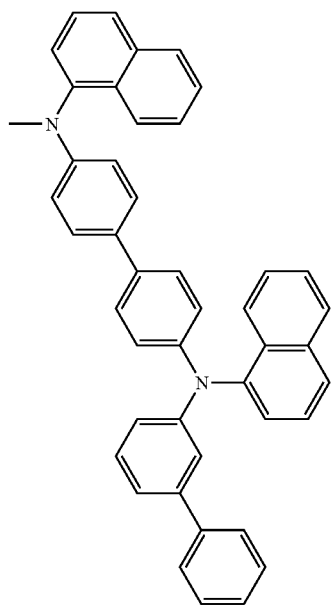
393
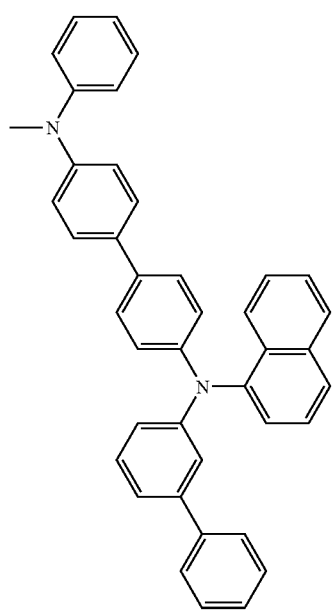
392
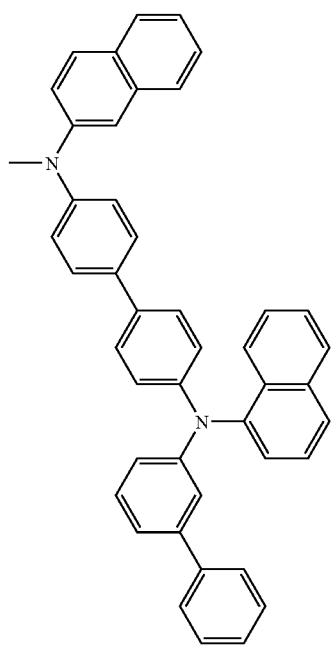
394

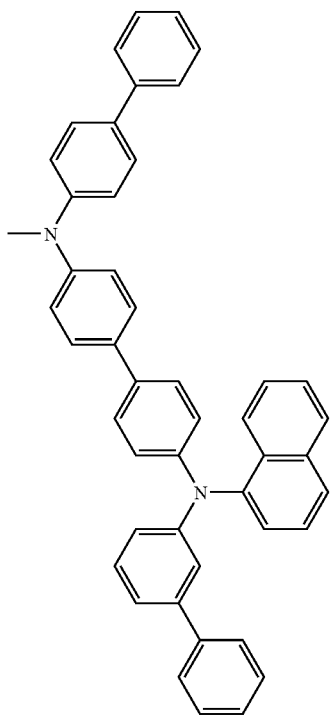
395
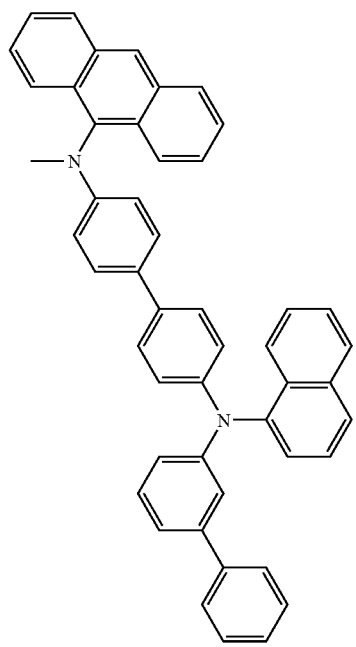
397
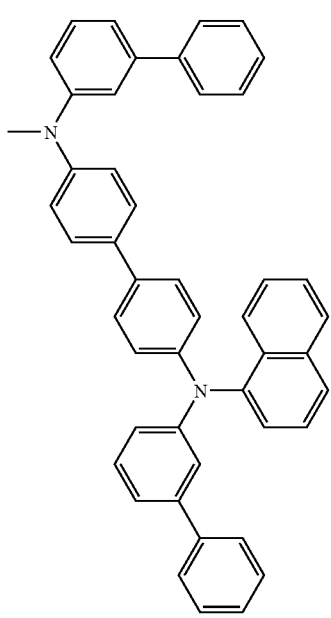
396

159
-continued
160
-continued
399
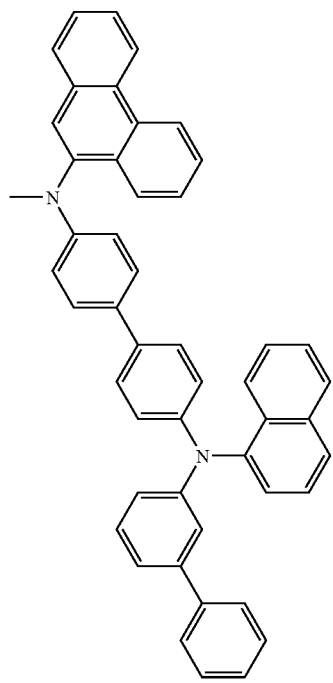
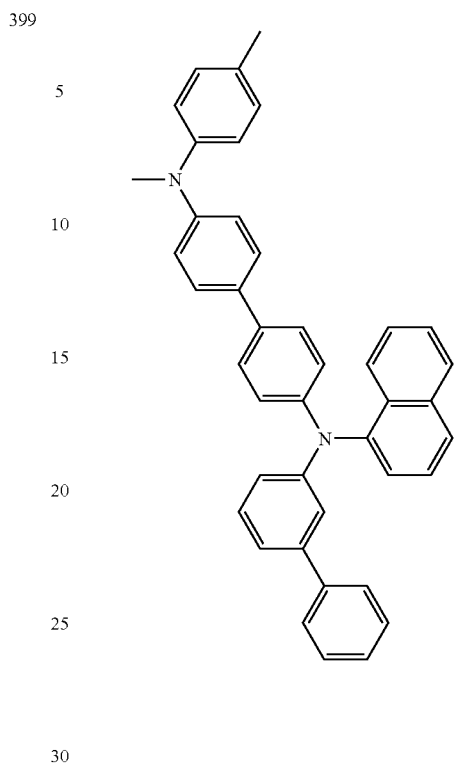
400
401
402
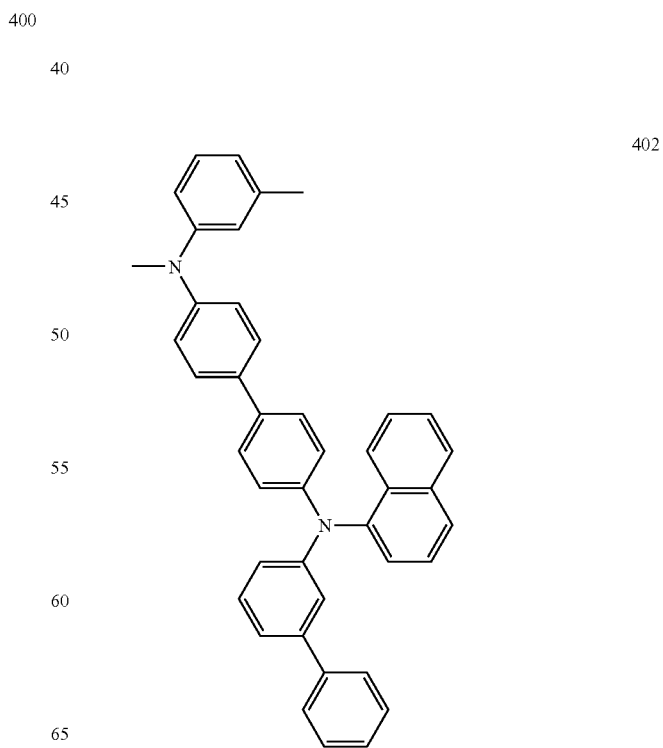

403
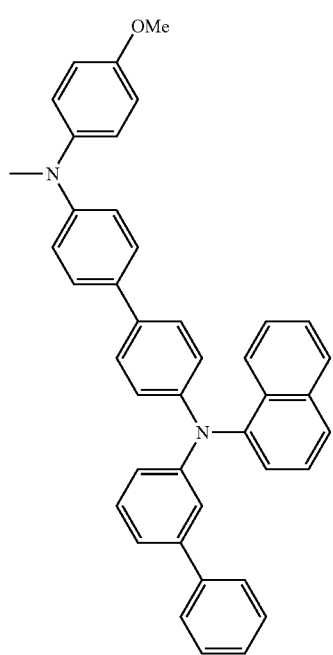
404
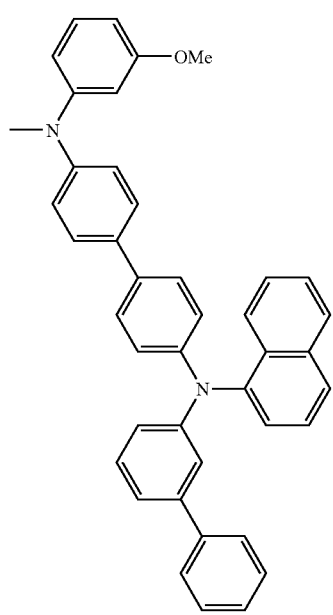
405
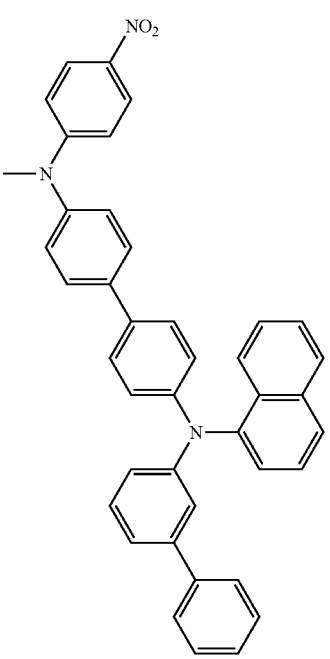
406
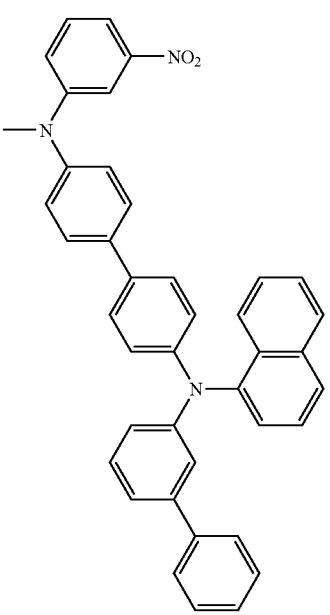

163
-continued
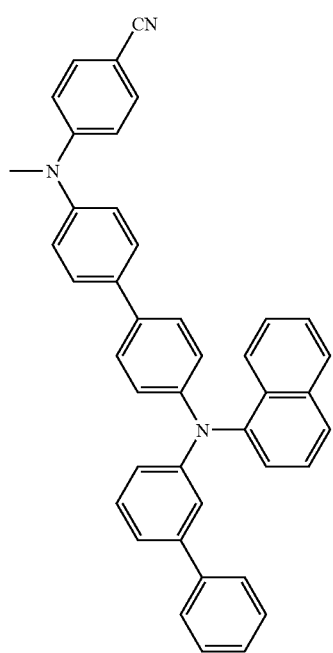
407
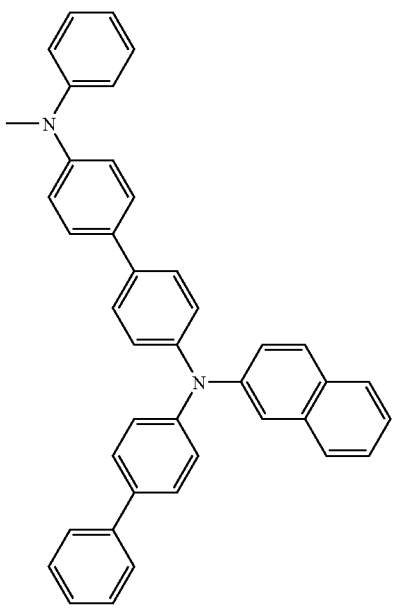
409
164
-continued
408
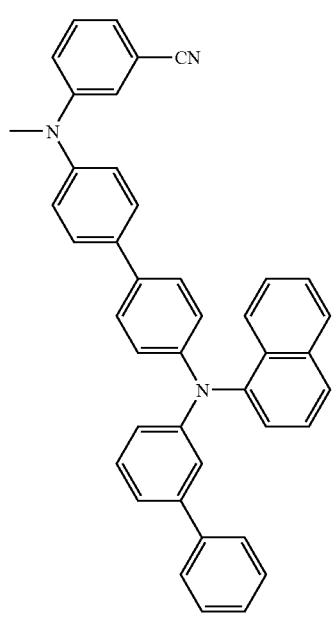
410
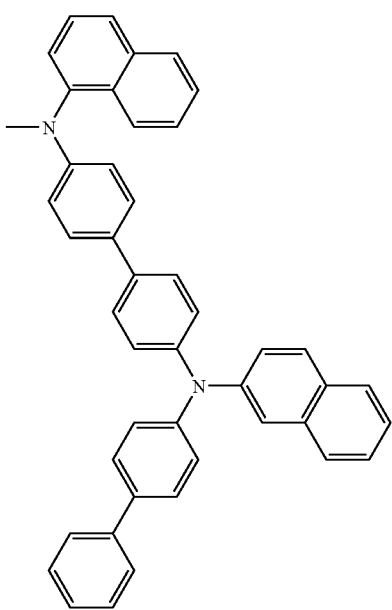

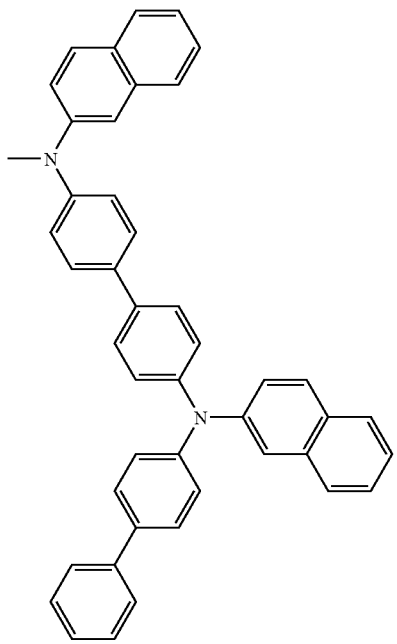
411
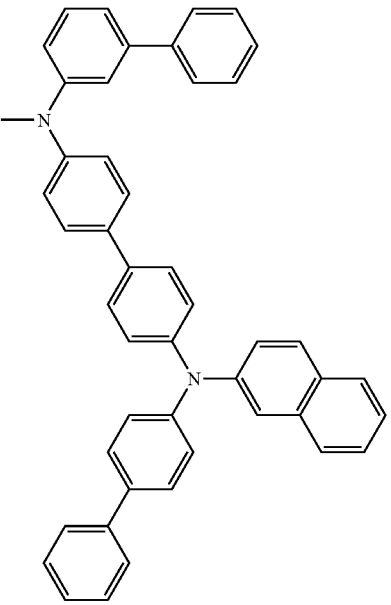
413
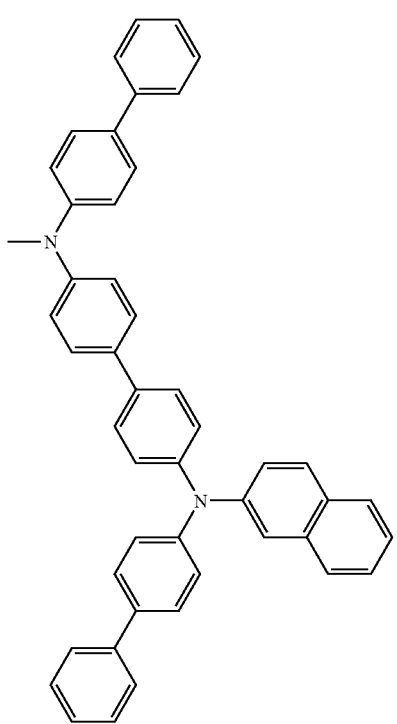
412
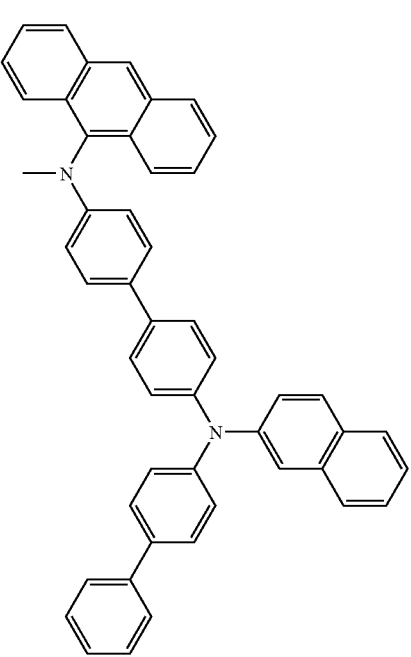
414

167
-continued
415
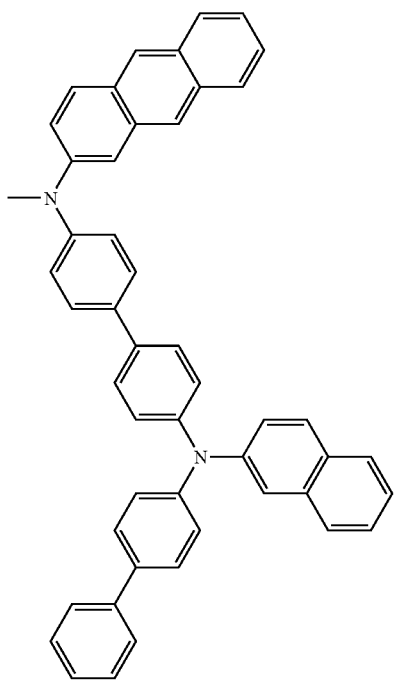
416
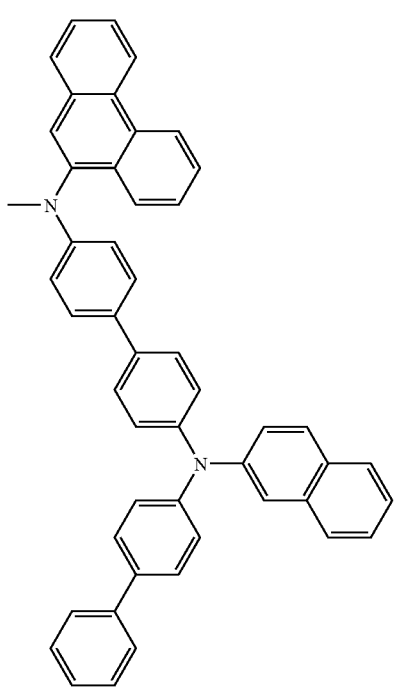
168
-continued
417
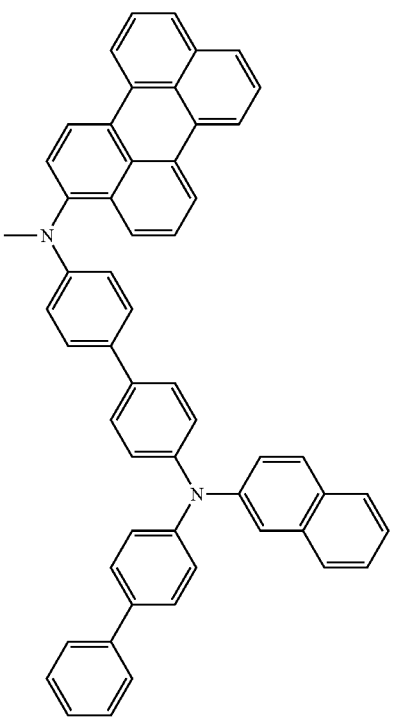
418
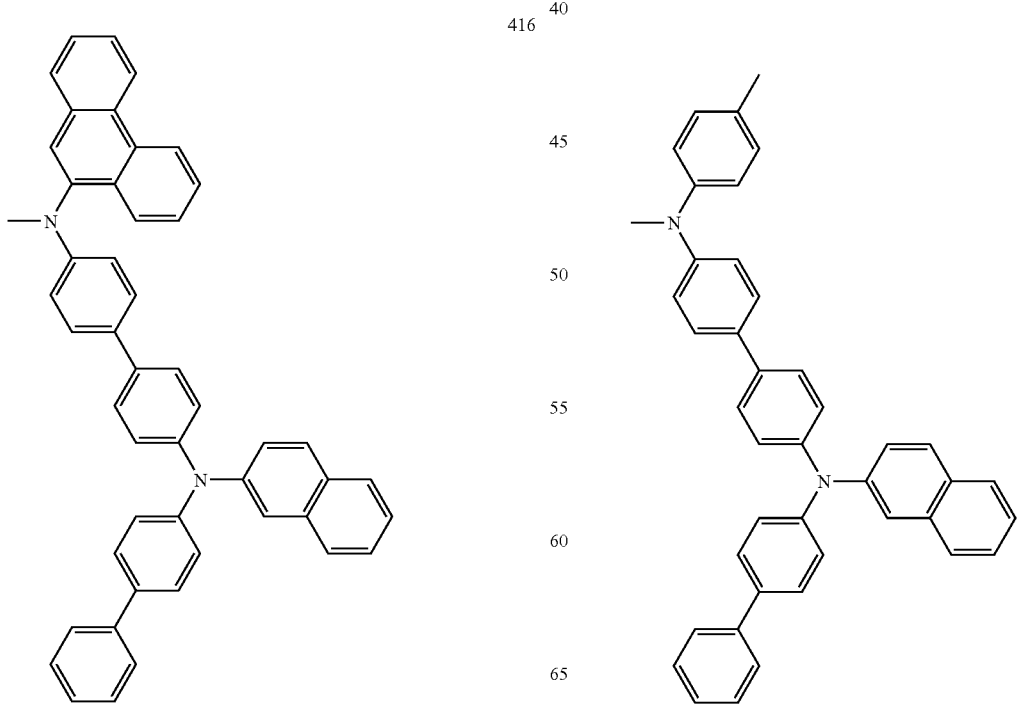

419
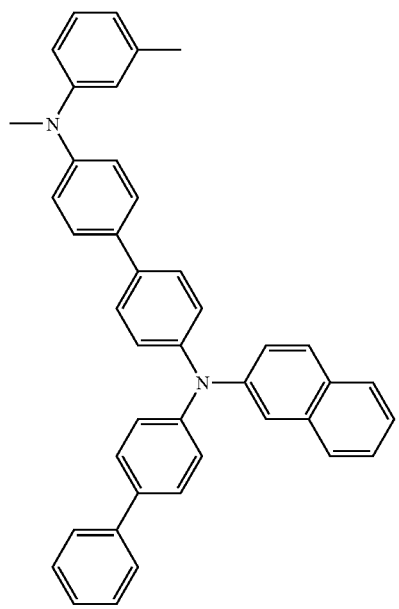
421
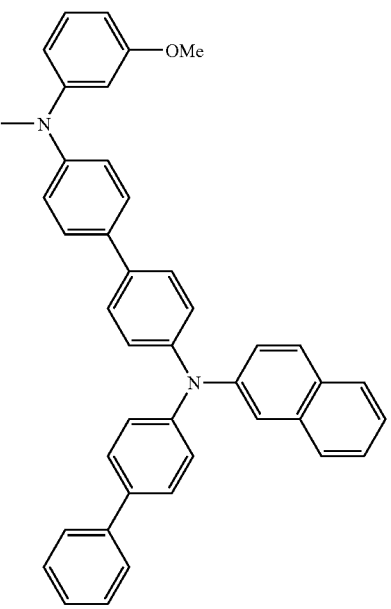
420
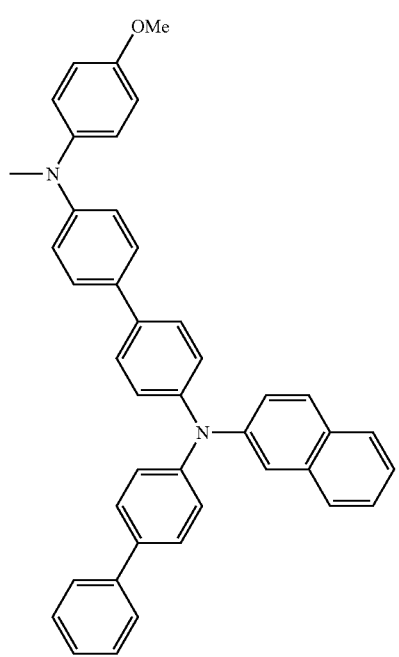
422
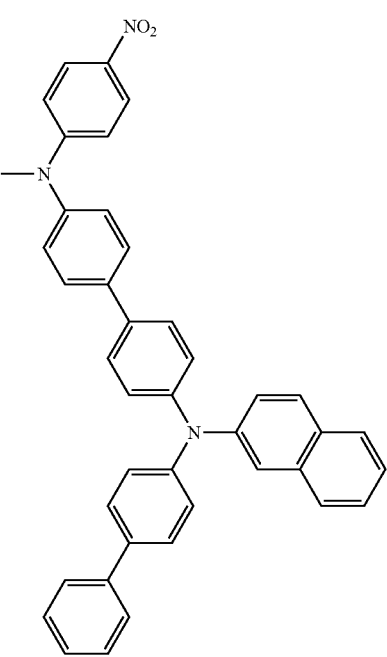

423
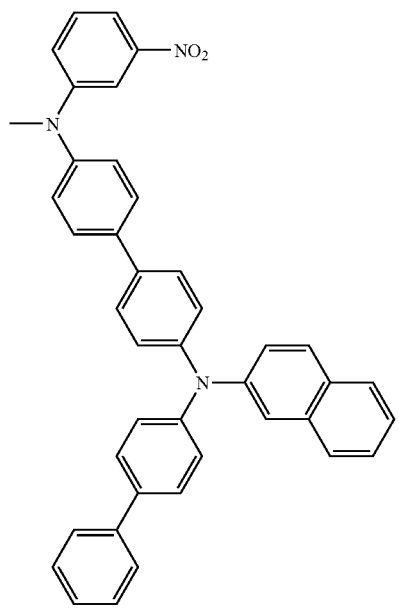
425
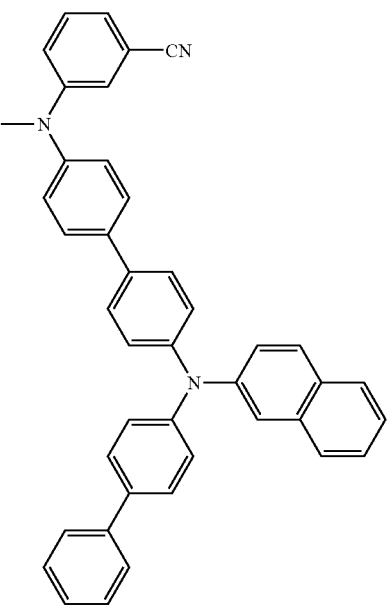
424
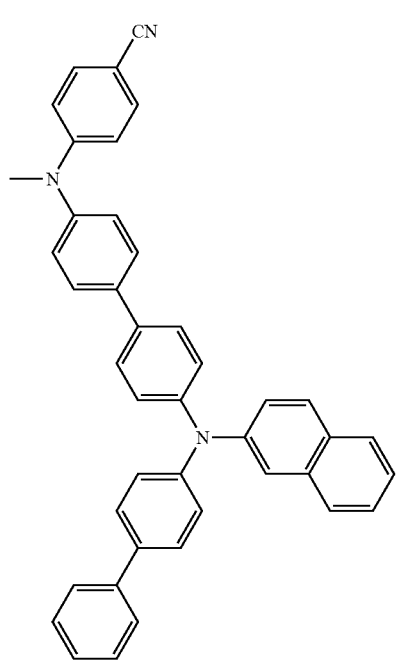
426
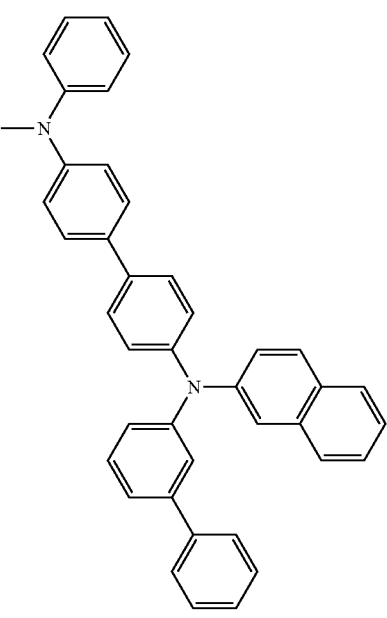

427
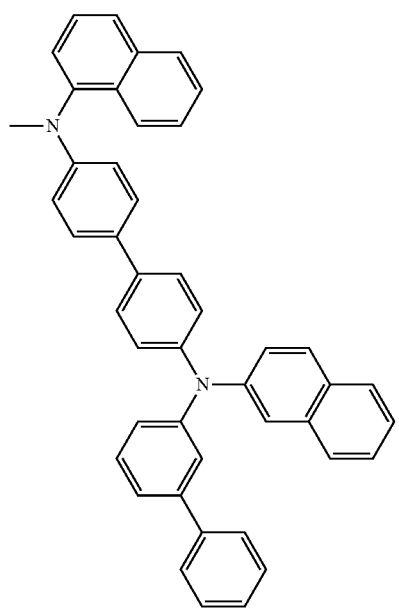
428
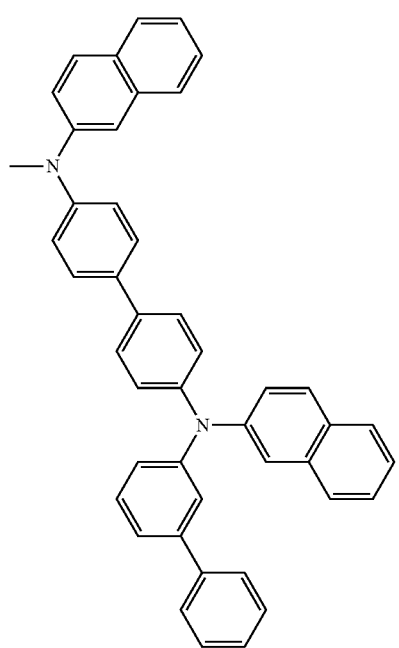
429
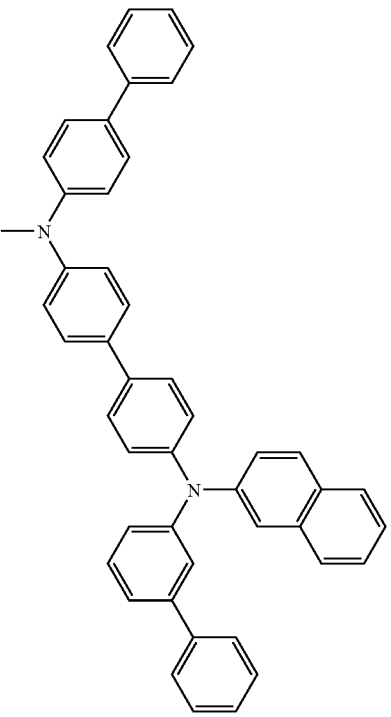
430
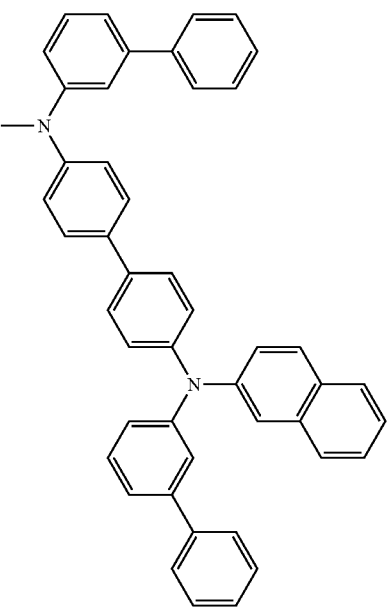

175
-continued
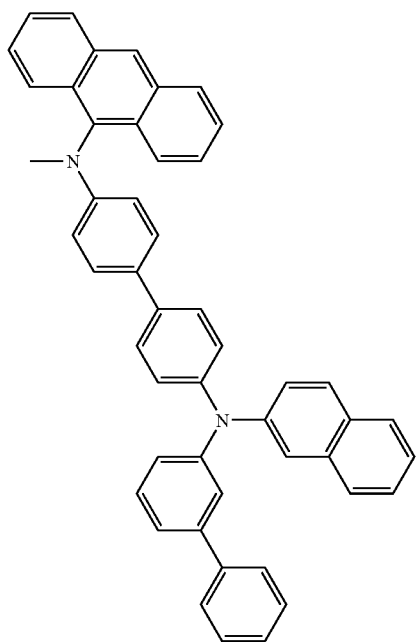
431
176
-continued
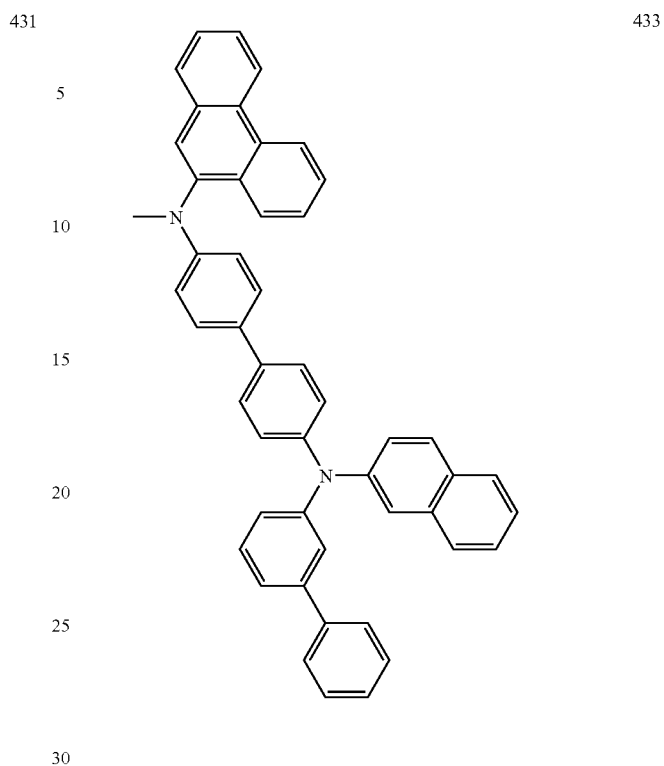
433
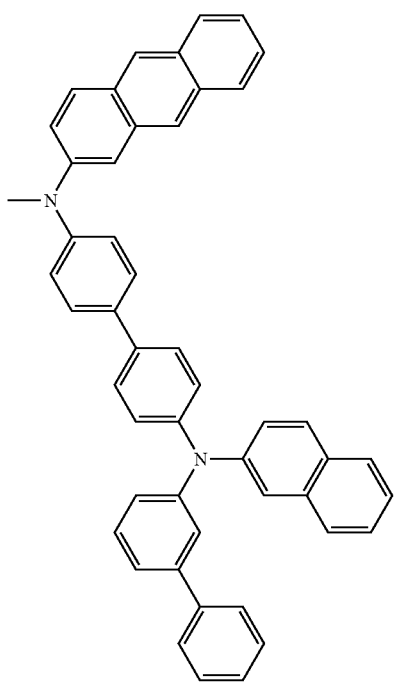
432
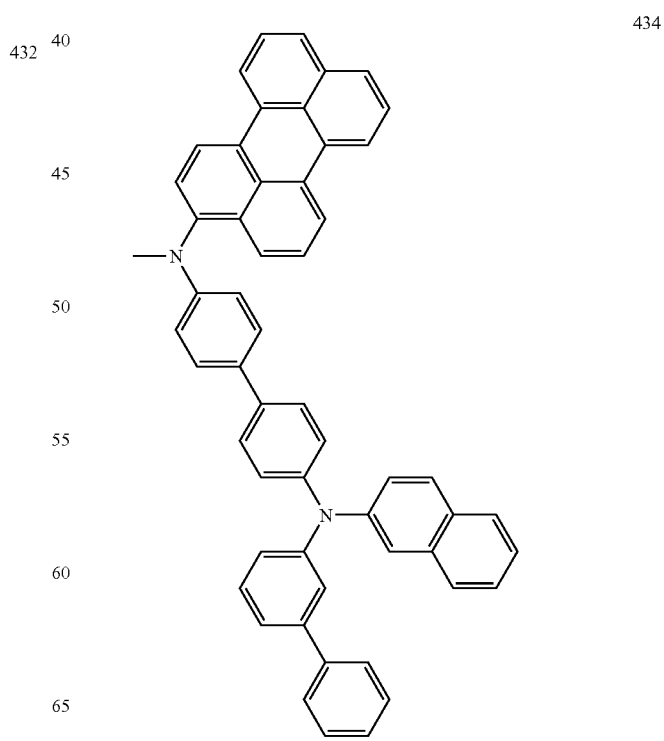
434

435
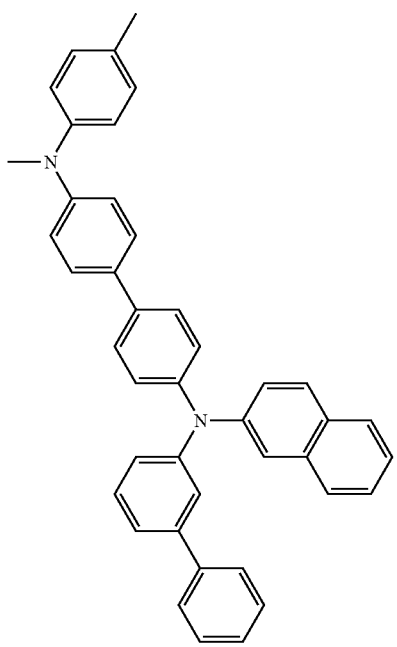
437
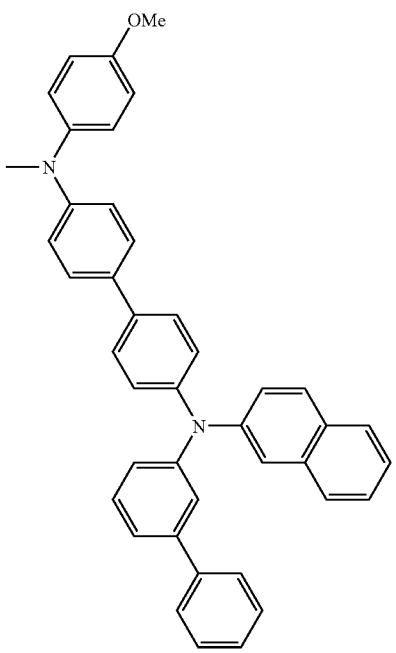
436
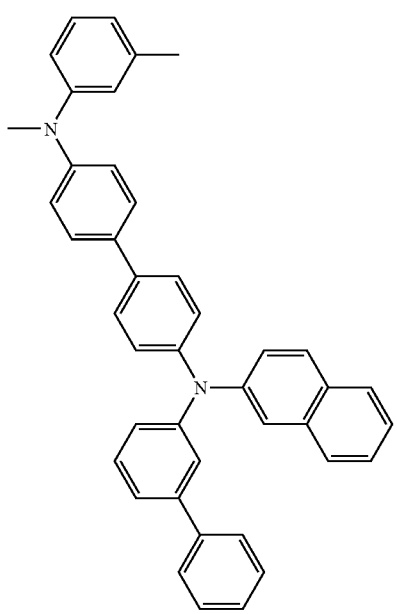
438
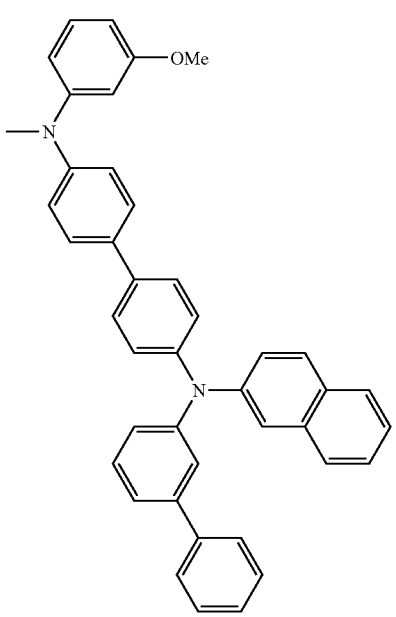

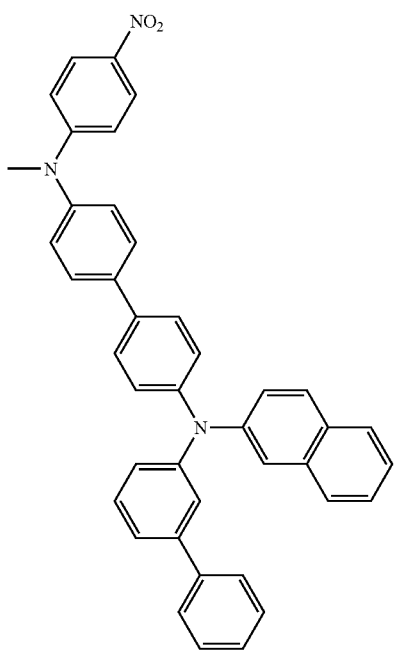
439
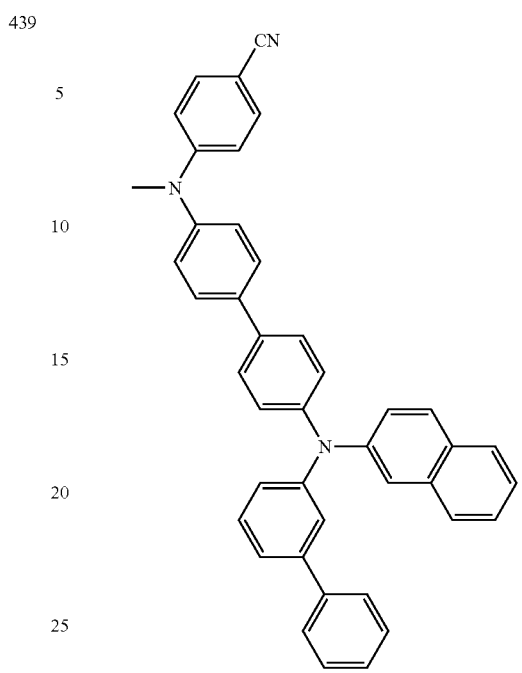
441
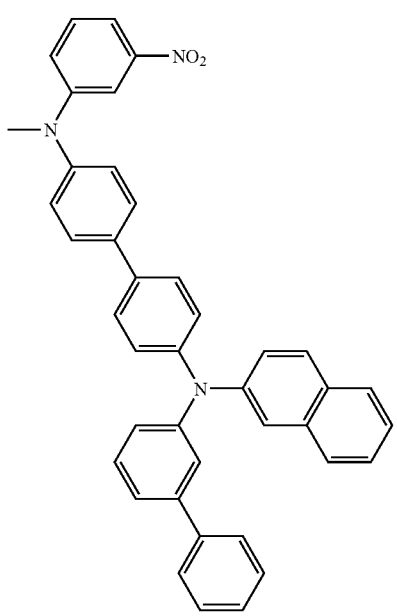
440
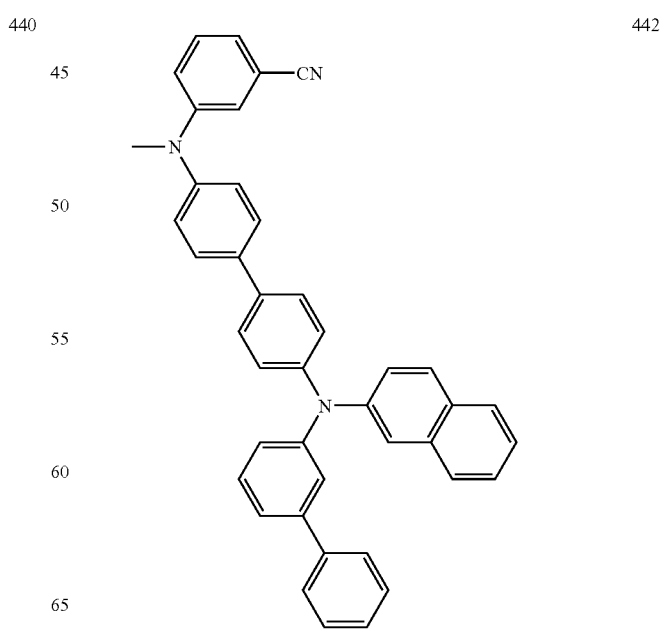
442

443
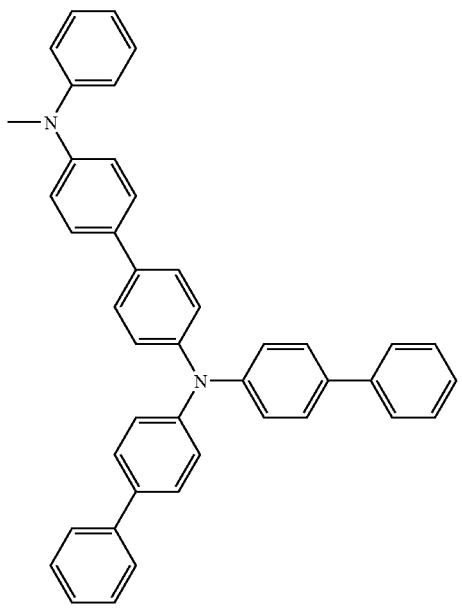
445
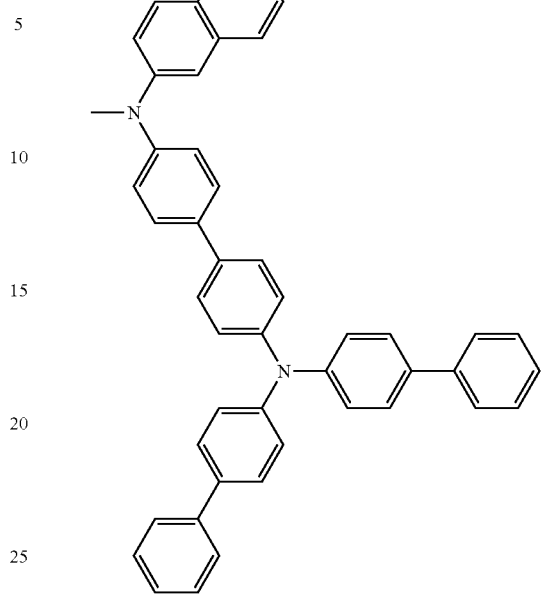
444
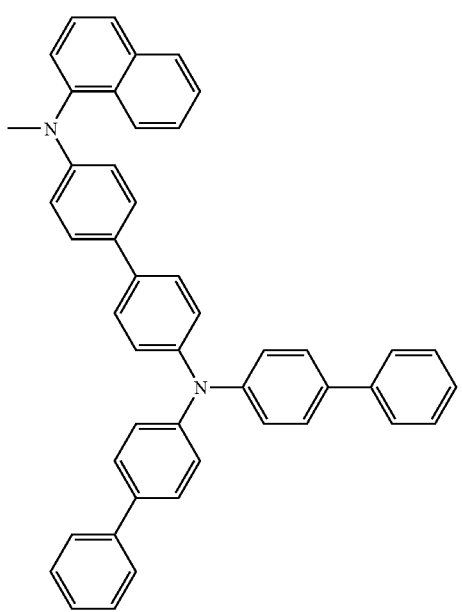
446
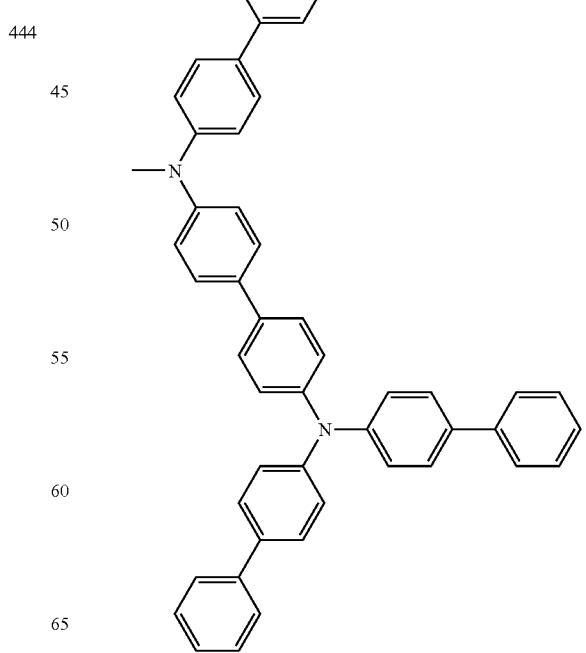

183
-continued
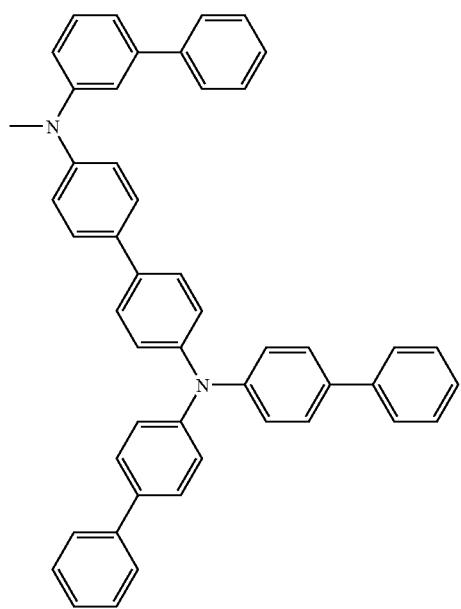
447
184
-continued
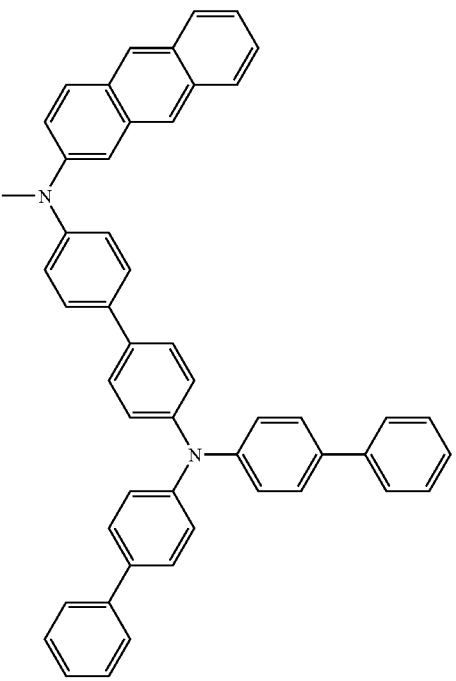
449
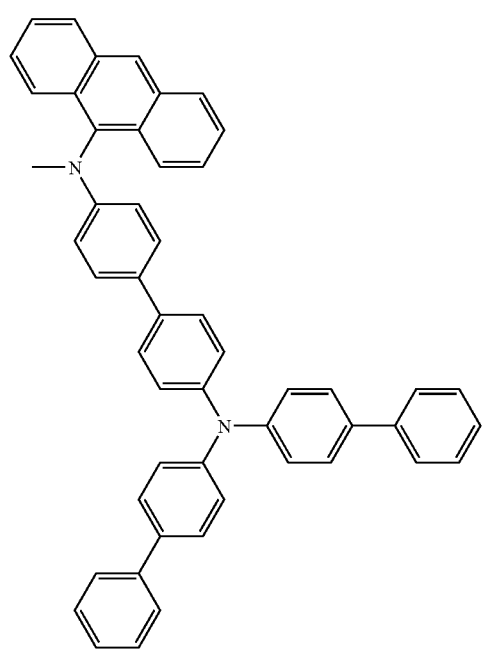
448
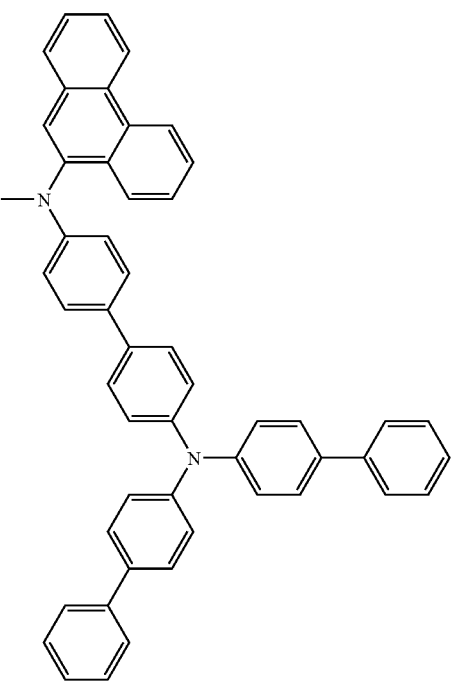
450

451
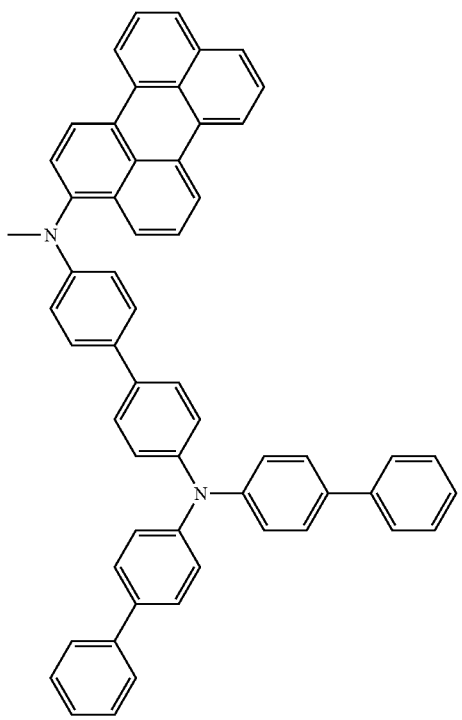
452
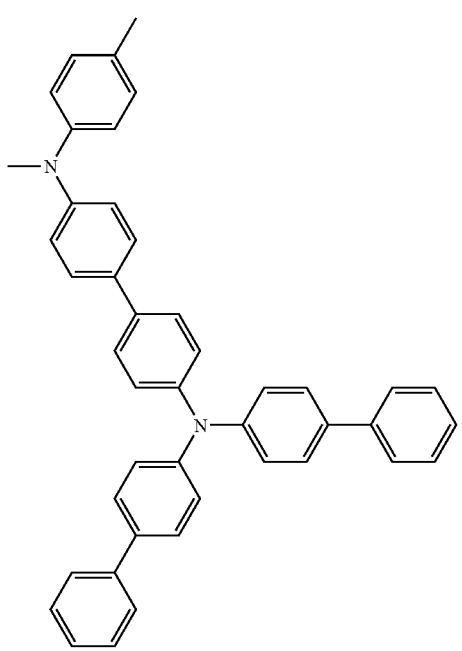
453
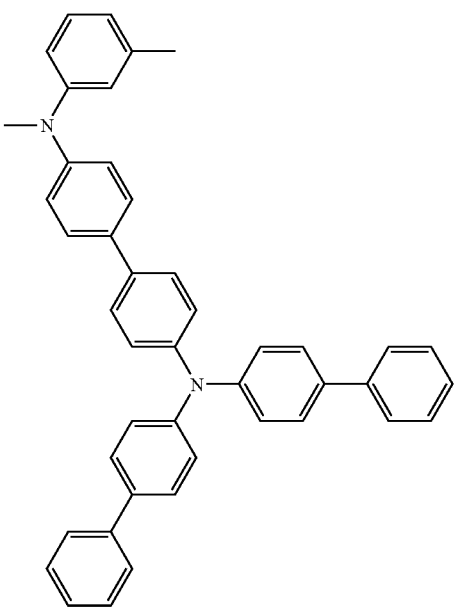
454
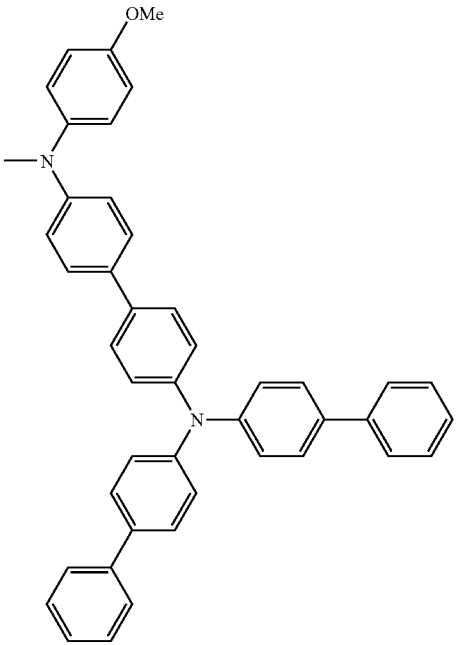

187
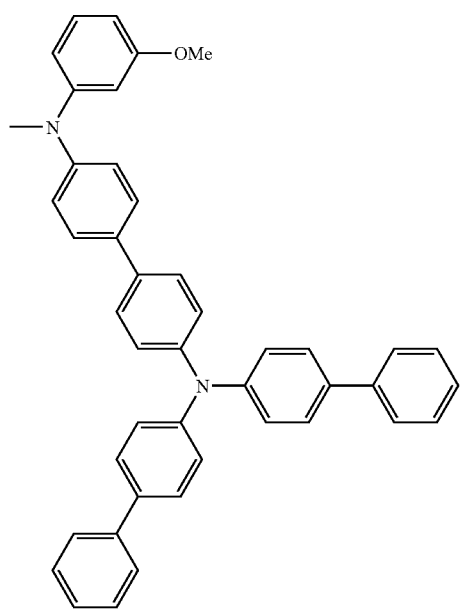
455
188
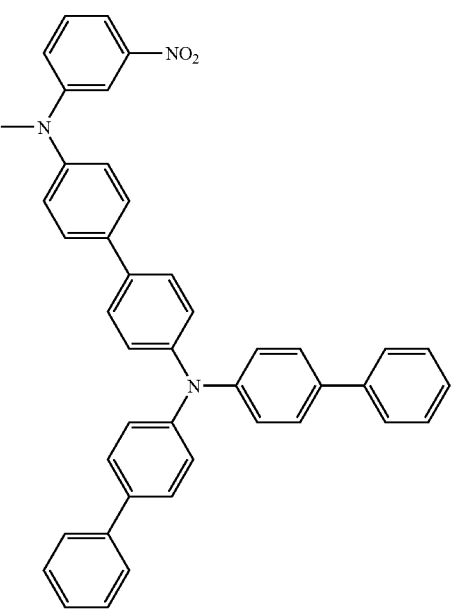
457
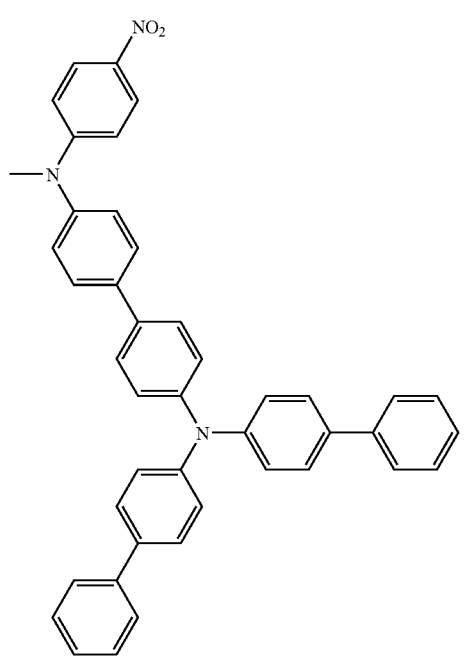
456
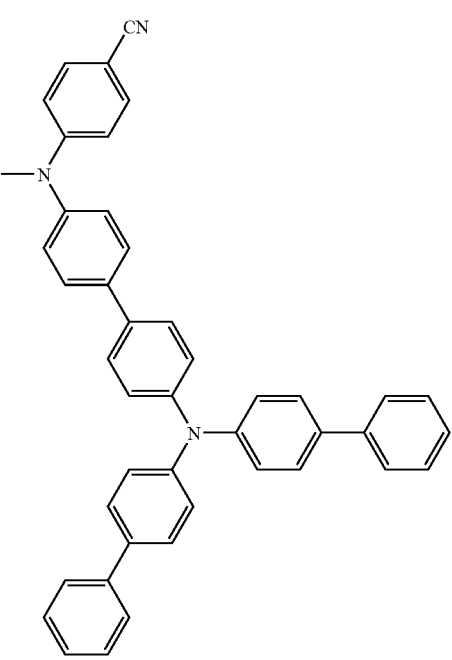
458

189
-continued
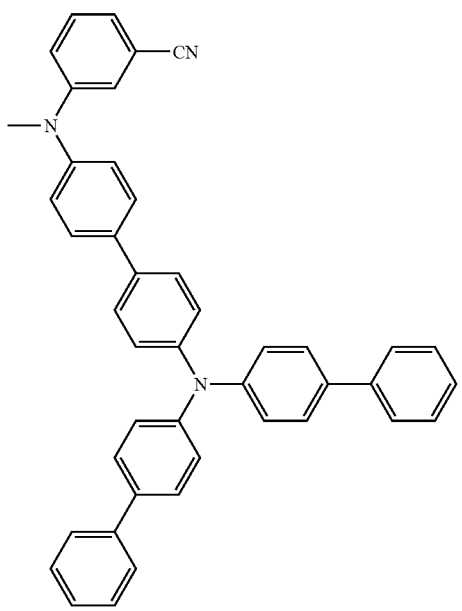
459
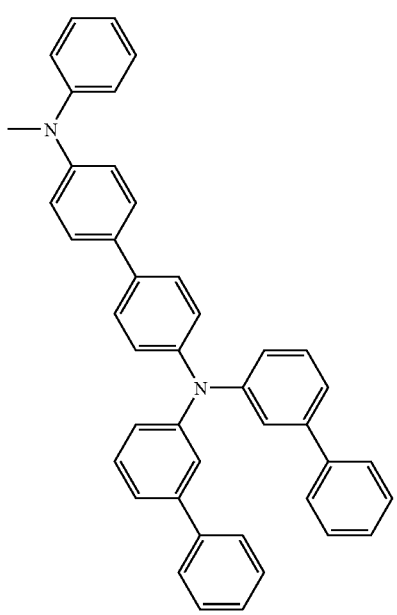
460
190
-continued
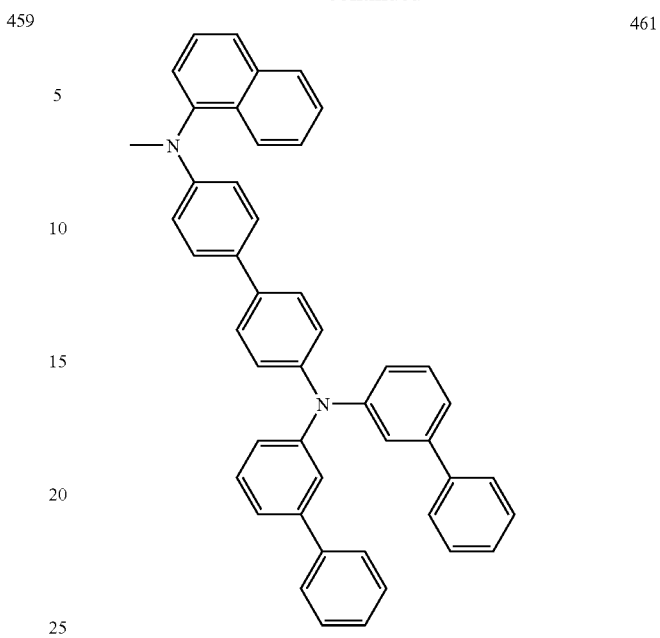
461
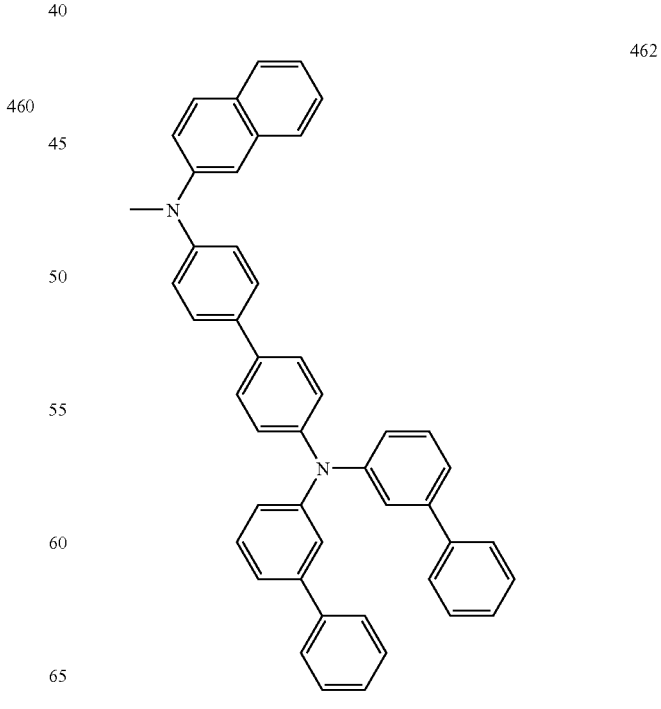
462

191
-continued
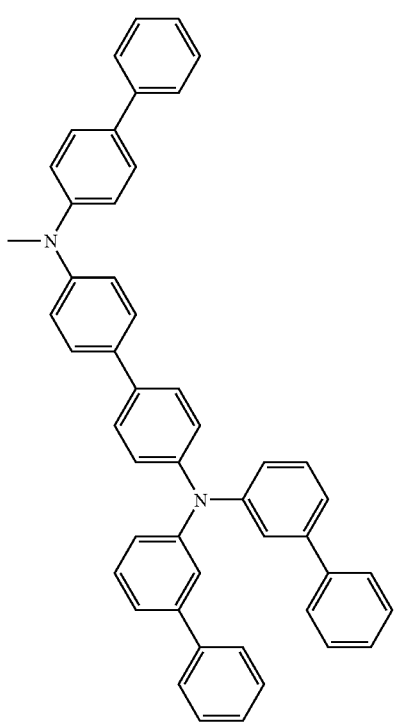
463
192
-continued
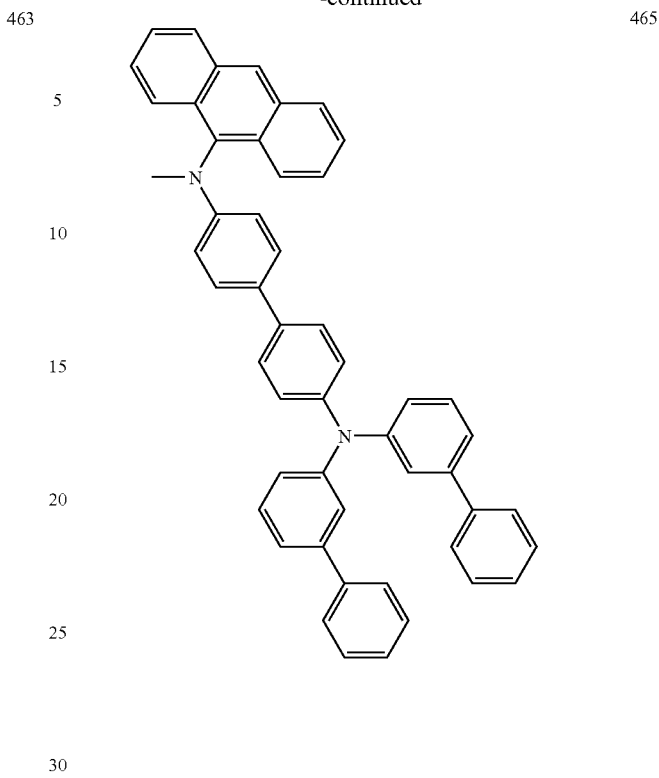
465
464
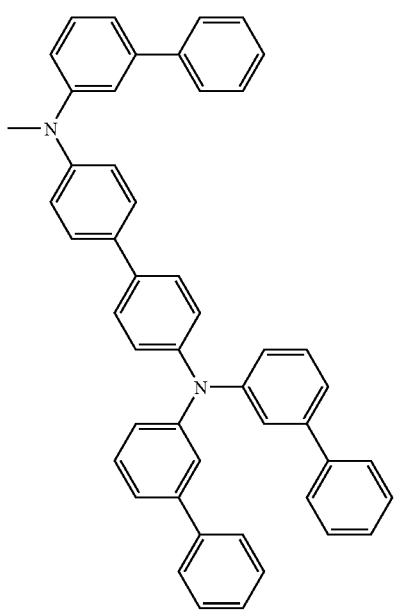
466
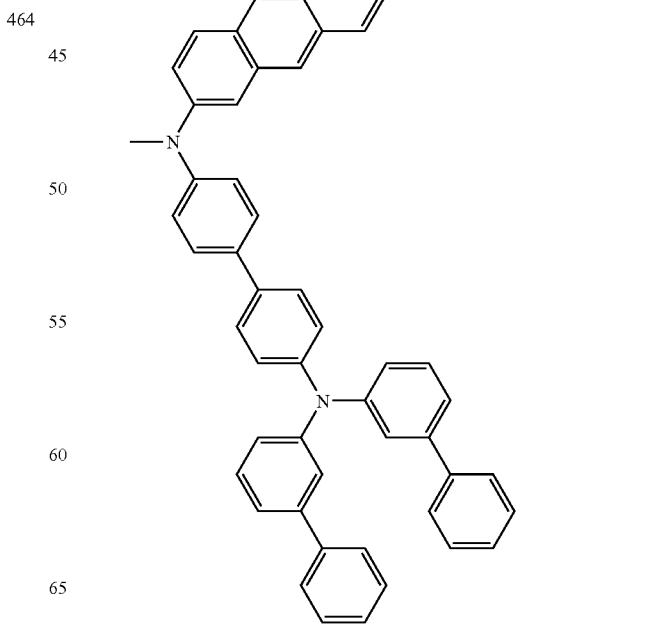

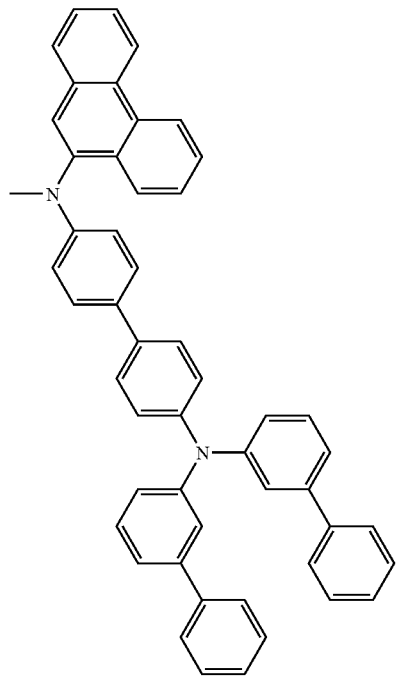
467
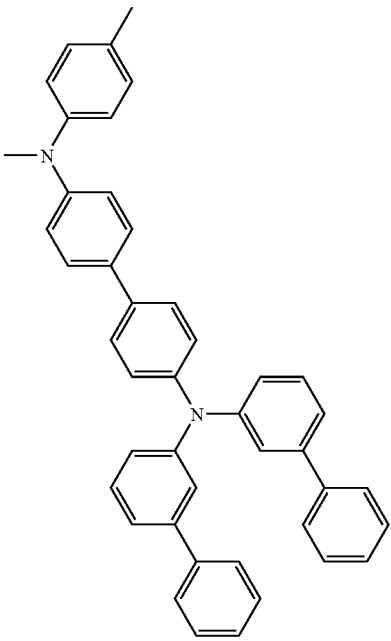
468
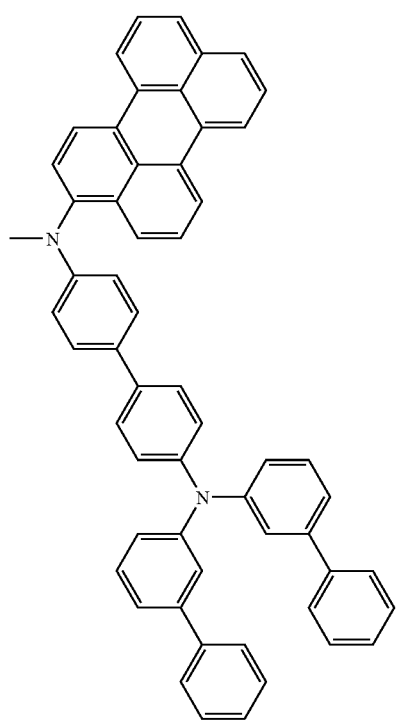
469
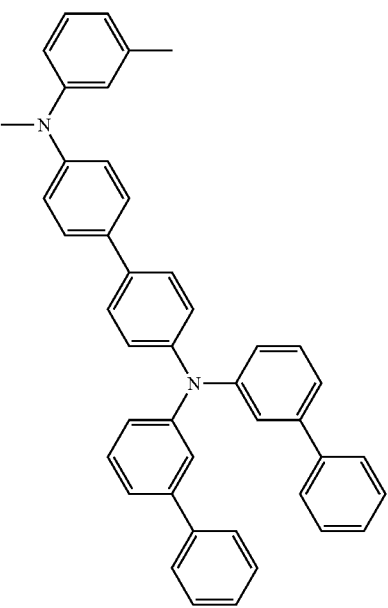
470

195
-continued
471
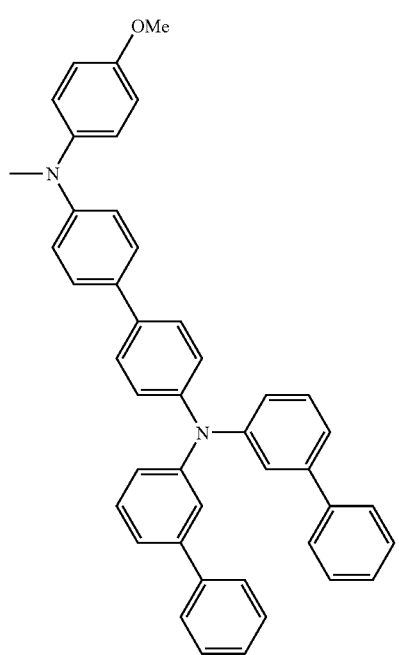
472
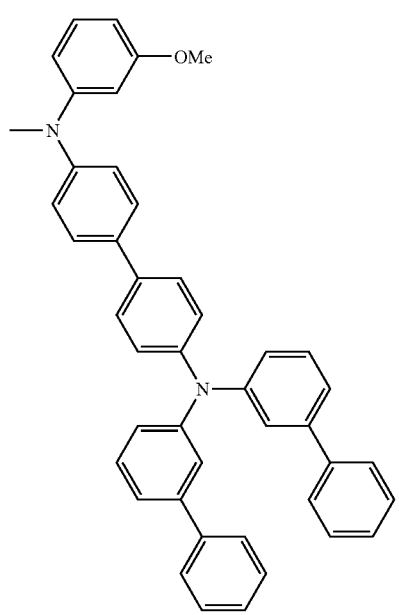
196
-continued
473
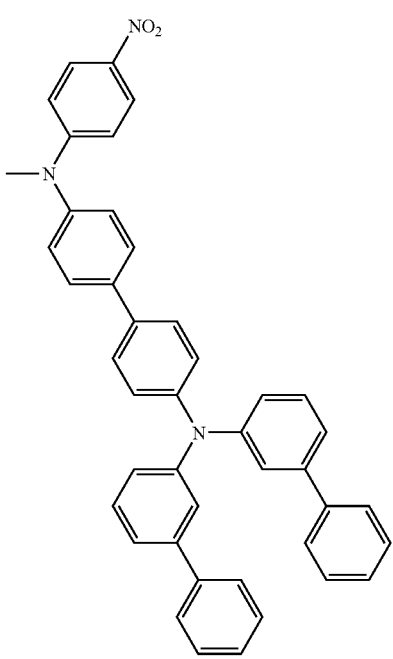
474
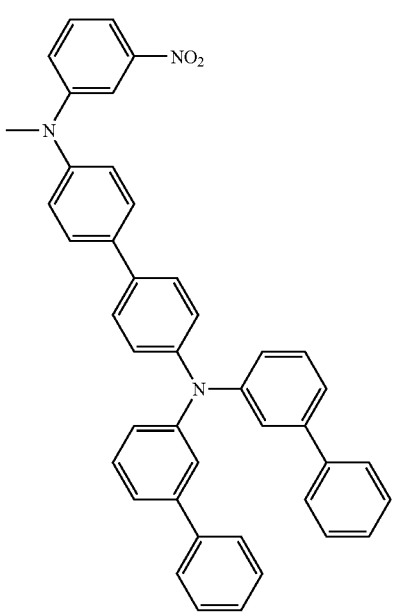

475
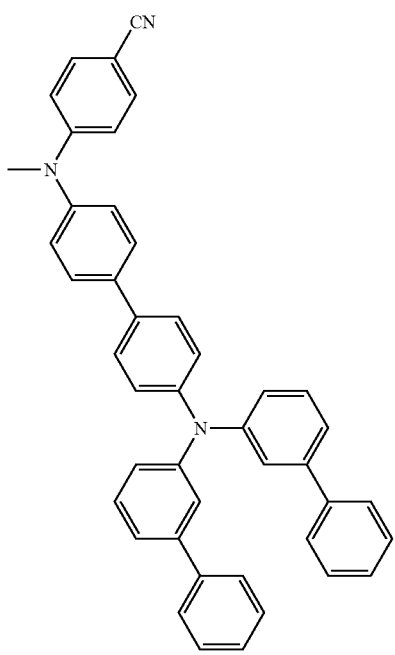
476
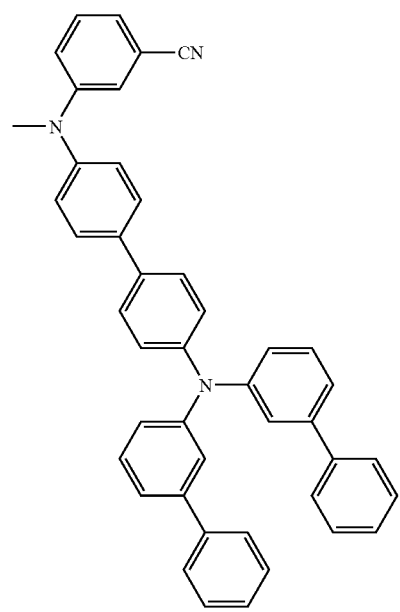
477
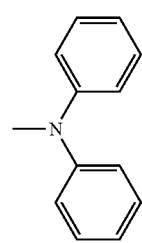
478
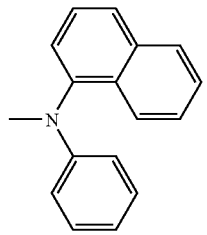
479
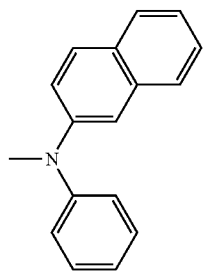
480
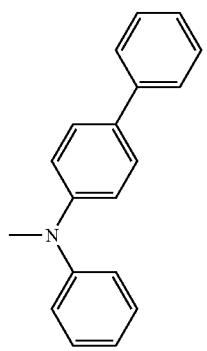
481
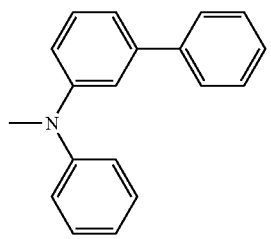
482
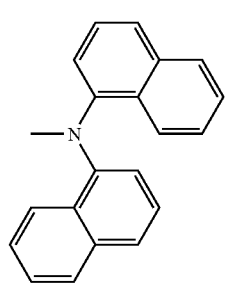

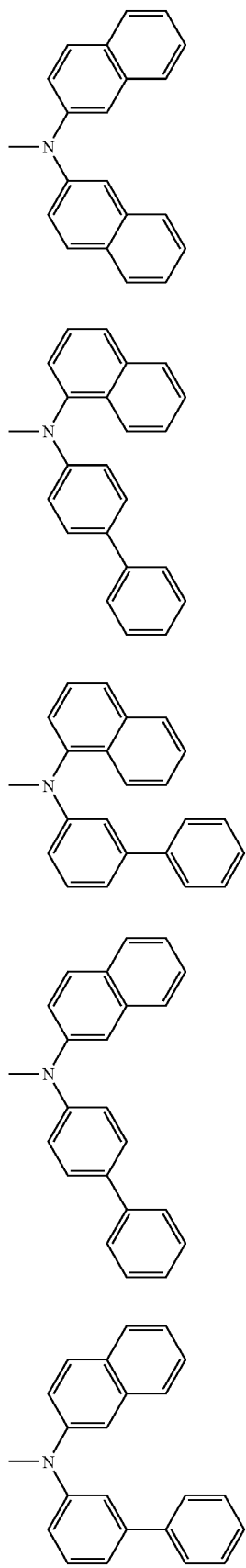
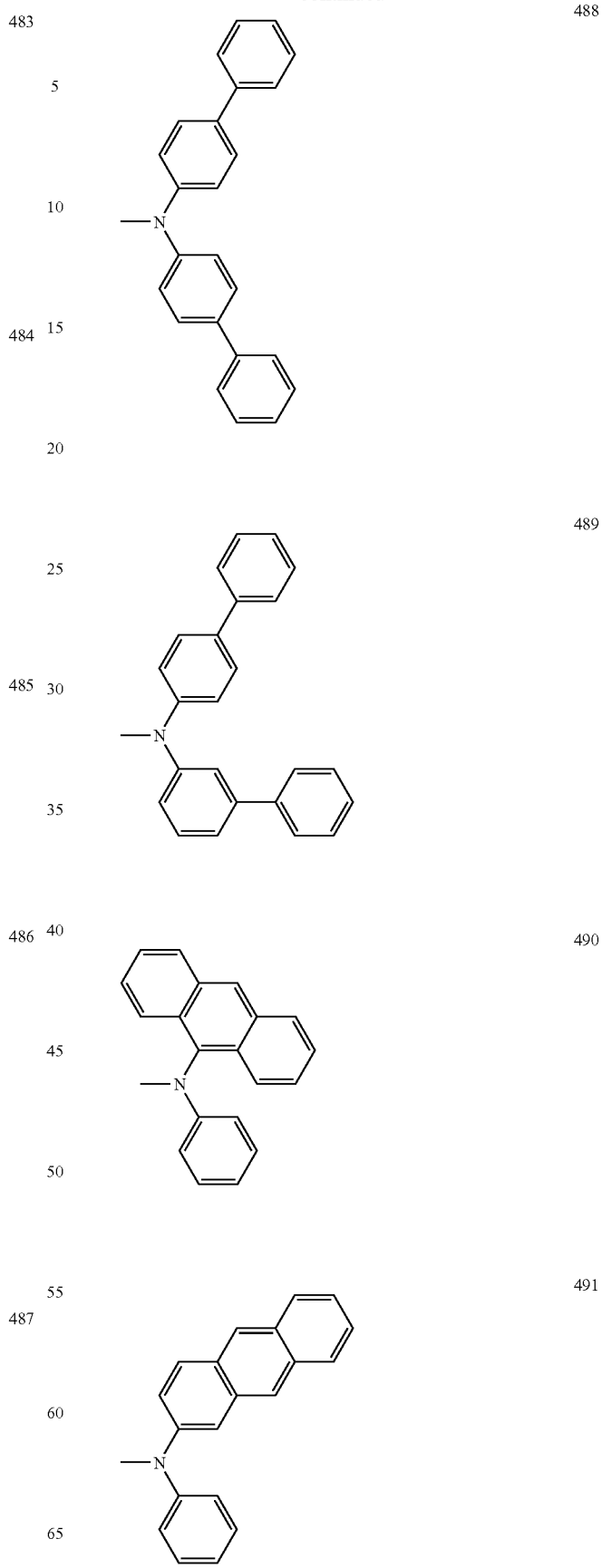

| 201 | 202 |
|---|---|
| 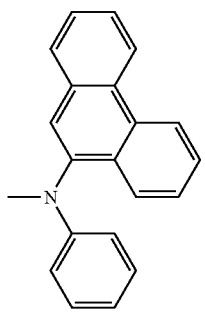 492 | 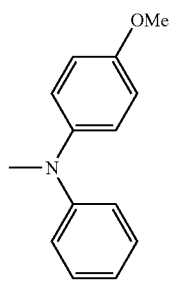 497 |
| 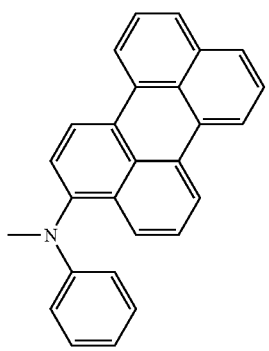 493 | 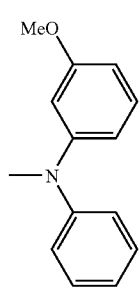 498 |
| 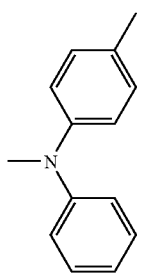 494 | 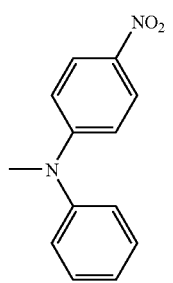 499 |
| 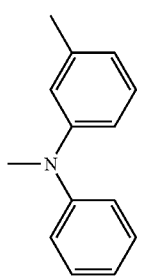 495 | 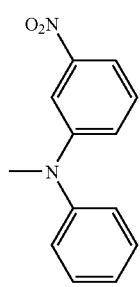 500 |
| 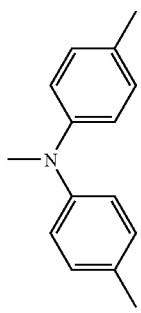 496 | 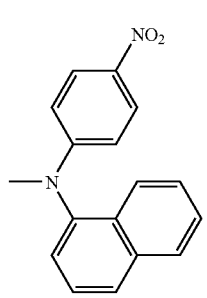 501 |

-continued
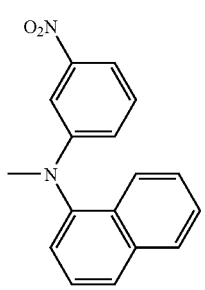
502
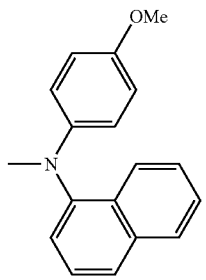
507
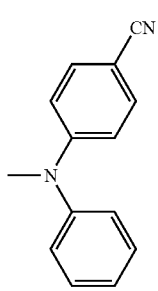
503
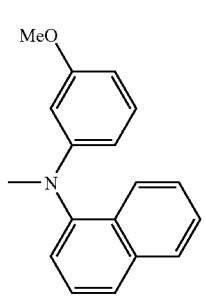
508
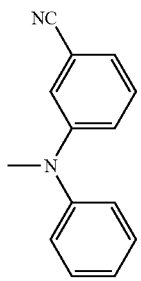
504
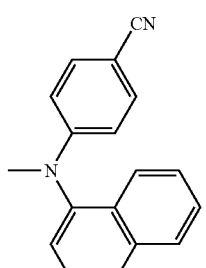
509
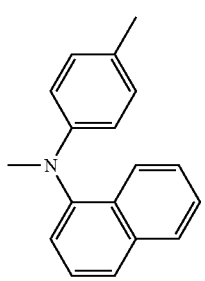
505
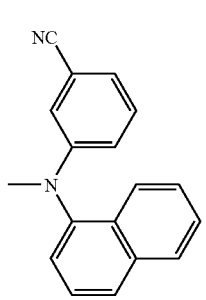
510
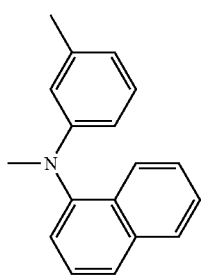
506
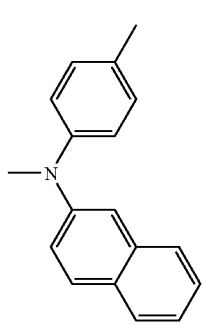
511

205
-continued
512 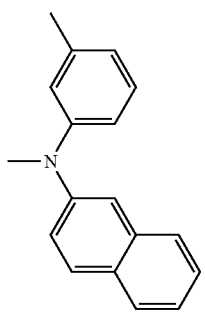
513 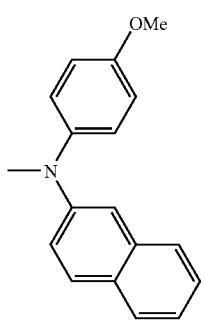
514 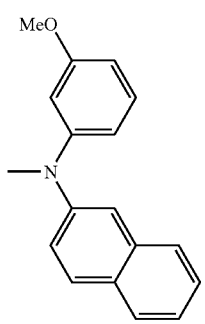
515 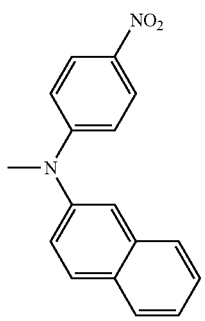
516 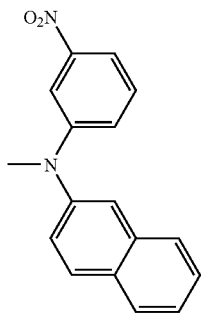
206
-continued
517 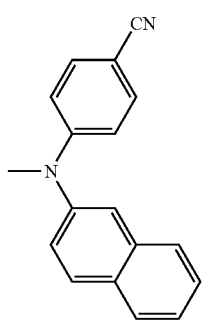
518 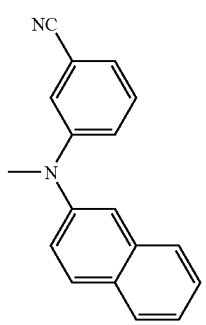
519 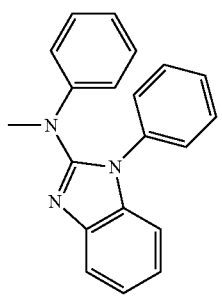
520 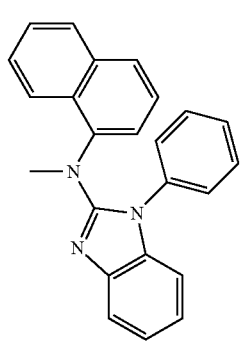
521 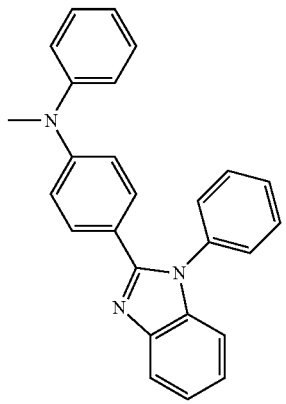

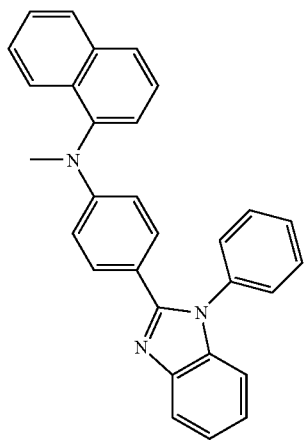
522
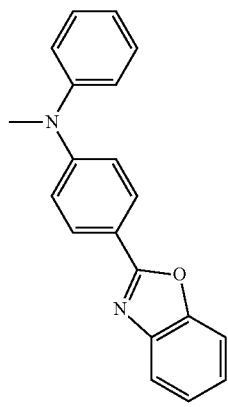
525
523
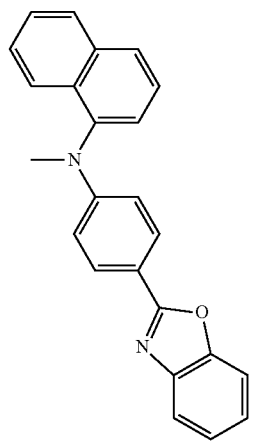
526
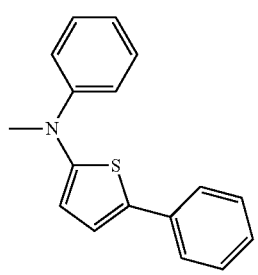
527
524
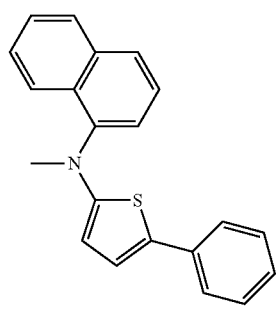
528

529

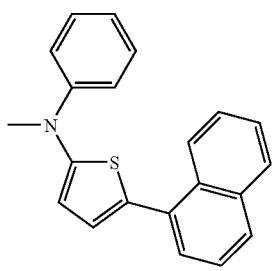

530

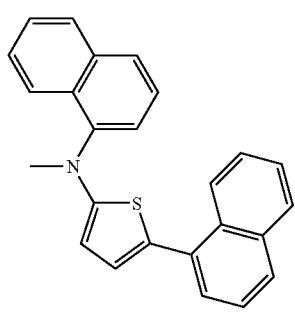

531

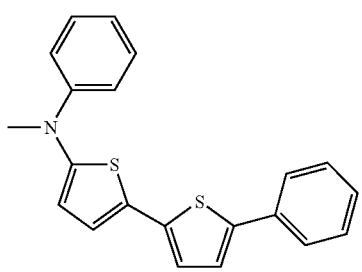

532

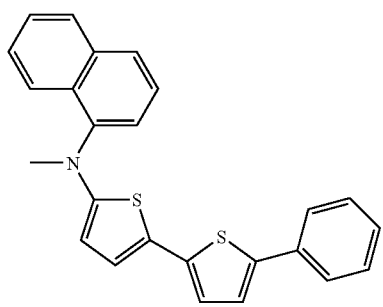

533

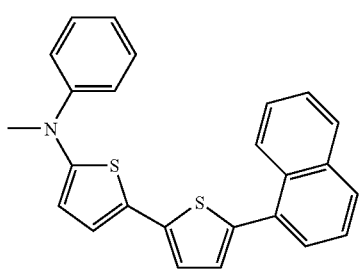

544

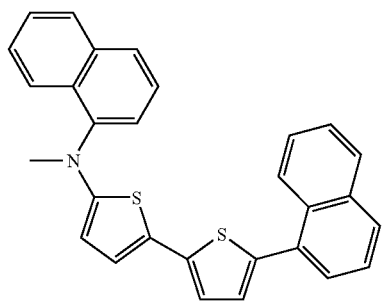

545

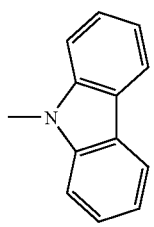

546

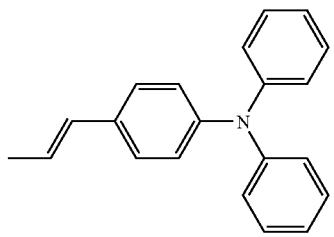

547

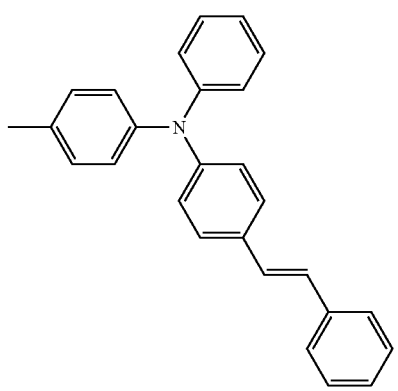

548

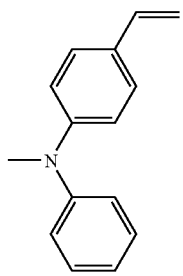

Various substituent groups are introduced into a core structure shown in Formula 1, in detail, the core structure in which a benzophenone group is bonded to a combination of an acridine group and a carbazole group to form an open spiro structure, thereby the compound of Formula 1 has characteristics suitable for application to an organic material layer used in an organic light emitting diode. This will be described in detail, below.

The steric core structure of the compound of Formula 1 can be divided into two portions, I and II as shown in the following Formula.

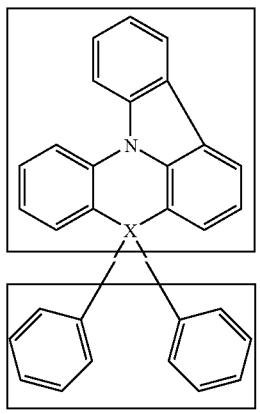

The compound of Formula 1 has the steric core structure, in which a plane I meets a plane II at a more planar angle being close to a right angle, unlike the closed spiro structure, in which a plane I is at a complete right angle with a plane II around X, and conjugation does not occur between the I and II portions around X. Furthermore, since one nitrogen atom is positioned among three aryl groups in the plane I, conjugation is limited in the plane I.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to R1 to R15 positions and Z1 to Z2 positions of the core structure having the large energy band gap so as to produce compounds having various energy band gaps. Generally, it is easy to control the energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO and LUMO energy levels of the compound by introducing various substituent groups into R1 to R15 and Z1 to Z4 positions of the core structure.

Additionally, by introducing various substituent groups into the core structure, compounds having intrinsic characteristics of the substituent groups can be obtained. For example, substituent groups, which are frequently applied to hole injection layer material, hole transport layer material, light emitting layer material, and electron transport layer materials during the production of the organic light emitting diode, are introduced into the core structure so as to produce substances capable of satisfying the requirements of each organic material layer. Particularly, since the core structure of the compound of Formula 1 includes the arylamine structure, it has an energy level suitable for the hole injection and/or hole transport materials in the organic light emitting diode. In the present invention, the compound having the proper energy level is selected depending on the substituent group among the compounds of Formula 1 to be used in the organic light emitting diode, whereby it is possible to realize a device having a low actuating voltage and a high light efficiency.

Furthermore, various substituent groups are nonsymmetrically introduced into the core structure (the A portion is located at one side of the core structure) so as to precisely control the energy band gap, improve interfacial characteristics with organic materials, and apply the compound to various fields.

In addition, if the number of amine contained in the substituent group A is set to 1 or more (if Z1 and Z2 are a heteroaromatic amine compound, the number of nitrogen atom contained therein is not included), it is possible to precisely control the HOMO or LUMO energy levels and the energy band gap, on the other hand, to improve interfacial characteristics with the organic materials, and apply the compound to various fields.

Additionally, various substituent groups are introduced into the steric structure of the compound of Formula 1 using open spiro bonding to control the three-dimensional structure of the organic material, so as to minimize π-π interaction in the organic material, thereby preventing formation of excimers.

With respect to the energy band gap and the energy level, for example, since the compound of Formula 2-2 of Example 1 of the present invention, in which arylamine is introduced into the hole transport material or the hole injection material of the structure of Formula 1, has HOMO of 5.31 eV, it has an energy level suitable for the hole injection layer or the hole transport layer. Meanwhile, the compound of Formula 2-2 of Example 1 has the band gap of 2.99 eV, which is still larger than that of NPB, typically used as the hole transport layer material, thus it has a LUMO value of about 2.32 eV, which is considered to be very high. If a compound having a high LUMO value is used as the hole transport layer, it increases the energy wall of LUMO of the material constituting the light emitting layer to prevent the movement of electrons from the light emitting layer to the hole transport layer. Accordingly, the above-mentioned compound improves the light emission efficiency of the organic light emitting diode so that efficiency is higher than that of conventionally used NPB (HOMO 5.4 eV, LUMO 2.3 eV, and energy band gap 3.1 eV). In the present invention, the energy band gap is calculated by a typical method using a UV-VIS spectrum.

As well, the compound of Formula 1 has stable redox characteristics. Redox stability is estimated using a CV (cyclovoltammetry) method. For example, if oxidation voltage is repeatedly applied to the compound of Formula 2-2 of Example 1, oxidation repeatedly occurs at the same voltage and the current amount is constant. This means that the compound has excellent stability to oxidation.

Meanwhile, since the compound of Formula 1 has a high glass transition temperature (Tg), it has excellent thermal stability. For example, the compound of Formula 2-2 of Example 1 of the present invention has a glass transition temperature of 150° C., which is still higher than that of conventionally used NPB (Tg: 96° C.). Such increase in thermal stability is an important factor providing actuating stability to the device.

Furthermore, the compound of Formula 1 may be used to form the organic material layer using a vacuum deposition process or a solution coating process during the production of the organic light emitting diode. In connection with this, examples of the solution coating process include a spin coating process, a dip coating process, an inkjet printing process, a screen printing process, a spray process, and a roll coating process, but are not limited thereto.

Tertiary alcohol, which is produced by a reaction of a lithiated aryl and keto group, is heated in the presence of an acid catalyst to form a hexagonal cyclic structure while water is removed, thereby producing the compound of the present invention. The above-mentioned procedure for producing the compound is well known in the art, and those skilled in the art can change the production conditions during the production of the compound of Formula 1. The production will be described in detail in the preparation examples later.

Further, the present invention provides an organic light emitting diode which comprises a first electrode, at least one organic material layer, and a second electrode, wherein the first electrode, the organic material layer(s), and the second electrode form a layered structure and at least one layer of the organic material layers includes a compound represented by Formula 1 of the present invention.

The organic light emitting diode of the present invention can be produced using known materials through a known process, modified only in that at least one layers of organic material layer(s) include the compound of the present invention, that is, the compound of Formula 1.

The organic material layer(s) of the organic light emitting diode according to the present invention may have a single layer structure, or alternatively, a multilayered structure in which two or more organic material layers are layered. For example, the organic light emitting diode of the present invention may comprise a hole injection layer, a hole transport layer, a light emitting layer, an electron transport layer, and an electron injection layer as the organic material layers. However, the structure of the organic light emitting diode is not limited to this, but may comprise a smaller number of organic material layers.

If the organic light emitting diode according to the present invention has a multilayered structure of organic material layer, the compound of Formula 1 can be contained in a hole injection layer, a hole transport layer, a hole injection and transport layer, a light emitting layer, and a hole transport layer. In the present invention, the compound of Formula 1 is preferably contained in a hole injection layer, a hole transport layer, or a hole injection and transport layer.

The organic light emitting diode of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

MODE FOR THE INVENTION

A better understanding of a method of producing a compound of Formula 1 and the production of an organic light emitting diode using the same may be obtained in light of the following preparation examples and examples which are set forth to illustrate, but are not to be construed to limit the present invention.

In order to produce the compound represented by Formula 1, any one of the compounds of the following Formulae a to b may be used as a starting material.

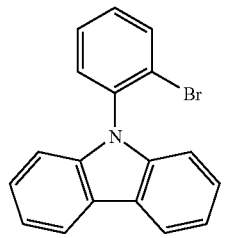

[Formula a]

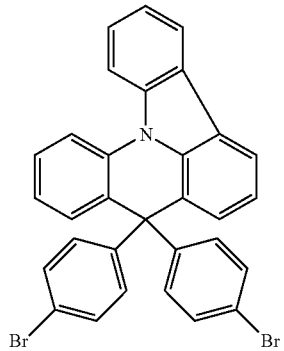

[Formula b]

Preparation Example 1

Preparation of Starting Material Represented by Formula a

Carbazole (1.672 g, 10 mmol), 1-bromo-2-iodobenzene (1.5 ml, 12 mmol), potassium carbonate ($K_2CO_3$, 2.7646 g, 20 mmol), copper iodide (CuI, 95 mg, 0.5 mmol), and 25 ml of xylene were refluxed in a nitrogen atmosphere. After cooling to normal temperature was conducted, a product was extracted with ethyl acetate, water was removed with anhydrous magnesium sulfate ($MgSO_4$), and the solvent was removed at a reduced pressure. The resulting product was passed through a silica gel column using a hexane solvent to produce a compound, the solvent was removed at a reduced pressure, and vacuum drying was conducted to produce the desired white solid compound (800 mg, yield 25%).

MS: $[M+H]^+=323$.

Preparation Example 2

Preparation of Starting Material Represented by Formula b

The starting material represented by Formula a (4.19 g, 13 mmol) was dissolved in 50 ml of purified THF and cooled to −78° C., and n-BuLi (2.5 M in hexane, 4.8 ml, 12 mmol) was slowly dropped thereon. Stirring was conducted at the same temperature for 45 min, and 4-bromobenzophenone (2.61 g, 10.0 mmol) was added thereto. After Stirring was conducted at the same temperature for 1 hour, the temperature was raised to normal temperature and stirring was carried out for an additional 2 hours. The reaction was completed in an ammonium chloride ($NH_4Cl$) aqueous solution, and an organic material was extracted with ethyl ether. Water was removed, and an organic solvent was then removed therefrom to give a yellow solid. The produced solid was dispersed in ethanol, stirred, filtered, and vacuum dried to produce 4.5 g of intermediate material. The intermediate solid was dispersed in 40 ml of acetic acid, twelve drops of concentrated sulfuric acid were added thereto, and reflux was conducted for 3 hours. After cooling to normal temperature was conducted, the resulting solid was filtered, washed with ethanol, and vacuum dried to give 3.98 g of a product (yield 82.2%).

MS: [M+H]$^+$=486.

Example 1

Preparation of Compound Represented by Following Formula 2-2

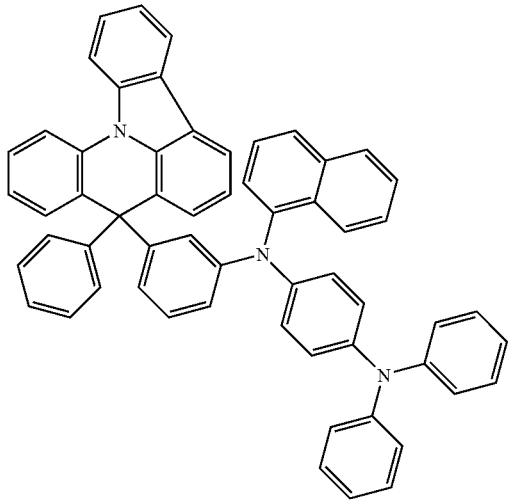

[Formula 2-2]

1) Production of arylamine(4-(N-phenyl-N-phenylamino) phenyl-1-naphthylamine) to Produce the Compound Represented by Formula 2-2

4-bromophenyl-N-phenyl-N-phenylamine (15.0 g, 46.3 mmol) and 1-naphthylamine (7.29 g, 50.9 mmol) were dissolved in 200 ml of toluene, sodium-tertiary-butoxide (13.34 g, 138.8 mmol), bisdibenzylidene acetone palladium (0) (0.53 g, 0.93 mmol), and 50 wt % tri-tertiary-butylphosphine toluene solution (0.56 ml, 1.39 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (13 g, yield 73%).

MS: [M+H]$^+$=386.

2) The compound of Formula b (5.00 g, 10.3 mmol) and 4-(N-phenyl-N-phenylamino)phenyl-1-naphthylamine (4.78 g, 12.4 mmol) were dissolved in 50 ml of toluene, and sodium-tertiary-butoxide (5.89 g, 61.3 mmol), bisdibenzylidene acetone palladium(0) (0.12 g, 0.21 mmol), and 50 wt % tri-tertiary-butylphosphine toluene solution (0.15 ml, 0.31 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=4/1), stirring was conducted using petroleum ether, and vacuum drying was conducted to produce the compound of Formula 2-2 (4.3 g, yield 53%).

MS: [M+H]$^+$=781.

Example 2

Preparation of Compound Represented by Following Formula 2-256

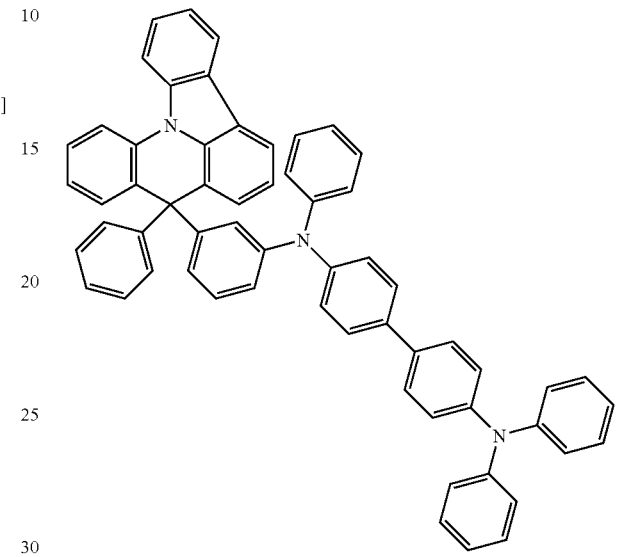

[Formula 2-256]

1) Production of arylamine(4-(N,N-diphenylamino)-biphenyl-N'-phenylamine) to Produce the Compound Represented by Formula 2-256

4-chlorobiphenyl-N,N'-diphenylamine (4.00 g, 11.2 mmol) and aniline (1.13 ml, 12.4 mmol) were dissolved in 100 ml of toluene, sodium-tertiary-butoxide (2.70 g, 28.1 mmol), bisdibenzylidene acetone palladium (0) (0.13 g, 0.23 mmol), and 50 wt % tri-tertiary-butylphosphine toluene solution (0.17 ml, 0.34 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (3.8 g, yield 81%).

MS: [M+H]$^+$=413.

2) The compound of Formula b (3.62 g, 7.47 mmol) and 4-(N,N-diphenylamino)-biphenyl-N'-phenylamine (3.4 g, 8.2 mmol) were dissolved in 40 ml of toluene, and sodium-tertiary-butoxide (1.94 g, 22.4 mmol), bisdibenzylidene acetone palladium(0) (0.09 g, 0.16 mmol), and 50 wt % tri-tertiary-butylphosphine toluene solution (0.11 ml, 0.22 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-256 (3.5 g, yield 53%).

MS: [M+H]$^+$=819.

Example 3

Preparation of Compound Represented by Following Formula 2-257

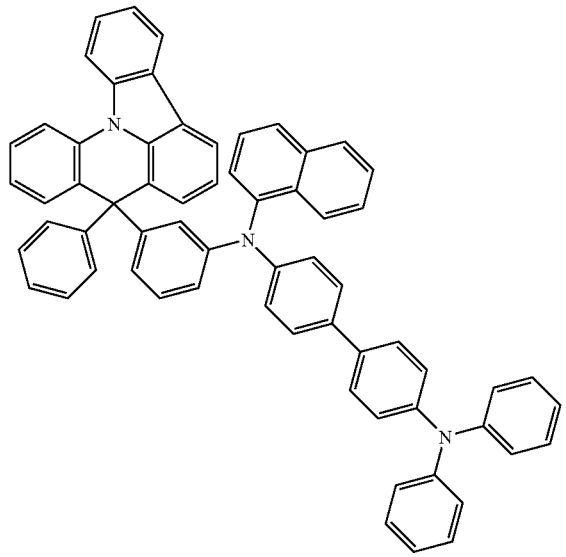

[Formula 2-257]

1) Production of arylamine(4-(N,N-diphenylamino)-biphenyl-N'-naphthylamine) to Produce the Compound Represented by Formula 2-257

4-chlorobiphenyl-N,N'-diphenylamine (8.80 g, 24.7 mmol) and 1-naphthylamine (5.31 g, 37.1 mmol) were dissolved in 200 ml of toluene, sodium-tertiary-butoxide (5.94 g, 61.8 mmol), bisdibenzylidene acetone palladium (0) (0.43 g, 0.74 mmol), and 50 wt % tri-tertiary-butylphosphine toluene solution (0.61 ml, 1.24 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (7.0 g, yield 61%).

MS: $[M+H]^+$=413.

2) The compound of Formula b (3.62 g, 7.47 mmol) and 4-(N,N-diphenylamino)-biphenyl-N'-naphthylamine (3.8 g, 8.2 mmol) were dissolved in 40 ml of toluene, and sodium-tertiary-butoxide (1.94 g, 22.4 mmol), bisdibenzylidene acetone palladium(0) (0.09 g, 0.16 mmol), and 50 wt % tri-tertiary-butylphosphine toluene solution (0.11 ml, 0.22 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-257 (3.5 g, yield 54%).

MS: $[M+H]^+$=869.

Example 4

Preparation of Compound Represented by Following Formula 2-259

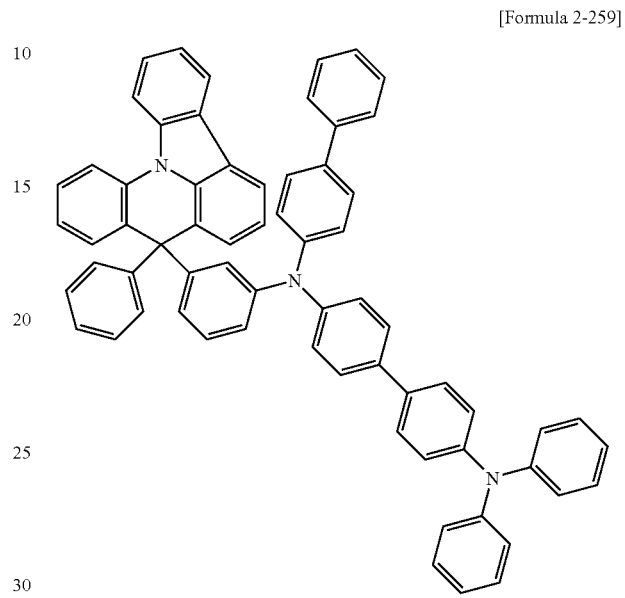

[Formula 2-259]

1) Production of arylamine(4-(N,N-diphenylamino)-biphenyl-N'-biphenylamine) to Produce the Compound Represented by Formula 2-259

4-chlorobiphenyl-N,N-diphenylamine (8.80 g, 24.7 mmol) and 4-aminobiphenyl (6.28 g, 37.1 mmol) were dissolved in 200 ml of toluene, sodium-tertiary-butoxide (5.94 g, 61.8 mmol), bisdibenzylidene acetone palladium (0) (0.43 g, 0.74 mmol), and 50 wt % tri-tertiary-butylphosphine toluene solution (0.61 ml, 1.24 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (7.0 g, yield 58%).

MS: $[M+H]^+$=489.

2) The compound of Formula b (3.62 g, 7.47 mmol) and 4-(N,N-diphenylamino)-biphenyl-N'-biphenylamine (4.0 g, 8.2 mmol) were dissolved in 40 ml of toluene, and sodium-tertiary-butoxide (1.94 g, 22.4 mmol), bisdibenzylidene acetone palladium(0) (0.09 g, 0.16 mmol), and 50 wt % tri-tertiary-butylphosphine toluene solution (0.11 ml, 0.22 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-259 (3.5 g, yield 53%).

MS: $[M+H]^+$=895.

Example 5

Preparation of Compound Represented by Following Formula 2-273

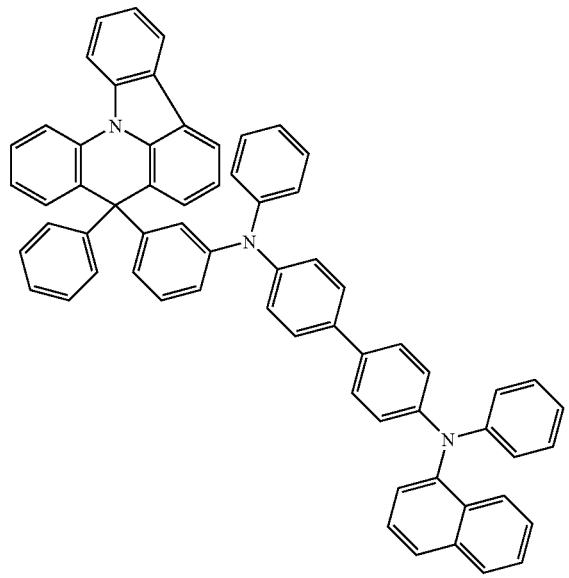

[Formula 2-273]

1) Production of arylamine(4-(N-phenyl-N-naphthylamino)-biphenyl-N'-phenylamine) to Produce the Compound Represented by Formula 2-273

4-chlorobiphenyl-N-phenyl-N-naphthylamine (4.08 g, 10.1 mmol) and aniline (1.38 ml, 15.1 mmol) were dissolved in 100 ml of toluene, sodium-tertiary-butoxide (2.90 g, 30.2 mmol), bisdibenzylidene acetone palladium (0) (0.17 g, 0.30 mmol), and 50 wt % tri-tertiary-butylphosphine toluene solution (0.26 ml, 0.53 mmol) were added thereto, and reflux was conducted in a nitrogen atmosphere for 7 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (3.8 g, yield 82%).

MS: $[M+H]^+=463$.

2) The compound of Formula b (3.13 g, 6.47 mmol) and 4-(N-phenyl-N-naphthylamino)-biphenyl-N'-phenylamine (3.3 g, 7.1 mmol) were dissolved in 40 ml of toluene, and sodium-tertiary-butoxide (1.94 g, 22.4 mmol), bisdibenzylidene acetone palladium(0) (0.08 g, 0.14 mmol), and 50 wt % tri-tertiary-butylphosphine toluene solution (0.11 ml, 0.22 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-273 (2.5 g, yield 45%).

MS: $[M+H]^+=869$.

Example 6

Preparation of Compound Represented by Following Formula 2-274

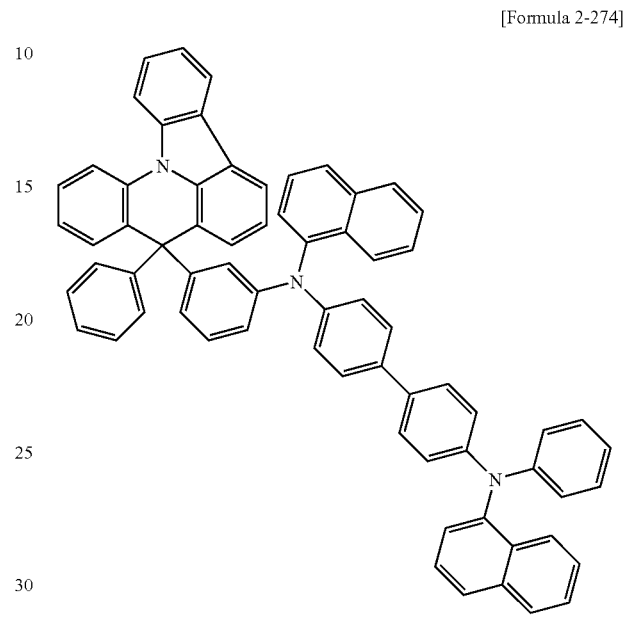

[Formula 2-274]

1) Production of arylamine(4-(N-phenyl-N-naphthylamino)-biphenyl-N'-naphthylamine) to produce the compound represented by Formula 2-274

4-chlorobiphenyl-N-phenyl-N-naphthylamine (4.08 g, 10.1 mmol) and 1-naphthylamine (2.16 g, 15.1 mmol) were dissolved in 100 ml of toluene, sodium-tertiary-butoxide (2.90 g, 30.2 mmol), bisdibenzylidene acetone palladium (0) (0.17 g, 0.30 mmol), and 50 wt % tri-tertiary-butylphosphine toluene solution (0.26 ml, 0.53 mmol) were added thereto, and reflux was conducted in a nitrogen atmosphere for 7 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (3.8 g, yield 74%).

MS: $[M+H]^+=513$.

2) The compound of Formula b (3.62 g, 7.47 mmol) and 4-(N-phenyl-N-naphthylamino)-biphenyl-N'-naphthylamine (3.8 g, 7.4 mmol) were dissolved in 40 ml of toluene, and sodium-tertiary-butoxide (1.94 g, 22.4 mmol), bisdibenzylidene acetone palladium(0) (0.089 g, 0.16 mmol), and 50 wt % tri-tertiary-butylphosphine toluene solution (0.11 ml, 0.22 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-274 (3.0 g, yield 44%).

MS: $[M+H]^+=919$.

Example 7

Preparation of Compound Represented by Following Formula 2-276

[Formula 2-276]

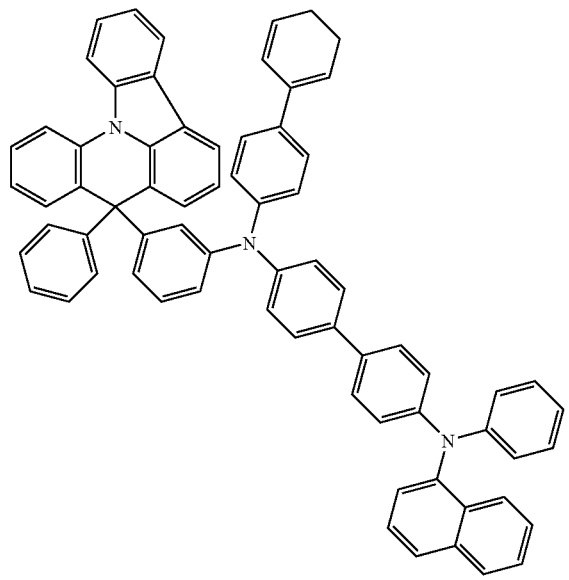

1) Production of arylamine(4-(N-phenyl-N-naphthylamino)-biphenyl-N'-biphenylamine) to Produce the Compound Represented by Formula 2-276

4-chlorobiphenyl-N-phenyl-N-naphthylamine (4.08 g, 10.1 mmol) and 4-aminobiphenyl (2.55 g, 15.1 mmol) were dissolved in 100 ml of toluene, sodium-tertiary-butoxide (2.90 g, 30.2 mmol), bisdibenzylidene acetone palladium(0) (0.17 g, 0.30 mmol), and 50 wt % tri-tertiary-butylphosphine toluene solution (0.26 ml, 0.53 mmol) were added thereto, and reflux was conducted in a nitrogen atmosphere for 7 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (3.8 g, yield 70%).

MS: $[M+H]^+=539$.

2) The compound of Formula b (3.13 g, 6.47 mmol) and 4-(N-phenyl-N-naphthylamino)-biphenyl-N'-biphenylamine (3.8 g, 7.1 mmol) were dissolved in 40 ml of toluene, and sodium-tertiary-butoxide (1.94 g, 22.4 mmol), bisdibenzylidene acetone palladium(0) (0.081 g, 0.14 mmol), and 50 wt % tri-tertiary-butylphosphine toluene solution (0.11 ml, 0.22 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-276 (2.5 g, yield 41%).

MS: $[M+H]^+=945$.

Example 8

Preparation of Compound Represented by Following Formula 2-307

[Formula 2-307]

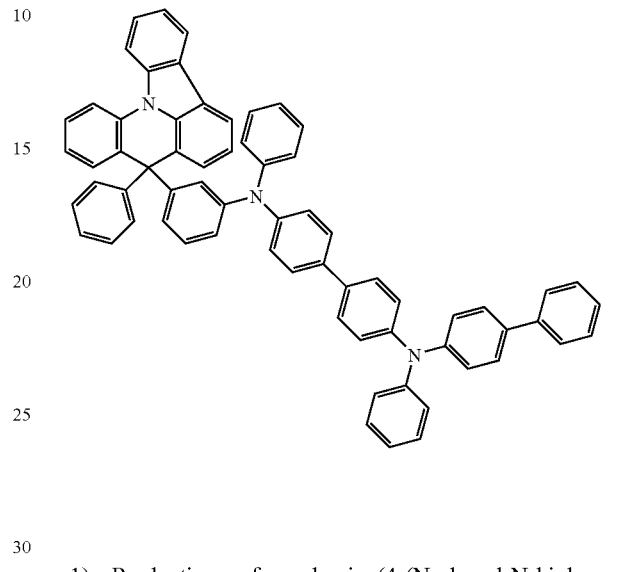

1) Production of arylamine(4-(N-phenyl-N-biphenylamino)-biphenyl-N'-phenylamine) to Produce the Compound Represented by Formula 2-307

4-chlorobiphenyl-N-phenyl-N-biphenylamine (4.86 g, 11.2 mmol) and aniline (1.13 ml, 12.4 mmol) were dissolved in 100 ml of toluene, sodium-tertiary-butoxide (2.70 g, 28.1 mmol), bisdibenzylidene acetone palladium(0) (0.13 g, 0.23 mmol), and 50 wt % tri-tertiary-butylphosphine toluene solution (0.17 ml, 0.34 mmol) were added thereto, and reflux was conducted in a nitrogen atmosphere for 7 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (3.8 g, yield 69%).

MS: $[M+H]^+=489$.

2) The compound of Formula b (3.13 g, 6.47 mmol) and 4-(N-phenyl-N-biphenylamino)-biphenyl-N'-phenylamine (3.5 g, 7.1 mmol) were dissolved in 40 ml of toluene, and sodium-tertiary-butoxide (1.94 g, 22.4 mmol), bisdibenzylidene acetone palladium(0) (0.081 g, 0.14 mmol), and 50 wt % tri-tertiary-butylphosphine toluene solution (0.11 ml, 0.22 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-307 (2.6 g, yield 45%).

MS: $[M+H]^+=895$.

Example 9

Preparation of Compound Represented by Following Formula 2-308

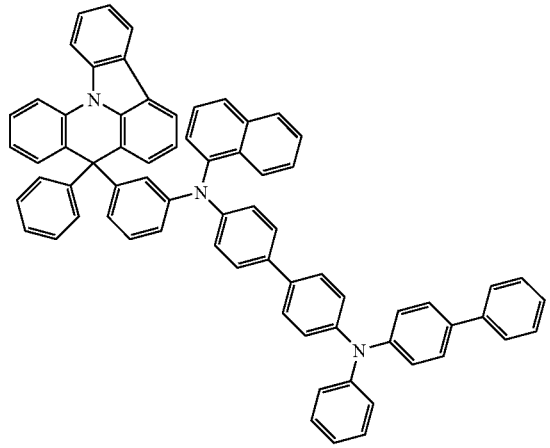

[Formula 2-308]

1) Production of arylamine(4-(N-phenyl-N-biphenylamino)-biphenyl-N'-naphthylamine) to Produce the Compound Represented by Formula 2-308

4-chlorobiphenyl-N-phenyl-N-biphenylamine (4.86 g, 11.2 mmol) and 1-naphthylamine (1.78 nil, 12.4 mmol) were dissolved in 100 ml of toluene, sodium-tertiary-butoxide (2.70 g, 28.1 mmol), bisdibenzylidene acetone palladium(0) (0.13 g, 0.23 mmol), and 50 wt % tri-tertiary-butylphosphine toluene solution (0.17 ml, 0.34 mmol) were added thereto, and reflux was conducted in a nitrogen atmosphere for 7 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (4.0 g, yield 69%).

MS: $[M+H]^+$=539.

2) The compound of Formula b (3.13 g, 6.47 mmol) and 4-(N-phenyl-N-biphenylamino)-biphenyl-N'-naphthylamine (3.8 g, 7.1 mmol) were dissolved in 40 ml of toluene, and sodium-tertiary-butoxide (1.94 g, 22.4 mmol), bisdibenzylidene acetone palladium(0) (0.081 g, 0.14 mmol), and 50 wt % tri-tertiary-butylphosphine toluene solution (0.11 ml, 0.22 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-308 (3.1 g, yield 51%).

MS: $[M+H]^+$=945.

Example 10

Preparation of Compound Represented by Following Formula 2-310

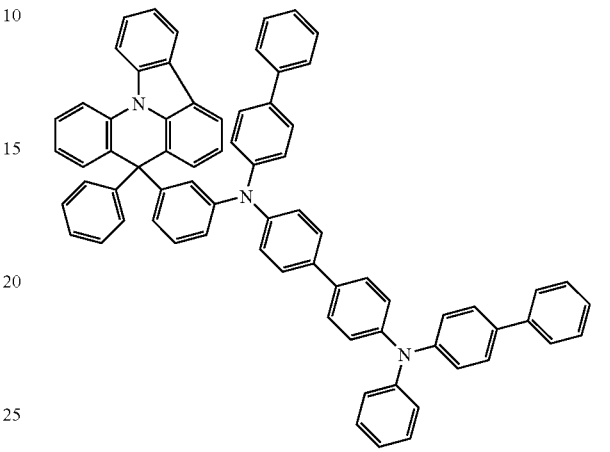

[Formula 2-310]

1) Production of arylamine(4-(N-phenyl-N-biphenylamino)-biphenyl-N'-biphenylamine) to Produce the Compound Represented by Formula 2-310

4-chlorobiphenyl-N-phenyl-N-biphenylamine (4.86 g, 11.2 mmol) and 4-aminobiphenyl (2.09 ml, 12.4 mmol) were dissolved in 100 ml of toluene, sodium-tertiary-butoxide (230 g, 28.1 mmol), bisdibenzylidene acetone palladium(0) (0.13 g, 0.23 mmol), and 50 wt % tri-tertiary-butylphosphine toluene solution (0.17 ml, 0.34 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran (n-hexane/THF=10/1), stirring was conducted using petroleum ether, and vacuum drying was conducted to produce an arylamine connection group (3.6 g, yield 56%).

MS: $[M+H]^+$=565.

2) The compound of Formula b (2.92 g, 6.02 mmol) and 4-(N-phenyl-N-biphenylamino)-biphenyl-N'-biphenylamine (3.57 g, 6.32 mmol) were dissolved in 40 ml of toluene, and sodium-tertiary-butoxide (1.94 g, 22.4 mmol), bisdibenzylidene acetone palladium(0) (0.073 g, 0.13 mmol), and 50 wt % tri-tertiary-butylphosphine toluene solution (0.10 ml, 0.19 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=8/1), stirring was conducted using petroleum ether, and vacuum drying was conducted to produce the compound of Formula 2-310 (2.5 g, yield 43%).

MS: $[M+H]^+$=971.

Example 11

Preparation of Compound Represented by Following Formula 3-2

[Formula 3-2]

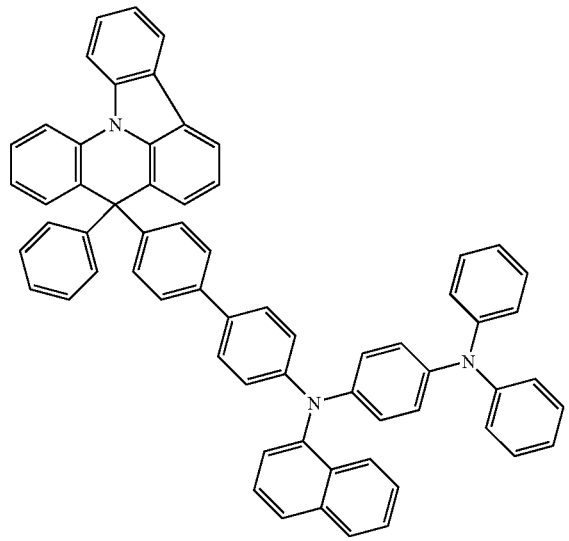

1) Production of arylamine(4-(N-phenyl-N-phenylamino) phenyl-1-naphthylamine) to Produce the Compound Represented by Formula 3-2

Synthesis was conducted through the same procedure as in synthesis of the arylamine connection group of the compound represented by Formula 2-2.

2) The compound of Formula b (5.0 g, 10.32 mmol) was completely dissolved in 40 ml of THF, 4-chloro-phenylboronic acid (2.42 g, 15.48 mmol), 2 M potassium carbonate solution, tetrakis(triphenylphosphine)palladium(0) (0.31 mmol, 0.36 g), and 10 ml of ethanol were added thereto, and reflux was conducted for 24 hours. After the reaction was completed, cooling to normal temperature was conducted, and filtration was conducted. Washing was conducted with water and ethanol several times. Recrystallization was conducted with ethanol, and vacuum drying was conducted to produce a compound (4.97 g, 93% yield).

MS: $[M+H]^+=517$.

The compound obtained by the above reaction (4.97 g, 9.63 mmol) and 4-(N-phenyl-N-phenylamino)phenyl-1-naphthylamine (5.58 g, 12.4 mmol) were dissolved in 50 ml of toluene, and sodium-tertiary-butoxide (1.85 g, 19.3 mmol), bis-dibenzylidene acetone palladium(0) (0.11 g, 0.19 mmol), and 50 wt % tri-tertiary-butylphosphine toluene solution (0.14 ml, 0.29 mmol) were added thereto. After reflux was conducted in a nitrogen atmosphere for 2 hours, distilled water was added to the reaction solution to complete the reaction. The organic layer was extracted, and a column separation process was conducted using a solvent of n-hexane and tetrahydrofuran (n-hexane/THF=4/1), stirring was conducted using petroleum ether, and vacuum drying was conducted to produce the compound of Formula 3-2 (4.5 g, yield 54%).

MS: $[M+H]^+=867$.

Experimental Example 1

Production of Organic Light Emitting Diode

Hexanitrile hexaazatriphenylene (hereinafter, referred to as "HAT") of the following Formula was vacuum deposited to a thickness of 500 by heating on a transparent ITO electrode, which was prepared through the above procedure, so as to form an anode including an ITO conductive layer and an N-type organic material.

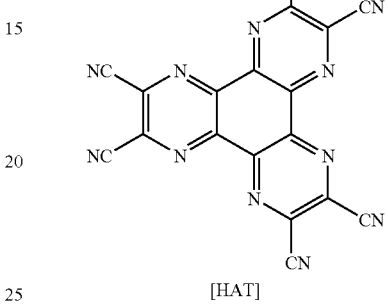

[HAT]

The compound of Formula 2-2 (400 Å) was vacuum deposited on the layer to form a hole transport layer. Then, $Alq_3$ was vacuum deposited to a thickness of 300 on the hole transport layer to form a light emitting layer. An electron transport layer material of the following Formula was deposited to a thickness of 200 on the light emitting layer to form an electron transport layer.

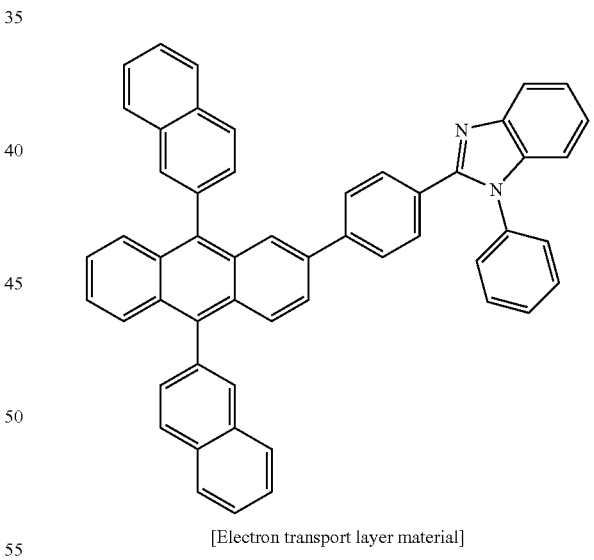

[Electron transport layer material]

Lithium fluoride (LiF) having a thickness of 12 and aluminum having a thickness of 2,000 were sequentially deposited on the electron transport layer to form a cathode.

In the above procedure, the deposition speed of an organic material was maintained at 0.3 to 0.8 Å/sec. Furthermore, lithium fluoride and aluminum were deposited at speeds of 0.3 Å/sec and 1.5 to 2.5 Å/sec, respectively, on the cathode. During the deposition, a vacuum was maintained at 1 to 3 $10^{-7}$.

The resulting device had an electric field of 7.44 V at a forward current density of 100 mA/cm², and a spectrum having a light efficiency of 1.69 lm/W. The operation and light emission of the device at the above-mentioned actuating voltage mean that the compound of Formula 2-2, which formed the layer between the hole injection layer and the light emitting layer, functions to transport holes.

Experimental Example 2

Production of Organic Light Emitting Diode

HAT was deposited to a thickness of 80 on an ITO electrode, which was prepared by the same method as in Experimental Example 1, so as to form a thin film. Interfacial characteristic between the substrate and hole injection layer can be improved by the thin film. Subsequently, the compound of Formula 2-2 was deposited to a thickness of 800 on the thin film to form a hole injection layer.

NPB was deposited to a thickness of 300 on the hole injection layer to form a hole transport layer. Then, $Alq_3$ was deposited to a thickness of 300 on the hole transport layer to form a light emitting layer. An electron transport layer and a cathode were formed on the light emitting layer by the same method as in Experimental Example 1.

The resulting device had an electric field of 9.36 V at a forward current density of 100 mA/cm$^2$, and a spectrum having a light efficiency of 2.38 lm/W. The operation and light emission of the device at the above-mentioned actuating voltage mean that the compound of Formula 2-2, which formed the layer between the thin film formed on the substrate and the hole transport layer, functions to inject holes.

Experimental Example 3

Production of Organic Light Emitting Diode

The procedure of Experimental Example 1 was repeated to produce a device except that instead of the compound of Formula 2-2, the compound of Formula 2-256 was used as a hole transport layer.

The resulting device had an electric field of 8.05 V at a forward current density of 100 mA/cm$^2$, and a spectrum having a light efficiency of 2.01 lm/W.

Experimental Example 4

Production of Organic Light Emitting Diode

The procedure of Experimental Example 1 was repeated to produce a device except that instead of the compound of Formula 2-2, the compound of Formula 2-257 was used as a hole transport layer.

The resulting device had an electric field of 8.08 V at a forward current density of 100 mA/cm$^2$, and a spectrum having a light efficiency of 2.37 lm/W.

Experimental Example 5

Production of Organic Light Emitting Diode

The procedure of Experimental Example 1 was repeated to produce a device except that instead of the compound of Formula 2-2, the compound of Formula 2-259 was used as a hole transport layer.

The resulting device had an electric field of 8.00 V at a forward current density of 100 mA/cm$^2$, and a spectrum having a light efficiency of 2.23 lm/W.

Experimental Example 6

Production of Organic Light Emitting Diode

The procedure of Experimental Example 1 was repeated to produce a device except that instead of the compound of Formula 2-2, the compound of Formula 2-273 was used as a hole transport layer.

The resulting device had an electric field of 8.02 V at a forward current density of 100 mA/cm$^2$, and a spectrum having a light efficiency of 2.16 lm/W.

Experimental Example 7

Production of Organic Light Emitting Diode

The procedure of Experimental Example 1 was repeated to produce a device except that instead of the compound of Formula 2-2, the compound of Formula 2-274 was used as a hole transport layer.

The resulting device had an electric field of 4.43 V at a forward current density of 100 mA/cm$^2$, and a spectrum having a light efficiency of 2.24 lm/W.

Example 8

Production of organic light emitting diode

The procedure of Experimental Example 1 was repeated to produce a device except that instead of the compound of Formula 2-2, the compound of Formula 2-276 was used as a hole transport layer.

The resulting device had an electric field of 8.13 V at a forward current density of 100 mA/cm$^2$, and a spectrum having a light efficiency of 2.32 lm/W.

Example 9

Production of Organic Light Emitting Diode

The procedure of Experimental Example 1 was repeated to produce a device except that instead of the compound of Formula 2-2, the compound of Formula 2-307 was used as a hole transport layer.

The resulting device had an electric field of 8.05 V at a forward current density of 100 mA/cm$^2$, and a spectrum having a light efficiency of 2.031 m/W.

Example 10

Production of Organic Light Emitting Diode

The procedure of Experimental Example 1 was repeated to produce a device except that instead of the compound of Formula 2-2, the compound of Formula 2-308 was used as a hole transport layer.

The resulting device had an electric field of 8.07 V at a forward current density of 100 mA/cm$^2$, and a spectrum having a light efficiency of 2.23 lm/W.

Example 11

Production of Organic Light Emitting Diode

The procedure of Experimental Example 1 was repeated to produce a device except that instead of the compound of Formula 2-2, the compound of Formula 2-310 was used as a hole transport layer.

The resulting device had an electric field of 8.01 V at a forward current density of 100 mA/cm², and a spectrum having a light efficiency of 2.19 lm/W.

Example 12

Production of Organic Light Emitting Diode

The procedure of Experimental Example 1 was repeated to produce a device except that instead of the compound of Formula 2-2, the compound of Formula 3-2 was used as a hole transport layer.

The resulting device had an electric field of 7.34 V at a forward current density of 100 mA/cm², and a spectrum having a light efficiency of 1.73 lm/W.

The invention claimed is:
1. A compound represented by the following Formula 1:

[Formula 1]

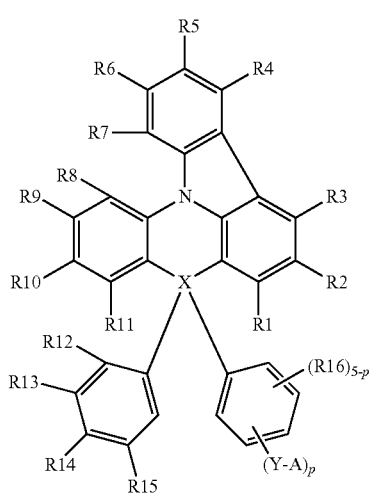

wherein, X is C or Si,
Ys are directly connected to each other; bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy, and amino groups,
R1 to R11 are the same or different from each other, and each independently hydrogen, a substituted or unsubstituted alkyl group, a substituted or un-substituted alkoxy group, a substituted or unsubstituted alkenyl group, a substituted or unsubstituted aryl group, a substituted or unsubstituted arylamine group, a substituted or unsubstituted heterocyclic group, an amino group, a nitrile group, a nitro group, a halogen group, an amide group, or an ester group, in which they may form aliphatic, aromatic or hetero condensation rings along with adjacent groups,
R12 and R16 are the same or different from each other, and each independently hydrogen, a substituted or unsubstituted alkyl group, a substituted or unsubstituted alkoxy group, a substituted or unsubstituted alkenyl group, a substituted or unsubstituted aryl group, a substituted or unsubstituted heterocyclic group, an amino group, a nitrile group, a nitro group, a halogen group, an amide group, or an ester group, in which they may form aliphatic, aromatic or hetero condensation rings along with adjacent groups,
R7 and R8 are directly connected to each other, or form a condensation ring along with a group selected from the group consisting of O, S, NR, PR, C=O,
CRR' and SiRR' in which R and R' are the same or different from each other, each independently hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, or an ester group, and form a condensation ring to form a spiro compound,
p is an integer of 1 to 5,
A is

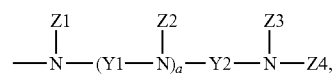

a is an integer of 0 to 10,
Y1 and Y2 are the same or different from each other, and each independently bivalent aromatic hydrocarbons; bivalent aromatic hydrocarbons which are substituted with at least one substituent group selected from the group consisting of nitro, nitrile, halogen, alkyl, alkoxy, and amino groups; a bivalent heterocyclic group; or a bivalent heterocyclic group which is substituted with at least one substituent group selected from the group consisting of nitro, nitrile, halogen, alkyl, alkoxy and amino groups, and
Z1 to Z4 are the same or different from each other, and each independently hydrogen; aliphatic hydrocarbons having 1 to 20 carbon atoms; aromatic hydrocarbons; aromatic hydrocarbons which are substituted with at least one substituent group selected from the group consisting of nitro, nitrile, halogen, alkyl, alkoxy, amino, aromatic hydrocarbon, and heterocyclic groups; a silicon group substituted with aromatic hydrocarbons; a heterocyclic group; a heterocyclic; group which is substituted with at least one substituent group selected from the group consisting of nitro, nitrile, halogen, alkyl, alkoxy, amino, aromatic hydrocarbon, and heterocyclic groups; a thiophene group which is substituted with aliphatic hydrocarbons having 1 to 20 carbon atoms or aromatic hydrocarbons having 6 to 20 carbon atoms; or a boron group which is substituted with aromatic hydrocarbons.

2. The compound according to in claim 1, wherein the bivalent aromatic hydrocarbon of Y, Y1 and Y2 of Formula 1 is selected from the group consisting of phenylene, biphenylene, terphenylene, naphthylene, anthracenylene, pyrenylene, and perylenylene.

3. The compound according to in claim 1, wherein the bivalent heterocyclic group of Y, Y1 and Y2 of Formula 1 is selected from the group consisting of thiophenylene, furylene, pynolyiene, imidazolylene, thiazolylene, oxazolylene, oxa-diazolylene, thiadiazolylene, triazolylene, pyridylene, pyridazylene, pyrazinylene, quinolylene and isoquinolylene.

4. The compound according to claim 1, wherein the aromatic hydrocarbon of Z1 to Z4 of Formula 1 is selected from the group consisting of phenyl, biphenyl, terphenyl, naphthyl, anthracenyl, pyrenyl, and perylenyl.

5. The compound according to claim 1, wherein the heterocyclic group of Z1 to Z4 of Formula 1 is selected from the group consisting of thiophene, furan, pyrrole, imidazole, thiazole, oxazole, oxadiazole, thiadiazole, triazole, pyridyl, pyridazyl, pyrazine, quinoline and isoquinoline.

6. The compound according to claim 1, wherein the aliphatic hydrocarbon having 1 to 20 carbon atoms of Z1 to Z4 of Formula is selected from the group consisting of a methyl group, an ethyl group, an n-propyl group, an iso-propyl group, an n-butyl group, a sec-butyl group, an iso-butyl group, a ter-butyl group, a pentyl group, a hexyl group, a styryl group, and an acetylene group.

7. The compound according to claim 1, wherein the aryl group of R1 to R16 of Formula 1 is selected from the group consisting of a phenyl group, a biphenyl group, a terphenyl group, a stilbene group, a naphthyl group, an anthracenyl group, a phenanthrene group, a pyrenyl group, and a perylenyl group.

8. The compound according to claim 1, wherein the arylamine group of R1 to R11 of Formula 1 is selected from the group consisting of a diphenylamine group, a dinaphthylamine group, a dibiphenylamine group, a phenylnaphthylamine group, a phenyldiphetylamine, group, a ditolylamine group, a phenyltolylamine group, a carbazolyl group, and a triphenylamine group.

9. The compound according to claim 1, wherein the heterocyclic group of R1 to R16 of Formula 1 is selected from the group consisting of a thiophene group, a furan group, a pyrrole group, an imidazole group, a thiazole group, an oxazole group, an oxadiazole group, a triazole group, a pyridyl group, a pyradazine group, a quinolinyl group, an isoquinoline group, and an acridyl group.

10. The compound according to claim 1, wherein the alkenyl, aryl, arylamine, and heterocyclic groups of R1 to R16 of Formula 1 are selected from the group consisting of the following Formulae:

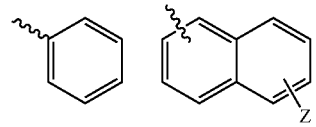

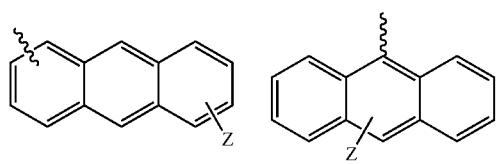

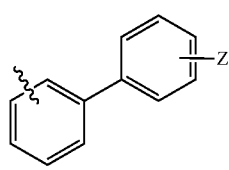

-continued

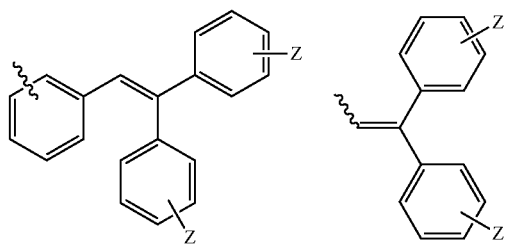

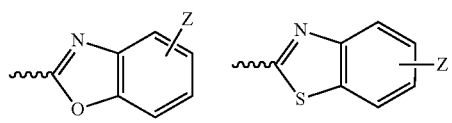

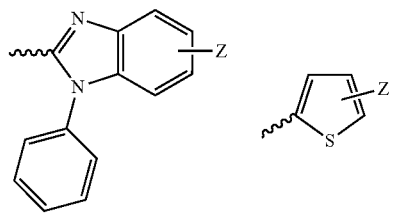

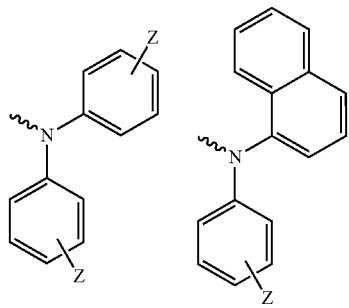

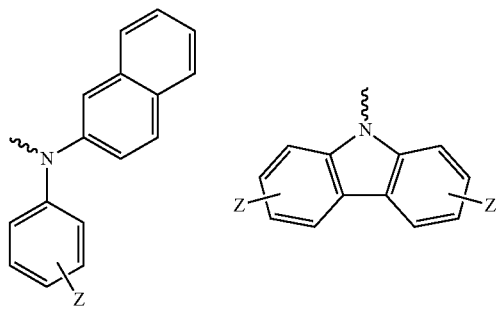

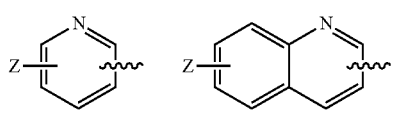

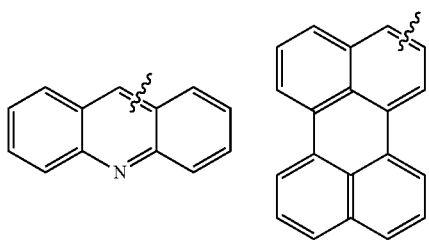
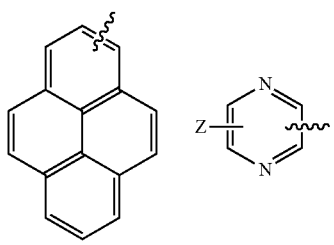
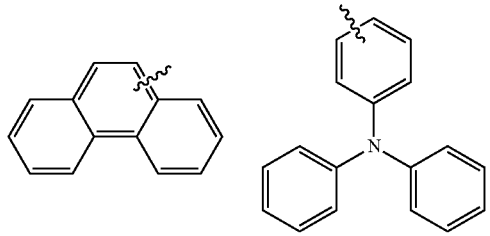
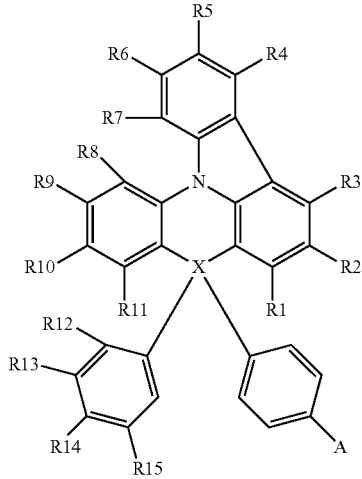

wherein Z is a group selected from the group consisting of hydrogen, aliphatic hydrocarbons having 1 to 20 carbon atoms, an alkoxy group, an arylamine group, an aryl group, a heterocyclic group, a nitrile group, and an acetylene group.

11. The compound according to claim 1, wherein Formula 1 is represented by any one of the following Formulae 2 to 7:

[Formula 2]

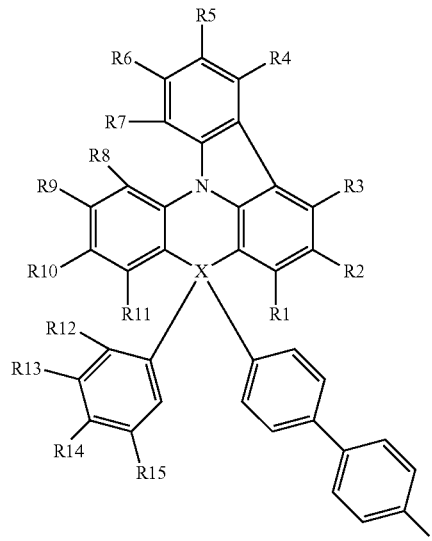

[Formula 3]

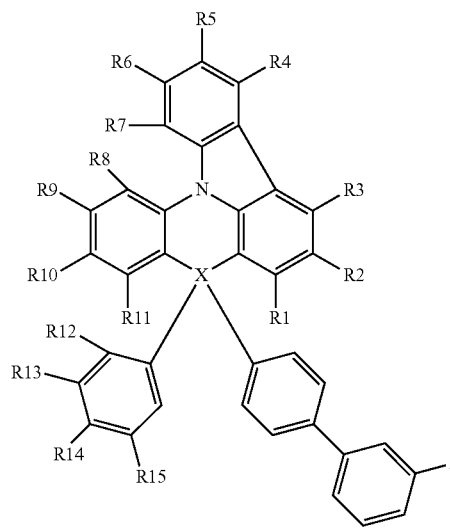

[Formula 4]

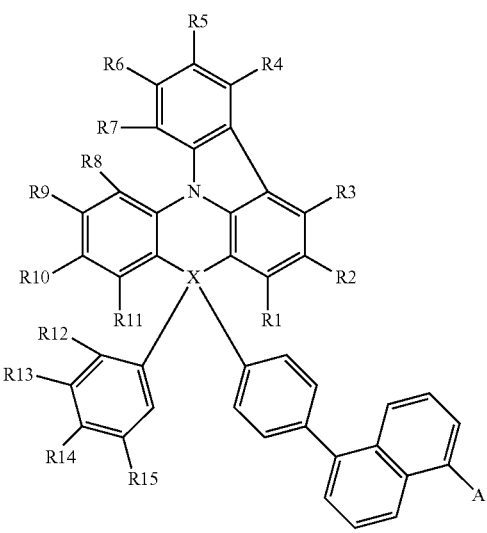

[Formula 5]

[Formula 6]
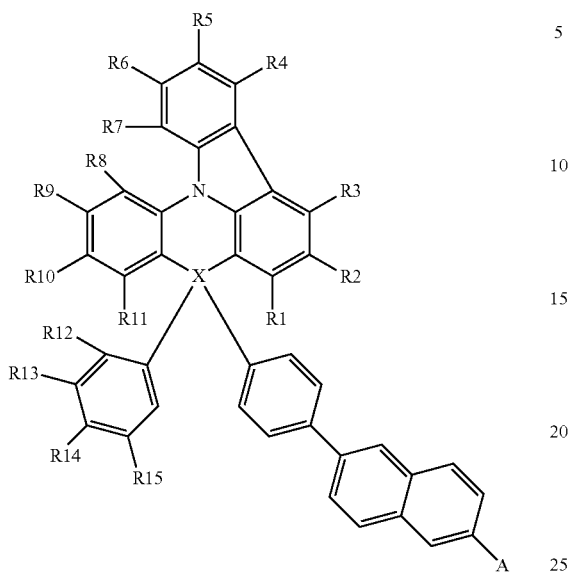
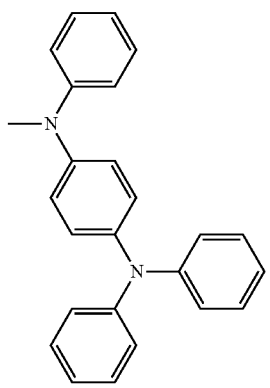
1
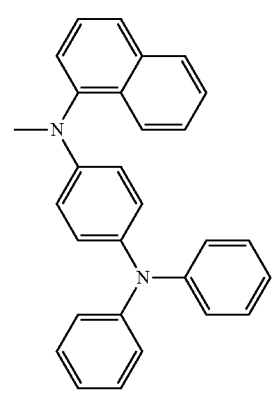
2
[Formula 7]
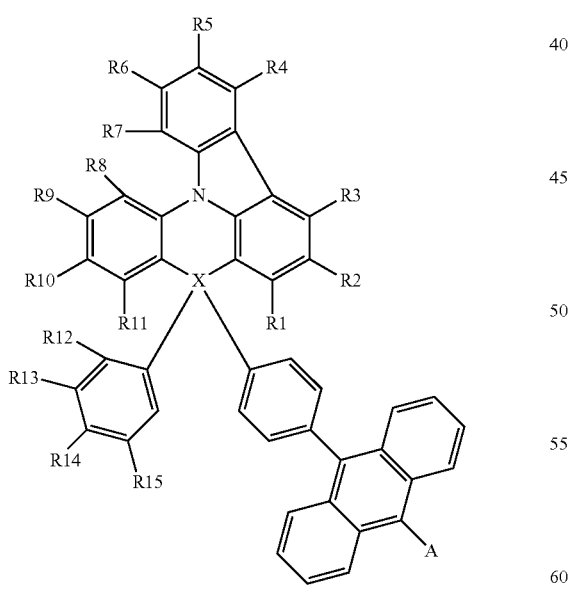
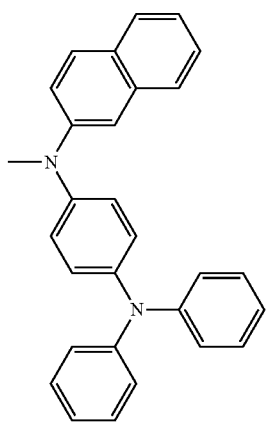
3
wherein X, R1 to R15, and A are as defined in Formula 1.
12. The compound according to claim 1, wherein A of Formula 1 is selected from the group consisting of the following groups:

4
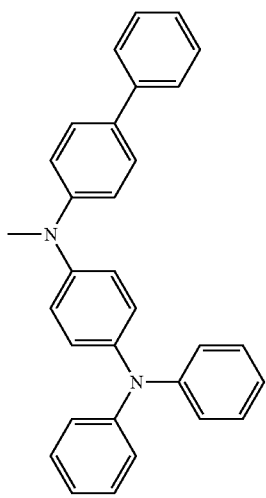
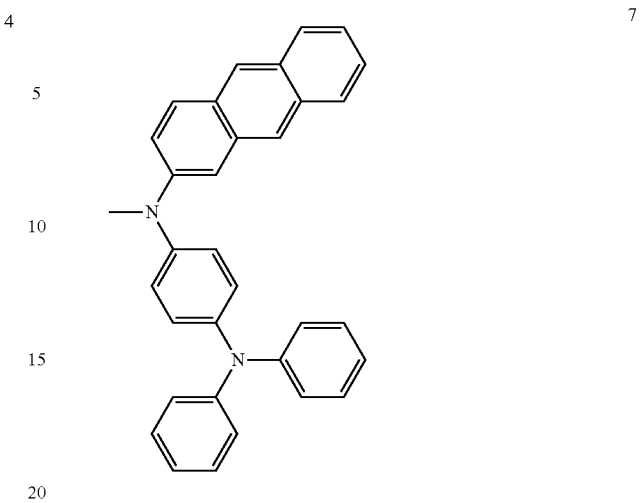
5
5
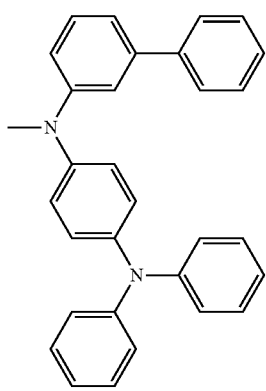
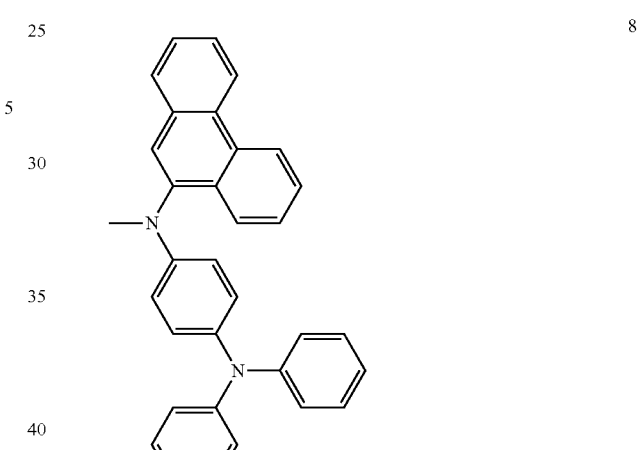
6
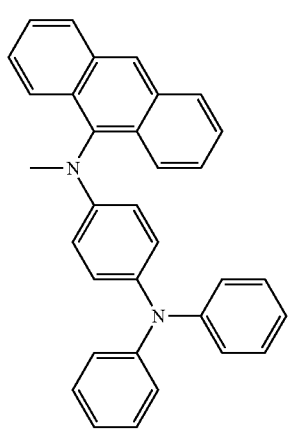
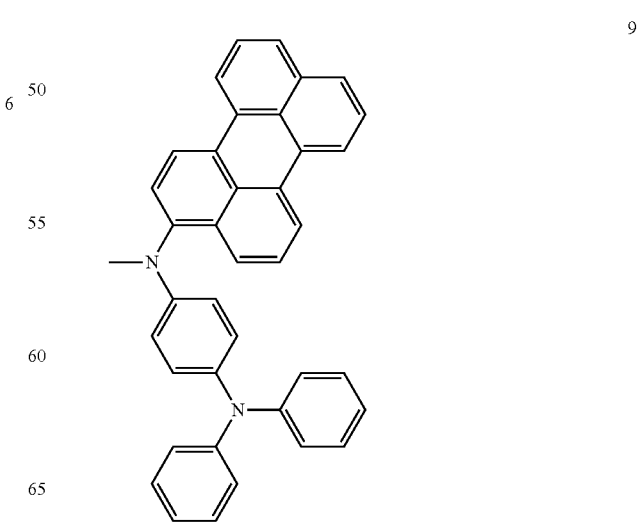

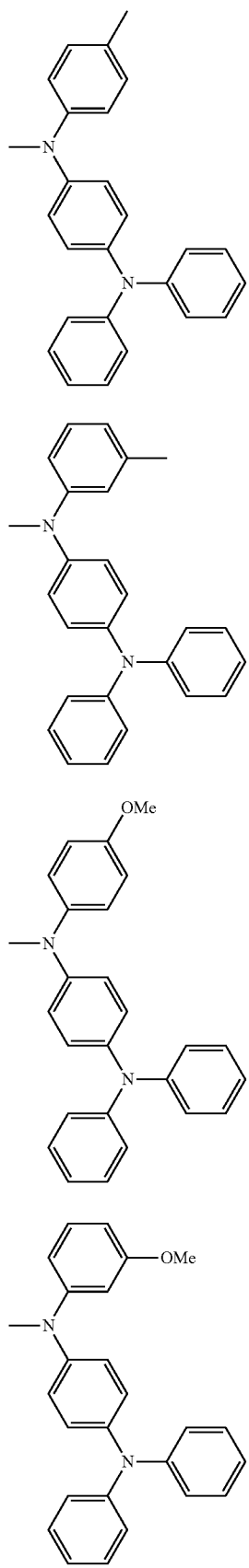
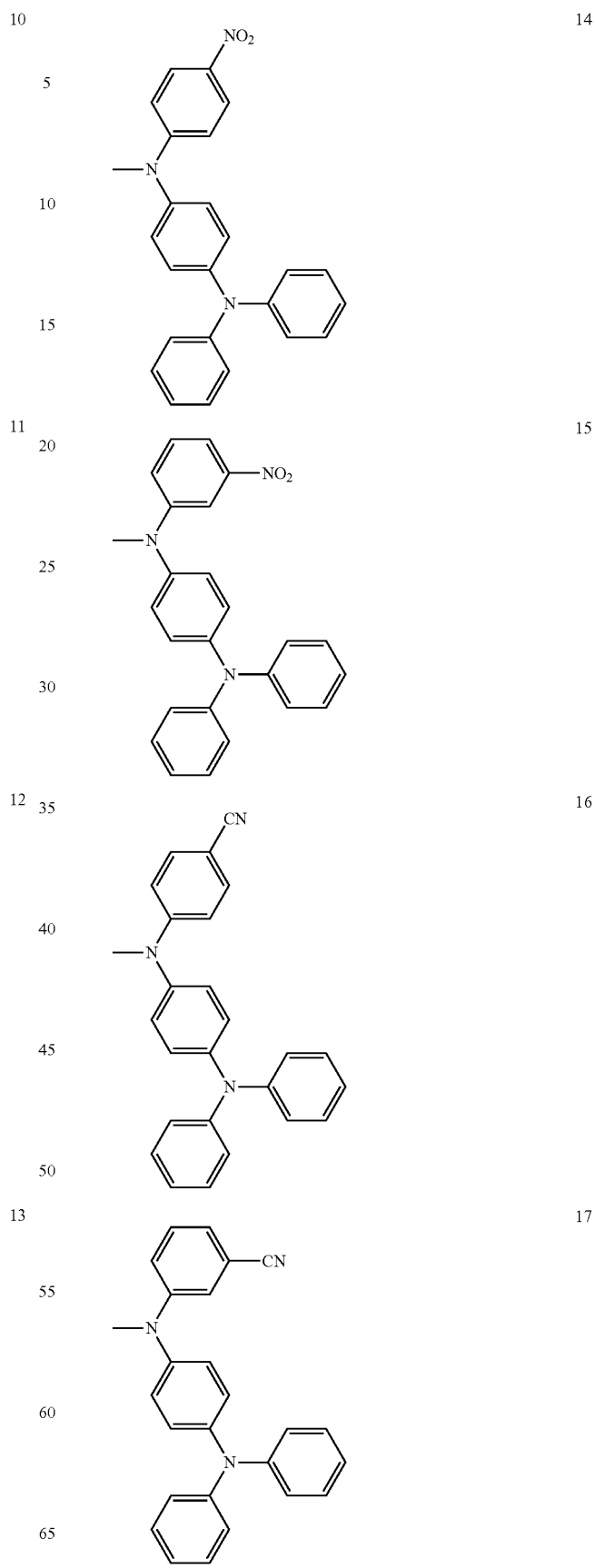

18
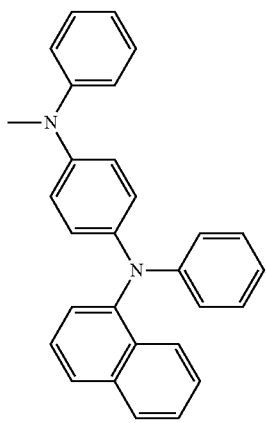
19
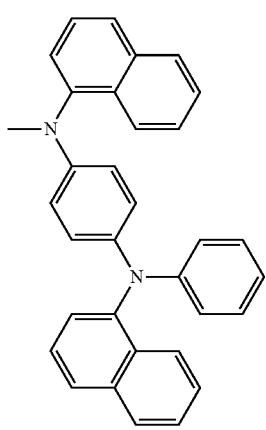
20
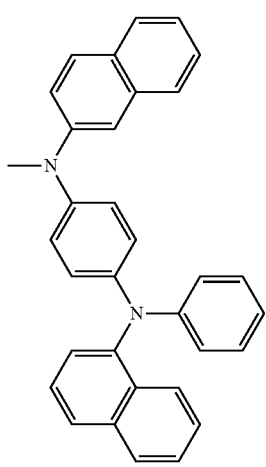
21
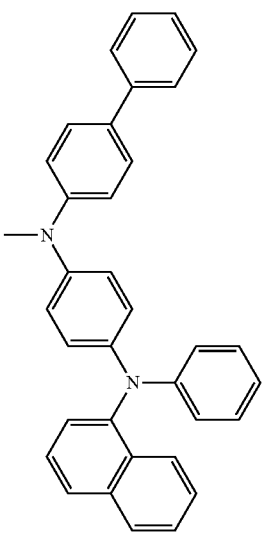
22
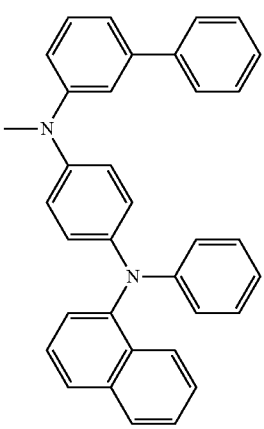
23
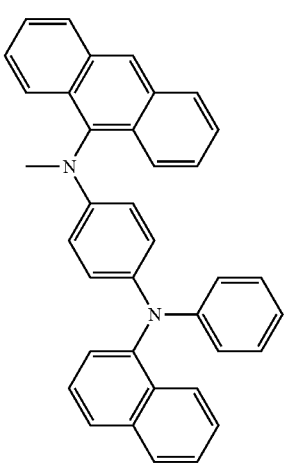

24
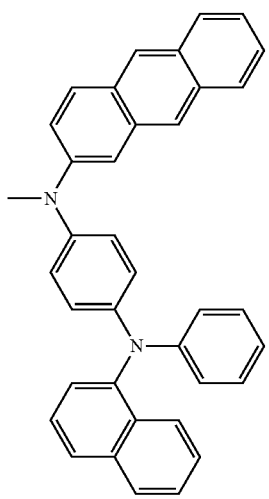
25
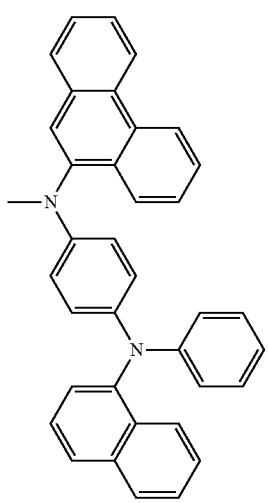
26
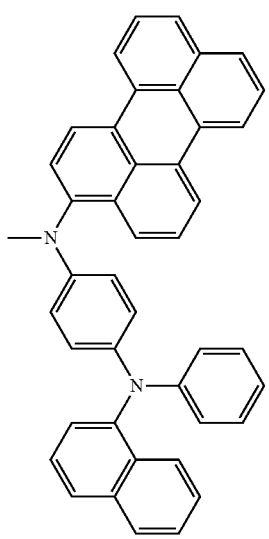
27
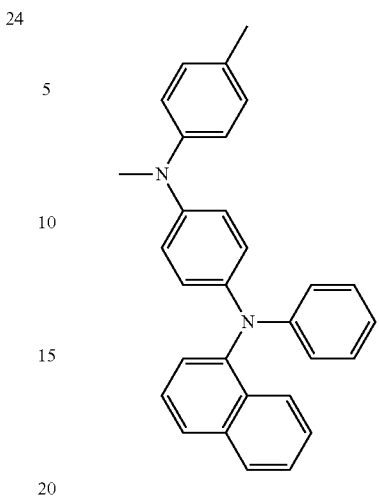
28
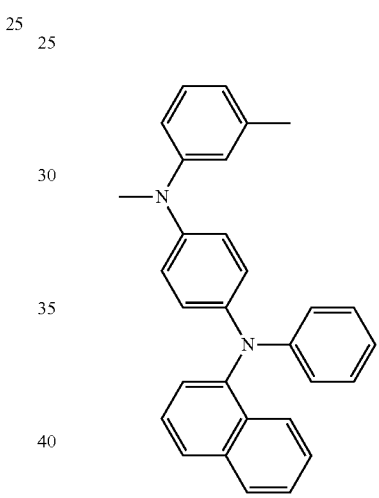
29
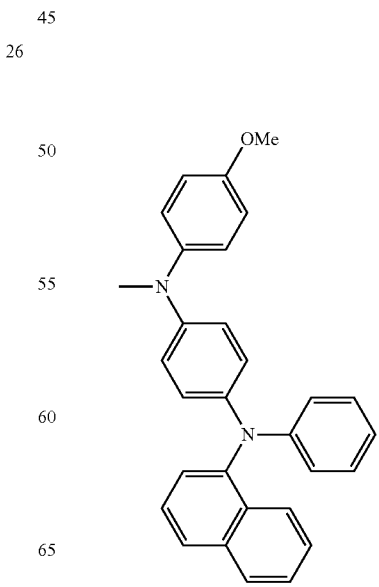

245
-continued
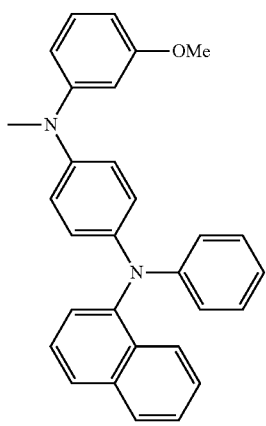
30
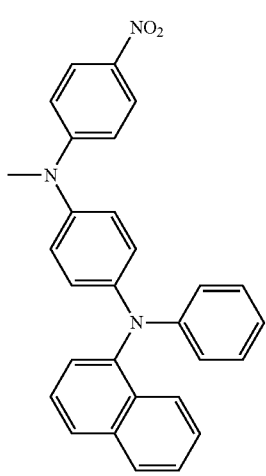
31
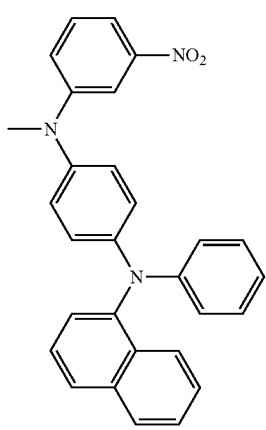
32
246
-continued
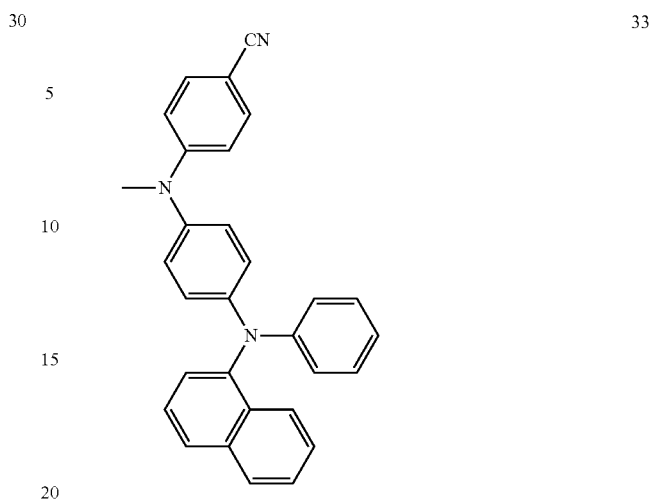
33
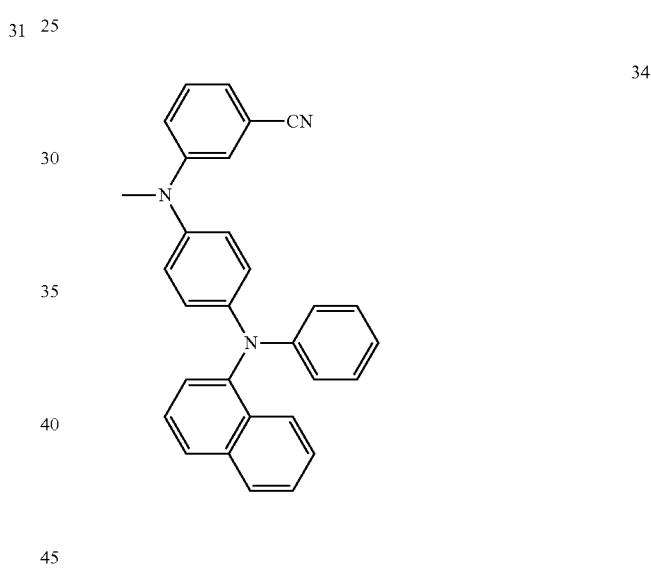
34
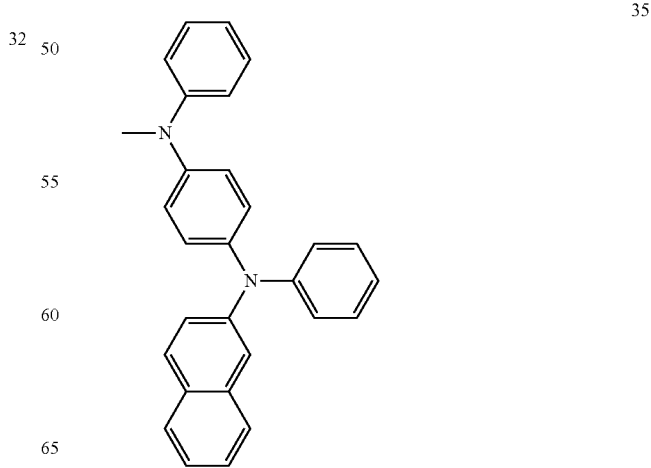
35

36
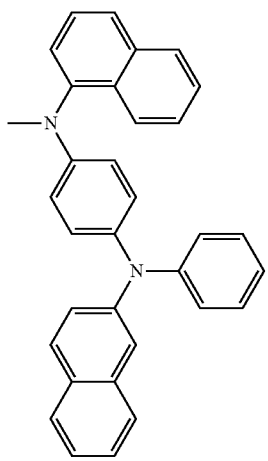
37
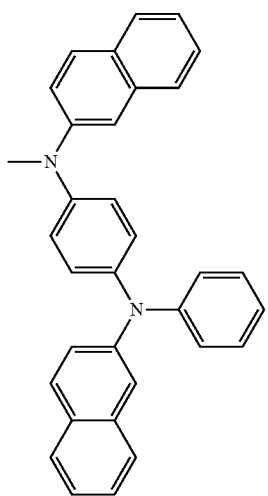
38
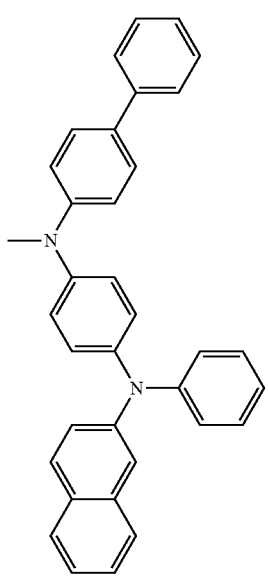
39
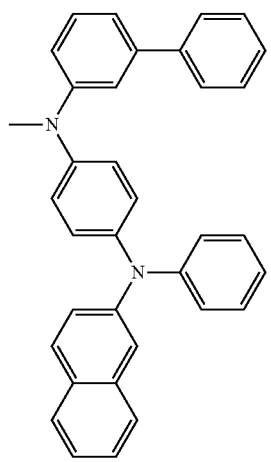
40
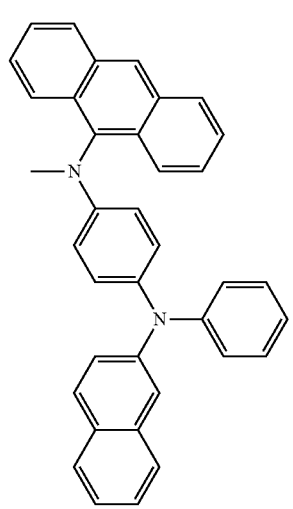
41
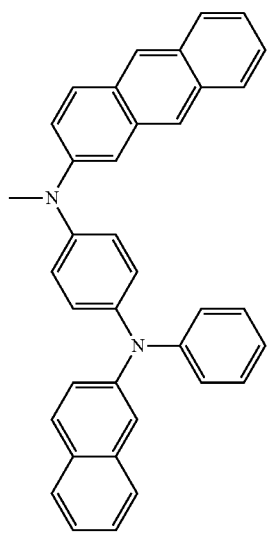

249
-continued
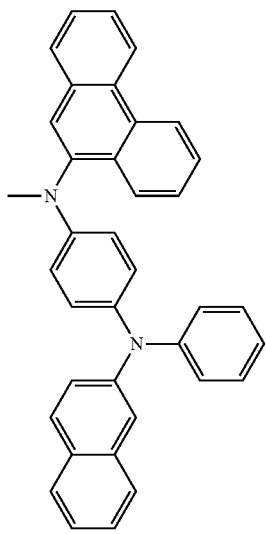
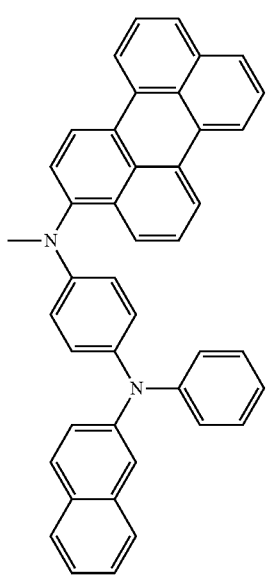
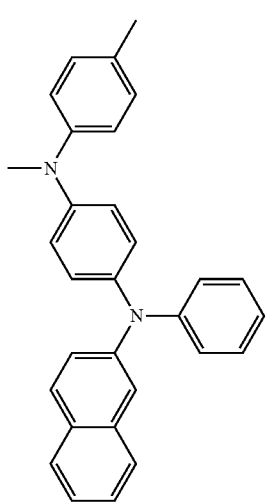
250
-continued
42
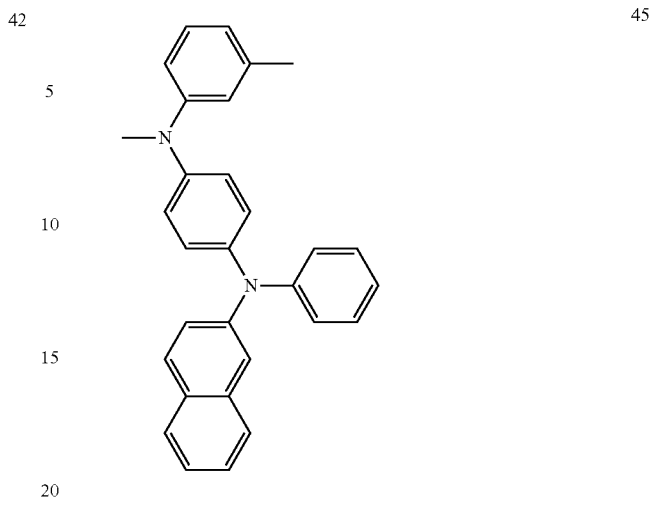
43
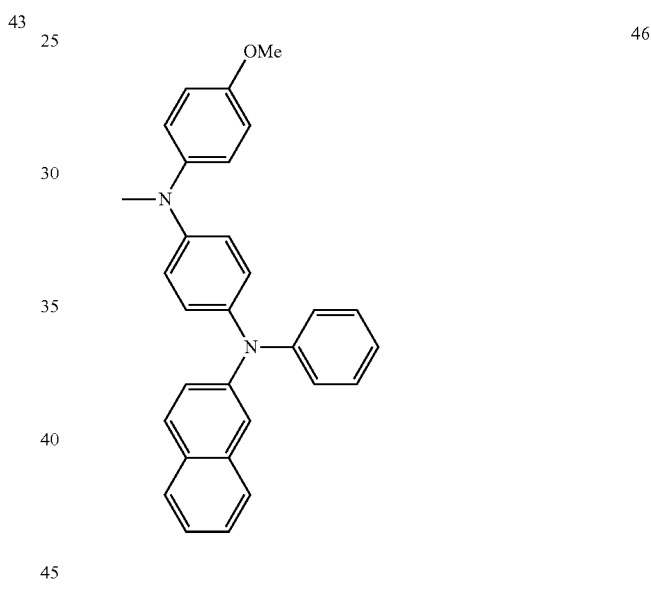
44
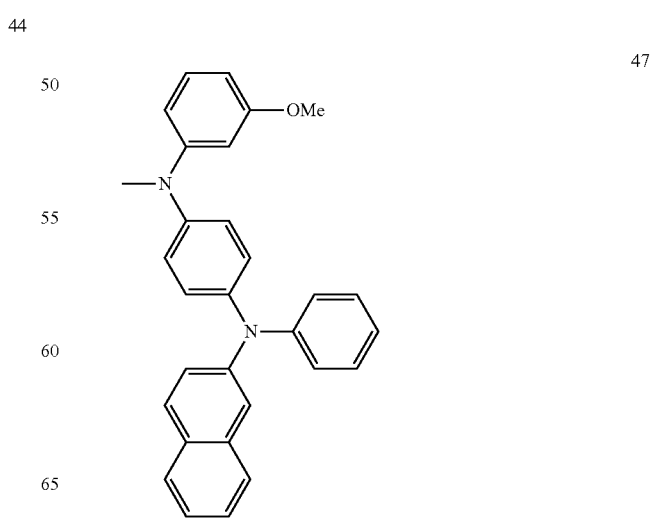

48
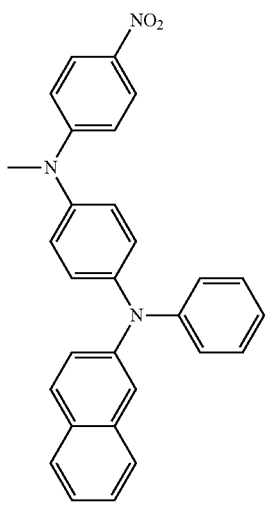
49
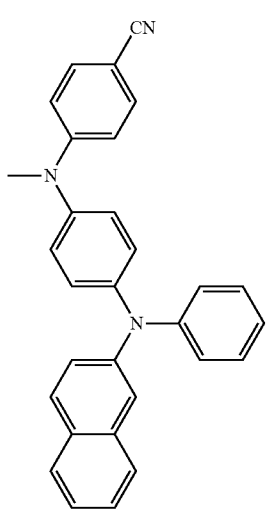
51
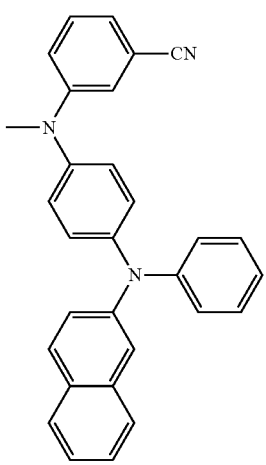
52
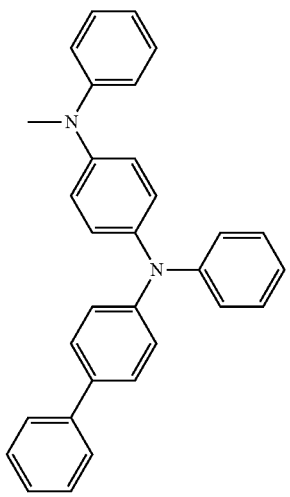
53
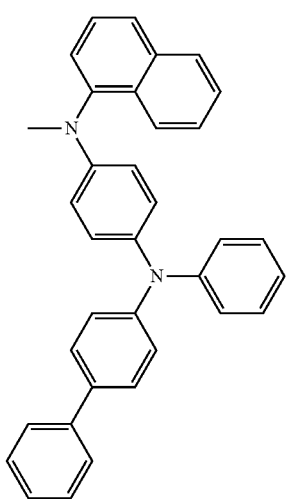

54
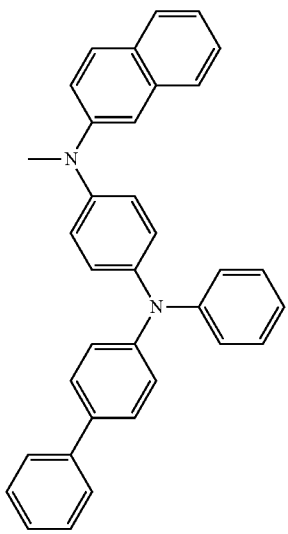
55
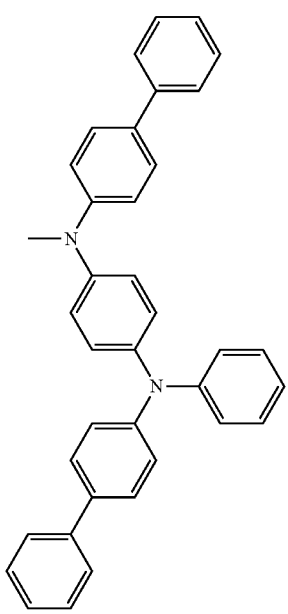
56
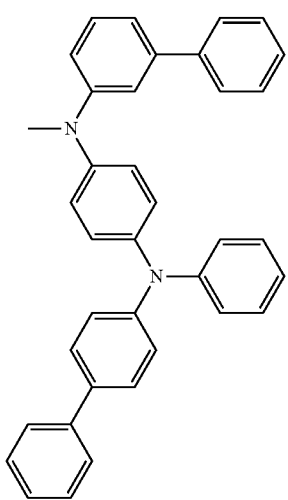
57
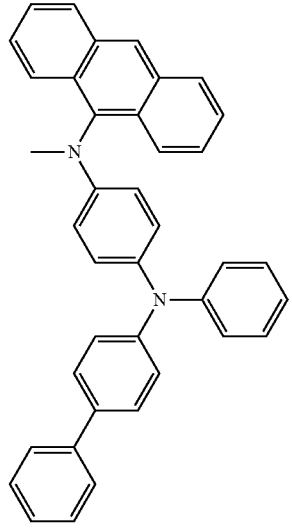
58
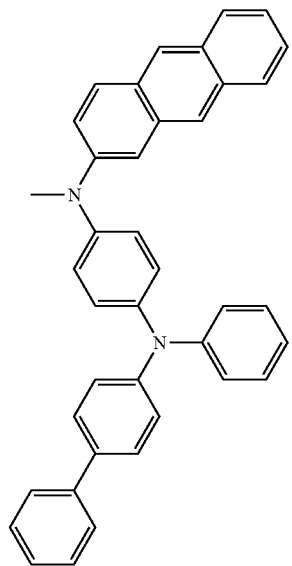
59
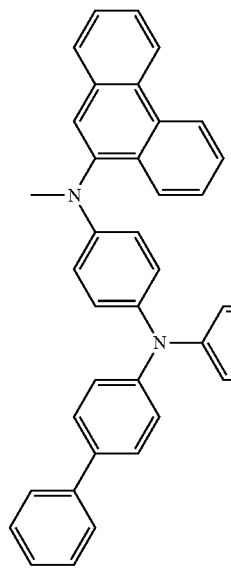

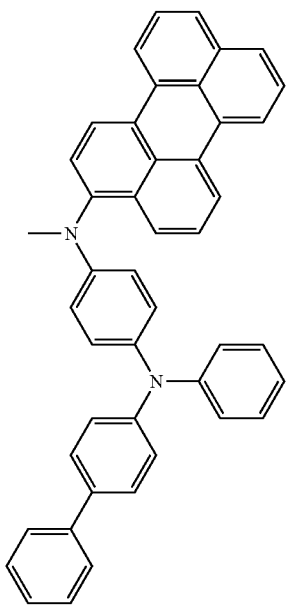
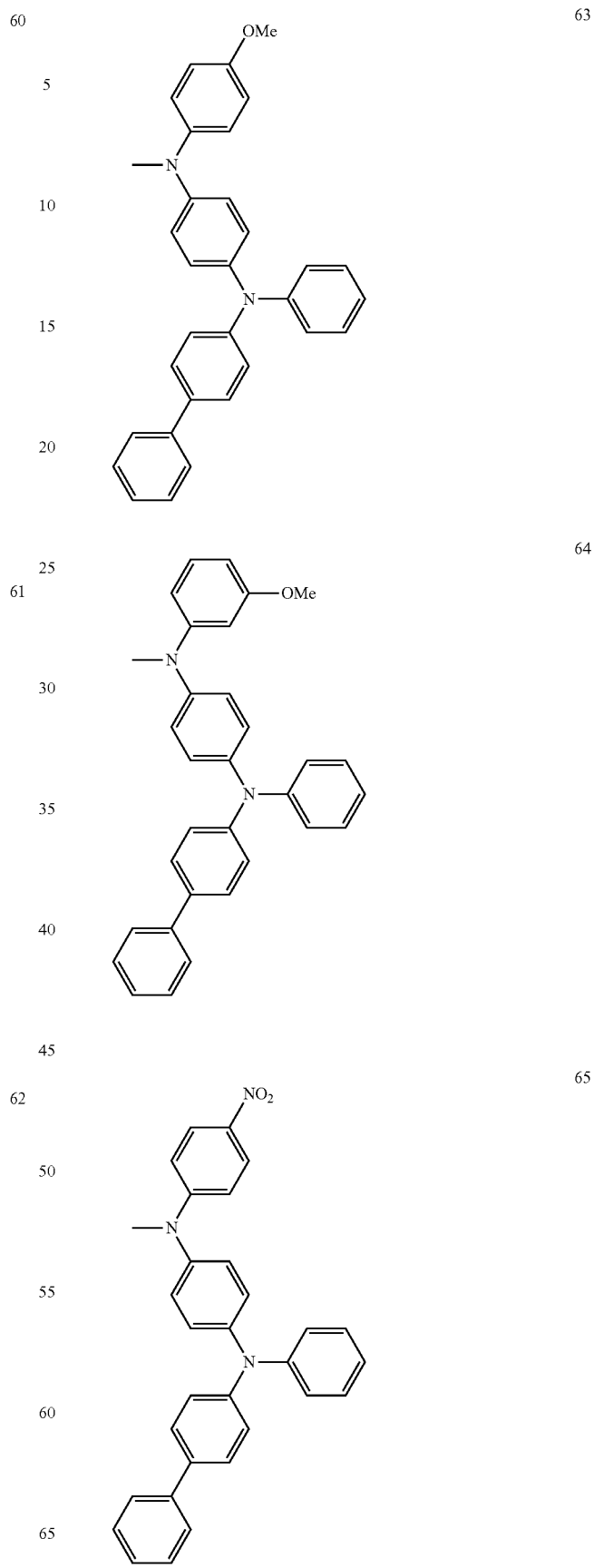

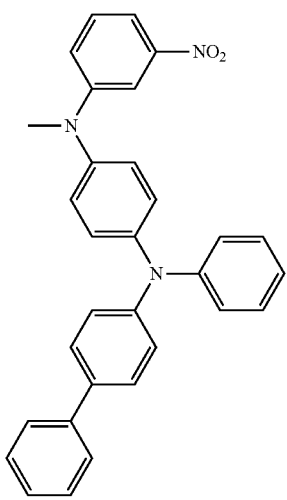
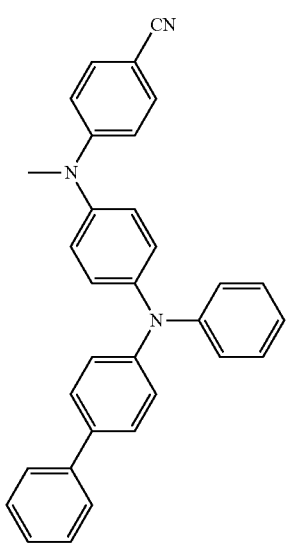
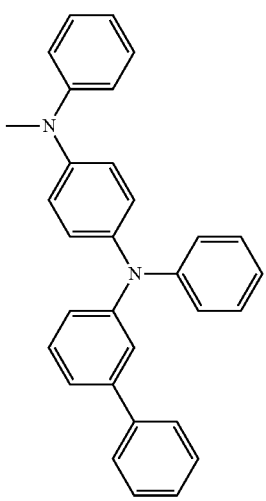
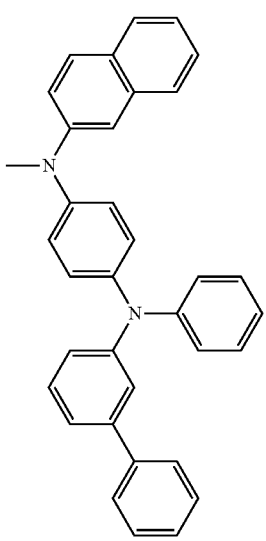

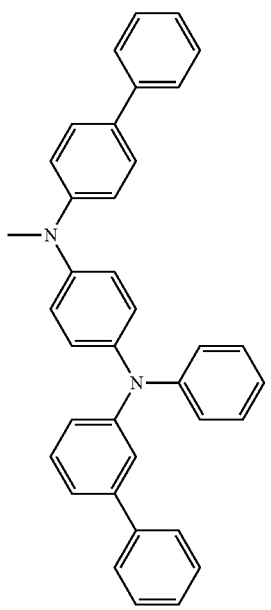
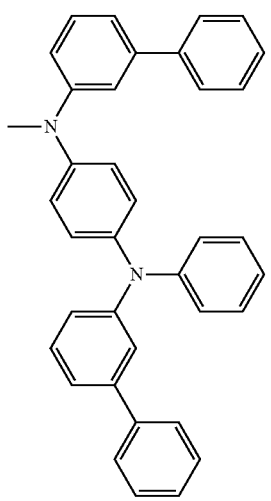
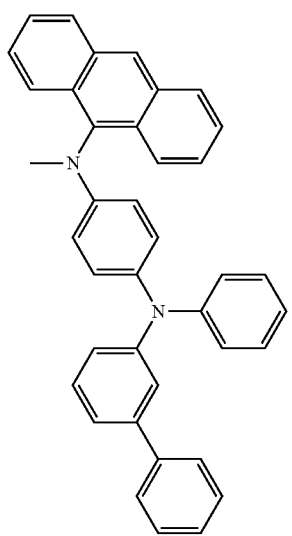
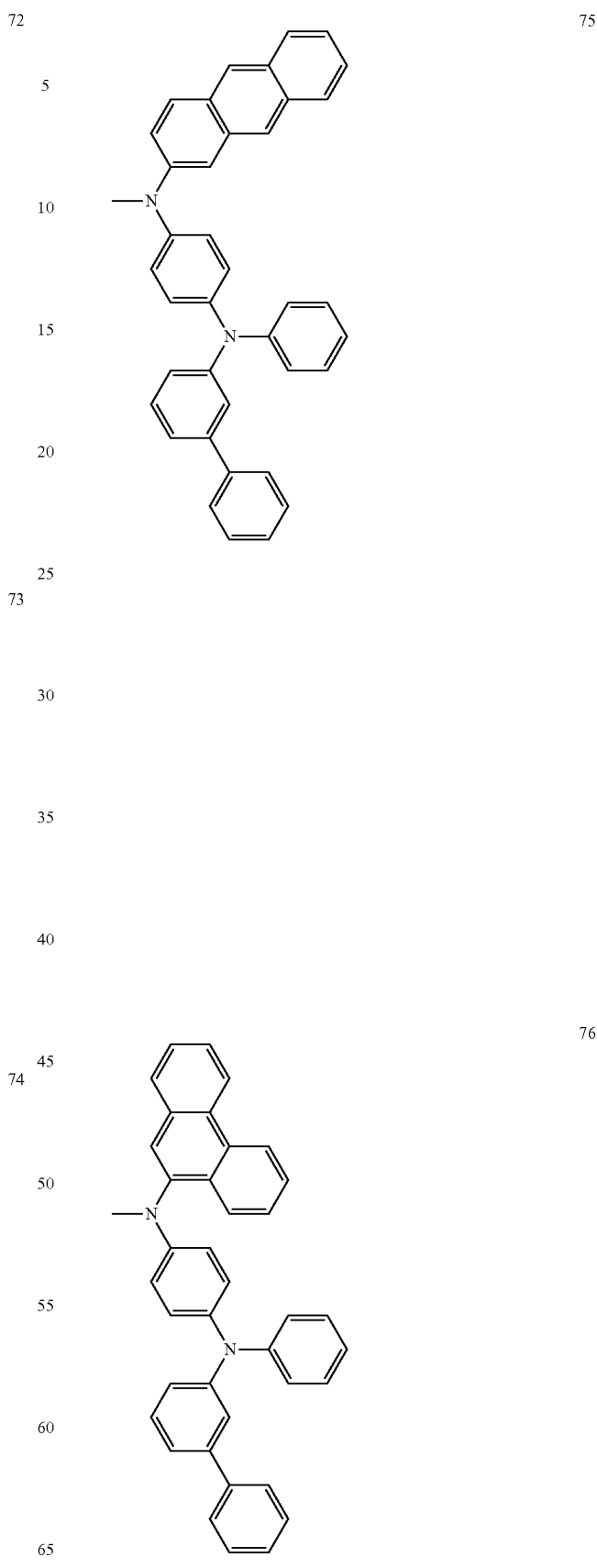

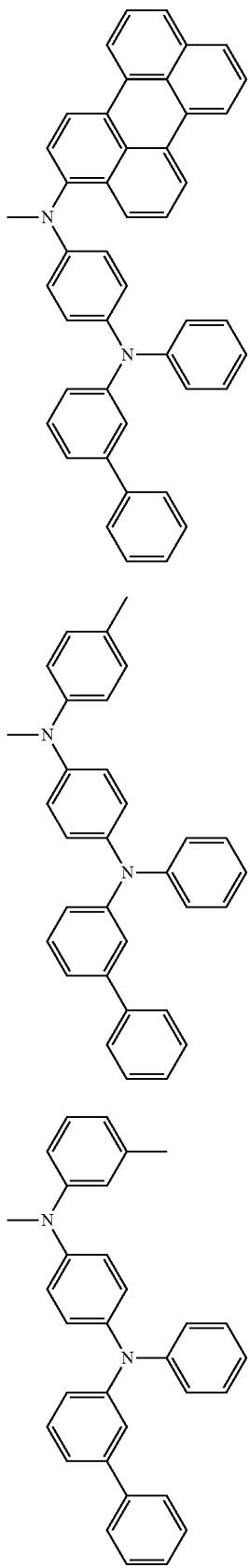
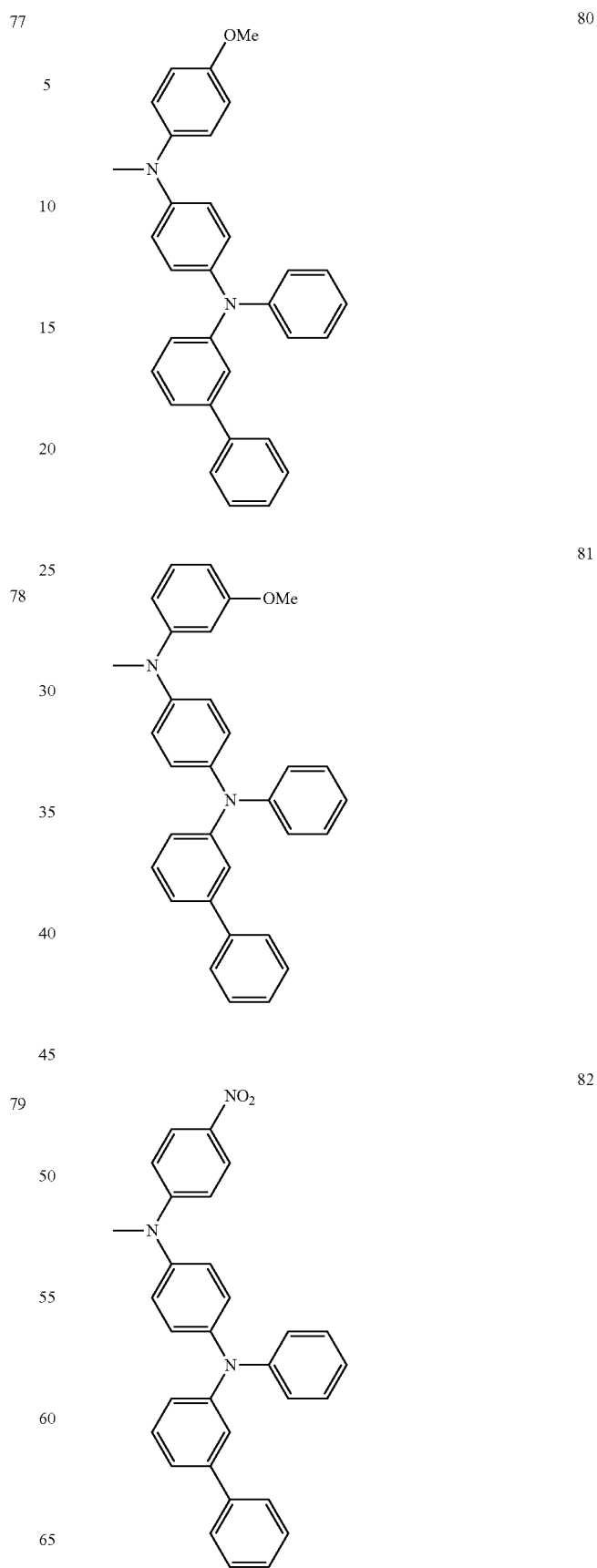

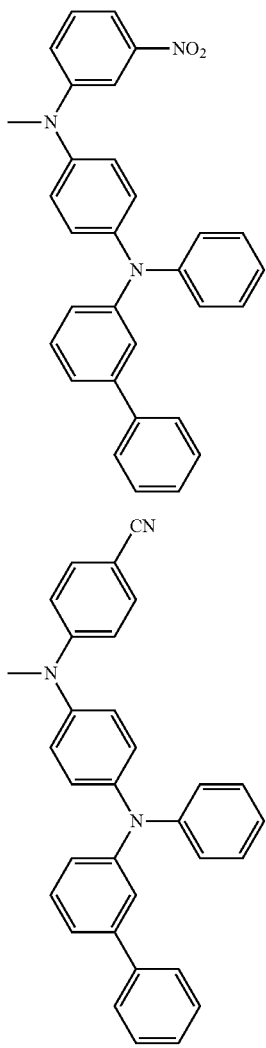

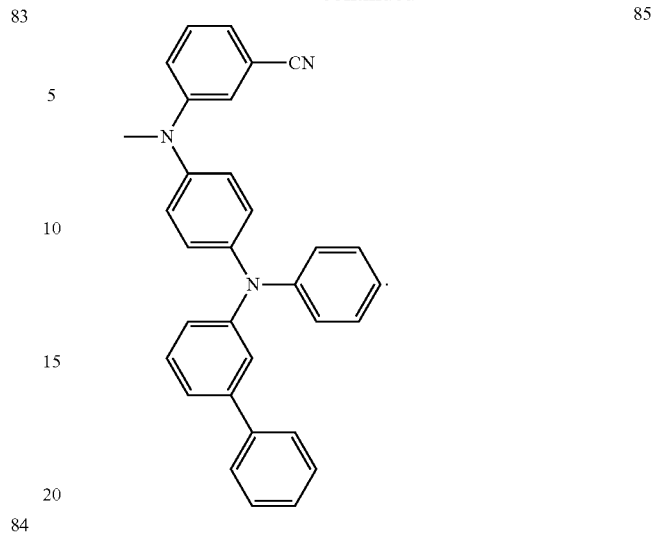

13. An organic light emitting diode comprising a first electrode, at least one organic material layer, and a second electrode, wherein the first electrode, the organic material layer(s), and the second electrode form a layered structure and at least one layer of the organic material layers includes the compound of claim 1.

14. The organic light emitting diode according to claim 13, wherein the organic material layer comprises a hole transport layer, and the hole transport layer contains the compound.

15. The organic light emitting diode according to claim 13, wherein the organic material layer comprises a hole injection layer, and the hole injection layer contains the compound.

16. The organic light emitting diode according to claim 13, wherein the organic material layer comprises a hole injection and transport, layer, and the hole injection and transport layer contains the compound.

* * * * *